US012668641B2

(12) United States Patent
De Jong et al.

(10) Patent No.: US 12,668,641 B2
(45) Date of Patent: Jun. 30, 2026

(54) ANTIBODY VARIANT COMBINATIONS AND USES THEREOF

(71) Applicant: GENMAB B.V., Utrecht (NL)

(72) Inventors: Rob De Jong, Utrecht (NL); Frank Beurskens, Utrecht (NL); Gijs Zom, Utrecht (NL); Janine Schuurman, Diemen (NL); Xiaoguang Xue, Utrecht (NL)

(73) Assignee: GENMAB B.V., Utrecht (NL)

( * ) Notice: Subject to any disclaimer, the term of this patent is extended or adjusted under 35 U.S.C. 154(b) by 1000 days.

(21) Appl. No.: 17/774,333

(22) PCT Filed: Nov. 6, 2020

(86) PCT No.: PCT/EP2020/081389
§ 371 (c)(1),
(2) Date: May 4, 2022

(87) PCT Pub. No.: WO2021/089850
PCT Pub. Date: May 14, 2021

(65) Prior Publication Data
US 2022/0411529 A1     Dec. 29, 2022

(30) Foreign Application Priority Data
Nov. 6, 2019     (DK) ................................. 2019 01296

(51) Int. Cl.
*C07K 16/28*          (2006.01)
(52) U.S. Cl.
CPC ...... *C07K 16/2887* (2013.01); *C07K 16/2878* (2013.01); *C07K 16/2893* (2013.01); *C07K 16/2896* (2013.01); *C07K 2317/21* (2013.01); *C07K 2317/24* (2013.01); *C07K 2317/41* (2013.01); *C07K 2317/72* (2013.01); *C07K 2317/734* (2013.01); *C07K 2317/75* (2013.01)
(58) Field of Classification Search
None
See application file for complete search history.

(56) References Cited

U.S. PATENT DOCUMENTS

| | | | |
|---|---|---|---|
| 10,759,867 | B2 | 9/2020 | Parren et al. |
| 10,882,913 | B2 | 1/2021 | Overdijk et al. |
| 11,034,772 | B2 | 6/2021 | Oostindie et al. |
| 11,180,572 | B2 | 11/2021 | De Jong et al. |
| 11,396,553 | B2 | 7/2022 | Oostindie et al. |
| 11,512,137 | B2 | 11/2022 | Oostindie et al. |
| 12,049,512 | B2 | 7/2024 | Parren et al. |
| 12,173,076 | B2 | 12/2024 | Beurskens et al. |
| 12,247,080 | B2 | 3/2025 | Overdijk et al. |
| 12,338,289 | B2 | 6/2025 | De Jong et al. |
| 12,448,459 | B2 | 10/2025 | Oostindie et al. |
| 2005/0095244 | A1 | 5/2005 | Jure-Kunkel et al. |
| 2014/0242075 | A1 | 8/2014 | Parren et al. |

| | | | | |
|---|---|---|---|---|
| 2015/0175707 | A1* | 6/2015 | De Jong | ............ C07K 16/2809 424/9.1 |
| 2015/0337049 | A1* | 11/2015 | Labrijn | ................. C07K 16/00 530/387.3 |
| 2015/0353636 | A1 | 12/2015 | Parren et al. | |
| 2019/0144554 | A1 | 5/2019 | Overdijk et al. | |
| 2019/0202926 | A1 | 7/2019 | Beurskens et al. | |
| 2019/0276549 | A1 | 9/2019 | De Jong et al. | |
| 2019/0315877 | A1 | 10/2019 | Overdijk et al. | |
| 2020/0181277 | A1 | 6/2020 | Beurskens et al. | |
| 2020/0270359 | A1 | 8/2020 | Oostindie et al. | |
| 2020/0291124 | A1 | 9/2020 | Oostindie et al. | |
| 2021/0024647 | A1 | 1/2021 | Oostindie et al. | |
| 2021/0107988 | A1 | 4/2021 | Oostindie et al. | |
| 2021/0163619 | A1 | 6/2021 | Parren et al. | |
| 2021/0230301 | A1 | 7/2021 | De Jong et al. | |
| 2021/0238296 | A1 | 8/2021 | De Jong et al. | |
| 2021/0324096 | A1 | 10/2021 | Overdijk et al. | |
| 2021/0355232 | A1 | 11/2021 | Oostindie et al. | |
| 2022/0251231 | A1 | 8/2022 | Oostindie et al. | |
| 2023/0107363 | A1 | 4/2023 | De Jong et al. | |
| 2023/0399414 | A1 | 12/2023 | Oostindie et al. | |
| 2024/0076397 | A1 | 3/2024 | Oostindie et al. | |

(Continued)

FOREIGN PATENT DOCUMENTS

| | | |
|---|---|---|
| JP | 2014520788 A | 8/2014 |
| JP | 2015524387 A | 8/2015 |

(Continued)

OTHER PUBLICATIONS

Wang et al. (Molecular Cell 63, 135-145, Jul. 7, 2016). (Year: 2016).*
Dekkers et al. (Front Immunol. Aug. 2, 2017;8:877). (Year: 2017).*
Lo et al. (JBC, vol. 292, No. 9, pp. 3900-3908, Mar. 3, 2017). (Year: 2017).*
Jefferis (Archives of Biochemistry and Biophysics 526 (2012) 159-166). (Year: 2012).*
Hristodorov et al. (Mol Biotechnol (2013) 53:326-335). (Year: 2013).*
Barbas, C. et al., "Molecular profile of an antibody response to HIV-1 as probed by combinatorial libraries," J Mol Biol., vol. 230(3):812-823 (1993).
Chodorge, M. et al., "A series of Fas receptor agonist antibodies that demonstrate an inverse correlation between affinity and potency," Cell Death Differ., vol. 19(7):1187-1195 (2012).

(Continued)

*Primary Examiner* — Zachary S Skelding
(74) *Attorney, Agent, or Firm* — Nelson Mullins Riley & Scarborough LLP; Jane E. Remillard, Esq.; Christopher L. Frank

(57)          ABSTRACT

The invention relates to combination therapy involving two or more antibodies, wherein the Fc regions of the two antibodies have been modified such that hetero-oligomerization between the antibodies is strongly favored over self-oligomerization when antibodies are bound to their corresponding target antigens and such that hetero-oligomerization-independent effector functions of one or both antibodies are eliminated or strongly reduced. The invention also relates to antibodies, compositions, and kits suitable for use in the combination therapy of the invention.

17 Claims, 48 Drawing Sheets

Specification includes a Sequence Listing.

(56) References Cited

U.S. PATENT DOCUMENTS

| | | | |
|---|---|---|---|
| 2024/0117064 A1 | 4/2024 | Oostindie et al. |
| 2024/0254252 A1 | 8/2024 | De Goeij et al. |
| 2025/0043018 A1 | 2/2025 | Parren et al. |
| 2025/0145720 A1 | 5/2025 | Parren et al. |
| 2025/0223374 A1 | 7/2025 | Parren et al. |
| 2025/0326854 A1 | 10/2025 | Beurskens et al. |

FOREIGN PATENT DOCUMENTS

| | | |
|---|---|---|
| WO | 2004035607 A2 | 4/2004 |
| WO | 2011112978 A1 | 9/2011 |
| WO | 2012130831 A1 | 10/2012 |
| WO | 2013004842 A2 | 1/2013 |
| WO | 2014/006217 A1 | 1/2014 |
| WO | 2014009358 A1 | 1/2014 |
| WO | 2014108198 A1 | 7/2014 |
| WO | 2017/093447 A1 | 6/2017 |
| WO | 2019145455 A1 | 8/2019 |

OTHER PUBLICATIONS

Cooke, B.A., et al., "Hormones and Their Actions, Part 2: Specific Action of Protein Hormones," New Comprehensive Biochemistry, vol. 18B (35): 1-46 (1988).

Crowe, J. et al., "Humanized monoclonal antibody CAMPATH-1H: myeloma cell expression of genomic constructs, nucleotide sequence of cDNA constructs and comparison of effector mechanisms of myeloma and Chinese hamster ovary cell-derived material," Clin Exp Immunol., vol. 87(1):105-110 (1992).

Diebolder, C. et al., "Complement is activated by IgG hexamers assembled at the cell surface," Science, vol. 343 (6176):1260-1263 (2014).

Edelman, G. et al., "The covalent structure of an entire gammaG immunoglobulin molecule," Proc Natl Acad Sci., vol. 63(1):78-85 (1969).

Fantl W I., et al., "Signalling by receptor tyrosine kinases," Annu. Rev. Biochem., vol. 62: 453-481 (1993).

Flower D R., "Modelling G-protein-coupled receptors for drug design," (Biochim. Biophys. Acta, vol. 1422(3): 207-234 (1999).

International Search Report and Written Opinion, PCT/EP2020/081389, Feb. 18, 2011, 16 pages.

Kabat, E. A., et al., Sequences of proteins om Imm interest, 5th Ed—extract, 680-718 (1991).

Labrijn, A.F., et al., "Efficient generation of stable bispecific IgG1 by controlled Fab-arm exchange," PNAS, vol. 110(13): 5145-5150 (2013).

Liu et al., "Heterogeneity of monoclonal antibodies," J Pharm Sci., vol. 97(7): 2426-2447 (2008).

Massague J., "Receptors for the TGF-beta family," Cell, vol. 69(7): 1067-1070 (1992).

Mimura, Y. et al., "Glycosylation engineering of therapeutic IgG antibodies: challenges for the safety, functionality and efficacy," Protein & Cell, vol. 9(1):47-62 (2018).

Miyajima A., et al., "Cytokine receptors and signal transduction," Annu. Rev. Immunol., vol. 10: 295-331 (1992).

Miyasaka, M. ed., Cell Technology, supplementary vol. Handbook series, "Handbook for Adhesion Factors" (1994) (Shujunsha, Tokyo, Japan).

Oostindie, S. et al., "CD20 and CD37 antibodies synergize to activate complement by Fc-mediated clustering," Haematologica, vol. 104(9):1841-1852 (2019).

Patthy L., "Homology of a domain of the growth hormone/prolactin receptor family with type III modules of fibronectin," Cell, vol. 61: 13-14 (1990).

Smith C A., et al., "The TNF receptor superfamily of cellular and viral proteins: activation, costimulation, and death," Cell, vol. 76(6): 959-962 (1994).

Taga T. and Kishimoto T., "Cytokine receptors and signal transduction," FASEB J., vol. 6 (15): 3387-3396 (1992).

Ullrich A., et al., "Signal transduction by receptors with tyrosine kinase activity," Cell, vol. 61(2): 203-212 (1990).

Vink, T. et al., "A simple, robust and highly efficient transient expression system for producing antibodies," Methods, vol. 65(1): 5-10 (2014).

* cited by examiner

Campath + 11B8

Campath + 11B8

IgG1-Campath-1H                    IgG1-11B8                    IgG1-b12

- - - - - - - - - - - - - - - - - - - - - - - - - - - - - - - - - - - - - - WT - - -
E430G - - - - - - - - - - - - - - - - - - - - E430G - - - - - - - - - - - - - - - - -
E430G-K439E-N297Q - - - - - - - - - - - - - - - - - - - - - - - - - - - WT - - -
- - - - - - - - - - - - - - - - - - - - - - - E430G-S440K - - - - - - - WT - - -
- - - - - - - - - - - - - - - - - - - - - - - E430G-S440K-N297Q - - WT - -
E430G-K439E-N297Q - - - - - - - - E430G-S440K - - - - - - - - - - -
E430G-K439E-N297Q - - - - - - - - E430G-S440K-N297Q - - - - - -

CDC Wien 133 - relative AUC

Relative AUC (%)

IgG1-Campath-1H                    IgG1-11B8                    IgG1-b12

- - - - - - - - - - - - - - - - - - - - - - - - - - - - - - - - - - - - - - WT - - -
E430G - - - - - - - - - - - - - - - - - - - - E430G - - - - - - - - - - - - - - - - -
E430G-K439E-N297Q - - - - - - - - - - - - - - - - - - - - - - - - - - - WT - - -
- - - - - - - - - - - - - - - - - - - - - - - E430G-S440K - - - - - - - WT - - -
- - - - - - - - - - - - - - - - - - - - - - - E430G-S440K-N297Q - - WT - -
E430G-K439E-N297Q - - - - - - - - E430G-S440K - - - - - - - - - - -
E430G-K439E-N297Q - - - - - - - - E430G-S440K-N297Q - - - - - -

Lysis at 40 µg/mL

Lysis (%)

Relative AUC (%) - Ramos
CD52

Relative AUC (%)

Cytotoxicity at 40 ug/mL - Ramos
CD52; CD20

Cytotoxicity (%)

CDC Wien 133
CD52

CDC Wien 133
Lysis at 40 ug/mL

CDC Ramos - Lysis at 40 µg/mL
CD52+CD52

CDC Wien 133 - Lysis at 40 µg/mL
CD52+CD20

FCGR2A activation
Raji + Jurkat reporter

FCGR2A activation
Raji + Jurkat reporter

CDC Wien 133
CD52

CDC Wien 133
Lysis at 40 ug/mL

CDC Ramos - CD52
Relative AUC (%)

CDC Ramos - CD52
Cytotoxicity at 40 µg/mL

CDC Wien 133 - CD52+CD20
Lysis at 40 μg/mL

Lysis (%)

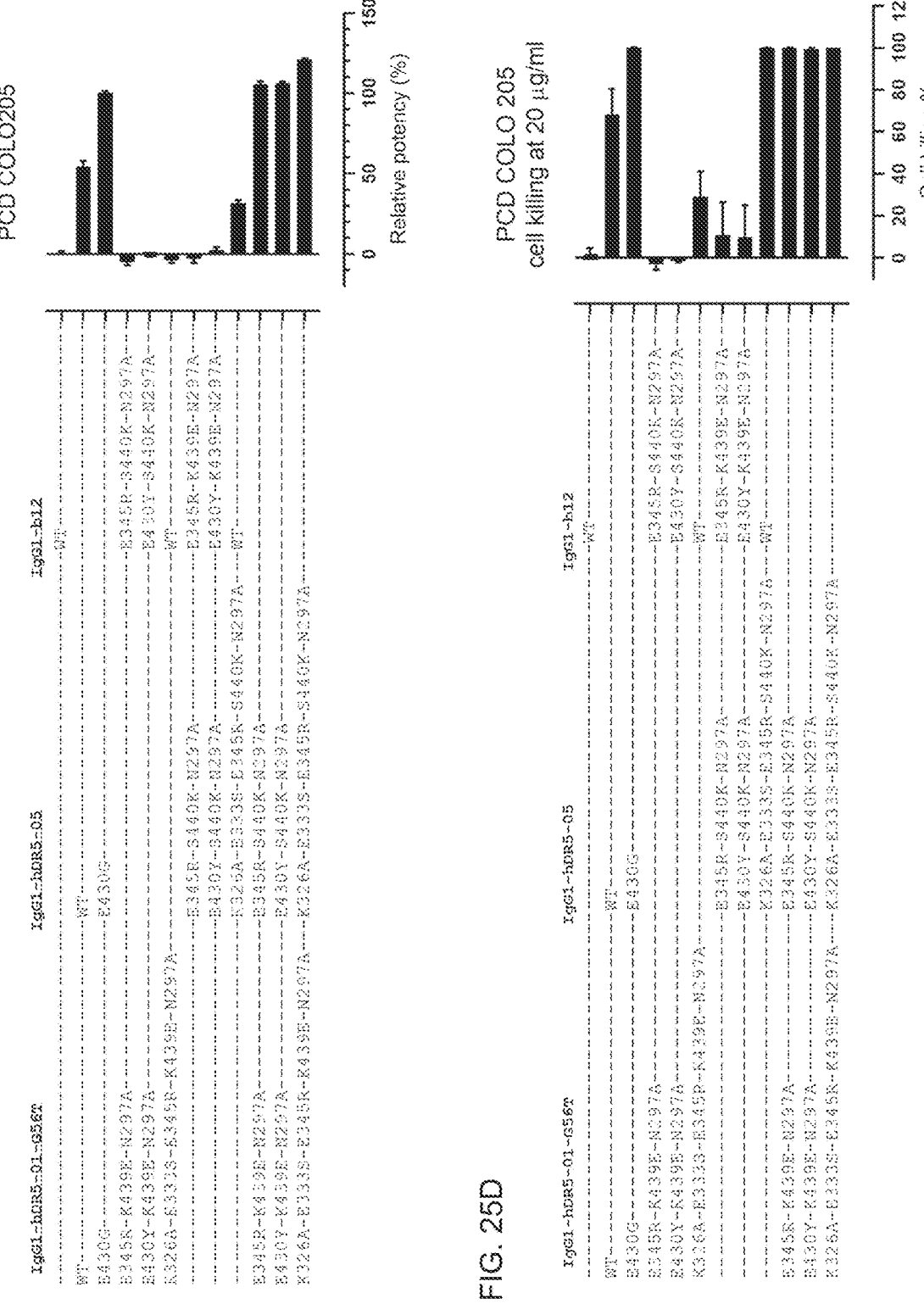

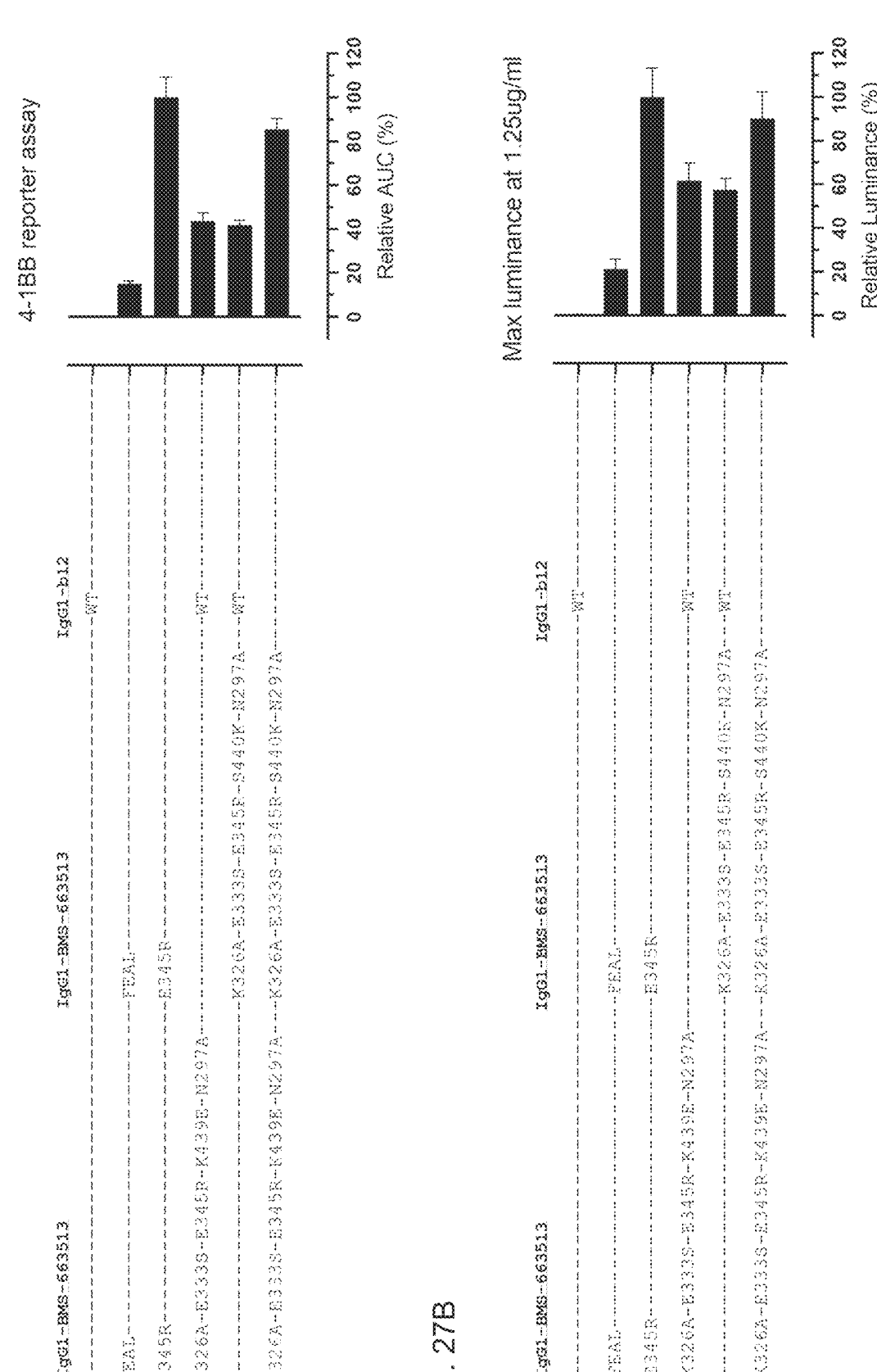

ANTIBODY VARIANT COMBINATIONS AND USES THEREOF

RELATED APPLICATIONS

This application is a 35 U.S.C. 371 national stage filing of International Application No. PCT/EP2020/081389, filed Nov. 6, 2020, which claims priority to Denmark Patent Application No. PA 2019 01296, filed Nov. 6, 2019, the contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on May 4, 2022, is named GMI-213US_SequenceListing_20220504.txt and is 229618 bytes in size.

FIELD OF THE INVENTION

The present invention relates to combination therapy involving two or more antibodies, wherein the Fc regions of the two antibodies have been modified such that hetero-oligomerization between the antibodies is strongly favored over self-oligomerization when antibodies are bound to their corresponding target antigens and such that hetero-oligomerization-independent effector functions of one or both antibodies are eliminated or strongly reduced. The invention also relates to antibodies, compositions, and kits suitable for use in the combination therapy of the invention.

BACKGROUND OF THE INVENTION

Antibodies are highly effective molecules which can have effects on target cells via various mechanisms. In some instances, the mere binding of an antibody to a target antigen on a cell surface can have an antagonistic or agonistic effect on the target antigen and thus on the target cell. Alternatively, or in addition, the effect of an antibody on a target cell is achieved through the ability of antibodies to induce effector functions, typically Fc-mediated effector functions, such as complement-dependent cytotoxicity (CDC), antibody-dependent cell-mediated cytotoxicity (ADCC), and antibody-dependent cell-mediated phagocytosis (ADCP). Fc-region-mediated effector functions, such as CDC, ADCC, and ADCP contribute to the therapeutic window of an antibody treatment, defined by efficacy and toxicity.

CDC is initiated by binding of C1q to the Fc regions of antibodies. C1q is a multimeric protein consisting of six globular binding heads attached to a stalk. The individual globular binding heads have low affinity for IgG, and C1q must gain avidity by binding multiple IgG1 molecules on a cell surface to trigger the classical complement pathway. ADCC and ADCP are initiated by binding of the IgG Fc region to Fcγ receptors (FcγR) on effector cells.

IgG hexamerization upon target binding on the cell surface has been shown to support avid C1q binding (Diebolder (2014) Science 343:1260). The hexamerization is mediated through intermolecular non-covalent Fc-Fc interactions, and Fc-Fc interactions can be enhanced by point mutations in the CH3 domain, including E345R and E430G.

The employment of effector functions by IgG antibodies is dependent on glycosylation status. In other words, a lack of glycosylation of the IgG Fc region strongly decreases the capacity of IgG antibodies to mediate effector functions. The Fc region of IgG antibodies contains a highly conserved N-glycosylation site at amino acid position N297. Wang et al. ((2016) Mol Cell 63:135) studied IgG variants that can form hexamers and bind C1q in solution. It was found that deglycosylation of the Fc region of these variants inhibited both the formation of hexamers and the C1q binding avidity of hexamers in solution.

WO2013/004842 discloses antibodies or polypeptides comprising variant Fc regions having one or more amino acid modifications resulting in modified effector functions such as CDC.

WO2014/108198 discloses polypeptides such as antibodies comprising variant Fc regions having one or more amino acid modifications resulting in increased CDC.

WO2012/130831 concerns Fc region-containing polypeptides that have altered effector function as a consequence of one or more amino acid substitutions in their Fc region.

Enhancing Fc-Fc interactions between antibodies may increase the potency of antibodies through enhancing effector functions such as CDC and/or ADCC. This may lead to cell death of the target cell to which the antibody binds. However, if the target antigen is broadly expressed in the body both on healthy cells and on disease-causing cells, then the antibody may become toxic by killing healthy cells. Thus, antibody therapy may lack selectivity for the target tissue, and non-diseased tissue may be affected by the antibody treatment, resulting in toxicity.

WO2019/145455 and Oostindie et al. 2019 Haematologica 104:1841 relate to medical treatment with two antibodies that bind two different target antigens wherein the Fc regions of the antibodies have been modified such that hetero-oligomerization of the two antibodies is strongly favored over self- (or auto- or homo-) oligomerization. As a result of these modifications, more antibody oligomerization will occur on cells that express both antigen targets (allowing efficient (hetero)oligomerization of the two antibodies), than on cells that only express one of the targets (resulting in inefficient or no (self)oligomerization). As oligomerization generally enhances the efficacy of antibodies, the antibody combination treatment will be more efficacious against cells that co-express the targets than against cells that only express one of the targets. Thus, the antibody combination treatment has an improved selectivity for cells or tissue expressing both target antigens. Accordingly, by selecting two antigens that are co-expressed in a desired target cell population, but not, or less, co-expressed in cell populations that should not be targeted, a combined antibody treatment can be designed which will have an improved selective effect against the desired target cell populations.

SUMMARY OF THE INVENTION

While antibody-combination treatment strategies, such as those described in WO2019/145455 and Oostindie et al. 2019 Haematologica 104:1841, can be used to significantly enhance selectivity of antibody treatment towards the desired target cells populations, there may still be undesired residual activity of each of the antibodies of the combination towards healthy cells that express only one of the targets.

There is therefore a need for further improved forms of antibody treatment, in particular treatment with a further improved therapeutic window.

Surprisingly, it has now been found that the residual activity of individual antibodies used in a combination antibody treatment as described above can be strongly reduced by preventing or removing antibody glycosylation without strongly affecting the activity of the hetero-oligomer. Thus, undesired toxicity to healthy cells can be further reduced without strongly affecting desired efficacy against desired target cells.

Accordingly, it is an object of the present invention to provide a first antibody and a second antibody that are engineered to provide maximal activity on target cells bound by both antibodies simultaneously, wherein the first antibody provides no or minimal activity on target cells bound only by the first antibody, and wherein the second antibody provides minimal or reduced activity on target cells bound only by the second antibody, compared to the activity on cells bound by both antibodies simultaneously.

Thus, in a first aspect, the present invention provides a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises:

a. a substitution at position E430 or a substitution at position E345 or a combination of the substitutions K248E and T437R, and b. a K439E or S440K substitution, and said second Fc region comprises:

c. a substitution at position E430 or a substitution at position E345 or a combination of the substitutions K248E and T437R, and d. a K439E or S440K substitution, wherein the first Fc region has a K439E substitution and the second Fc region has an S440K substitution or the first Fc region has an S440K substitution and the second Fc region has a K439E substitution, and wherein the first antibody and/or the second antibody does not comprise N-linked glycosylation at position N297, wherein the amino acid positions correspond to human IgG1 according to the EU numbering system.

In a further aspect, the invention relates to an antibody comprising an Fc region of a human IgG and an antigen-binding region capable of binding to an antigen, wherein said Fc region comprises a. a substitution at position E430 or a substitution at position E345 or a combination of the substitutions K248E and T437R, and b. a K439E or S440K substitution, wherein the antibody does not comprise N-linked glycosylation at position N297.

In further aspects, the invention relates to methods for producing antibodies according to the invention and to compositions and kits comprising antibodies according to the invention.

In one aspect, the invention relates a method of producing an antibody, comprising the step of producing the antibody in a recombinant host cell which is capable of glycosylating the asparagine at position N297 of the antibody, followed by a step of removing the N-linked glycosylation from the produced antibody.

In another aspect, the invention relates to a method for producing an antibody, comprising the step of producing the antibody in a recombinant host cell, wherein said host cell is not capable of glycosylating the asparagine at position N297 of the antibody.

In another aspect, the invention relates to a composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein said first Fc region comprises a. a substitution at position E430 or a substitution at position E345 or a combination of the substitutions K248E and T437R, and b. a K439E or S440K substitution, and said second Fc region comprises c. a substitution at position E430 or a substitution at position E345 or a combination of the substitutions K248E and T437R, and d. a K439E or S440K substitution, wherein the first Fc region has a K439E substitution and the second Fc region has a S440K substitution or, the first Fc region has a S440K substitution and the second Fc region has a K439E substitution, and wherein the first antibody and/or the second antibody does not comprise N-linked glycosylation at position N297, wherein the amino acid positions correspond to human IgG1 according to EU numbering system.

In another aspect, the invention relates to a method of treating an individual having a disease comprising administering to said individual an effective amount of a first and a second antibody or a composition according to any aspect or embodiment described herein.

In another aspect, the invention relates to a method of depleting a cell population expressing a first antigen and a second antigen, which method comprises contacting said cell population with a first and second antibody or a composition according to any aspect or embodiment described herein.

In another aspect, the invention relates to a method of inducing proliferation in a cell population expressing a first antigen and a second antigen, which method comprises contacting said cell population with a first and second antibody, according to any aspect or embodiment described herein.

In another aspect, the invention relates to a kit comprising a first container comprising a first antibody as described in any aspect or embodiment herein and a second container comprising a second antibody as described in any aspect or embodiment herein.

In another aspect, the invention relates to a nucleic acid encoding an antibody or a first antibody or second antibody according to any aspect or embodiment herein.

In another aspect, the invention relates to a nucleic acid encoding a heavy chain of a first antibody or second antibody according to any aspect or embodiment herein.

In another aspect eh invention relates to an expression vector. In yet another aspect the invention relates to a delivery vehicle.

These and other aspects of the invention, particularly various uses and therapeutic applications for antibodies of the invention, are described in further detail below.

E430G-S440K. CDC efficacy is presented as (FIG. 1D) the AUC normalized to non-binding control antibody IgG1-b12 (0%) and the mixture of IgG1-CAMPATH-1H-E430G+IgG1-11B8-E430G (100%) and as (FIG. 1E) percentage lysis determined by the percentage PI-positive cells at an antibody concentration of 10 μg/mL.

FIGS. 2A-2D shows that deglycosylation increases selectivity of antibody variants containing an Fc-Fc interaction enhancing mutation and a self-oligomerization inhibiting mutation. Wien 133 cells were incubated with antibody concentration series in the presence of 20% NHS. (FIGS. 2A and 2B) Cell lysis through CDC by mixtures of IgG1-CAMPATH-1H antibody variants. (FIGS. 2C and 2D) Cell lysis through CDC by mixtures of IgG1-CAMPATH-1H and IgG1-11B8 antibody variants. CDC efficacy is presented as (FIGS. 2A and 2C) the AUC normalized to non-binding control antibody IgG1-b12 (0%) and the mixture of IgG1-CAMPATH-1H-E430G+IgG1-11B8-E430G (100%) and as (FIGS. 2B and 2D) percentage lysis determined by the percentage PI-positive cells at an antibody concentration of 10 μg/ml.

Figure 3A:
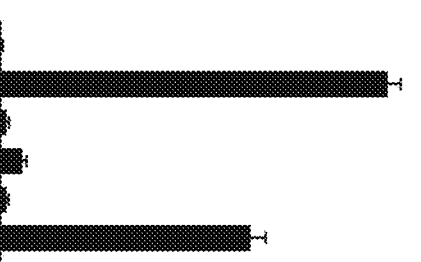
Figure 3B:
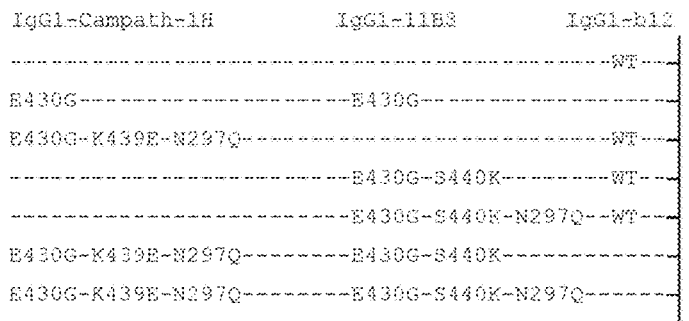
Figure 3B:
Figure 3B:
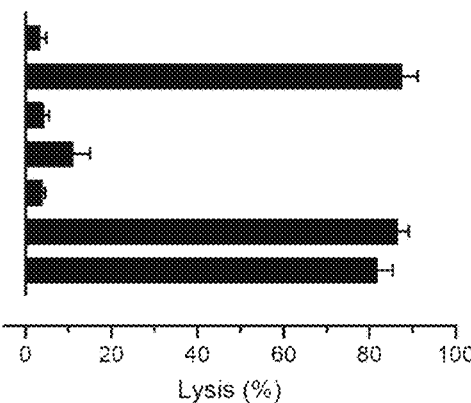

FIGS. 3A and 3B shows that aglycosylated antibody variants containing an Fc-Fc interaction enhancing mutation and a self-oligomerization inhibiting mutation demonstrate increased selectivity. Wien 133 cells were incubated with antibody concentration series in the presence of 20% NHS. (FIG. 3A) Cell lysis through CDC by mixtures of IgG1-CAMPATH-1H and IgG1-11B8 antibody variants, presented as the AUC normalized to non-binding control antibody IgG1-b12 (0%) and the mixture of IgG1-CAMPATH-1H-E430G+IgG1-11B8-E430G (100%). (FIG. 3B) Percentage of cell lysis through CDC at the highest concentration tested by mixtures of IgG1-CAMPATH-1H and IgG1-11B8 antibody variants, as determined by the percentage PI-positive cells at an antibody concentration of 40 μg/mL.

FIGS. 4A-4H shows the CDC activity of IgG1-CAMPATH-1H and IgG1-11B8 antibody variants harboring mutations that enhance Fc-Fc interactions and disrupt the N-linked glycosylation site. Ramos cells (FIGS. 4A, 4B, 4E and 4F) or Wien 133 cells (FIGS. 4C, 4D, 4G, and 4H) were incubated with IgG1-CAMPATH-1H (FIGS. 4A-4D) or IgG1-11B8 (FIGS. 4E-4H) antibody variant concentration series in the presence of 10% NHS (FIGS. 4A, 4B, 4E, and 4F), or 20% NHS (FIGS. 4C, 4D, 4G, and 4H). CDC efficacy is presented as (FIGS. 4A, 4C, 4E, and 4G) the AUC normalized to non-binding control antibody IgG1-b12 (0%) and positive control IgG1-CAMPATH-1H-E430G(100%) and as (FIG. 4B) percentage cytotoxicity normalized to positive control wells lysed with 0.02% Triton X-100 or (FIGS. 4D, 4F, and 4H) percentage lysis determined by the percentage PI-positive cells, at an antibody concentration of 40 μg/mL.

FIGS. 5A-5D shows that the aglycosylated antibody variants with Fc-Fc interaction enhancing mutations retained partial CDC activity compared to their glycosylated parental molecules. (-FIGS. 5A and 5B) Daudi cells were incubated with antibody concentration series in the presence of 10% NHS. CDC efficacy is presented as (FIG. 5A) the AUC normalized to non-binding control antibody IgG1-b12 (0%) and the mixture of IgG1-CD37-37-3-E430G+IgG1-11B8-E430G (100%) and as (FIG. 5B) Cytotoxicity determined at an antibody concentration of 40 μg/mL, normalized to positive control wells lysed with 0.02% Triton X-100. (FIGS. 5C and 5D) Raji cells were incubated with antibody concentration series in the presence of 10% NHS. CDC efficacy is presented as (FIG. 5C) the AUC normalized to non-binding control antibody IgG1-b12 (0%) and the mixture of IgG1-CD37-37-3-E430G+IgG1-11B8-E430G (100%) and as (FIG. 5D) percentage cytotoxicity at an antibody concentration of 40 μg/mL, normalized to positive control wells lysed with 0.02% Triton X-100.

FIGS. 6A-6D shows that disruption of the N297 glycosylation site improves the selectivity of CD52-targeting antibody variants with Fc-Fc interaction enhancing and self-oligomerization inhibiting mutations. (FIGS. 6A and 6B) Ramos cells were incubated with antibody concentration series in the presence of 10% NHS. CDC efficacy is presented as (FIG. 6A) the AUC normalized to non-binding control antibody IgG1-b12 (0%) and IgG1-CAMPATH-1H-E430G (100%) and as (FIG. 6B) percentage cytotoxicity determined at an antibody concentration of 40 μg/mL, normalized to positive control wells lysed with 0.02% Triton X-100. (FIGS. 6C and 6D) Wien 133 cells were incubated with antibody concentration series in the presence of 20% NHS. CDC efficacy is presented as (FIG. 6C) the AUC normalized to non-binding control antibody IgG1-b12 (0%) and IgG1-CAMPATH-1H-E430G (100%) and as (FIG. 6D) percentage lysis determined by the percentage PI-positive cells at an antibody concentration of 40 μg/mL.

FIGS. 7A-7D shows that disruption of the N297 glycosylation site improves the selectivity of CD52- and CD20-targeting antibody variants with Fc-Fc interaction enhancing and self-oligomerization inhibiting mutations. (FIGS. 7A and 7B) Wien 133 cells were incubated with antibody concentration series in the presence of 20% NHS. CDC efficacy is presented as (FIG. 7A) the AUC normalized to non-binding control antibody IgG1-b12 (0%) and the mixture of IgG1-CAMPATH-1H-E430G+IgG1-11B8-E430G (100%) and as (FIG. 7B) percentage lysis determined by the percentage PI-positive cells at an antibody concentration of 40 μg/mL. (FIGS. 7C and 7D) Ramos cells were incubated with antibody concentration series in the presence of 10% NHS. CDC efficacy is presented as (FIG. 7C) the AUC normalized to non-binding control antibody IgG1-b12 (0%) and the mixture of IgG1-CAMPATH-1H-E430G+IgG1-11B8-E430G (100%) and as (FIG. 7D) percentage cytotoxicity determined at an antibody concentration of 40 μg/mL, normalized to positive control wells lysed with 0.02% Triton X-100.

FIGS. 8A-8D shows that disruption of the N297 glycosylation site improves the selectivity of CD37- and CD20-targeting antibody variants with Fc-Fc interaction enhancing and self-oligomerization inhibiting mutations. (FIGS. 8A and 8B) Raji cells were incubated with antibody concentration series in the presence of 10% NHS. CDC efficacy is presented as (FIG. 8A) the AUC normalized to non-binding control antibody IgG1-b12 (0%) and the mixture of IgG1-CD37-37-3-E430G+IgG1-11B8-E430G (100%) and as (FIG. 8B) percentage cytotoxicity determined at an antibody concentration of 40 μg/mL, normalized to positive control wells lysed with 0.02% Triton X-100. (FIGS. 8C and 8D) Daudi cells were incubated with antibody concentration series in the presence of 10% NHS. CDC efficacy is presented as (FIG. 8C) the AUC normalized to non-binding control antibody IgG1-b12 (0%) and the mixture of IgG1-CD37-37-3-E430G+IgG1-11B8-E430G (100%) and as (FIG. 8D) percentage cytotoxicity determined at an antibody concentration of 40 μg/mL, normalized to positive control wells lysed with 0.02% Triton X-100.

Figure 9A:
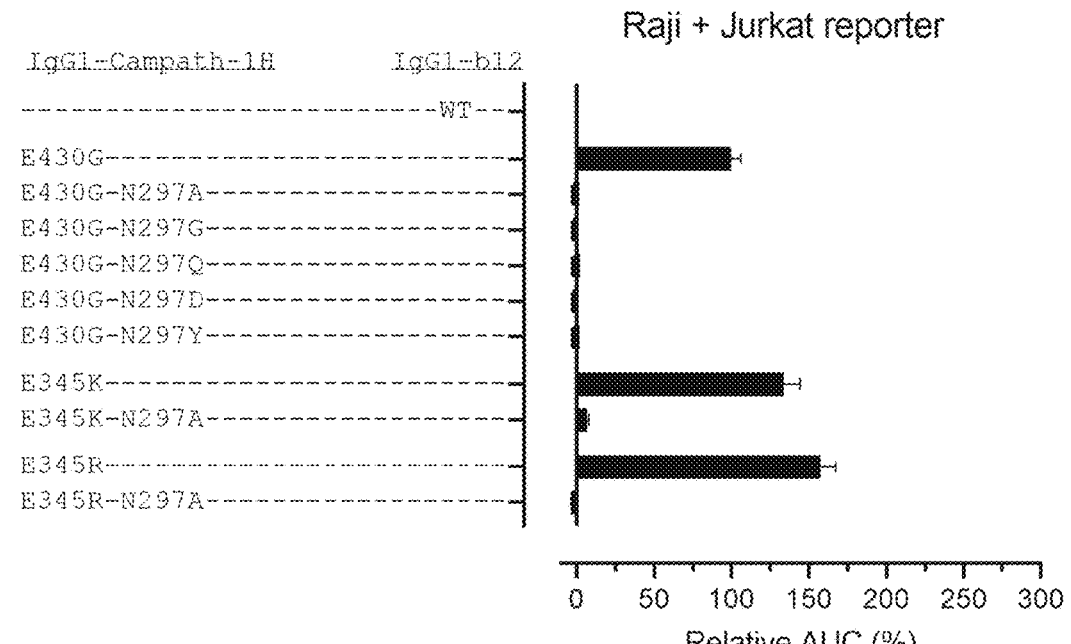
Figure 9B:
Figure 9B:
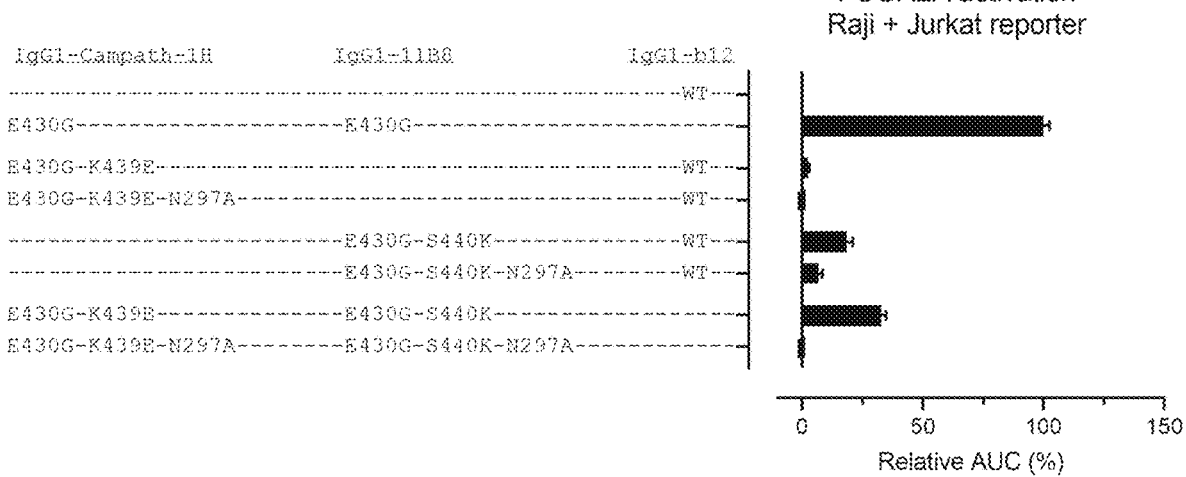

FIGS. 9A and 9B shows that aglycosylated antibody variants of IgG1-CAMPATH-1H and IgG1-11B8 harboring an Fc-Fc interaction enhancing and self-oligomerization inhibiting mutation were suppressed in their capacity to induce ADCP, as determined through an FcγRIIa activation reporter cell assay. Luciferase production was quantified by luminescence readout. Relative AUC: normalized area under the dose-response curves (0.15-40,000 ng/mL final concentrations in 4-fold dilutions). (FIG. 9A) Raji cells were incubated with titrated IgG1-CAMPATH-1H antibody variants and FcγRIIa-transduced Jurkat cells. (FIG. 9B) Raji cells were incubated with titrated IgG1-CAMPATH-1H and IgG1-11B8 antibody variants and FcγRIIa-transduced Jurkat cells.

Figure 10:
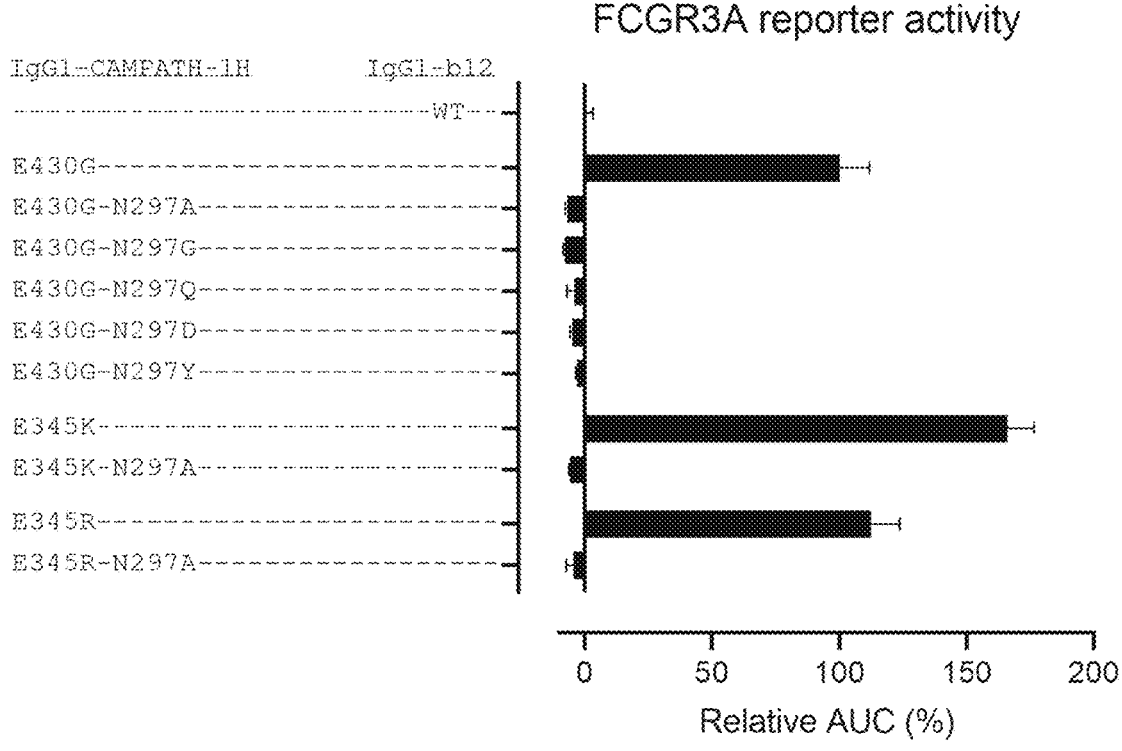

FIG. 10 shows that mutations preventing glycosylation in IgG1-CAMPATH-1H antibody variants harboring an Fc-Fc interaction enhancing mutation inhibit antibody-dependent cellular cytotoxicity, as determined through an FcγRIIIa activation reporter cell assay. Raji cells were incubated with titrated IgG1-CAMPATH-1H antibody variants and FcγRIIIa-expressing Jurkat cells. Luciferase production was quantified by luminescence readout on a Tecan Spark luminescence plate reader.

FIGS. 11A-11D shows that disruption of the N297 glycosylation site in IgG1-CAMPATH-1H-K248E-T437R had limited impact on its CDC activity. (FIGS. 11A and 11B) Wien 133 cells were incubated with antibody concentration series in the presence of 20% NHS. CDC efficacy is presented as (FIG. 11A) the AUC normalized to non-binding control antibody IgG1-b12 (0%) and the IgG1-CAMPATH-1H-E430G positive control (100%) and as (FIG. 11B) percentage lysis determined by the percentage PI-positive cells at an antibody concentration of 40 μg/mL. (FIGS. 11C and 11D) Ramos cells were incubated with antibody concentration series in the presence of 10% NHS. CDC efficacy is presented as (FIG. 11C) the AUC normalized to non-binding control antibody IgG1-b12 (0%) and the IgG1-CAMPATH-1H-E430G positive control (100%) and as (FIG. 11D) percentage cytotoxicity determined at an antibody concentration of 40 μg/mL, normalized to positive control wells lysed with 0.02% Triton X-100.

FIGS. 12A-12D shows that disruption of the N297 glycosylation site improves the selectivity of antibody variants harboring the K248E-T437R Fc-Fc interaction enhancing and the K439E or S440K self-oligomerization inhibiting mutations. (FIGS. 12A-12D) Wien 133 cells were incubated with antibody concentration series in the presence of 20% NHS. CDC efficacy is presented as (FIG. 12A) the AUC normalized to non-binding control antibody IgG1-b12-K439E+IgG1-b12-S440K (FIG. 12A) or IgG1-b12 (FIG. 12C) (0%) and the IgG1-CAMPATH-1H-E430G+IgG1-11B8-E430G positive control (100%) and as (FIGS. 12B and 12D) percentage lysis determined by the percentage PI-positive cells at an antibody concentration of 40 μg/mL.

Figures 13A, 13B:
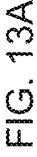

FIGS. 13A and 13B shows that aglycosylated CD37- and CD20-targeting antibody variants with the E430G or E345R Fc-Fc interaction enhancing and K439E or S440K self-oligomerization inhibiting mutations induce CDC in mutually dependent fashion. (FIGS. 13A and 13B) Daudi cells were incubated with antibody concentration series in the presence of 20% NHS. CDC efficacy is presented as (FIG. 13A) the AUC normalized to non-binding control antibody IgG1-b12 (0%) and the mixture of IgG1-CD37-37-3-E430G+IgG1-11B8-E430G (100%) and as (FIG. 13B) percentage cytotoxicity determined at an antibody concentration of 20 μg/mL.

Figures 14A, 14B:
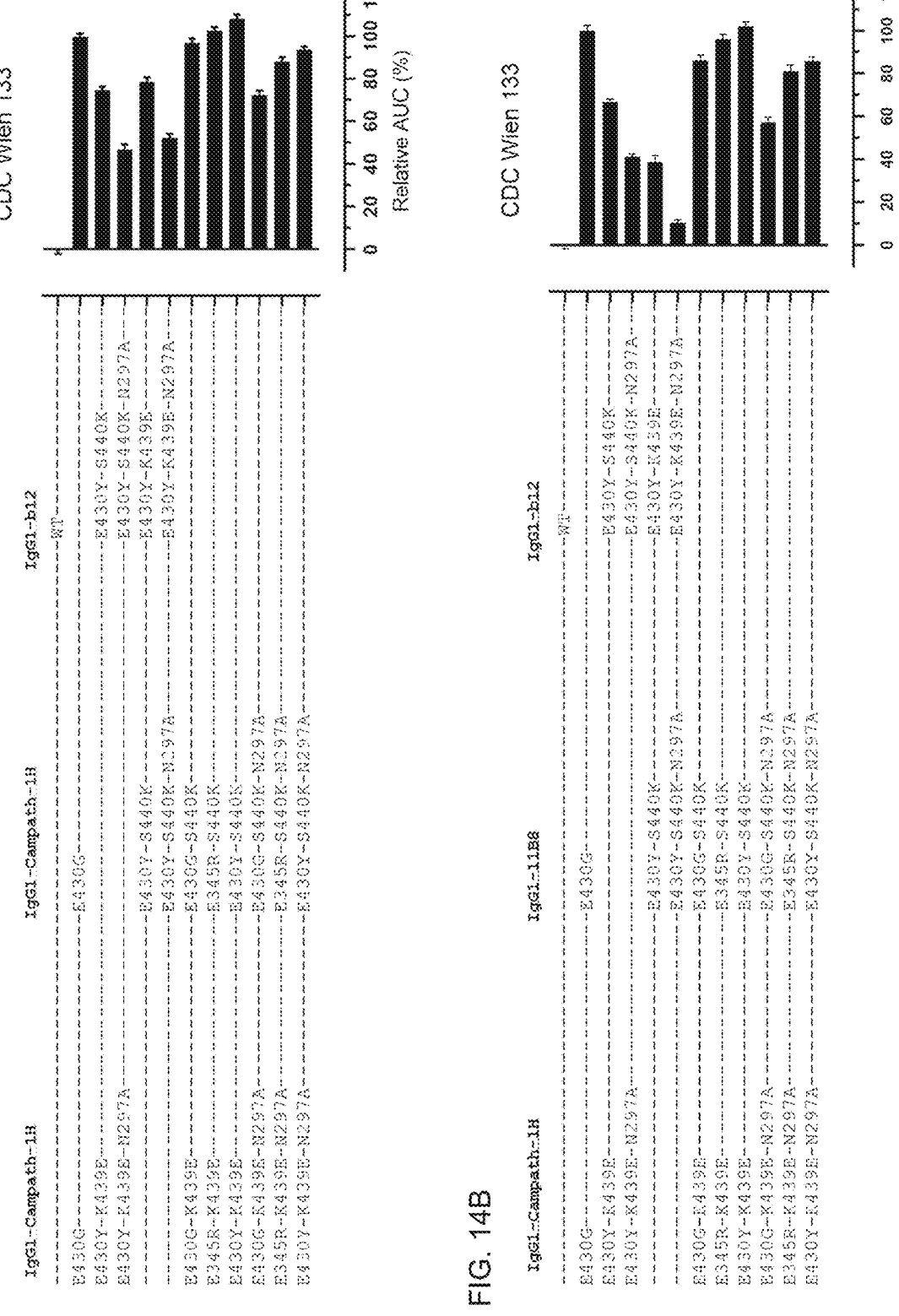

FIGS. 14A and 14B shows selectivity in CDC activity on Wien 133 cells of glycosylated and aglycosylated IgG1-CAMPATH-1H and IgG1-11B8 antibody variants harboring a self-oligomerization inhibiting mutation and the E430Y Fc-Fc interaction enhancing mutation, as compared to variants harboring the E430G and E345R mutations. The potency to induce CDC was normalized to non-binding antibody control IgG1-b12 (0%) and IgG1-CAMPATH-1H-E430G (100%; FIG. 14A) or IgG1-CAMPATH-1H-E430G+IgG1-11B8-E430G (100%; FIG. 14B). (FIG. 14A) Wien 133 cells were incubated with IgG1-CAMPATH-1H antibody variants or mixtures thereof in a concentration series in the presence of 20% NHS. (FIG. 14B) Wien 133 cells were incubated with IgG1-CAMPATH-1H, IgG1-11B8 and/or IgG1-b12 antibody variants or mixtures thereof in a concentration series in the presence of 20% NHS.

Figures 15A, 15B:

FIGS. 15A and 15B shows selectivity in CDC induction on Wien 133 cells by aglycosylated IgG1-CAMPATH-1H and IgG1-11B8 antibody variants that harbor Fc-Fc interaction enhancing mutation E345K, self-oligomerization inhibiting mutations K439E or S440K and C1q binding enhancing mutations K326A and E333S. The potency to induce CDC was normalized to non-binding antibody control IgG1-b12 (0%) and IgG1-CAMPATH-1H-E430G (100%; FIG. 15A) or IgG1-CAMPATH-1H-E430G+IgG1-11B8-E430G (100%; FIG. 15B). (FIG. 15A) Wien 133 cells were incubated with IgG1-CAMPATH-1H antibody variants or mixtures thereof in a concentration series in the presence of 20% NHS. (FIG. 15B) Wien 133 cells were incubated with IgG1-CAMPATH-1H and IgG1-11B8 antibody variants or mixtures thereof in a concentration series in the presence of 20% NHS.

Figures 16A, 16B:
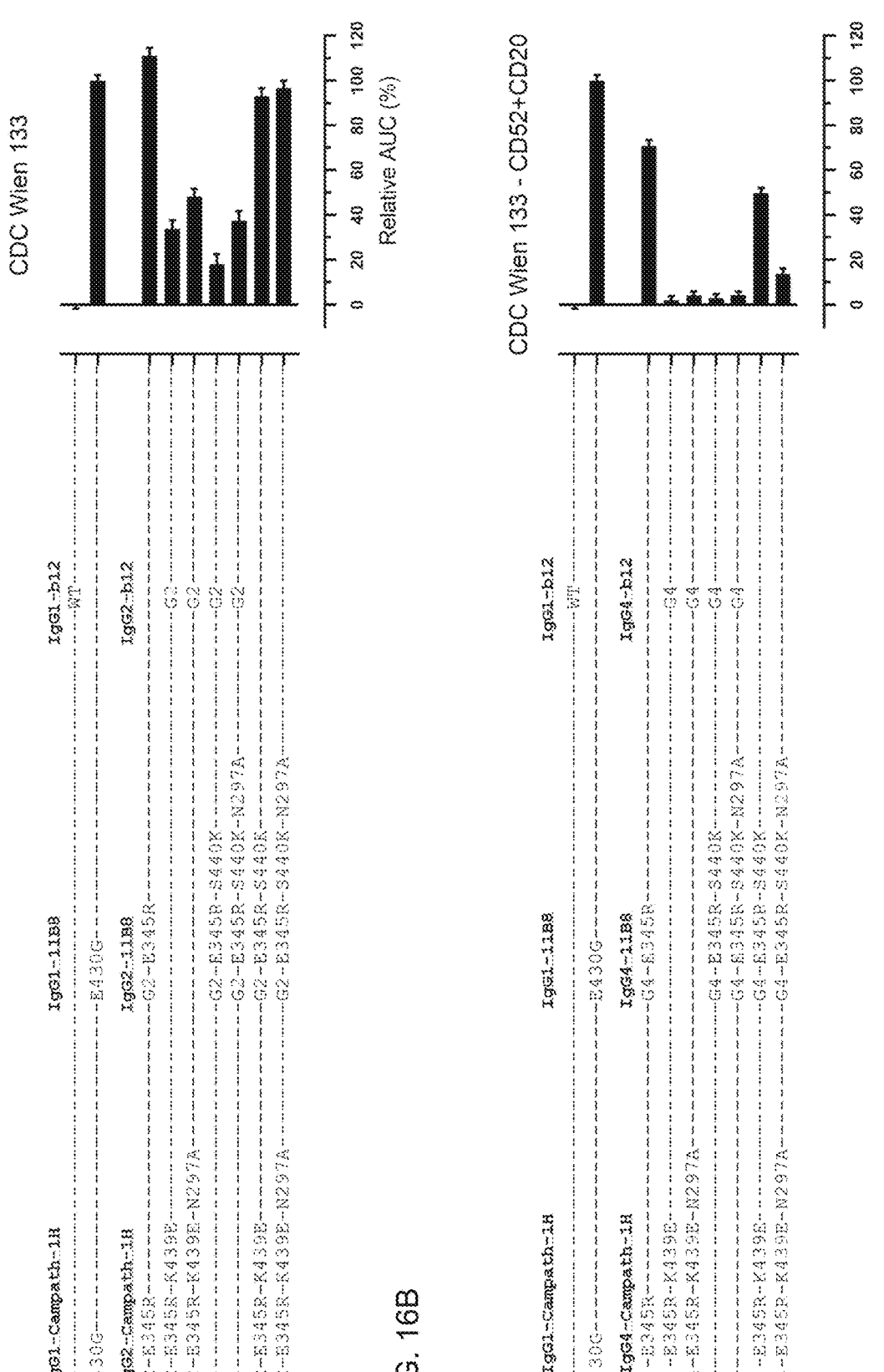

FIGS. 16A and 16B shows selectivity in CDC induction on Wien 133 cells by aglycosylated CAMPATH-1H and 11B8 antibody variants of the IgG2 or IgG4 subclass, which harbor Fc-Fc interaction enhancing mutation E345R and self-oligomerization inhibiting mutations K439E or S440K. The potency to induce CDC was normalized to non-binding antibody control IgG1-b12 (0%) and IgG1-CAMPATH-1H-E430G+IgG1-11B8-E430G (100%). (FIG. 16A) Wien 133 cells were incubated with IgG2-CAMPATH-1H and IgG2-11B8 antibody variants or mixtures thereof in a concentration series in the presence of 20% NHS. (FIG. 16B) Wien 133 cells were incubated with IgG4-CAMPATH-1H and IgG4-11B8 antibody variants or mixtures thereof in a concentration series in the presence of 20% NHS.

Figure 17A:
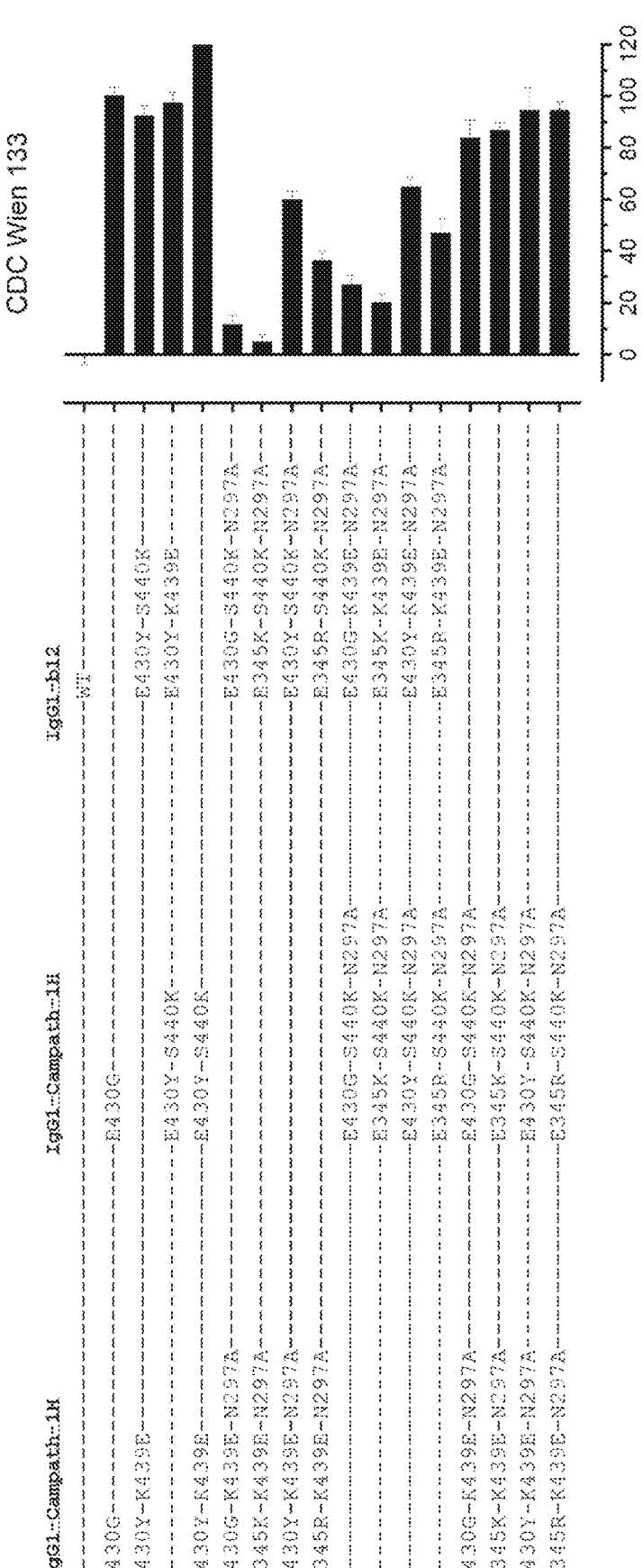
Figure 17B:
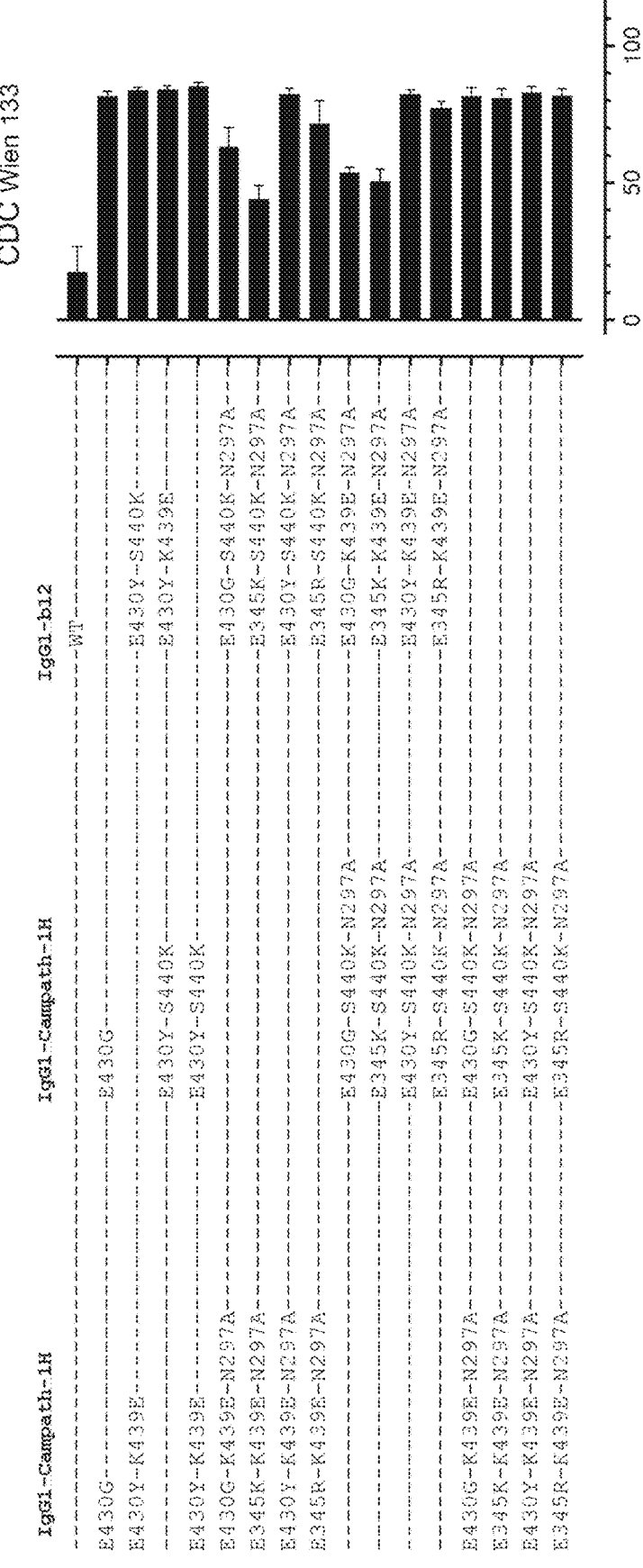

FIGS. 17A and 17B shows selectivity in CDC induction on Wien 133 cells by aglycosylated IgG1-CAMPATH-1H antibody variants that harbor Fc-Fc interaction enhancing mutations E430G, E430Y, E345K or E345R and self-oligomerization inhibiting mutations K439E or S440K. The potency to induce CDC was normalized to non-binding antibody control IgG1-b12 (0%) and IgG1-CAMPATH-1H-E430G (100%). Wien 133 cells were incubated with IgG1-CAMPATH-1H antibody variants or mixtures thereof in a concentration series in the presence of 20% NHS. (FIG. 17A) Relative CDC potency as induced on Wien 133 cells incubated with IgG1-CAMPATH-1H antibody variants or mixtures thereof in a concentration series in the presence of 20% NHS. (FIG. 17B) Percentage of cell lysis of Wien 133 cells incubated with IgG1-CAMPATH-1H antibody variants or mixtures thereof in a concentration series in the presence of 20% NHS.

Figure 18A:
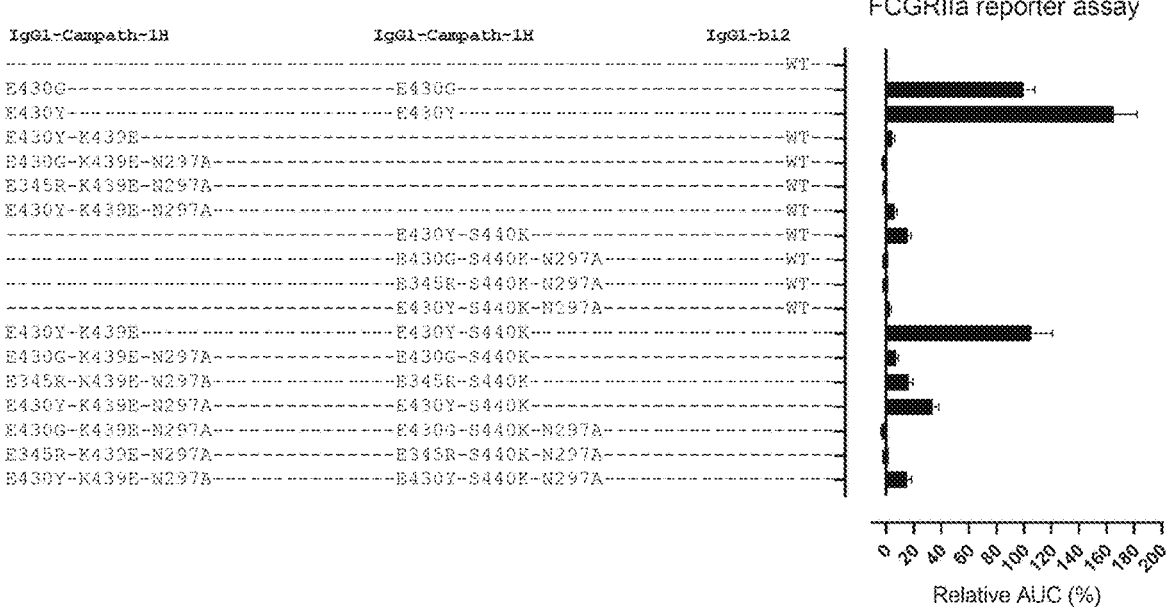
Figure 18B:
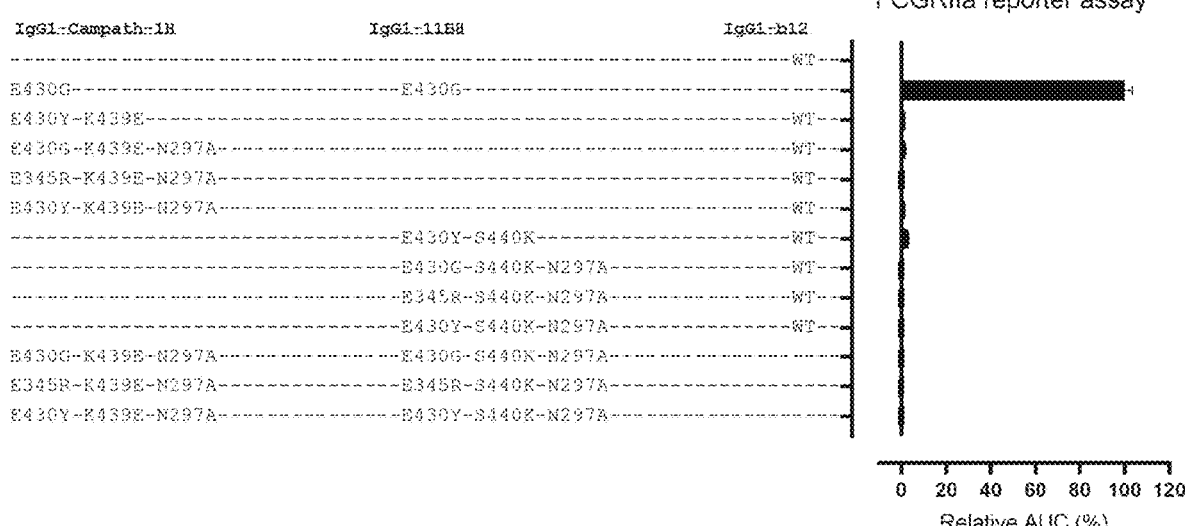

FIGS. 18A and 18B shows the capacity to induce ADCP, as determined through an FcγRIIa activation reporter cell assay, by aglycosylated antibody variants of IgG1-CAMPATH-1H and IgG1-11B8 harboring an Fc-Fc interaction enhancing, a self-oligomerization inhibiting mutation, and C1q binding enhancing mutations K326A-E333S. Luciferase production was quantified by luminescence readout. Data are presented as relative AUCs of area under the antibody dose-response curves (0.2-40,000 ng/mL in 4-fold dilutions) normalized to the AUC value measured for the non-binding negative control IgG1-b12 (0%) and the AUC value measured for the positive control IgG1-CAMPATH-1H-E430G (100%; FIG. 18A), or IgG1-CAMPATH-E430G+IgG1-11B8-E430G (100%; FIG. 18B). (FIG. 18A) Raji cells were incubated with titrated IgG1-CAMPATH-1H antibody variants and FcγRIIa-transduced Jurkat cells. (FIG. 18B) Raji cells were incubated with titrated IgG1-CAMPATH-1H and IgG1-11B8 antibody variants and FcγRIIa-transduced Jurkat cells.

Figures 19A, 19B:
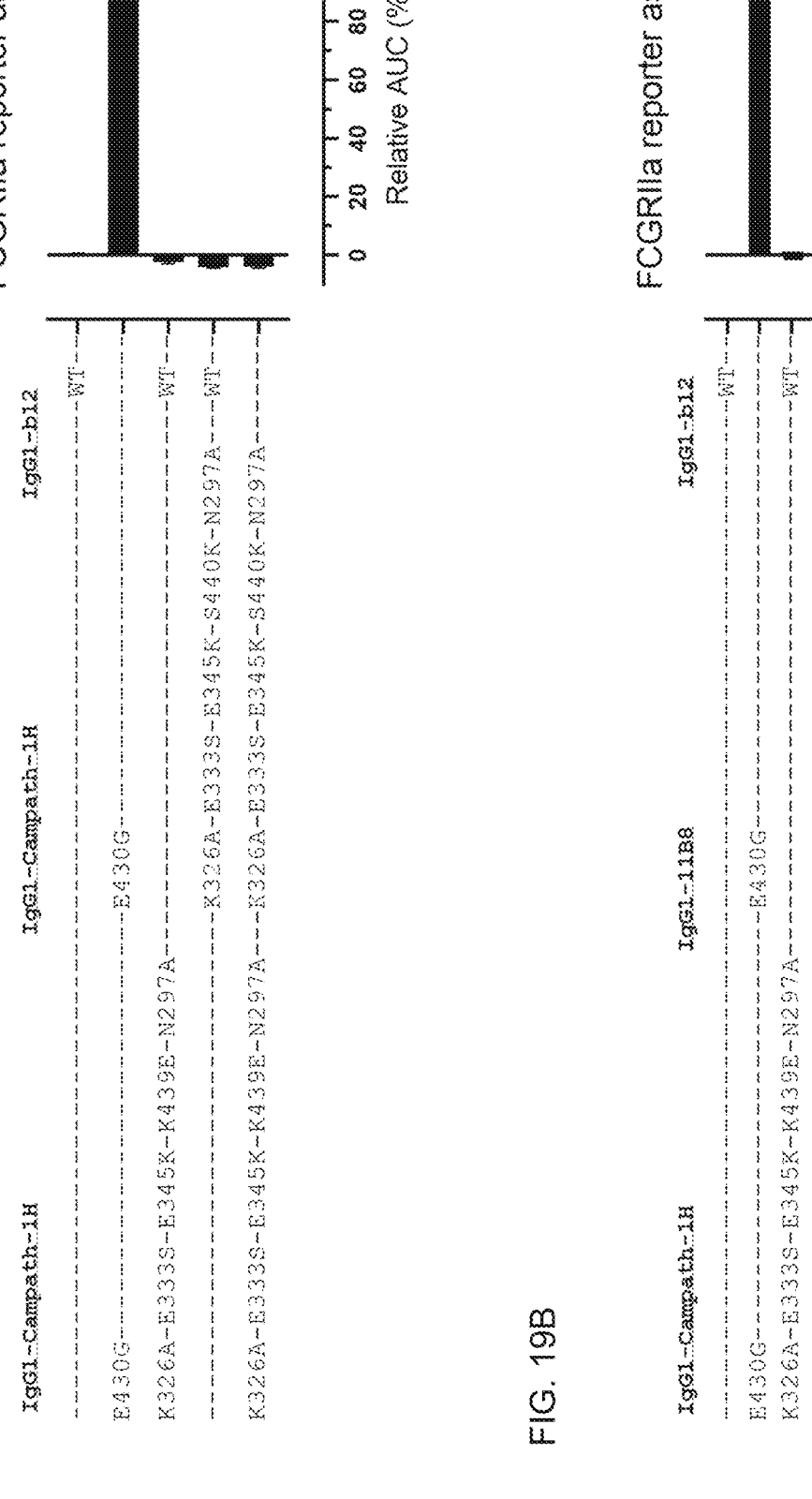

FIGS. 19A and 19B show the effects of IgG1-CAMPATH-1H antibody variants harboring the indicated Fc region mutations on FcγRIIa activation.

Figure 20A:
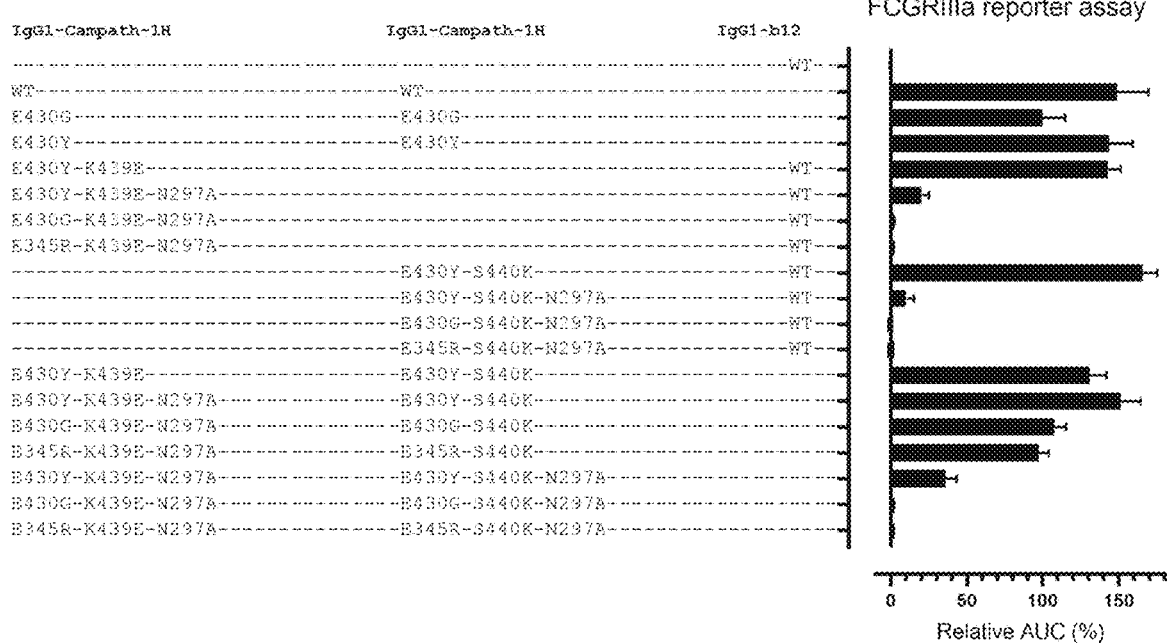
Figure 20B:
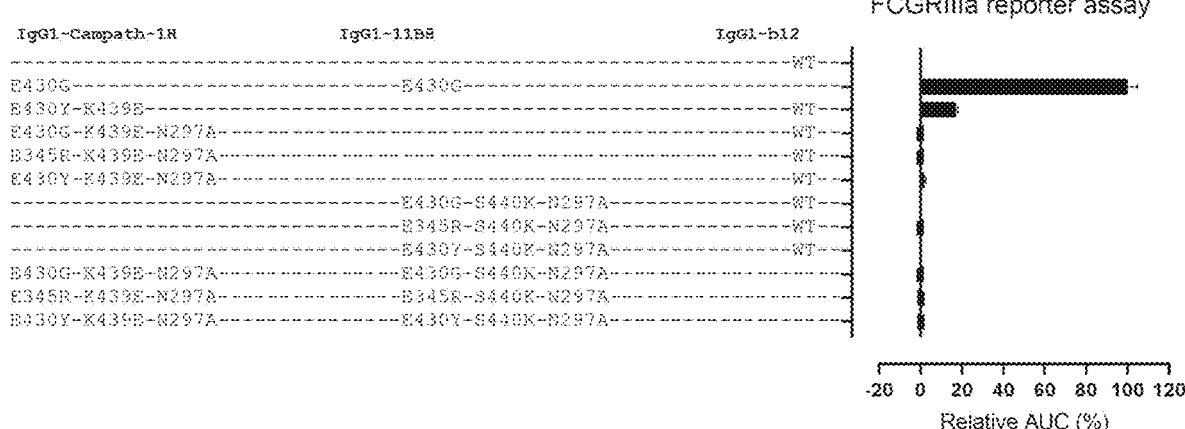

FIGS. 20A and 20B shows the capacity to induce ADCC, as determined through an FcγRIIIa activation reporter cell assay, by aglycosylated antibody variants of IgG1-CAMPATH-1H and IgG1-11B8 harboring an Fc-Fc interaction enhancing and a self-oligomerization inhibiting mutation. Luciferase production was quantified by luminescence read-out. Data are presented as relative AUCs of area under the antibody dose-response curves (0.2-40,000 ng/mL in 4-fold dilutions) normalized to the AUC value measured for the non-binding negative control IgG1-b12 (0%) and the AUC value measured for the positive control IgG1-CAMPATH-1H-E430G (100%; FIG. 20A), or IgG1-CAMPATH-E430G+IgG1-11B8-E430G (100%; FIG. 20B). (FIG. 20A) Raji cells were incubated with titrated IgG1-CAMPATH-1H antibody variants and FcγRIIIa-transduced Jurkat cells. (FIG. 20B) Raji cells were incubated with titrated IgG1-CAMPATH-1H and IgG1-11B8 antibody variants and FcγRIIIa-transduced Jurkat cells.

Figures 21A, 21B:

FIGS. 21A and 21B shows the capacity to induce ADCC, as determined through an FcγRIIIa activation reporter cell assay, by aglycosylated antibody variants of IgG1-CAMPATH-1H and IgG1-11B8 harboring an Fc-Fc interaction enhancing, a self-oligomerization inhibiting mutation and C1q binding enhancing mutations. Luciferase production was quantified by luminescence readout. Data are presented as relative AUCs of area under the antibody dose-response curves (0.2-40,000 ng/mL in 4-fold dilutions) normalized to the AUC value measured for the non-binding negative control IgG1-b12 (0%) and the AUC value measured for the positive control IgG1-CAMPATH-1H-E430G (100%; FIG. 21A), or IgG1-CAMPATH-E430G+IgG1-11B8-E430G (100%; FIG. 21B). (FIG. 21A) Raji cells were incubated with titrated IgG1-CAMPATH-1H antibody variants and FcγRIIIa-transduced Jurkat cells. (FIG. 21B) Raji cells were incubated with titrated IgG1-CAMPATH-1H and IgG1-11B8 antibody variants and FcγRIIIa-transduced Jurkat cells.

Figures 22A, 22B:
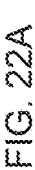

FIGS. 22A and 22B shows the capacity to induce ADCP, as determined through an FcγRIIa activation reporter cell assay, by aglycosylated CAMPATH-1H and 11B8 antibody variants of the IgG2 and IgG4 subclass, which harbor an Fc-Fc interaction enhancing and self-oligomerization inhibiting mutation. Luciferase production was quantified by luminescence readout. Data are presented as relative AUCs of area under the antibody dose-response curves (0.6-40,000 ng/mL in 4-fold dilutions) normalized to the AUC value measured for the non-binding negative control IgG1-b12 (0%) and the AUC value measured for the positive control IgG1-CAMPATH-1H-E430G+IgG1-11B8-E430G (100%). (FIG. 22A) Raji cells were incubated with titrated IgG2-CAMPATH-1H and/or IgG2-11B8 antibody variants, and FcγRIIa-transduced Jurkat cells. (FIG. 22B) Raji cells were incubated with titrated IgG4-CAMPATH-1H and/or IgG4-11B8 antibody variants, and FcγRIIa-transduced Jurkat cells.

Figures 23A, 23B:
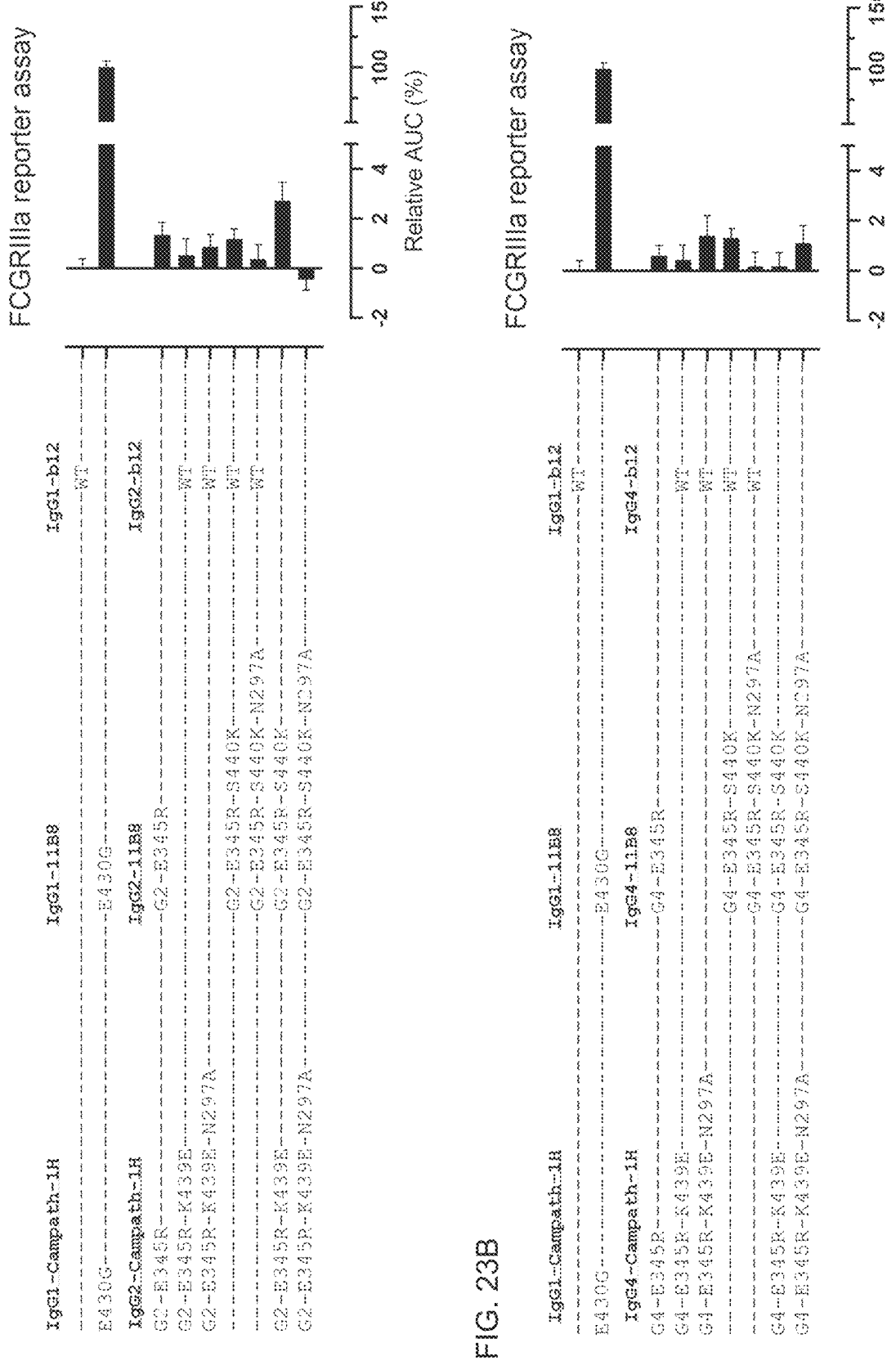

FIGS. 23A and 23B shows the capacity to induce ADCC, as determined through an FcγRIIIa activation reporter cell assay, by aglycosylated CAMPATH-1H and 11B8 antibody variants of the IgG2 and IgG4 subclass, which harbor an Fc-Fc interaction enhancing and self-oligomerization inhibiting mutation. Luciferase production was quantified by luminescence readout. Data are presented as relative AUCs of area under the antibody dose-response curves (0.2-40,000 ng/mL in 4-fold dilutions) normalized to the AUC value measured for the non-binding negative control IgG1-b12 (0%) and the AUC value measured for the positive control IgG1-CAMPATH-1H-E430G+IgG1-11B8-E430G (100%). (FIG. 23A) Raji cells were incubated with titrated IgG2-CAMPATH-1H and/or IgG2-11B8 antibody variants, and FcγRIIIa-transduced Jurkat cells. (FIG. 23B) Raji cells were incubated with titrated IgG4-CAMPATH-1H and/or IgG4-11B8 antibody variants, and FcγRIIIa-transduced Jurkat cells.

Figures 24A, 24B:
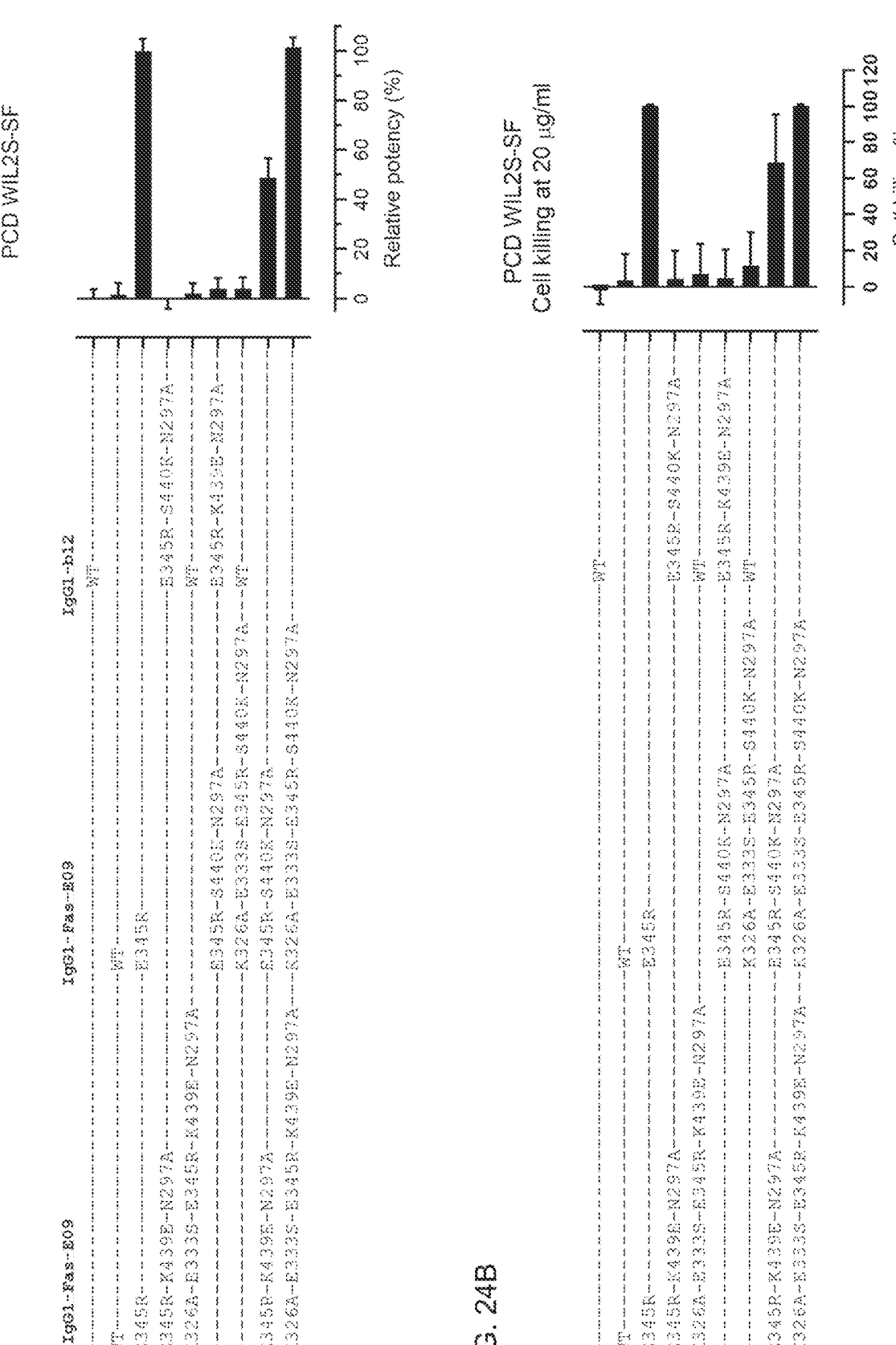

FIGS. 24A and 24B shows the relative potency to induce programmed cell death (PCD) of WIL2S-SF B cell lymphoblast target cells by aglycosylated anti-Fas-E09 antibody variants harboring mutations that enhance Fc-Fc interactions, inhibit self-oligomerization and enhance C1q binding. (FIG. 24A) PCD efficacy is presented as the killing potency [AUC (IgG1-b12)—AUC (sample)], normalized to IgG1-Fas-E09-E345R (100%). (FIG. 24B) Cell death induction of WIL2S-SF cells induced at 20 μg/mL antibody variant concentrations.

FIGS. 25A-25D shows the relative potency to induce programmed cell death (PCD) of BxPC-3 and COL0205 cancer cells by two aglycosylated non-competing anti-DR5 antibody variants (IgG1-hDR5-01-G56T and IgG1-hDR5-05) and mixtures thereof harboring mutations that enhance Fc-Fc interactions, inhibit self-oligomerization and enhance C1q binding. PCD efficacy is presented as the killing potency [AUC (IgG1-b12)—AUC (sample)], normalized to IgG1-hDR5-01-G56T-E430G+IgG1-hDR5-05-E430G (100%). (FIG. 25A) Relative potency to induce cell death of BxPC-3 cancer cells. (FIG. 25B) Maximal cell death of BxPC-3 cells induced by the indicated antibody variants and mixtures thereof at a concentration of 20 μg/mL. (FIG. 25C) Relative potency to induce cell death of COL0205 cancer cells. (FIG. 25D) Maximal cell death of COL0205 cells induced by the indicated antibody variants and mixtures thereof at a concentration of 20 μg/mL.

Figures 26A, 26B:
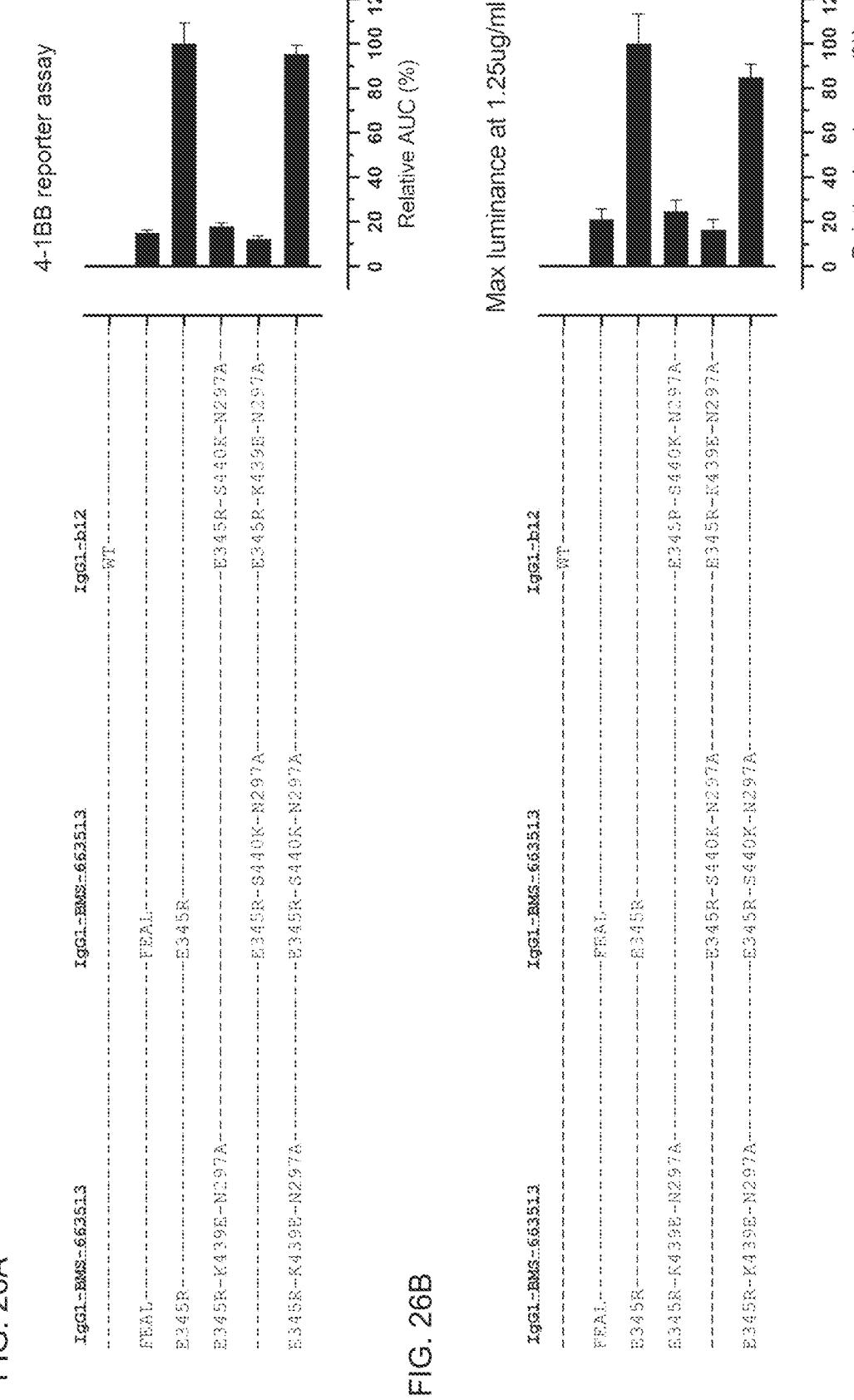

FIGS. 26A and 26B shows the selective induction of 4-1BB-mediated activation of a reporter cell engineered to stably express 4-1BB and a nuclear factor of activated T cells (NFAT)-response element driving expression of firefly luciferase by antibody variants of IgG1-BMS663513 harboring mutations that enhance Fc-Fc interactions, inhibit self-oligomerization and yield aglycosylated antibodies. 4-1BB-expressing Jurkat cells were incubated with IgG1-BMS663513 antibody variants or mixtures thereof in a concentration series in the presence of C1q. (FIG. 26A) The potency to induce 4-1BB-mediated reporter cell activation is presented as relative AUC normalized to non-binding antibody control IgG1-b12 (0%) and IgG1-BMS663513-E345R (100%). (FIG. 26B) Potency to induce 4-1BB-mediated reporter cell activation at an antibody concentration of 1.25 μg/mL, presented as the measured luminescence, normalized to non-binding antibody control IgG1-b12 (0%) and IgG1-BMS663513-E345R (100%).

FIGS. 27A and 27B shows the selective induction of 4-1BB-mediated activation of a reporter cell engineered to stably express 4-1BB and a nuclear factor of activated T cells (NFAT)-response element driving expression of firefly luciferase by antibody variants of IgG1-BMS663513 harboring mutations that enhance Fc-Fc interactions, inhibit self-oligomerization, yield aglycosylated antibodies and enhance C1q binding. 4-1BB-expressing Jurkat cells were incubated with IgG1-BMS663513 antibody variants or mixtures thereof in a concentration series in the presence of C1q. (FIG. 27A) The potency to induce 4-1BB-mediated reporter cell activation is presented as relative AUC normalized to non-binding antibody control IgG1-b12 (0%) and IgG1-BMS663513-E345R (100%). (FIG. 27B) Potency to induce 4-1BB-mediated reporter cell activation at an antibody concentration of 1.25 µg/mL, presented as the luminescence measured, normalized to non-binding antibody control IgG1-b12 (0%) and IgG1-BMS663513-E345R (100%).

DETAILED DESCRIPTION OF THE INVENTION

Definitions

The term "immunoglobulin" refers to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region typically is comprised of three domains, CH1, CH2, and CH3. The heavy chains are inter-connected via disulfide bonds in the so-called "hinge region". Each light chain typically is comprised of a light chain variable region (abbreviated herein as VL) and a light chain constant region. The light chain constant region typically is comprised of one domain, CL. The VH and VL regions may be further subdivided into regions of hyper-variability (or hypervariable regions which may be hyper-variable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)). Unless otherwise stated or contradicted by context, CDR sequences herein are identified according to IMGT rules using DomainGapAlign (Lefranc M P., Nucleic Acids Research 1999; 27:209-212 and Ehrenmann F., Kaas Q. and Lefranc M.-P. Nucleic Acids Res., 38, D301-307 (2010); see also internet http address www.imqt.org/.

Unless otherwise stated or contradicted by context, reference to amino acid positions in the Fc region/Fc domain in the present invention is according to the Eu-numbering (Edelman et al., Proc Natl Acad Sci USA. 1969 May; 63(1):78-85; Kabat et al., Sequences of proteins of immunological interest. 5th Edition—1991 NIH Publication No. 91-3242).

The Fc-region of an immunoglobulin is defined as the fragment of an antibody which would be typically generated after digestion of an antibody with papain (which is known for someone skilled in the art) which includes the two CH2-CH3 regions of an immunoglobulin and a connecting region, e.g. a hinge region. The constant domain of an antibody heavy chain defines the antibody isotype/subclass, e.g. IgG1, IgG2, IgG3, IgG4, IgA1, IgA2, IgM, IgD, or IgE. The Fc-region mediates the effector functions of antibodies with cell surface receptors called Fc receptors and proteins of the complement system.

The term "hinge region" as used herein is intended to refer to the hinge region of an immunoglobulin heavy chain. Thus, for example the hinge region of a human IgG1 antibody corresponds to amino acids 216-230 according to the Eu numbering.

The term "CH2 region" or "CH2 domain" as used herein is intended to refer to the CH2 region of an immunoglobulin heavy chain. Thus, for example the CH2 region of a human IgG1 antibody corresponds to amino acids 231-340 according to the Eu numbering. However, the CH2 region may also be any of the other subtypes as described herein.

The term "CH3 region" or "CH3 domain" as used herein is intended to refer to the CH3 region of an immunoglobulin heavy chain. Thus, for example the CH3 region of a human IgG1 antibody corresponds to amino acids 341-447 according to the Eu numbering. However, the CH3 region may also be any of the other subtypes as described herein.

The term "antibody" (Ab) in the context of the present invention refers to an immunoglobulin molecule, a fragment of an immunoglobulin molecule, or a derivative of either thereof, which has the ability to specifically bind to an antigen. The antibody of the present invention comprises an Fc region of an immunoglobulin and an antigen-binding region. An antibody generally contains two CH2-CH3 regions and a connecting region, e.g. a hinge region, e.g. at least an Fc region. The variable regions of the heavy and light chains of the immunoglobulin molecule contain a binding domain that interacts with an antigen. As described above, the constant or "Fc" regions of the antibodies may mediate the binding of the immunoglobulin to host tissues or factors, including various cells of the immune system (such as effector cells) and components of the complement system such as C1q, the first component in the classical pathway of complement activation. An antibody may also be a multi-specific antibody, such as a bispecific antibody or similar molecule. The term "bispecific antibody" refers to an antibody having specificities for at least two different, typically non-overlapping, epitopes. Such epitopes may be on the same or different targets. If the epitopes are on different targets, such targets may be on the same cell or different cells or cell types. As indicated above, unless otherwise stated or clearly contradicted by the context, the term antibody herein includes fragments of an antibody which comprise at least a portion of an Fc-region and which retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. Examples of binding fragments encompassed within the term "Ab" or "antibody" include, without limitation, monovalent antibodies (described in WO2007059782 by Genmab); heavy-chain antibodies, consisting only of two heavy chains and naturally occurring in e.g. camelids (e.g., Hamers-Casterman (1993) Nature 363: 446); ThioMabs (Roche, WO2011069104), strand-exchange engineered domain-bodies (SEED or Seed-body molecules), which are asymmetric and bispecific antibody-like molecules (Merck, WO2007110205); Triomab (Pharma/Fresenius Biotech, Lindhofer et al. 1995 J Immunol 155:219; WO2002020039); FcAAdp (Regeneron, WO2010151792), Azymetric Scaffold (Zymeworks/Merck, WO2012/058768), mAb-Fv (Xencor, WO2011/028952), Xmab (Xencor), Dual variable domain immunoglobulins (Abbott, DVD-Ig, U.S. Pat. No. 7,612,181); Dual domain double head antibodies (Unilever; Sanofi Aventis, WO20100226923), Di-diabody molecules (ImClone/Eli Lilly), Knobs-into-holes antibody formats (Genentech, WO9850431); DuoBody molecules (Genmab, WO 2011/131746); DuetMab (MedImmune, US2014/0348839), Electrostatic steering antibody formats (Amgen, EP1870459 and WO2009089004; Chugai, US201000155133; Oncomed, WO2010129304A2); bispe-cific IgG1 and IgG2 (Rinat neurosciences Corporation, WO11143545), CrossMAbs (Roche, WO2011117329), LUZ-Y (Genentech), Biclonic molecules (Merus, WO2013157953), Dual Targeting domain antibodies (GSK/ Domantis), Two-in-one Antibodies or Dual action Fabs recognizing two targets (Genentech, NovImmune, Adimab), Cross-linked Mabs (Karmanos Cancer Center), covalently fused mAbs (AIMM), CovX-body (CovX/Pfizer), FynomAbs (Covagen/Janssen ilag), DutaMab (Dutalys/ Roche), iMab (MedImmune), IgG-like Bispecific molecules (ImClone/Eli Lilly, Shen, J., et al. J Immunol Methods, 2007. 318(1-2): p. 65-74), TIG-body, DIG-body and PIG-body molecules (Pharmabcine), Dual-affinity retargeting molecules (Fc-DART or Ig-DART, by Macrogenics, WO/2008/157379, WO/2010/080538), BEAT (Glenmark), Zybodies (Zyngenia), approaches with common light chain (Crucell/Merus, U.S. Pat. No. 7,262,028) or common heavy chains (dkBodies by NovImmune, WO2012023053), as well as fusion proteins comprising a polypeptide sequence fused to an antibody fragment containing an Fc-region like scFv-fusions, like BsAb by ZymoGenetics/BMS, HERCULES by Biogen Idec (U.S. Pat. No. 7,951,918), SCORPIONS by Emergent BioSolutions/Trubion and Zymogenetics/BMS, Ts2Ab (MedImmune/AZ (Dimasi, N., et al. J Mol Biol, 2009. 393(3): p. 672-92), scFv fusion by Genentech/Roche, scFv fusion by Novartis, scFv fusion by Immunomedics, scFv fusion by Changzhou Adam Biotech Inc (CN 102250246), TvAb by Roche (WO 2012025525, WO 2012025530), mAb² by f-Star (WO2008/003116), and dual scFv-fusions. It also should be understood that the term antibody, unless specified otherwise, also includes poly-clonal antibodies, monoclonal antibodies (such as human monoclonal antibodies), antibody mixtures (recombinant polyclonals) for instance generated by technologies exploited by Symphogen and Merus (Oligoclonics), multi-meric Fc proteins as described in WO2015/158867, fusion proteins as described in WO2014/031646 and antibody-like polypeptides, such as chimeric antibodies and humanized antibodies. An antibody as generated can potentially possess any isotype.

The term "full-length antibody" when used herein, refers to an antibody (e.g., a parent antibody) which contains all heavy and light chain constant and variable domains corre-sponding to those that are normally found in a wild-type antibody of that isotype.

The term "human antibody", as used herein, is intended to include antibodies having variable and constant regions derived from human germline immunoglobulin sequences. The human antibodies of the invention may include amino acid residues not encoded by human germline immuno-globulin sequences (e.g., mutations, insertions or deletions introduced by random or site-specific mutagenesis in vitro or by somatic mutation in vivo). However, the term "human antibody", as used herein, is not intended to include anti-bodies in which CDR sequences derived from the germline of another mammalian species, such as a mouse, have been grafted onto human framework sequences.

The term "chimeric antibody", as used herein, refers to an antibody in which both chain types, i.e. heavy chain and light chain, are chimeric as a result of antibody engineering. A chimeric chain is a chain that contains a foreign variable domain (originating from a non-human species, or synthetic or engineered from any species including human) linked to a constant region of human origin.

The term "humanized antibody", as used herein, refers to an antibody in which both chain types are humanized as a result of antibody engineering. A humanized chain is typi-cally a chain in which the complementarity determining regions (CDR) of the variable domains are foreign (origi-nating from a species other than human, or synthetic) whereas the remainder of the chain is of human origin. Humanization assessment is based on the resulting amino acid sequence, and not on the methodology per se, which allows protocols other than grafting to be used.

The terms "monoclonal antibody", "monoclonal Ab", "monoclonal antibody composition", "mAb", or the like, as used herein refer to a preparation of Ab molecules of single molecular composition. A monoclonal antibody composition displays a single binding specificity and affinity for a par-ticular epitope. Accordingly, the term "human monoclonal antibody" refers to Abs displaying a single binding speci-ficity which have variable and constant regions derived from human germline immunoglobulin sequences. The human mAbs may be generated by a hybridoma which includes a B cell obtained from a transgenic or trans-chromosomal non-human animal, such as a transgenic mouse, having a genome comprising a human heavy chain transgene repertoire and a light chain transgene repertoire, rearranged to produce a functional human antibody, fused to an immortalized cell.

The term "isotype" as used herein, refers to the immu-noglobulin class (for instance IgG, IgD, IgA1, IgGA2, IgE, or IgM. IgGs may by further classified as subclasses IgG1, IgG2, IgG3 or IgG4. The term "subclass" as used herein, referrers to the IgG1, IgG2, IgG3 and IgG4 subclasses of the IgG isotype. The IgG1 subclass may be further classified according to allotypes thereof such as IgG1m(za) and IgG1m(f)) that is encoded by heavy chain constant region genes. Further, each heavy chain isotype can be combined with either a kappa (☐) or lambda (☐) light chain. The term "mixed isotype" or "mixed subclass" used herein refers to the Fc region of an immunoglobulin generated by combining structural features of one isotype with the analogous region from another isotype thereby generating a hybrid isotype. A mixed isotype may comprise an Fc region having a sequence comprised of two or more isotypes selected from the fol-lowing IgG1, IgG2, IgG3, IgG4, IgD, IgA1, IgGA2, IgE, or IgM thereby generating combinations such as e.g. IgG1/ IgG3, IgG1/IgG4, IgG2/IgG3, IgG2/IgG4, or IgG1/IgA.

The term "antigen-binding region", "antigen binding region", "binding region" or "antigen binding domain", as used herein, refers to a region of an antibody which is capable of binding to the antigen. This binding region is typically defined by the VH and VL domains of the antibody which may be further subdivided into regions of hypervari-ability (or hypervariable regions which may be hypervari-able in sequence and/or form of structurally defined loops), also termed complementarity determining regions (CDRs), interspersed with regions that are more conserved, termed framework regions (FRs). The antigen can be any molecule, such as a polypeptide, e.g. present on a cell, bacterium, or virion.

The term "target" or "target antigen" as used herein, refers to a molecule to which the antigen-binding region of the antibody binds. The target includes any antigen towards which the antibody is directed. The term "antigen" and "target" may in relation to an antibody be used interchangeably and constitute the same meaning and purpose with respect to any aspect or embodiment of the present invention.

The term "epitope" means a molecular determinant capable of specific binding to an antibody variable domain. Epitopes usually consist of surface groupings of molecules such as amino acids, sugar side chains, or a combination thereof and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding.

The term "parent antibody", is to be understood as an antibody which is identical to an antibody according to the invention, but wherein the parent antibody does not have one or more of the specified mutations. A "variant" or "antibody variant" or a "variant of a parent antibody" of the present invention is an antibody molecule which comprises one or more mutations as compared to a "parent antibody". The different terms may be used interchangeably and constitute the same meaning and purpose with respect to any aspect or embodiment of the present invention. Exemplary parent antibody formats include, without limitation, a wild-type antibody, a full-length antibody or Fc-containing antibody fragment, a bispecific antibody, a human antibody, humanized antibody, chimeric antibody or any combination thereof. The different terms may be used interchangeably and constitute the same meaning and purpose with respect to any aspect or embodiment of the present invention. Amino acid substitutions may exchange a native amino acid for another naturally-occurring amino acid, or for a non-naturally-occurring amino acid derivative. The amino acid substitution may be conservative or non-conservative. In the context of the present invention, conservative substitutions may be defined by substitutions within the classes of amino acids reflected in one or more of the following three tables:

Amino Acid Residue Classes for Conservative Substitutions

| | |
|---|---|
| Acidic Residues | Asp (D) and Glu I |
| Basic Residues | Lys (K), AI(R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged ResidueLys (C), Met (M), and Pro (P) | |
| Aromatic Residues | Phe (F), Tyr (Y), and Trp (W) |

Alternative Conservative Amino Acid Residue Substitution Classes

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, N, D, E, and R |

In the context of the present invention, a substitution in a variant is indicated as:

Original amino acid—position—substituted amino acid;

The three letter code, or one letter code, are used, including the codes Xaa and X to indicate amino acid residue. Accordingly, the notation "E345R" or "Glu345Arg" means that the variant comprises a substitution of glutamic acid with arginine in the variant amino acid position corresponding to the amino acid in position 345 in the parent antibody.

Where a position as such is not present in an antibody, but the variant comprises an insertion of an amino acid, for example:

Position—substituted amino acid; the notation, e.g., "448E" is used.

Such notation is particularly relevant in connection with modification(s) in a series of homologous polypeptides or antibodies.

Similarly, when the identity of the substitution amino acid residue(s) is immaterial:

Original amino acid—position; or "E345".

For a modification where the original amino acid(s) and/or substituted amino acid(s) may comprise more than one, but not all amino acid(s), the substitution of glutamic acid with arginine, lysine or tryptophan in position 345:

"Glu345Arg, Lys,Trp" or "E345R,K,W" or "E345R/K/ W" or "E345 to R, K or W" may be used interchangeably in the context of the invention.

Furthermore, the term "a substitution" embraces a substitution into any one of the other nineteen natural amino acids, or into other amino acids, such as non-natural amino acids. For example, a substitution of amino acid E in position 345 includes each of the following substitutions: 345A, 345C, 345D, 345G, 345H, 345F, 345I, 345K, 345L, 345M, 345N, 345P, 345Q, 345R, 345S, 345T, 345V, 345W, and 345Y. This is equivalent to the designation 345X, wherein the X designates any amino acid. These substitutions can also be designated E345A, E345C, etc., or E345A, C, etc., or E345A/C/etc. The same applies to analogy to each and every position mentioned herein, to specifically include herein any one of such substitutions.

As used herein, the term "effector cell" refers to an immune cell which is involved in the effector phase of an immune response, as opposed to the recognition and activation phases of an immune response. Exemplary immune cells include cells of a myeloid or lymphoid origin, for instance lymphocytes (such as B cells and T cells including cytolytic T cells (CTLs)), killer cells, natural killer cells, macrophages, monocytes, and polymorphonuclear cells or granulocytes, such as neutrophils, mast cells, eosinophils, and basophils. Some effector cells express Fc receptors (FcRs) or complement receptors and carry out specific immune functions. In some embodiments, an effector cell such as, e.g., a natural killer cell, is capable of inducing ADCC. For example, monocytes, macrophages, neutrophils, dendritic cells and Kupffer cells which express FcRs, are involved in specific killing of target cells and presenting antigens to other components of the immune system, or in binding to cells that present antigens. In some embodiments the ADCC can be further enhanced by antibody-driven classical complement activation, resulting in the deposition of activated C3 fragments on the target cell. C3 cleavage products are ligands to complement receptors (CRs), such as CR3, expressed on myeloid cells. The recognition of complement fragments by CRs on effector cells may promote enhanced Fc receptor-mediated ADCC. In some embodiments, antibody-driven classical complement activation leads to C3 fragments on the target cell. These C3 cleavage products may promote direct complement-dependent cellular cytotoxicity (CDCC). In some embodiments, an effector cell may phagocytose a target antigen, target particle or target cell. The expression of a particular FcR or complement receptor on an effector cell may be regulated by humoral factors such as cytokines. For example, expression of FcγRI has been found to be up-regulated by interferon γ (IFNγ) and/or G-CSF. This enhanced expression increases the cytotoxic activity of FcγRI-bearing cells against targets. An effector cell can phagocytose a target antigen or phagocytose or lyse a target cell. In some embodiments, antibody-driven classical complement activation leads to C3 fragments on the target cell. These C3 cleavage products may promote direct phagocytosis by effector cells or indirectly by enhancing antibody-mediated phagocytosis.

The term "Fc effector functions," or "Fc-mediated effector functions," as used herein, is intended to refer to functions that are a consequence of binding a polypeptide or antibody to its target, such as an antigen, on a cell membrane wherein the Fc effector function is attributable to the Fc region of the polypeptide or antibody. Examples of Fc effector functions include (i) Clq-binding, (ii) complement activation, (iii) complement-dependent cytotoxicity (CDC), (iv) antibody-dependent cell-mediated cytotoxicity (ADCC), (v) Fc-gamma receptor-binding, (vi) antibody-dependent cellular phagocytosis (ADCP), (vii) complement-dependent cellular cytotoxicity (CDCC), (viii) complement-enhanced cytotoxicity, (ix) binding to complement receptor of an opsonized antibody mediated by the antibody, (x) opsonization, and (xi) a combination of any of (i) to (x).

The term "clustering-dependent functions," as used herein, is intended to refer to functions that are a consequence of the formation of antigen complexes after oligomerization of polypeptides or antibodies bound to their antigens, optionally on a cell, on a cell membrane, on a virion, or on another particle. Examples of clustering-dependent effector functions include (i) antibody oligomer formation, (ii) antibody oligomer stability, (iii) antigen oligomer formation, (iv) antigen oligomer stability, (v) induction of apoptosis, (vi) proliferation modulation, such as proliferation reduction, inhibition or stimulation, and (vii) a combination of any of (i) to (vi).

The term "vector" as used herein, is intended to refer to a nucleic acid molecule capable of inducing transcription of a nucleic acid segment ligated into the vector. One type of vector is a "plasmid" which is in the form of a circular double stranded DNA loop. Another type of vector is a viral vector, wherein the nucleic acid segment may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

The term "delivery vehicle" as used herein refers to a composition or formulation intended to protect e.g. a nucleic acid, a peptide, a polypeptide, e.g. an antibody, a small molecule, or other pharmacologically active substance from degradation upon administration. A delivery vehicle for nucleic acids may be a vector, which is to be understood as a nucleic acid molecule capable of inducing transcription of a nucleic acid segment ligated into the vector. Such a vector may comprise nucleic acid sequences encoding the heavy and light chain of a polypeptide variant. Furthermore, a delivery vehicle may be a lipid formulation, composed of constituents such as lipids, ionizable aminolipids, PEG-lipids, cholesterol or any combination thereof. Nucleic acids may be encapsulated in a delivery vehicle. Such a delivery vehicle may be modified in such a way that delivery to the relevant tissue is optimally achieved, e.g. by external attachment of target-specific antibodies, vehicle size adjustment or by means of modulating physico-chemical properties of the vehicle.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NSO cells, and lymphocytic cells, and prokaryotic cells such as E. coli and other eukaryotic hosts such as plant cells and fungi.

The term "transfectoma", as used herein, includes recombinant eukaryotic host cells expressing the Ab or a target antigen, such as CHO cells, PER.C6, NSO cells, HEK-293 cells, plant cells, or fungi, including yeast cells.

The term "preparation" refers to preparations of antibody variants and mixtures of different antibody variants which can have an increased ability to form oligomers when interacting with antigen associated with a cell (e.g., an antigen expressed on the surface of the cell), a cell membrane, a virion or other structure, which may result in enhanced signaling and/or activation by the antigen.

As used herein, the term "affinity" is the strength of binding of one molecule, e.g. an antibody, to another, e.g. a target or antigen, at a single site, such as the monovalent binding of an individual antigen binding site of an antibody to an antigen.

As used herein, the term "avidity" refers to the combined strength of multiple binding sites between two structures, such as between multiple antigen binding sites of antibodies simultaneously interacting with a target or e.g. between antibody and Clq. When more than one binding interactions are present, the two structures will only dissociate when all binding sites dissociate, and thus, the dissociation rate will be slower than for the individual binding sites, thereby providing a greater effective total binding strength (avidity) compared to the strength of binding of the individual binding sites (affinity).

As used herein, the term "oligomer" refers to a molecule that consists of more than one but a limited number of monomer units (e.g. antibodies) in contrast to a polymer that, at least in principle, consists of an unlimited number of monomers. Exemplary oligomers are dimers, trimers, tetramers, pentamers and hexamers. Greek prefixes are often used to designate the number of monomer units in the oligomer, for example a tetramer being composed of four units and a hexamer of six units.

The term "oligomerization", as used herein, is intended to refer to a process that converts monomers to a finite degree of polymerization. Herein, it is observed that antibodies comprising target-binding regions according to the invention can form oligomers, such as hexamers, via non-covalent association of Fc-regions after target binding, e.g., at a cell surface. In the context of the present application, "self-oligomerization", "homo-oligomerization" or "auto-oligomerization" is intended to refer to a process of oligomerization between antibody molecules that have identical protein sequences disregarding post-translational modifications. The term "hetero-oligomerization", as used herein, is intended to refer to a process of oligomerization between antibody molecules that have different protein sequences, disregarding post-translational modifications. Different antibodies participating in hetero-oligomerization could for instance bind different antigens, such as different target proteins, glycoproteins, glycans, or glycolipids.

The term "self-oligomerization inhibiting substitution" or "self-oligomerization inhibiting-substitution" is intended to refer to a substitution in an antibody comprising an Fc region of an immunoglobulin and an antigen binding region that inhibits the process of oligomerization between antibody molecules that have identical protein sequences disregarding post-translational modifications. Inhibition of self-oligomerization can for example result in an increased EC50 of CDC activity or a reduction in maximal CDC lysis activity of the polypeptide, measured according to the methods described in the Examples herein, e.g. Examples 2 and 5. Examples of self-oligomerization inhibiting substitutions are K439E and S440K. Thus, e.g. a first antibody having a K439E substitution has a low propensity form oligomers with another antibody having a K439E substitution, but an antibody having a K439E substitution has a high propensity to form oligomers with another antibody having an S440K substitution. An antibody having an S440K substitution has a low propensity to form oligomers with another antibody having an S440K substitution.

The term "clustering", as used herein, is intended to refer to oligomerization of antibodies, polypeptides, antigens or other proteins through non-covalent interactions.

The term "Fc-Fc enhancing", as used herein, is intended to refer to increasing the binding strength between, or stabilizing the interaction between, the Fc regions of two Fc-region containing antibodies or polypeptides so that the polypeptides form oligomers upon target binding. Fc-Fc enhancing substitutions, as used herein, refer to substitutions in E430 and E345, or the combination of the K248E and T437R substitutions (WO2018/031258), with the amino acid numbering corresponding to human IgG1 according to the Eu numbering.

When used herein in the context of two antigens, the term "co-expressed" or grammatical variations thereof, is intended to refer, on one hand, to situations where the two antigens are co-expressed on the same cell. The antigens may already be adjacent to each other on the cell or the antigens may be brought together via oligomerization of the binding polypeptides, e.g. antibodies, of the invention. Furthermore, the term "co-expressed" is also intended to refer to situations wherein the two antigens are expressed on different cells, but wherein such cells are located in close proximity to each other.

The term "co-dependent", as used herein, is intended to refer to a functional effect that is dependent on the simultaneous binding of two or more different Fc region containing antibodies with self-oligomerization inhibiting substitutions to the same target, cell, or virion. In the context of the present invention, functional effects that can be co-dependent include clustering-dependent functions, Fc-mediated effector functions, and the binding of effector molecules such as FcγR or C1, but not necessarily the individual binding of Fc region containing antibodies to their target antigens. As used herein, different Fc region containing antibodies with self-oligomerization inhibiting substitutions may each individually bind different targets, cells, or virions, but the co-dependent functional outcome is dependent on simultaneous binding of two or more different components to the same target, cell or virion. As used herein, co-dependent functional effects are recovered specifically by the two or more different Fc region containing antibodies with self-oligomerization inhibiting substitutions by virtue of the restoration of non-covalent Fc-Fc interactions between different components in the co-dependent Fc-containing polypeptide mixture.

The term "C1q binding" as used herein, is intended to refer to the direct interaction between C1q and antibody. Direct C1q binding can be evaluated for example by using immobilized antibody on artificial surface. The multivalent interaction resulting in high avidity binding of C1q to an antibody oligomer can be evaluated when bound to a predetermined antigen on a cellular or virion surface.

C1q binding to a polypeptide or an antibody may be determined in an ELISA assay using the following steps i) coat a 96-well Microlon ELISA plate with 1 μg/mL of polypeptide or antibody in 100 μl PBS at 4° C. overnight, ii) incubate the plate with 100 μL/well of a serial dilution series of C1q, final C1q concentration range 30-0.01 μg/mL in 3-fold dilutions for 1 h at 37° C., iii) incubate the plate with 100 μl/well of rabbit anti-human C1q for 1 h at RT, iv) incubate the plate with 100 μl/well swine anti-rabbit IgG-HRP for 1 h at RT, v) incubate the plate with 100 μL/well of substrate with 1 mg/mL 2,2'-azino-bis (3-ethylbenzothiazoline-6-sulfonic acid) for 15 min at RT, vi) stop the reaction by adding 100 μL 2% oxalic acid/well. The absorbance is measured at 405 nm in a BioTek EL808 Microplate reader.

The term "C1q binding substitution" as used herein, is intended to refer to a substitution in a polypeptide comprising an Fc region of an immunoglobulin and an antigen binding region, that enhances the direct interaction with C1q. Enhanced C1q binding can for example result in a decreased EC50 of the interaction between C1q and the antibody, measured according to the method to determine C1q binding described above.

As used herein, the term "complement activation" refers to the activation of the classical complement pathway, which is initiated by a large macromolecular complex, called C1, binding to antibody-antigen complexes on a surface. C1 is a complex that consists of 6 recognition proteins, C1q, and a hetero-tetramer of serine proteases, C1r2C1s2. C1 is the first protein complex in the early events of the classical complement cascade that involves a series of cleavage reactions that starts with the cleavage of C4 into C4a and C4b and C2 into C2a and C2b. C4b is deposited and forms together with C2a an enzymatic active convertase called C3 convertase, which cleaves complement component C3 into C3b and C3a, which forms a C5 convertase. This C5 convertase splits C5 in C5a and C5b and the last component is deposited on the membrane and that in turn triggers the late events of complement activation in which terminal complement components C5b, C6, C7, C8, and C9 assemble into the membrane attack complex (MAC). The complement cascade results in the creation of pores in the cell membrane, which causes lysis of the cell, also known as complement-dependent cytotoxicity (CDC). Complement activation can e.g. be evaluated using C1q efficacy, CDC kinetics, or CDC assays (as described in WO2013/004842, WO2014/108198) or by the method Cellular deposition of C3b and C4b described in Beurskens et al. in Journal of Immunology, 2012 vol. 188 no. 7, April 1, 3532-3541.

The term "complement-dependent cytotoxicity" ("CDC"), as used herein, is intended to refer to the process of antibody-mediated complement activation leading to lysis of the cell or virion as a result of pores in the membrane that are created by MAC assembly when the antibody is bound to its target on a cell or virion.

The term "antibody-dependent cell-mediated cytotoxicity" ("ADCC") as used herein, is intended to refer to a mechanism of killing of antibody-coated target cells or virions by cells expressing Fc receptors that recognize the constant region of the bound antibody. The term "antibody-dependent cellular phagocytosis" ("ADCP") as used herein is intended to refer to a mechanism of elimination of antibody-coated target cells or virions by internalization by phagocytes. The internalized antibody-coated target cells or virions are contained in a vesicle called a phagosome, which then fuses with one or more lysosomes to form a phagolysosome. ADCP may be evaluated by using an in vitro cytotoxicity assay with macrophages as effector cells and video microscopy as described by van Bij et al. in Journal of Hepatology Volume 53, Issue 4, October 2010, Pages 677-685.

The term "complement-dependent cellular cytotoxicity" ("CDCC") as used herein is intended to refer to a mechanism of killing of target cells or virions by cells expressing complement receptors that recognize complement 3 (C3) cleavage products that are covalently bound to the target cells or virions as a result of antibody-mediated complement activation. CDCC may be evaluated in a similar manner as described for ADCC.

The term "plasma half-life" as used herein indicates the time it takes to reduce the concentration of polypeptide in the blood plasma to one half of its initial concentration during elimination (after the distribution phase). For antibodies the distribution phase will typically be 1-3 days, during which there is about 50% decrease in blood plasma concentration due to redistribution between plasma and tissues. The plasma half-life can be measured by methods well-known in the art.

The term "plasma clearance rate" as used herein is a quantitative measure of the rate at which a polypeptide is removed from the blood upon administration to a living organism. The plasma clearance rate may be calculated as the dose/AUC (mL/day/kg), wherein the AUC (area under the curve) value is determined from a concentration-time curve.

The term "antibody-drug conjugate", as used herein refers to an antibody or Fc-containing polypeptide having specificity for at least one type of malignant cell, a drug, and a linker coupling the drug to e.g. the antibody. The linker is cleavable or non-cleavable in the presence of the malignant cell; wherein the antibody-drug conjugate kills the malignant cell.

The term "antibody-drug conjugate uptake", as used herein refers to the process in which antibody-drug conjugates are bound to a target on a cell, followed by uptake/engulfment by the cell membrane, thereby drawing the antibody-drug conjugates into the cell. Antibody-drug conjugate uptake may be evaluated as "antibody-mediated internalization and cell killing by anti-TF ADC in an in vitro killing assay" as described in WO 2011/157741.

The term "apoptosis", as used herein refers to the process of programmed cell death (PCD) that may occur in a cell. Biochemical events lead to characteristic cell changes (morphology) and death. These changes include blebbing, cell shrinkage, nuclear fragmentation, chromatin condensation, and chromosomal DNA fragmentation. Binding of an antibody to a certain receptor may induce apoptosis.

The term "programmed cell-death" or "PCD", as used herein refers to the death of a cell in any form mediated by an intracellular program. Different forms of PCD exist, the various types of PCD have in common that they are executed by active cellular processes that can be intercepted by interfering with intracellular signaling. In a particular embodiment, the occurrence of any form of PCD in a cell or tissue may be determined by staining the cell or tissue with conjugated Annexin V, correlating to phosphatidylserine exposure.

The term "Annexin V", as used herein, refers to a protein of the annexin group that binds phosphatidylserine (PS) on the cell surface.

The term "FcRn", as used herein is intended to refer to neonatal Fc receptor which is an Fc receptor. It was first discovered in rodents as a unique receptor capable of transporting IgG from mother's milk across the epithelium of newborn rodent's gut into the newborn's bloodstream. Further studies revealed a similar receptor in humans. In humans, however, it is found in the placenta to help facilitate transport of mother's IgG to the growing fetus and it has also been shown to play a role in monitoring IgG turnover. FcRn binds IgG at acidic pH of 6.0-6.5 but not at neutral or higher pH. Therefore, FcRn can bind IgG from the intestinal lumen (the inside of the gut) at a slightly acidic pH and ensure efficient unidirectional transport to the basolateral side (inside the body) where the pH is neutral to basic (pH 7.0-7.5). This receptor also plays a role in adult salvage of IgG through its occurrence in the pathway of endocytosis in endothelial cells. FcRn receptors in the acidic endosomes bind to IgG internalized through pinocytosis, recycling it to the cell surface, releasing it at the basic pH of blood, thereby preventing it from undergoing lysosomal degradation. This mechanism may provide an explanation for the greater half-life of IgG in the blood compared to other isotypes.

The term "Protein A", as used herein is intended to refer to a 56 kDa MSCRAMM surface protein originally found in the cell wall of the bacterium *Staphylococcus aureus*. It is encoded by the spa gene and its regulation is controlled by DNA topology, cellular osmolarity, and a two-component system called ArlS-ArlR. It has found use in biochemical research because of its ability to bind immunoglobulins. It is composed of five homologous Ig-binding domains that fold into a three-helix bundle. Each domain is able to bind proteins from many mammalian species, most notably IgGs. It binds the heavy chain Fc region of most immunoglobulins (overlapping the conserved binding site of FcRn receptors) and also interacts with the Fab region of the human VH3 family. Through these interactions in serum, IgG molecules bind the bacteria via their Fc region instead of solely via their Fab regions, by which the bacteria disrupts opsonization, complement activation and phagocytosis.

The term "Protein G", as used herein is intended to refer to an immunoglobulin-binding protein expressed in group C and G streptococcal bacteria much like Protein A but with differing specificities. It is a 65 kDa (G148 protein G) or a 58 kDa (C40 protein G) cell surface protein that has found application in purifying antibodies through its binding to the Fc region.

"Treatment" refers to the administration of an effective amount of a therapeutically active compound of the present invention with the purpose of easing, ameliorating, arresting or eradicating (curing) symptoms or disease states.

An "effective amount" or "therapeutically effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

The term "glycosylation", as used herein, refers to the post-translational modification that involves selective attachment of glycans to a polypeptide, e.g. an antibody, in order to stabilize the structure of the polypeptide or convey function to the polypeptide. The term "deglycosylation" as used herein refers to the removal, e.g. enzymatic removal, of glycans from a polypeptide, e.g. from an antibody. The term "aglycosylated" as used herein refers to the characteristic of a polypeptide, e.g. an antibody, having no attached glycans, effectuated by genetic engineering, by recombinant technologies or by deglycosylation, such as enzymatic deglycosylation.

Specific Embodiments of the Invention

As described above, in a first aspect, the invention relates to a first antibody comprising a first Fc region of a human IgG and a first antigen-binding region capable of binding to a first antigen, for use as a medicament in combination with a second antibody comprising a second Fc region of a human IgG and a second antigen-binding region capable of binding to a second antigen, wherein said first Fc region comprises a. a substitution at position E430 or a substitution at position E345 or a combination of the substitutions K248E and T437R, and b. a K439E or S440K substitution, and said second Fc region comprises c. a substitution at position E430 or a substitution at position E345 or a combination of the substitutions K248E and T437R, and d. a K439E or S440K substitution, wherein the first Fc region has a K439E substitution and the second Fc region has a S440K substitution or the first Fc region has a S440K substitution and the second Fc region has a K439E substitution, and wherein the first antibody and/or the second antibody does not comprise N-linked glycosylation at position N297, wherein the amino acid positions correspond to human IgG1 according to the Eu numbering system (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

A substitution at a position corresponding to E430, E345 or a combination of the substitutions K248E and T437R is considered an Fc-Fc enhancing substitution according to the present invention, i.e. such a substitution/substitutions introduce(s) the effect of enhanced Fc-Fc interactions and oligomerization in the polypeptide or antibody. The enhanced oligomerization occurs when the antigen binding region of the antibody is bound to the corresponding target antigen. The enhanced oligomerization generates oligomers such as e.g. hexamers. The generation of oligomeric structures, such as hexamers, has the effect of increasing Fc effector functions, e.g. CDC, by increasing the C1q binding avidity of the polypeptide.

In one embodiment, the first antibody comprises at most one substitution at a position corresponding to E430 or E345. In one embodiment, the second antibody comprises at most one substitution at a position corresponding to E430 or E345. Thus, in one embodiment the Fc region comprises at most one substitution at a position corresponding to E430 or E345.

In one embodiment of the invention, the first Fc region and the second Fc region comprise a substitution selected from the group consisting of: E430G, E345K, E430S, E430F, E430T, E430Y, E345Q, E345R and E345Y or the combination of the substitutions K248E and T437R.

In one embodiment of the invention, the first Fc region and the second Fc region comprise a substitution selected from the group consisting of: E345K, E430G, E345R, E430Y, E345Q, E345Y, E430S, E430T, and E430F and or the combination of the substitutions K248E and T437R.

In one embodiment, the first Fc region and the second Fc region comprise a substitution selected from the group consisting of: E430G and E345K.

In one embodiment, the first Fc region and the second Fc region comprise a substitution selected from the group consisting of: E345R and E430Y.

In one embodiment, the first Fc region and the second Fc region comprise the combination of the substitutions K248E and T437R.

In one embodiment, the first Fc region may have an E430G substitution and the second Fc region may have an E345K substitution. In another embodiment, the first Fc region may have an E345K substitution and the second antibody may have an E430G substitution. The substitution in the first Fc region and the second Fc region may be selected independently from the group of Fc-Fc enhancing substitutions.

In one embodiment of the invention, the first Fc region and second Fc region comprise a substitution selected from the group consisting of: E345K, E430G, E345R, E430Y. In one embodiment of the invention, the first Fc region and second Fc region comprise a substitution selected from the group consisting of: E430G, E345K and E345R. In one embodiment of the invention, the first Fc region and second Fc region comprise an E430G substitution. In one embodiment of the invention, the first Fc region and second Fc region comprise an E345K substitution. In one embodiment of the invention, the first Fc region and second Fc region comprise an E345R substitution. In one embodiment of the invention, the first Fc region and second Fc region comprise an E430Y substitution.

The first Fc region and the second Fc region further comprise a K439E or a S440K substitution which are considered complementary oligomerization-inhibiting substitutions according to the present invention. Thus, e.g. a first antibody having a K439E substitution has a low propensity form oligomers with another antibody having a K439E substitution, but an antibody having a K439E substitution has a high propensity to form oligomers with another antibody having an S440K substitution. An antibody having an S440K substitution has a low propensity to form oligomers with another antibody having an S440K substitution. Thus, in one embodiment of the invention the first Fc region comprises a K439E substitution and the second Fc region comprises a S440K substitution. In one embodiment of the invention, the first Fc region comprises a S440K substitution and the second Fc region comprises a K439E substitution.

In a further embodiment,
the first Fc region comprises a K439E substitution and a Y436N substitution and the second Fc region comprises a S440K substitution and a Q438R substitution, or
the first Fc region comprises a K439E substitution and a Q438R substitution and the second Fc region comprises a S440K substitution and a Y436N substitution, or
the first Fc region comprises a S440K substitution and a Y436N substitution and the second Fc region comprises a K439E substitution and a Q438R substitution, or
the first Fc region comprises a S440K substitution and a Q438R substitution and the second Fc region comprises a K439E substitution and a Y436N substitution.
Y436N and Q438R are also considered complementary oligomerization-inhibiting substitutions according to the present invention.

In one embodiment, neither the first antibody nor the second antibody comprises a substitution of the amino acid at position G237 or one or more substitutions selected from the group consisting of: G236R, G236K, K322A, E269K, L234A, L234F, L235A, L235Q and L235E.

In one embodiment, neither the first antibody nor the second antibody comprises a substitution of the amino acid at position P329 or a K322E substitution.

In one embodiment, neither the first antibody nor the second antibody comprises one or more substitutions selected from the group consisting of: K326A, K326W, E333A and E333S.

In one embodiment, neither the first antibody nor the second antibody comprises a substitution of the amino acid at position G237 or P329 or one or more substitutions selected from the group consisting of: G236R, G236K, K322A, K332E, E269K, L234A, L234F, L235A, L235Q and L235E.

Furthermore, the first antibody and/or the second antibody does not comprise N-linked glycosylation at position N297.

IgG antibodies are normally glycosylated at position N297 if the antibody is produced in an eukaryotic cell capable of glycosylating polypeptides. At least one of the antibodies used in the invention is not glycosylated at position N297. This can e.g. be achieved by mutating the N-glycosylation consensus sequence (N-X/S/T) around N297, by producing the antibody in a system wherein N-linked glycosylation at N297 does not take place, such as a prokaryotic, e.g. bacterial, expression system or by removing glycosylation, e.g. enzymatically. The effect of the lack of glycosylation at position N297 is that the antibody has a strongly reduced ability to execute effector functions as a single agent. The present inventors have surprisingly found that the lack of glycosylation does not strongly affect the ability of the antibody to form a highly active hetero-oligomer with the other antibody of the pair.

In one embodiment, the first antibody and/or second antibody comprises an amino acid substitution, deletion or insertion that prevents N-linked glycosylation at position N297.

In one embodiment, the first Fc region and/or second Fc region comprises an amino acid substitution at position N297 or at position T299, wherein the substitution at position T299 is not T299S.

In one embodiment, the first Fc region and/or second Fc region comprises a substitution selected from the group consisting of: N297A, N297G, N297Y, N297Q, N297D, N297S, N297T, T299A and T299G.

In one embodiment, the first Fc region and/or second Fc region comprises an N297A substitution or an N297G substitution. In one embodiment, the first Fc region and second Fc region comprises an N297A substitution. In one embodiment, the first Fc region and second Fc region comprises an N297G substitution. In one embodiment, the first Fc region and second Fc region comprises an N297Y substitution. In one embodiment, the first Fc region and second Fc region comprises an N297Q substitution. In one embodiment, the first Fc region and second Fc region comprises an N297D substitution. In one embodiment, the first Fc region and second Fc region comprises an N297S substitution. In one embodiment, the first Fc region and second Fc region comprises an N297T substitution. In one embodiment, the first Fc region and second Fc region comprises a T299A substitution. In one embodiment, the first Fc region and second Fc region comprises a T299G substitution.

In one embodiment, the first antibody and/or second antibody does not comprise N-linked glycosylation at any position in the antibody.

The following Tables provide non-limiting lists of embodiments, describing combinations of a first polypeptide and a second polypeptide with specific substitutions. Thus, for example, embodiment 1 of the first Table below is a combination of a first antibody comprising substitutions at positions corresponding to E430G and K439E and lacking glycosylation at position N297 (Aglyc), with a second antibody comprising E430G and S440K substitutions. As described herein, the first antibody and second antibody of all of the embodiments listed can optionally comprise further substitutions.

| Embodiment | First antibody | Second antibody |
|---|---|---|
| 1 | K439E E430G Aglyc | S440K E430G |
| 2 | K439E E430G | S440K E430G Aglyc |
| 3 | K439E E430G Aglyc | S440K E430G Aglyc |
| 4 | K439E E345K Aglyc | S440K E345K |
| 5 | K439E E345K | S440K E345K Aglyc |
| 6 | K439E E345K Aglyc | S440K E345K Aglyc |
| 7 | K439E E345R Aglyc | S440K E345R |
| 8 | K439E E345R | S440K E345R Aglyc |
| 9 | K439E E345R Aglyc | S440K E345R Aglyc |
| 10 | K439E K248E T437R Aglyc | S440K K248E T437R |
| 11 | K439E K248E T437R | S440K K248E T437R Aglyc |
| 12 | K439E K248E T437R Aglyc | S440K K248E T437R Aglyc |

-continued

| Embodiment | First antibody | Second antibody |
|---|---|---|
| 13 | K439E E430G Aglyc | S440K E345K |
| 14 | K439E E430G | S440K E345K Aglyc |
| 15 | K439E E430G Aglyc | S440K E345K Aglyc |
| 16 | K439E E430G Aglyc | S440K E345R |
| 17 | K439E E430G | S440K E345R Aglyc |
| 18 | K439E E430G Aglyc | S440K E345R Aglyc |
| 19 | K439E E345K Aglyc | S440K E430G |
| 20 | K439E E345K | S440K E430G Aglyc |
| 21 | K439E E345K Aglyc | S440K E430G Aglyc |
| 22 | S440K E345K Aglyc | S440K E430G |
| 23 | S440K E345K | S440K E430G Aglyc |
| 24 | S440K E345R Aglyc | S440K E430G Aglyc |
| 25 | K439E E345K Aglyc | S440K E345R |
| 26 | K439E E345K | S440K E345R Aglyc |
| 27 | K439E E345K Aglyc | S440K E345R Aglyc |
| 28 | K439E K248E T437R Aglyc | S440K E345K |
| 29 | K439E K248E T437R | S440K E345K Aglyc |
| 30 | K439E K248E T437R Aglyc | S440K E345K Aglyc |
| 31 | K439E E430G N297A | S440K E430G |
| 32 | K439E E430G | S440K E430G N297A |
| 33 | K439E E430G N297A | S440K E430G N297A |
| 34 | K439E E345K N297A | S440K E345K |
| 35 | K439E E345K | S440K E345K N297A |
| 36 | K439E E345K N297A | S440K E345K N297A |
| 37 | K439E E345R N297A | S440K E345R |
| 38 | K439E E345R | S440K E345R N297A |
| 39 | K439E E345R N297A | S440K E345R N297A |
| 40 | K439E K248E T437R N297A | S440K K248E T437R N297A |
| 41 | K439E K248E T437R | S440K K248E T437R N297A |
| 42 | K439E K248E T437R N297A | S440K K248E T437R N297A |
| 43 | K439E E430G N297A | S440K E345K |
| 44 | K439E E430G | S440K E345K N297A |
| 45 | K439E E430G N297A | S440K E345K N297A |
| 46 | K439E E430G N297A | S440K E345R |
| 47 | K439E E430G | S440K E345R N297A |
| 48 | K439E E430G N297A | S440K E345R N297A |
| 49 | K439E E345K N297A | S440K E430G |
| 50 | K439E E345K | S440K E430G N297A |
| 51 | K439E E345K N297A | S440K E430G N297A |
| 52 | S440K E345R N297A | S440K E430G |
| 53 | S440K E345R | S440K E430G N297A |
| 54 | S440K E345R N297A | S440K E430G N297A |
| 55 | K439E E345K N297A | S440K E345R |
| 56 | K439E E345K | S440K E345R N297A |
| 57 | K439E E345K N297A | S440K E345R N297A |
| 58 | K439E K248E T437R N297A | S440K E345K |
| 59 | K439E K248E T437R | S440K E345K N297A |
| 60 | K439E K248E T437R N297A | S440K E345K N297A |

| Embodiment | First antibody | Second antibody |
|---|---|---|
| 61 | K439E E430G N297G | S440K E430G |
| 62 | K439E E430G | S440K E430G N297G |
| 63 | K439E E430G N297G | S440K E430G N297G |
| 64 | K439E E345K N297G | S440K E345K |
| 65 | K439E E345K | S440K E345K N297G |
| 66 | K439E E345K N297G | S440K E345K N297G |
| 67 | K439E E345R N297G | S440K E345R |
| 68 | K439E E345R | S440K E345R N297G |
| 69 | K439E E345R N297G | S440K E345R N297G |
| 70 | K439E K248E T437R N297G | S440K K248E T437R N297G |
| 71 | K439E K248E T437R | S440K K248E T437R N297G |
| 72 | K439E K248E T437R N297G | S440K K248E T437R N297G |
| 73 | K439E E430G N297G | S440K E345K |
| 74 | K439E E430G | S440K E345K N297G |
| 75 | K439E E430G N297G | S440K E345K N297G |

-continued

| Embodiment | First antibody | Second antibody |
|---|---|---|
| 76 | K439E E430G N297G | S440K E345R |
| 77 | K439E E430G | S440K E345R N297G |
| 78 | K439E E430G N297G | S440K E345R N297G |
| 79 | K439E E345K N297G | S440K E430G |
| 80 | K439E E345K | S440K E430G N297G |
| 81 | K439E E345K N297G | S440K E430G N297G |
| 82 | S440K E345K N297G | S440K E430G |
| 83 | S440K E345R | S440K E430G N297G |
| 84 | S440K E345R N297G | S440K E430G N297G |
| 85 | K439E E345K N297G | S440K E345R |
| 86 | K439E E345K | S440K E345R N297G |
| 87 | K439E E345K N297G | S440K E345R N297G |
| 88 | K439E K248E T437R N297G | S440K E345K |
| 89 | K439E K248E T437R | S440K E345K N297G |
| 90 | K439E K248E T437R N297G | S440K E345K N297G |

| Embodiment | First antibody | Second antibody |
|---|---|---|
| 91 | K439E E430G T299A | S440K E430G |
| 92 | K439E E430G | S440K E430G T299A |
| 93 | K439E E430G T299A | S440K E430G T299A |
| 94 | K439E E345K T299A | S440K E345K |
| 95 | K439E E345K | S440K E345K T299A |
| 96 | K439E E345K T299A | S440K E345K T299A |
| 97 | K439E E345R T299A | S440K E345R |
| 98 | K439E E345R | S440K E345R T299A |
| 99 | K439E E345R T299A | S440K E345R T299A |
| 100 | K439E K248E T437R T299A | S440K K248E T437R T299A |
| 101 | K439E K248E T437R | S440K K248E T437R T299A |
| 102 | K439E K248E T437R T299A | S440K K248E T437R T299A |
| 103 | K439E E430G T299A | S440K E345K |
| 104 | K439E E430G | S440K E345K T299A |
| 105 | K439E E430G T299A | S440K E345K T299A |
| 106 | K439E E430G T299A | S440K E345R |
| 107 | K439E E430G | S440K E345R T299A |
| 108 | K439E E430G T299A | S440K E345R T299A |
| 109 | K439E E345K T299A | S440K E430G |
| 110 | K439E E345K | S440K E430G T299A |
| 111 | K439E E345K T299A | S440K E430G T299A |
| 112 | S440K E345R T299A | S440K E430G |
| 113 | S440K E345R | S440K E430G T299A |
| 114 | S440K E345R T299A | S440K E430G T299A |
| 115 | K439E E345K T299A | S440K E345R |
| 116 | K439E E345K | S440K E345R T299A |
| 117 | K439E E345K T299A | S440K E345R T299A |
| 118 | K439E K248E T437R T299A | S440K E345K |
| 119 | K439E K248E T437R | S440K E345K T299A |
| 120 | K439E K248E T437R T299A | S440K E345K T299A |

| Embodiment | First antibody | Second antibody |
|---|---|---|
| 121 | K439E E430G K326A S333S N297A | S440K E430G K326A S333S N297A |
| 122 | K439E E430Y K326A S333S N297A | S440K E430Y K326A S333S N297A |
| 123 | K439E E345K K326A S333S N297A | S440K E345K K326A S333S N297A |
| 124 | K439E E345R K326A S333S N297A | S440K E345R K326A S333S N297A |
| 125 | K439E E430Y N297A | S440K E430Y |
| 126 | K439E E430Y | S440K E430Y N297A |
| 127 | K439E E430Y N297A | S440K E430Y N297A |

In one embodiment of the invention, the first and/or second antibody is human, humanized or chimeric. In one embodiment of the invention, the first and second antibody is human, humanized or chimeric. In one embodiment of the invention, the first and second antibody is human. In one embodiment of the invention, the first and second antibody is humanized. In one embodiment of the invention, the first antibody is human and the second antibody is humanized. In one embodiment of the invention the first antibody is humanized and the second antibody is human.

In one embodiment of the invention, the first and/or second antibody is a monoclonal antibody. In one embodiment of the invention, the first and second antibody is a monoclonal antibody. In one embodiment of the invention, the first and second antibody is a bispecific antibody. In one embodiment, the first antibody is a monoclonal antibody and the second antibody is a bispecific antibody. In one embodiment, the first antibody is a bispecific antibody and the second antibody is a monoclonal antibody.

It is to be understood that the embodiments described herein with reference to an antibody refers to an antibody comprising an Fc region of an immunoglobulin and an antigen-binding region. An antibody may also be a multispecific antibody such as a bispecific antibody having a first Fc region of an immunoglobulin and a first antigen-binding region, and a second polypeptide or antibody having a second Fc region of an immunoglobulin and a second antigen-binding region.

In one embodiment of the invention, the first and/or second antibody is an IgG1, IgG2, IgG3 or IgG4 subclass. In one embodiment of the invention, the first and second antibody is an IgG1, IgG2, IgG3 or IgG4 subclass. In one embodiment of the invention, the first and second antibody is a human IgG1, IgG2, IgG3 or IgG4 subclass. In one embodiment of the invention, the first and second antibody is an IgG1, IgG2 or IgG4 subclass. In one embodiment of the invention, the first and second antibody is a human IgG1, IgG2 or IgG4 subclass. In one embodiment of the invention, the first and/or second antibody is an IgG1 subclass. In one embodiment of the invention, the first and/or second antibody is a human IgG1 subclass. In one embodiment of the invention, the first and second antibody is an IgG1 subclass. In one embodiment, the first and second antibody is an IgG2 subclass. In one embodiment of the invention, the first and second antibody is an IgG4 subclass. In one embodiment of the invention, the first antibody is an IgG1 subclass and the second antibody is an IgG2 subclass. In one embodiment of the invention, the first antibody is an IgG2 subclass and the second antibody is an IgG1 subclass.

In one embodiment of the invention, the first antibody comprises a heavy chain of an IgG1 subclass. In one embodiment of the invention, the second antibody comprises a heavy chain of an IgG1 subclass. In one embodiment of the invention, the first antibody comprises a heavy chain of an IgG2 subclass. In one embodiment of the invention, the second antibody comprises a heavy chain of an IgG2 subclass. In one embodiment of the invention, the first antibody comprises a heavy chain of an IgG3 subclass. In one embodiment of the invention, the second antibody comprises a heavy chain of an IgG3 subclass. In one embodiment of the invention, the first antibody comprises a heavy chain of an IgG4 subclass. In one embodiment of the invention, the second antibody comprises a heavy chain of an IgG4 subclass.

In one embodiment of the invention, the first antibody comprises a heavy chain of an IgG1 subclass and the second antibody comprises a heavy chain of an IgG1 subclass.

In a preferred embodiment, said first antibody comprises a first Fc region of a human IgG1 subclass and/or said second antibody comprises a second Fc region of a human IgG1 subclass.

In one embodiment of the invention, the antibody, or the first and/or second antibody comprises a first and/or second constant region comprising a sequence selected from Table 1.

In one embodiment of the invention, the antibody, or the first and/or second antibody comprises a first and/or second constant region comprising a sequence selected from the group consisting of SEQ ID NO: 42 to 53, 57, 58, 61 or 62. In one embodiment of the invention, the antibody, or the first and/or second antibody comprises a first and/or second constant region comprising a sequence selected from the group consisting of SEQ ID NO: 42 to 49, 61 to 62, 64 to 68, 79 to 86, 127 to 128, 132 to 133.

In one embodiment of the invention, the antibody, or the first and/or second antibody comprises a constant region or a first and/or second constant region comprising the sequence set forth in SEQ ID NO: 42. In one embodiment of the invention, the antibody, or the first and/or second antibody comprises a constant region or a first and/or second constant region comprising the sequence set forth in SEQ ID NO: 43. In one embodiment of the invention, the antibody, or the first and/or second antibody comprises a constant region or a first and/or second constant region comprising the sequence set forth in SEQ ID NO: 44. In one embodiment of the invention, the antibody, or the first and/or second antibody comprises a constant region or a first and/or second constant region comprising the sequence set forth in SEQ ID NO: 45. In one embodiment of the invention, the antibody, or the first and/or second antibody comprises a constant region or a first and/or second constant region comprising the sequence set forth in SEQ ID NO: 46. In one embodiment of the invention, the antibody, or the first and/or second antibody comprises a constant region or a first and/or second constant region comprising the sequence set forth in SEQ ID NO: 47. In one embodiment of the invention, the antibody, or the first and/or second antibody comprises a constant region or a first and/or second constant region comprising the sequence set forth in SEQ ID NO: 48. In one embodiment of the invention, the antibody, or the first and/or second antibody comprises a constant region or a first and/or second constant region comprising the sequence set forth in SEQ ID NO: 49. In one embodiment of the invention, the antibody, or the first and/or second antibody comprises a constant region or a first and/or second constant region comprising the sequence set forth in SEQ ID NO: 61. In one embodiment of the invention, the antibody, or the first and/or second antibody comprises a constant region or a first and/or second constant region comprising the sequence set forth in SEQ ID NO: 62. In one embodiment of the invention, the antibody, or the first and/or second antibody comprises a constant region or a first and/or second constant region comprising the sequence set forth in SEQ ID NO: 64. In one embodiment of the invention, the antibody, or the first and/or second antibody comprises a constant region or a first and/or second constant region comprising the sequence set forth in SEQ ID NO: 65. In one embodiment of the invention, the antibody, or the first and/or second antibody comprises a constant region or a first and/or second constant region comprising the sequence set forth in SEQ ID NO: 66. In one embodiment of the invention, the antibody, or the first and/or second antibody comprises a constant region or a first and/or second constant region comprising the sequence set forth in SEQ ID NO: 67. In one embodiment of the invention, the antibody, or the first and/or second antibody comprises a constant region or a first and/or second constant region comprising the sequence set forth in SEQ ID NO: 68. In one embodiment of the invention, the antibody, or the first and/or second antibody comprises a constant region or a first and/or second constant region comprising the sequence set forth in SEQ ID NO: 79. In one embodiment of the invention, the antibody, or the first and/or second antibody comprises a constant region or a first and/or second constant region comprising the sequence set forth in SEQ ID NO: 80. In one embodiment of the invention, the antibody, or the first and/or second antibody comprises a constant region or a first and/or second constant region comprising the sequence set forth in SEQ ID NO: 81. In one embodiment of the invention, the antibody, or the first and/or second antibody comprises a constant region or a first and/or second constant region comprising the sequence set forth in SEQ ID NO: 82. In one embodiment of the invention, the antibody, or the first and/or second antibody comprises a constant region or a first and/or second constant region comprising the sequence set forth in SEQ ID NO: 83. In one embodiment of the invention, the antibody, or the first and/or second antibody comprises a constant region or a first and/or second constant region comprising the sequence set forth in SEQ ID NO: 84. In one embodiment of the invention, the antibody, or the first and/or second antibody comprises a constant region or a first and/or second constant region comprising the sequence set forth in SEQ ID NO: 85. In one embodiment of the invention, the antibody, or the first and/or second antibody comprises a constant region or a first and/or second constant region comprising the sequence set forth in SEQ ID NO: 86. In one embodiment of the invention, the antibody, or the first and/or second antibody comprises a constant region or a first and/or second constant region comprising the sequence set forth in SEQ ID NO: 127. In one embodiment of the invention, the antibody, or the first and/or second antibody comprises a constant region or a first and/or second constant region comprising the sequence set forth in SEQ ID NO: 128.

In one embodiment of the invention, the antibody, or the first and/or second antibody comprises a constant region or a first and/or second constant region comprising the sequence set forth in SEQ ID NO: 132. In one embodiment of the invention, the antibody, or the first and/or second antibody comprises a constant region or a first and/or second constant region comprising the sequence set forth in SEQ ID NO: 133.

In one embodiment of the invention, the first and/or second antibody comprises a first and/or second heavy chain constant region comprising a sequence selected from the group consisting of SEQ ID NO: 42 to 53, 57, 58, 61 or 62, wherein the first and second heavy chain sequence are selected independently from the group.

In one embodiment of the invention, the antibody, or the first and/or second antibody comprises a first and/or second constant region comprising a sequence selected from the group consisting of SEQ ID NO: 24 to 53, 57, 58, 61 or 62, wherein at most 5 additional substitutions are introduced, such as at most 4 additional substitutions, such as at most 3 additional substitutions, such as at most 2 additional substitutions, such as at most 1 additional substitution.

In one embodiment of the invention, the antibody, or the first and/or second antibody comprises a constant region or a first and/or second constant region comprising a sequence selected from the group consisting of SEQ ID NO: 42 to 49, 61 to 62, 64 to 68, 79 to 86, 127 to 128, 132 to 133, wherein the C-terminal lysin has been removed. The C-terminal lysin may be removed from the expression sequence e.g. from the nucleic acid vectors or the C-terminal lysine may be removed by post-translational modification such as by carboxypeptidase processing.

In one embodiment of the invention, the first and second antigens are both cell surface-exposed molecules. In one embodiment of the invention, the first and second antigens are both cell surface-expressed molecules. In one embodiment, the first and second antigens are co-expressed in cells or tissues that are target cells or target tissue for the disease or disorder to be treated.

In one embodiment of the invention, the first and second antigens are not identical.

In one embodiment, the first antibody and second antibody in combination deplete a population of cells co-expressing the first and second antigen. In one embodiment, the first antibody and second antibody in combination deplete a cell population co-expressing the first and second antigen. In one embodiment, the first antibody and second antibody in combination induces cell death in a cell population co-expressing the first and second antigen.

In one embodiment hereof, cell population is a tumor cell population. In a further embodiment, the cell population is a hematological tumor cell population or a solid tumor cell population.

In one embodiment, the cell population is a leukocyte cell population.

In one embodiment, the cell population is a lymphocyte, such as a lymphocyte cell population.

In one embodiment, the cell population is a B cell population, T cell population, an NK cell population, a regulatory T cell population, myeloid derived suppressor cell population.

In one embodiment, the cell population is a B cell population, such as a subset of a B cell population.

In one embodiment, the cell population is a T cell, such as a T cell population, such as a subset of a T cell population. In one embodiment of the invention the cell population is a regulatory T cell.

In one embodiment, the cell population is an NK cell population. In one embodiment, the cell population is a myeloid derived suppressor cell population. In one embodiment, the cell population is a tumor associated macrophage population.

Hereby embodiments are described wherein the first antibody and second antibody according to the invention are used as a medicament to deplete a specific cell population expressing a first and second antigen recognized by the first and second antibody. Thus, a first and second antibody according to the present invention may be used to deplete tumor cells that express a first and second antigen recognized by the first and second antibody, while the first and second antibody may not deplete the healthy tissue expressing only the first or the second antigen. A first and second antibody according to the present invention may also be particularly useful in depleting specific cell populations of the immune system, such as specific subsets of lymphocytes e.g. B cells or T cells or even subsets of B cells or subsets of T cells. For applications where cell depletion are desired the following mutations may be particularly preferred E345K, E430G.

In another embodiment of the invention, the first antibody and second antibody in combination induces proliferation in a cell population expressing a first antigen and a second antigen. Hereby embodiments are described wherein the first antibody and second antibody according to the invention are used as a medicament to activate a specific cell population i.e. by inducing proliferation of the specific cell population expressing a first and second antigen recognized by the first and second antibody. For applications where agonistic effect are desired the following mutations may be particularly preferred E345R, E430Y, E430F.

In a further main aspect, the invention relates to an antibody comprising an Fc region of a human IgG and an antigen-binding region capable of binding to an antigen, wherein said Fc region comprises a. a substitution at position E430 or a substitution at position E345 or a combination of the substitutions K248E and T437R, and b. a K439E or S440K substitution, wherein the antibody does not comprise N-linked glycosylation at position N297.

In one embodiment, the antibody comprises an amino acid substitution, deletion or insertion that prevents N-linked glycosylation at position N297.

In one embodiment, the Fc region comprises an amino acid substitution at position N297 or at position T299, wherein the substitution at position T299 is not T299S.

In one embodiment, the Fc region comprises a substitution selected from the group consisting of: N297A, N297G, N297Y, N297Q, N297D, N297S, N297T, T299A and T299G.

In one embodiment, the antibody does not comprise N-linked glycosylation at any position in the antibody.

In one embodiment, the Fc region comprises:

a K439E substitution and a Y436N substitution, or a K439E substitution and a Q438R substitution, or a S440K substitution and a Y436N substitution, or a S440K substitution and a Q438R substitution.

In one embodiment, the Fc region comprises a substitution selected from the group consisting of: E430G, E345K, E430S, E430F, E430T, E430Y, E345Q, E345R and E345Y or the combination of the substitutions K248E and T437R. In one embodiment, the Fc region comprises a substitution selected from the group consisting of: E345K, E430G, E345R, E430Y, E345Q, E345Y, E430S, E430T, and E430F and or the combination of the substitutions K248E and T437R.

In one embodiment, the Fc region comprises a substitution selected from the group consisting of: E345K, E430G, E345R, E430Y.

In one embodiment, the Fc region comprises a substitution selected from the group consisting of: E430G and E345K. In one embodiment, the Fc region comprises a substitution selected from the group consisting of: E345R and E430Y. In one embodiment, the Fc region comprises a E345K substitution. In one embodiment, the Fc region comprises a E430G substitution. In one embodiment, the Fc region comprises a E345R substitution. In one embodiment, the Fc region comprises a E430Y substitution. In one embodiment, the Fc region comprises a E345Q substitution. In one embodiment, the Fc region comprises a E345Y substitution. In one embodiment, the Fc region comprises a E430S substitution. In one embodiment, the Fc region comprises a E430T substitution. In one embodiment, the Fc region comprises a E430F substitution. In one embodiment, the Fc region comprises the combination of the substitutions K248E and T437R.

In one embodiment, the Fc region comprises one or more substitution(s) selected from the group consisting of: E333S, K326A, E333A, K326W. In one embodiment, the Fc region comprises E333S and K326A substitution.

In one embodiment, the antibody is a human IgG1, IgG2, IgG3 or IgG4 subclass.

In one embodiment, the antibody is a human IgG1, IgG2 or IgG4 subclass. In one embodiment, the antibody is a human IgG1 subclass. In one embodiment, the antibody is a human IgG2 subclass. In one embodiment, the antibody is a human IgG4 subclass.

Targets and Method of Use

The first antibody and second antibody according to the present invention may bind targets that are expressed on the same cell. In one embodiment the target is a target that activates, inhibits, modulates and/or regulates a signal transduction pathway.

Examples of targets that may be particularly suitable as targets according to the present invention are cell surface receptors and ligands. The following protein classes may also be particularly suitable as antigen binding targets for the first and/or second antibody according to the invention: tumor necrosis receptor super family, GPI-anchored proteins, Lipidated proteins, Hydrolases (EC 3.) and regulators superfamilies, B7 family-related protein, immunoglobulin superfamily, interleukin receptor family, Integrins, Ig-like cell adhesion molecule family, Receptor type Protein Tyrosine Phosphatases, C-type lectins, Tetraspanins, Membrane spanning 4-domains, Activating leukocyte immunoglobulin like receptors, C—C motif chemokine receptors, G protein-coupled receptors, Toll like receptors, Receptor Tyrosine Kinases. In one embodiment of the invention the first and second antigen binding regions are capable of binding to a target antigen from the same protein class. In one embodiment of the invention the first and second antigen binding regions are capable of binding to a target antigen from different protein classes.

In one embodiment of the invention, the first antigen binding region is capable of binding to a target antigen from the protein class of GPI-anchored proteins and the second antigen binding region is capable of binding to a target antigen from the protein class of Tetraspanins. In one embodiment of the invention the first antigen binding region is capable of binding to a target antigen from the protein class of Tetraspanins and the second antigen binding region is capable of binding to a target antigen from the protein class of GPI-anchored proteins.

In one embodiment of the invention, the first antigen binding region is capable of binding to a target antigen from the protein class of GPI-anchored proteins and the second antigen binding region is capable of binding to a target antigen from the protein class of Membrane spanning 4-domains. In one embodiment of the invention the first antigen binding region is capable of binding to a target antigen from the protein class of Membrane spanning 4-domains and the second antigen binding region is capable of binding to a target antigen from the protein class of GPI-anchored proteins.

In one embodiment of the invention, the first antigen binding region is capable of binding to a target antigen from the protein class of tumor necrosis receptor super family and the second antigen binding region is capable of binding to a target antigen from the protein class of tumor necrosis receptor super family. In one embodiment of the invention the first antigen and/or second antigen is a member of the TNFR-SF. In one embodiment of the invention the first antigen and second antigen is a member of the TNFR-SF.

In one embodiment of the invention, the first antigen binding region is capable of binding to a target antigen from the protein class of tumor necrosis receptor super family and the second antigen binding region is capable of binding to a target antigen from the protein class of immunoglobulin superfamily.

Cell surface receptors include, for example, receptors that belong to receptor families such as the hematopoietic factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. Various references that relate to receptors belonging to these receptor families and their characteristics are available and include, for example, Cooke B A., King R J B., van der Molen H J. ed. New Comprehensive Biochemistry Vol. 18B "Hormones and their Actions Part 2" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim. Biophys. Acta, 1422: 207-234; and M. Miyasaka ed., Cell Technology, supplementary volume, Handbook series, "Handbook for Adhesion Factors" (1994) (Shujun-sha, Tokyo, Japan).

In one embodiment of the invention, the antibody comprises an antigen binding region wherein the antigen binding region binds to a member of the tumor necrosis factor receptor super family (TNFR-SF) or G-protein Coupled Receptor (GPCR) superfamily.

In one embodiment of the invention, the first and/or second antibody binds to a cell surface receptor, for example, hormone receptors and cytokine receptors. Exemplary cytokine receptors include, for example, hematopoietic factor receptor, lymphokine receptor, growth factor receptor, differentiation control factor receptor and the like. Examples of cytokine receptors are erythropoietin (EPO) receptor, thrombopoietin (TPO) receptor, granulocyte colony stimulating factor (G-CSF) receptor, macrophage colony stimulating factor (M-CSF) receptor, granular macrophage colony stimulating factor (GM-CSF) receptor, tumor necrosis factor (TNF) receptor, interleukin-1 (IL-1) receptor, interleukin-2 (IL-2) receptor, interleukin-3 (IL-3) receptor, interleukin-4 (IL-4) receptor, interleukin-5 (IL-5) receptor, interleukin-6 (IL-6) receptor, interleukin-7 (IL-7) receptor, interleukin-9 (IL-9) receptor, interleukin-10 (IL-10) receptor, interleukin-11 (IL-11) receptor, interleukin-12 (IL-12) receptor, interleukin-13 (IL-13) receptor, interleukin-15 (IL-15) receptor, interferon-alpha (IFN-alpha) receptor, interferon-beta (IFN-beta) receptor, interferon-gamma (IFN-gamma) receptor, growth hormone (GH) receptor, insulin receptor, blood stem cell proliferation factor (SCF) receptor, vascular epidermal growth factor (VEGF) receptor, epidermal cell growth factor (EGF) receptor, nerve growth factor (NGF) receptor, fibroblast growth factor (FGF) receptor, platelet-derived growth factor (PDGF) receptor, transforming growth factor-beta (TGF-beta) receptor, leukocyte migration inhibitory factor (LIF) receptor, ciliary neurotrophic factor (CNTF) receptor, oncostatin M (OSM) receptor, and Notch family receptor.

The tumor necrosis factor receptor superfamily (TN-FRSF) is a group of receptors characterized by the ability to bind ligands of the tumor necrosis factor superfamily (TNFSF) via an extracellular cysteine-rich domain. The TNF receptors form trimeric complexes in the plasma membrane. The TNFRSF include the following list of 29 proteins; TNFR1 (Uniprot P19438), FAS (Uniprot P25445), DR3 (Uniprot Q93038), DR4(Uniprot 000220), DR5 (Uniprot 014763), DR6 (Uniprot 075509), NGFR (Uniprot P08138), EDAR (Uniprot Q9UNEO), DcR1 (Uniprot 014798), DcR2(Uniprot Q9UBN6), DcR3 (Uniprot 095407), OPG (Uniprot 000300), TROY (Uniprot Q9NS68), XEDAR (Uniprot Q9HAV5), LTbR (Uniprot P36941), HVEM (Uniprot Q92956), TWEAKR (Uniprot Q9NP84), CD120b (Uniprot P20333), OX40 (Uniprot P43489), CD40 (Uniprot P25942), CD27 (Uniprot P26842), CD30 (Uniprot P28908), 4-1BB (Uniprot Q07011), RANK (Uniprot Q9Y6Q6), TACI (Uniprot 014836), BLySR (Uniprot Q96RJ3), BCMA (Uniprot Q02223), GITR (Uniprot Q9Y5U5), RELT (Uniprot Q969Z4).

In one embodiment of the invention, the antibody, the first and/or second antibody comprises an antigen-binding region capable of binding to an antigen selected from the group consisting of: DR4, DR5, CD20, CD37, CD52, HLA-DR, CD3, CD5, 4-1BB and PD-1.

In one embodiment of the invention, the antibody, the first and/or second antibody comprises an antigen-binding region capable of binding to an antigen selected from the group consisting of: DR4, DR5, CD20, CD37, CD52, HLA-DR, CD3, CD5, 4-1BB, PD-1, FAS.

In one embodiment, the antigen-binding region is capable of binding to DR4. In one embodiment the antigen-binding region is capable of binding to DR5. In one embodiment the antigen-binding region is capable of binding to CD20. In one embodiment the antigen-binding region is capable of binding to CD37. In one embodiment the antigen-binding region is capable of binding to CD52. In one embodiment the antigen-binding region is capable of binding to HLA-DR. In one embodiment the antigen-binding region is capable of binding to CD3. In one embodiment the antigen-binding region is capable of binding to CD5. In one embodiment the antigen-binding region is capable of binding to 4-1BB. In one embodiment the antigen-binding region is capable of binding to PD-1. In one embodiment the antigen-binding region is capable of binding to FAS. In one embodiment the antigen-binding region is capable of binding to a member of the TNFR-SF.

In one embodiment of the invention, the antibody, or the first and/or second antibody comprises an antigen-binding region comprising:

a VH region comprising a CDR1 sequence as set forth in SEQ ID NO:9, a CDR2 sequence as set forth in SEQ ID NO:10 and a CDR3 sequence as set forth SEQ ID NO:11, and a VL region comprising a CDR1 sequence as set forth in SEQ ID NO: 13, a CDR2 sequence as set forth in: DAS and a CDR3 sequence as set forth SEQ ID NO:14 [CD20, 1118];

a VH region comprising a CDR1 sequence as set forth in SEQ ID NO:43, a CDR2 sequence as set forth in SEQ ID NO:44 and a CDR3 sequence as set forth SEQ ID NO:45, and a VL region comprising a CDR1 sequence as set forth in SEQ ID NO:47, a CDR2 sequence as set forth in: VAT and a CDR3 sequence as set forth SEQ ID NO:48 [CD37];

a VH region comprising a CDR1 sequence as set forth in SEQ ID NO:2, a CDR2 sequence as set forth in SEQ ID NO:3 and a CDR3 sequence as set forth SEQ ID NO:4, and a VL region comprising a CDR1 sequence as set forth in SEQ ID NO:6, a CDR2 sequence as set forth in: NTN, and a CDR3 sequence as set forth SEQ ID NO:7 [CD52, CAMPATH-1H];

a VH region comprising a CDR1 sequence as set forth in SEQ ID NO:118, a CDR2 sequence as set forth in SEQ ID NO:119, and a CDR3 sequence as set forth SEQ ID NO:120 and a VL region comprising a CDR1 sequence as set forth in SEQ ID NO: 122, a CDR2 sequence as set forth in SEQ ID NO: 123 and a CDR3 sequence as set forth SEQ ID NO:124 [CD52, h2E8];

a VH region comprising a CDR1 sequence as set forth in SEQ ID NO:104, a CDR2 sequence as set forth in SEQ ID NO: 105 and a CDR3 sequence as set forth SEQ ID NO:106, and a VL region comprising a CDR1 sequence as set forth in SEQ ID NO:108, a CDR2 sequence as set forth in: YNN and a CDR3 sequence as set forth SEQ ID NO:109 [Fas, Fas-E09];

a VH region comprising a CDR1 sequence as set forth in SEQ ID NO:111, a CDR2 sequence as set forth in SEQ ID NO:112 and a CDR3 sequence as set forth SEQ ID NO:113, and a VL region comprising a CDR1 sequence as set forth in SEQ ID NO:115, a CDR2 sequence as set forth in: DAS and a CDR3 sequence as set forth SEQ ID NO:116 [4-1BB, BMS-663513];

a VH region comprising a CDR1 sequence as set forth in SEQ ID NO:90, a CDR2 sequence as set forth in SEQ ID NO:91 and a CDR3 sequence as set forth SEQ ID NO:92, and a VL region comprising a CDR1 sequence as set forth in SEQ ID NO:94, a CDR2 sequence as set forth in: FAS, and a CDR3 sequence as set forth SEQ ID NO:95 [DR5, hDR5-01-G56T];

a VH region comprising a CDR1 sequence as set forth in SEQ ID NO:97, a CDR2 sequence as set forth in SEQ ID NO:98 and a CDR3 sequence as set forth SEQ ID NO:99, and a VL region comprising a CDR1 sequence as set forth in SEQ ID NO: 101, a CDR2 sequence as set forth in: RTS, and a CDR3 sequence as set forth SEQ ID NO:102 [DR5, hDR5-05].

In a further aspect, the present invention relates to a composition comprising a first and a second antibody wherein the first antibody comprises a first antigen-binding region and a first Fc region according to any embodiment disclosed herein and the second antibody comprises a second antigen-binding region and a second Fc region according to any aspect or embodiment disclosed herein.

In a further aspect, the invention relates to a composition comprising a first and a second antibody, wherein the first antibody comprises a first antigen-binding region capable of binding to a first antigen and a first Fc region of a human IgG, and the second antibody comprises a second antigen-binding region capable of binding to a second antigen and a second Fc region of a human IgG, wherein said first Fc region comprises a. a substitution at position E430 or a substitution at position E345 or a combination of the substitutions K248E and T437R, and b. a K439E or S440K substitution, and said second Fc region comprises c. a substitution at position E430 or a substitution at position E345 or a combination of the substitutions K248E and T437R, and d. a K439E or S440K substitution, wherein the first Fc region has a K439E substitution and the second Fc region has a S440K substitution or, the first Fc region has a S440K substitution and the second Fc region has a K439E substitution, and wherein the first antibody and/or the second antibody does not comprise N-linked glycosylation at position N297, wherein the amino acid positions correspond to human IgG1 according to the Eu numbering system.

In one embodiment, the first Fc region and second Fc region of the antibodies present in the composition comprise a substitution selected from the group consisting of: E430G, E345K, E430S, E430F, E430T, E430Y, E345Q, E345R and E345Y or the combination of the substitutions K248E and T437R.

In one embodiment, the first antibody and the second antibody are present in the composition at molar ratio of about 1:50 to 50:1, such as a molar ratio of about 1:1, a molar ratio of about 1:2, a molar ratio of about 1:3, a molar ratio of about 1:4, a molar ratio of about 1:5, a molar ratio of about 1:6, a molar ratio of about 1:7, molar ratio of about 1:8, a molar ratio of about 1:9, a molar ratio of about 1:10, a molar ratio of about 1:15, a molar ratio of about 1:20, a molar ratio of about 1:25, a molar ratio of about 1:30, a molar ratio of about 1:35, a molar ratio of about 1:40, a molar ratio of about 1:45, a molar ratio of about 1:50, a molar ratio of about 50:1, a molar ratio of about 45:1, a molar ratio of about 40:1, a molar ratio of about 35:1, a molar ratio of about 30:1, a 25:1 molar ratio, a 20:1 molar ratio, a 15:1 molar ratio, a 10:1 molar ratio, a 9:1 molar ratio, a 8:1 molar ratio, a 7:1 molar ratio, a 6:1 molar ratio, a 5:1 molar ratio, a 4:1 molar ratio, a 3:1 molar ratio, a 2:1 molar ratio.

In another embodiment, the first antibody and the second antibody are present in the composition at molar ratio of about 1:50 to 50:1, such as a molar ratio of 1:40 to 40:1, such as a molar ratio of 1:30 to 30:1, such as a molar ratio of 1:20 to 20:1, such as a molar ratio of 1:10 to 10:1, such as a molar ratio of 1:9 to 9:1, such as a molar ratio of 1:5 to 5:1, such as a molar ration of 1:2 to 2:1.

In one embodiment, the first antibody and the second antibody are present in the composition at a molar ratio of 1:1.

In one embodiment, the composition further comprises a pharmaceutical carrier or excipient. In one embodiment, the composition is a pharmaceutical composition.

Therapeutic Applications

The first and second antibodies, antibodies or compositions according to any aspect or embodiment of the present invention may be used as a medicament, i.e. for therapeutic applications.

Thus, in one aspect the present invention provides a first and second antibody or a composition according to any aspect or embodiment disclosed herein for use as a medicament.

In another aspect, the present invention provides an antibody or a composition according to any aspect or embodiment disclosed herein for use in the treatment of cancer, autoimmune disease, inflammatory disease or infectious disease.

In another aspect the present invention relates to a method of treating an individual having a disease comprising administering to the individual an effective amount of a first and second antibody or composition according to any aspect or embodiment disclosed herein. In one embodiment the disease is selected from the group of: cancer, autoimmune disease, inflammatory disease and infectious disease.

In one embodiment of the invention, the method comprises administering an additional therapeutic agent.

In one embodiment of the invention, the additional therapeutic agent is one or more anti-cancer agent(s) selected from the group consisting of chemotherapeutics (including but not limited to paclitaxel, temozolomide, cisplatin, carboplatin, oxaliplatin, irinotecan, doxorubicin, gemcitabine, 5-fluorouracil, pemetrexed), kinase inhibitors (including but not limited to sorafenib, sunitinib or everolimus), apoptosis-modulating agents (including but not limited to recombinant human TRAIL or birinapant), RAS inhibitors, proteasome inhibitors (including but not limited to bortezomib), histone deacetylase inhibitors (including but not limited to vorinos-tat), nutraceuticals, cytokines (including but not limited to IFN-γ), antibodies or antibody mimetics (including but not limited to anti-EGFR, anti-IGF-1R, anti-VEGF, anti-CD20, anti-CD38, anti-HER2, anti-PD-1, anti-PD-L1, anti-CTLA4, anti-CD40, anti-CD137, anti-GITR antibodies and antibody mimetics), antibody-drug conjugates.

In a further aspect, the invention relates to a method of depleting a cell population expressing a first antigen and a second antigen, which method comprises contacting said cell population with a first and second antibody or compo-sition according to any aspect or embodiment disclosed herein.

In one embodiment, the cell population is a tumor cell population, such as a hematological tumor cell population or a solid tumor cell population.

In a further aspect, the invention relates to a method of inducing proliferation in a cell population expressing a first antigen and a second antigen, which method comprises contacting said cell population with a first and second antibody according to the invention or a composition according to the invention.

In one embodiment of the above-described methods, the cell population is present in the blood. In one embodiment, the cell population is a leukocyte, such as a leukocyte cell population. In one embodiment, the cell population is a subset of a leukocyte cell population. In one embodiment, the cell population is a lymphocyte cell population. In one embodiment, the cell population is a B cell population. In one embodiment of the invention the cell population is a subset of a B cell population. In one embodiment, the cell population is a T cell population. In one embodiment, the cell population is a subset of a T cell population. In one embodiment, the cell population is a regulatory T cell, such as a regulatory T cell population. In one embodiment, the cell population is a NK cell population. In one embodiment, the cell population is myeloid derived suppressor cell.

Kit-of-Parts

It is to be understood that the embodiments described below with reference to a first and second antibody refers to antibodies comprising an Fc region of an immunoglobulin and an antigen-binding region.

The invention also relates to kit-of-parts for simultaneous, separate or sequential use in therapy comprising a first and second antibody as described herein. Furthermore, such first and second may be obtained according to any method described herein.

In one aspect, the present invention relates to a kit of parts comprising an antibody or composition according to any aspect or embodiment described herein, wherein said first antibody and second antibody or composition are/is in one or more containers such as vials.

In one embodiment, the kit of parts comprises a first and second antibody or a composition according to any aspect or embodiment described herein, for simultaneous, separate or sequential use in therapy.

In another aspect, the present invention relates to use of a first and second antibody, a composition or kit-of-parts according to any of the embodiments herein described for use in a diagnostic method.

In another aspect, the present invention relates to a diagnostic method comprising administering a first and second antibody, a composition or a kit-of-parts according to any embodiments herein described to at least a part of the body of a human or other mammal.

In another aspect, the present invention relates to use of a first and second antibody, a composition or kit-of-parts according to any of the embodiments herein described in imaging at least a part of the body of a human or other mammal.

In another aspect, the present invention relates to a method for imaging of at least a part of the body of a human or other mammal, comprising administering a first and second antibody, a composition or a kit-of-parts according to any embodiments herein described.

Dosages

Efficient dosages and the dosage regimens for an antibody depend on the disease or condition to be treated and may be determined by the persons skilled in the art. An exemplary, non-limiting range for a therapeutically effective amount of an antibody of the present invention is about 0.1 to 100 mg/kg, such as about 0.1 to 50 mg/kg, for example about 0.1 to 20 mg/kg, such as about 0.1 to 10 mg/kg, for instance about 0.5, about such as 0.3, about 1, about 3, about 5, or about 8 mg/kg.

As mentioned, antibodies of the present invention may also be administered in combination therapy, i.e., combined with other therapeutic agents relevant for the disease or condition to be treated. Accordingly, in one embodiment, the antibody-containing medicament is for combination with one or more further therapeutic agents, such as a cytotoxic, chemotherapeutic or anti-angiogenic agents. Such combined administration may be simultaneous, separate or sequential.

In a further embodiment, the present invention provides a method for treating or preventing disease, such as cancer, which method comprises administration to a subject in need thereof of a therapeutically effective amount of a variant or pharmaceutical composition of the present invention, in combination with radiotherapy and/or surgery.

Method of Preparation

The invention also provides isolated nucleic acids and vectors encoding an antibody according to any one of the aspects described above, as well as recombinant host cells capable of production the antibodies. Suitable nucleic acid constructs, vectors and host cells for antibodies and variants thereof are known in the art, and described in the Examples. In embodiments wherein the variant antibody comprises not only a heavy chain (or Fc-containing fragment thereof) but also a light chain, the nucleotide sequences encoding the heavy and light chain portions may be present on the same or different nucleic acids or vectors.

Accordingly, in a further aspect, the invention relates to a nucleic acid, such as an isolated nucleic acid, encoding an antibody or a first antibody or second antibody according to the invention.

Furthermore, the invention relates to a nucleic acid, such as an isolated nucleic acid, encoding a heavy chain of an antibody or of a first antibody or second antibody according to the invention. Said nucleic acid may be used in combi-nation with a nucleic acid encoding a light chain.

In a further aspect, the invention provides an expression vector comprising a nucleic acid according to the invention or the combination of nucleic acids described above.

In a further aspect, the invention provides a delivery vehicle comprising a nucleic acid according to the invention or the combination of nucleic acids described above, option-ally in a composition with a pharmaceutically acceptable carrier. In one embodiment, said delivery vehicle is a particle. The invention also provides a method for produc-ing, in a host cell, an antibody according to any one of the aspects described above, wherein said method comprises the following steps:

a) providing a nucleotide construct encoding the antibody, b) expressing said nucleotide construct in a host cell, and c) recovering said antibody from a cell culture of said host cell.

In some embodiments, the antibody is a heavy-chain antibody. In most embodiments, however, the antibody will also contain a light chain and thus said host cell further expresses a light-chain-encoding construct, either on the same or a different vector.

Host cells suitable for the recombinant expression of antibodies are well-known in the art, and include CHO, HEK-293, Expi293, PER-C6, NS/0 and Sp2/0 cells.

In one embodiment, said host cell is a host cell which is not capable of efficiently removing C-terminal lysine K447 residues from antibody heavy chains. For example, Table 2 in Liu et al. (2008) J Pharm Sci 97: 2426 (incorporated herein by reference) lists a number of such antibody production systems, e.g. Sp2/0, NS/0 or transgenic mammary gland (goat), wherein only partial removal of C-terminal lysines is obtained.

As described above, antibodies of the invention lack N-linked glycosylation at position N297. In some embodiments, this may be achieved by mutating the antibody sequence such that the acceptor site around position N297 is no longer functional. In such embodiments, the host cell can be a cell which is capable of N-linked glycosylation of proteins, e.g. an eukaryotic cell, such as a mammalian cell, e.g. a human cell.

In another aspect, the invention relates to a method for producing an antibody according to the invention, comprising the step of producing the antibody in a recombinant host cell, wherein said host cell is not capable of glycosylating the asparagine at position 297 of the antibody. This may be e.g. be preferred if the sequence around position N297 is not mutated. Such a host cell may e.g. be a prokaryotic cell, such as a bacterial cell.

Thus, in one aspect, the invention provides a method for producing, in a host cell, an antibody according to any one of the aspects described above, wherein said method comprises the following steps:

a) providing a nucleotide construct encoding the antibody,
b) expressing said nucleotide construct in a host cell capable of glycosylating the asparagine at position 297 of the antibody, and
c) recovering said antibody from a cell culture of said host cell.

In a further aspect, the invention relates to a method for producing an antibody according to the invention, comprising the step of producing the antibody in a recombinant host cell which is capable of glycosylating the asparagine at position N297 of the antibody, followed by a step of removing the N-linked glycosylation from the produced antibody, e.g. enzymatically, such as through the use of deglycosylating enzyme PNGase F.

The invention also relates to an antibody obtained or obtainable by the method of the invention described above.

TABLE 1

| SEQ ID NO | Name | Sequence |
|---|---|---|
| 1. | VH CAMPATH-1H | QVQLQESGPGLVRPSQTLSLTCTVSGFTFTDFYMNWVRQPPGRGLEWIGFIRDK AKGYTTEYNPSVKGRVTMLVDTSKNQFSLRLSSVTAADTAVYYCAREGHTAAPF DYWGQGSLVTVSS |
| 2. | VH CAMPATH-1H CDR1 | GFTFTDFY |
| 3. | VH CAMPATH-1H CDR2 | IRDKAKGYTT |
| 4. | VH CAMPATH-1H CDR3 | AREGHTAAPFDY |
| 5. | VL CAMPATH-1H | DIQMTQSPSSLSASVGDRVTITCKASQNIDKYLNWYQQKPGKAPKLLIYNTNNL QTGVPSRFSGSGSGTDFTFTISSLQPEDIATYYCLQHISRPRTFGQGTKVEIK |
| 6. | VL CAMPATH-1H CDR1 | QNIDKY |
| | VL CAMPATH-1H CDR2 | NTN |
| 7. | VL CAMPATH-1H CDR3 | LQHISRPRT |
| 8. | VH CD37-37-3 | QVQVKESGPGLVAPSQSLSITCTVSGFSLTTSGVSWVRQPPGKGLEWLGVIWG DGSTNYHSALKSRLSIKKDHSKSQVFLKLNSLQTDDTATYYCAKGGYSLAHWG QGTLVTVSA |
| 9. | VH CD37-37-3 CDR1 | GFSLTTSG |
| 10. | VH CD37-37-3 CDR2 | IWGDGST |
| 11. | VH CD37-37-3 CDR3 | AKGGYSLAH |
| 12. | VL CD37-37-3 | DIQMTQSPASLSVSVGETVTITCRASENIRSNLAWYQQKQGKSPQLLVNVATNL ADGVPSRFSGSGSGTQYSLKINSLQSEDFGTYYCQHYWGTTWTFGGGTKLEIK |
| 13. | VL CD37-37-3 CDR1 | ENIRSN |
| | VL CD37-37-3 CDR2 | VAT |

TABLE 1-continued

| SEQ ID NO | Name | Sequence |
|---|---|---|
| 14. | VL CD37-37-3 CDR3 | QHYWGTTWT |
| 15. | VH 11B8 | EVQLVQSGGGLVHPGGSLRLSCTGSGFTFSYHAMHWVRQAPGKGLEWVSIIGT GGVTYYADSVKGRFTISRDNVKNSLYLQMNSLRAEDMAVYYCARDYYGAGSFY DGLYGMDVWGQGTTVTVSS |
| 16. | VH 11B8 CDR1 | GFTFSYHA |
| 17. | VH 11B8 CDR2 | IGTGGVT |
| 18. | VH 11B8 CDR3 | ARDYYGAGSFYDGLYGMDV |
| 19. | VL 11B8 | EIVLTQSPATLSLSPGERATLSCRASQSVSSYLAWYQQKPGQAPRLLIYDASNRA TGIPARFSGSGSGTDFTLTISSLEPEDFAVYYCQQRSDWPLT**FGGGTKVEIK |
| 20. | VL 11B8 CDR1 | QSVSSY |
| | VL 11B8 CDR2 | DAS |
| 21. | VL 11B8 CDR3 | QQRSDWPLT |
| 22. | VH gp120-b12 | QVQLVQSGAEVKKPGASVKVSCQASGYRFSNFVIHWVRQAPGQRFEWMGWIN PYNGNKEFSAKFQDRVTFTADTSANTAYMELRSLRSADTAVYYCARVGPYSWD DSPQDNYYMDVWGKGTTVIVSS |
| 23. | VH gp120-b12 CDR1 | GYRFSNFV |
| 24. | VH gp120-b12 CDR2 | INPYNGNK |
| 25. | VH gp120-b12 CDR3 | ARVGPYSWDDSPQDNYYMDV |
| 26. | VL gp120-b12 | EIVLTQSPGTLSLSPGERATFSCRSSHSIRSRRVAWYQHKPGQAPRLVIHGVSNR ASGISDRFSGSGSGTDFTLTITRVEPEDFALYYCQVYGASSYTFGQGTKLERK |
| 27. | VL gp120-b12 CDR1 | HSIRSRR |
| | VL gp120-b12 CDR2 | GVS |
| 28. | VL gp120-b12-CDR3 | QVYGASSYT |
| 29. | constant region human HC IgG1m(f)-N297A-E430G | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHGALHNHYTQKSLSLSPGK |
| 30. | constant region human HC IgG1m(f)-N297G-E430G | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYGSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHGALHNHYTQKSLSLSPGK |
| 31. | constant region human HC IgG1m(f)-N297Q-E430G | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYQSTYRVVSVLTVLHQDWLNGKEYKCKVSNKALPAPIEKTISKAK GQPREPQVYTLPPSREEMTKNQVSLTCLVKGFYPSDIAVEWESNGQPENNYKTTPP VLDSDGSFFLYSKLTVDKSRWQQGNVFSCSVMHGALHNHYTQKSLSLSPGK |
| 32. | constant region human HC IgG1m(f)-N297D-E430G | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYDSTYRVVSVLTVLHQDWLNGKEYKCKVSNKALPAPIEKTISKAK GQPREPQVYTLPPSREEMTKNQVSLTCLVKGFYPSDIAVEWESNGQPENNYKTTPP VLDSDGSFFLYSKLTVDKSRWQQGNVFSCSVMHGALHNHYTQKSLSLSPGK |
| 33. | constant region human HC IgG1m(f)-N297Y-E430G | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYYSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHGALHNHYTQKSLSLSPGK |
| 34. | constant region human HC IgG1m(f)- | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC |

TABLE 1-continued

| SEQ ID NO | Name | Sequence |
|---|---|---|
| | T299A-E430G | PAPELLGGPSVFLFPPKPKDTLMISRTPEVTCVVVDVSHEDPEVKFNWYVDGVEVH<br>NAKTKPREEQYNSAYRVVSVLTVLHQDWLNGKEYKCKVSNKALPAPIEKTISKAK<br>GQPREPQVYTLPPSREEMTKNQVSLTCLVKGFYPSDIAVEWESNGQPENNYKTTPP<br>VLDSDGSFFLYSKLTVDKSRWQQGNVFSCSVMHGALHNHYTQKSLSLSPGK |
| 35. | constant region human HC IgG1m(f)-N297A-E345K | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYASTYRVVSVLTVLHQDWLNGKEYKCKVSNKALPAPIEKTISKAKG<br>QPRKPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| 36. | constant region human HC IgG1m(f)-N297G-E345K | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYGSTYRVVSVLTVLHQDWLNGKEYKCKVSNKALPAPIEKTISKAKG<br>QPRKPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| 37. | constant region human HC IgG1m(f)-N297Q-E345K | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYQSTYRVVSVLTVLHQDWLNGKEYKCKVSNKALPAPIEKTISKAK<br>GQPRKPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |
| 38. | constant region human HC IgG1m(f)-T299A-E345K | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYNSAYRVVSVLTVLHQDWLNGKEYKCKVSNKALPAPIEKTISKAK<br>GQPRKPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |
| 39. | constant region human HC IgG1m(f)-N297A-E345R | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYASTYRVVSVLTVLHQDWLNGKEYKCKVSNKALPAPIEKTISKAKG<br>QPRRPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| 40. | constant region human HC IgG1m(f)-N297G-E345R | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYGSTYRVVSVLTVLHQDWLNGKEYKCKVSNKALPAPIEKTISKAKG<br>QPRRPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 41. | constant region human HC IgG1m(f)-N297Q-E345R | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYQSTYRVVSVLTVLHQDWLNGKEYKCKVSNKALPAPIEKTISKAK<br>GQPRRPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |
| 42. | constant region human HC IgG1m(f)-N297A-E430G-K439E | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYASTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHGALHNHYTQESLSLSPGK |
| 43. | constant region human HC IgG1m(f)-N297A-E430G-S440K | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYASTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHGALHNHYTQKKLSLSPGK |
| 44. | constant region human HC IgG1m(f)-N297A-E345K-K439E | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYASTYRVVSVLTVLHQDWLNGKEYKCKVSNKALPAPIEKTISKAKG<br>QPRKPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQESLSLSPGK |
| 45. | constant region human HC IgG1m(f)- | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC |

TABLE 1-continued

| SEQ ID NO | Name | Sequence |
|---|---|---|
| | N297A-E345K-S440K | PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNKALPAPIEKTISKAKG QPRKPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKKLSLSPGK |
| 46. | constant region human HC IgG1m(f)- N297A-E345R-K439E | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNKALPAPIEKTISKAKG QPRRPQVYTLPPSREEMTKNQVSLTCLVKGFYPSDIAVEWESNGQPENNYKTTPP VLDSDGSFFLYSKLTVDKSRWQQGNVFSCSVMHEALHNHYTQESLSLSPGK |
| 47. | constant region human HC IgG1m(f)- N297A-E345R-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNKALPAPIEKTISKAKG QPRRPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKKLSLSPGK |
| 48. | constant region human HC IgG1m(f)- N297Q-E345K-K439E | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYQSTYRVVSVLTVLHQDWLNGKEYKCKVSNKALPAPIEKTISKAK GQPRKPQVYTLPPSREEMTKNQVSLTCLVKGFYPSDIAVEWESNGQPENNYKTTP PVLDSDGSFFLYSKLTVDKSRWQQGNVFSCSVMHEALHNHYTQESLSLSPGK |
| 49. | constant region human HC IgG1m(f)- N297Q-E345K-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYQSTYRVVSVLTVLHQDWLNGKEYKCKVSNKALPAPIEKTISKAK GQPRKPQVYTLPPSREEMTKNQVSLTCLVKGFYPSDIAVEWESNGQPENNYKTTP PVLDSDGSFFLYSKLTVDKSRWQQGNVFSCSVMHEALHNHYTQKKLSLSPGK |
| 50. | constant region human HC IgG1m(f)- E345K-K439E | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPRKPQVYTLPPSREEMTKNQVSLTCLVKGFYPSDIAVEWESNGQPENNYKTTPP VLDSDGSFFLYSKLTVDKSRWQQGNVFSCSVMHEALHNHYTQESLSLSPGK |
| 51. | constant region human HC IgG1m(f)- E345K-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPRKPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKKLSLSPGK |
| 52. | constant region human HC IgG1m(f)- E345R-K439E | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPRRPQVYTLPPSREEMTKNQVSLTCLVKGFYPSDIAVEWESNGQPENNYKTTPP VLDSDGSFFLYSKLTVDKSRWQQGNVFSCSVMHEALHNHYTQESLSLSPGK |
| 53. | constant region human HC IgG1m(f)- E345R-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPRRPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKKLSLSPGK |
| 54. | constant region human HC IgG1m(f)- E430G | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHGALHNHYTQKSLSLSPGK |
| 55. | constant region human HC IgG1m(f)- E345K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPRKPQVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPGK |
| 56. | constant region human HC IgG1m(f)- | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC |

TABLE 1-continued

| SEQ ID NO | Name | Sequence |
|---|---|---|
| | E345R | PAPELLGGPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPRRPQVYTLPPSREEMTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 57. | constant region human HC IgG1m(f)-E430G-K439E | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHGALHNHYTQESLSLSPGK |
| 58. | constant region human HC IgG1m(f)-E430G-S440K | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHGALHNHYTQKKLSLSPGK |
| 59. | constant region human HC IgG1m(f) | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| 60. | Constant region human kappa LC | RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| 61. | constant region human HC IgG1m(f)-N297Q-E430G-K439E | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYQSTYRVVSVLTVLHQDWLNGKEYKCKVSNKALPAPIEKTISKAK<br>GQPREPQVYTLPPSREEMTKNQVSLTCLVKGFYPSDIAVEWESNGQPENNYKTTPP<br>VLDSDGSFFLYSKLTVDKSRWQQGNVFSCSVMHGALHNHYTQESLSLSPGK |
| 62. | constant region human HC IgG1m(f)-N297Q-E430G-S440K | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPKDTLMISRTPEVTCVVVDVSHEDPEVKFNWYVDGVEVH<br>NAKTKPREEQYQSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHGALHNHYTQKKLSLSPGK |
| 63. | constant region human HC IgG1m(f)-K248E-T437R | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPEDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYRQKSLSLSPGK |
| 64. | constant region human HC IgG1m(f)-K248E-N297A-T437R | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPEDTLMISRTPEVTCVVVDVSHEDPEVKFNWYVDGVEVH<br>NAKTKPREEQYASTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYRQKSLSLSPGK |
| 65. | constant region human HC IgG1m(f)-K248E-T437R-K439E | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPEDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYRQESLSLSPGK |
| 66. | constant region human HC IgG1m(f)-K248E-T437R-S440K | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPEDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYRQKKLSLSPGK |
| 67. | constant region human HC IgG1m(f)-K248E-N297A-T437R-K439E | ASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKRVEPKSCDKTHTCPPC<br>PAPELLGGPSVFLFPPKPEDTLMISRTPEVTCVVVDVSHEDPEVKFNWYVDGVEVH<br>NAKTKPREEQYASTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYRQESLSLSPGK |

TABLE 1-continued

| SEQ ID NO | Name | Sequence |
|---|---|---|
| 68. | constant region human HC IgG1m(f)-K248E-N297A-T437R-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPEDTLMISRTPEVTCVVVDVSHEDPEVKFNWYVDGVEVH NAKTKPREEQYASTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYRQKKLSLSPGK |
| 69. | constant region human HC IgG1m(f)-K439E | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQESLSLSPGK |
| 70. | constant region human HC IgG1m(f)-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKKLSLSPGK |
| 71. | constant region human HC IgG1m(z) | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 72. | constant region human HC IgG1m(a) | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKPVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 73. | constant region human HC IgG1m(x) | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKPVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEGLHNHYTQKSLSLSPGK |
| 74. | constant region human HC IgG2 | ASTKGPSVFPLAPCSRSTSESTAALGCLVKDYFPEPVTVSWNSGALTSGVHTFPAV LQSSGLYSLSSVVTVPSSNFGTQTYTCNVDHKPSNTKVDKTVERKCCVECPPCPAP PVAGPSVFLFPPKPKDTLMISRTPEVTCVVVDVSHEDPEVQFNWYVDGVEVHNAK TKPREEQFNSTFRVVSVLTVVHQDWLNGKEYKCKVSNKGLPAPIEKTISKTKGQPR EPQVYTLPPSREEMTKNQVSLTCLVKGFYPSDIAVEWESNGQPENNYKTTPPMLDS DGSFFLYSKLTVDKSRWQQGNVFSCSVMHEALHNHYTQKSLSLSPGK |
| 75. | constant region human HC IgG4 | ASTKGPSVFPLAPCSRSTSESTAALGCLVKDYFPEPVTVSWNSGALTSGVHTFPAV LQSSGLYSLSSVVTVPSSSLGTKTYTCNVDHKPSNTKVDKRVESKYGPPCPSCPAP EFLGGPSVFLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYKTTPPVL DSDGSFFLYSRLTVDKSRWQEGNVFSCSVMHEALHNHYTQKSLSLSLGK |
| 76. | constant region human HC IgG1m(f)-E430Y | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHYALHNHYTQKSLSLSPGK |
| 77. | constant region human HC IgG1m(f)-E430Y-K439E | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHYALHNHYTQESLSLSPGK |
| 78. | constant region human HC IgG1m(f)-E430Y-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHYALHNHYTQKKLSLSPGK |

TABLE 1-continued

| SEQ ID NO | Name | Sequence |
|---|---|---|
| 79. | constant region human HC IgG1m(f)-N297A-E430Y-K439E | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHYALHNHYTQESLSLSPGK |
| 80. | constant region human HC IgG1m(f)-N297A-E430Y-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHYALHNHYTQKKLSLSPGK |
| 81. | constant region human HC IgG1m(f)-N297A-K326A-E333S-E345K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNAALPAPISKTISKAKG QPRKPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 82. | constant region human HC IgG1m(f)-N297A-K326A-E333S-E345R | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNAALPAPISKTISKAKG QPRRPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 83. | constant region human HC IgG1m(f)-N297A-K326A-E333S-E345K-K439E | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNAALPAPISKTISKAKG QPRKPQVYTLPPSREEMTKNQVSLTCLVKGFYPSDIAVEWESNGQPENNYKTTPPV LDSDGSFFLYSKLTVDKSRWQQGNVFSCSVMHEALHNHYTQESLSLSPGK |
| 84. | constant region human HC IgG1m(f)-N297A-K326A-E333S-E345K-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNAALPAPISKTISKAKG QPRKPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKKLSLSPGK |
| 85. | constant region human HC IgG1m(f)-N297A-K326A-E333S-E345R-K439E | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNAALPAPISKTISKAKG QPRRPQVYTLPPSREEMTKNQVSLTCLVKGFYPSDIAVEWESNGQPENNYKTTPPV LDSDGSFFLYSKLTVDKSRWQQGNVFSCSVMHEALHNHYTQESLSLSPGK |
| 86. | constant region human HC IgG1m(f)-N297A-K326A-E333S-E345R-S440K | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYASTYRVVSVLTVLHQDWLNGKEYKCKVSNAALPAPISKTISKAKG QPRRPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKKLSLSPGK |
| 87. | constant region human HC IgG1m(f)-L234F-L235E-D265A-F405L | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPEFEGGPSVFLFPPKPKDTLMISRTPEVTCVVVAVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFLLYSKLTVDKSRWQQGNVFSCSVMHEALHNHYTQKSLSLSPGK |
| 88. | IgG1 constant region LC Lambda | GQPKAAPSVTLFPPSSEELQANKATLVCLISDFYPGAVTVAWKADSSPVKAGVETT TPSKQSNNKYAASSYLSLTPEQWKSHRSYSCQVTHEGSTVEKTVAPTECS |
| 89. | VH hDR5-01-G56T | EVQLQQSGAEVVKPGASVKLSCKASGFNIKDTFIHWVKQAPGQGLEWIGRIDP ANTNTKYDPKFQGKATITTDTSSNTAYMELSSLRSEDTAVYYCVRGLYTYYFDY WGQGTLVTVSS |
| 90. | VH hDR5-01-G56T CDR1 | GFNIKDTF |
| 91. | VH hDR5-01-G56T CDR2 | IDPANTNT |

TABLE 1-continued

| SEQ ID NO | Name | Sequence |
|---|---|---|
| 92. | VH hDR5-01-G56T CDR3 | VRGLYTYYFDY |
| 93. | VL hDR5-01-G56T | EIVMTQSPATLSVSPGERATLSCRASQSISNNLHWYQQKPGQAPRLLIKFASQSI TGIPARFSGSGSGTEFTLTISSLQSEDFAVYYCQQGNSWPYTFGQGTKLEIK |
| 94. | VL hDR5-01-G56T CDR1 | QSISNN |
|  | VL hDR5-01-G56T CDR2 | FAS |
| 95. | VL hDR5-01-G56T CDR3 | QQGNSWPYT |
| 96. | VH hDR5-05 | QVQLVQSGAEVKKPGASVKVSCKASGFNIKDTHMHWVRQAPGQRLEWIGRID PANGNTEYDQKFQGRVTITVDTSASTAYMELSSLRSEDTAVYYCARWGTNVYF AYWGQGTLVTVSS |
| 97. | VH hDR5-05 CDR1 | GFNIKDTH |
| 98. | VH hDR5-05 CDR2 | IDPANGNT |
| 99. | VH hDR5-05 CDR3 | ARWGTNVYFAY |
| 100. | VL hDR5-05 | DIQLTQSPSSLSASVGDRVTITCSASSSVSYMYWYQQKPGKAPKPWIYRTSNLA SGVPSRFSGSGSGTDFTLTISSLQPEDFATYYCQQYHSYPPTFGGGTKVEIK |
| 101. | VL hDR5-05 CDR1 | SSVSY |
|  | VL hDR5-05 CDR2 | RTS |
| 102. | VL hDR5-05 CDR3 | QQYHSYPPT |
| 103. | VH Fas-E09 | QLQLQESGPGLVKPSETLSLTCTVSGASISANSYYGVWVRQSPGKGLEWVGSI AYRGNSNSGSTYYNPSLKSRATVSVDTSKNQVSLRLTSVTAADTALYYCARRQL LDDGTGYQWAAFDVWGQGTMVTVSS |
| 104. | VH Fas-E09 CDR1 | GASISANSYY |
| 105. | VH Fas-E09 CDR2 | IAYRGNSNSGST |
| 106. | VH Fas-E09 CDR3 | ARRQLLDDGTGYQWAAFDV |
| 107. | VL Fas-E09 | QSVLTQPPSVSEAPRQTVTISCSGNSFNIGRYPVNWYQQLPGKAPKLLIYYNNLR FSGVSDRFSGSKSGTSASLAIRDLLSEDEADYYCSTWDDTLKGWVFGGGTKVT VL |
| 108. | VL Fas-E09 CDR1 | SFNIGRYP |
|  | VL Fas-E09 CDR2 | YNN |
| 109. | VL Fas-E09 CDR3 | STWDDTLKGWV |
| 110. | VH BMS-663513 | QVQLQQWGAGLLKPSETLSLTCAVYGGSFSGYYWSWIRQSPEKGLEWIGEINH GGYVTYNPSLESRVTISVDTSKNQFSLKLSSVTAADTAVYYCARDYGPGNYDW YFDLWGRGTLVTVSS |
| 111. | VH BMS-663513 CDR1 | GGSFSGYY |
| 112. | VH BMS-663513 CDR2 | INHGGYV |
| 113. | VH BMS-663513 CDR3 | ARDYGPGNYDWYFDL |
| 114. | VL BMS-663513 | EIVLTQSPATLSLSPGERATLSCRASQSVSSYLAWYQQKPGQAPRLLIYDASNRA TGIPARFSGSGSGTDFTLTISSLEPEDFAVYYCQQRSNWPPALTFGGGTKVEIK |
| 115. | VL BMS-663513 CDR1 | QSVSSY |
|  | VL BMS-663513 CDR2 | DAS |

TABLE 1-continued

| SEQ ID NO | Name | Sequence |
|---|---|---|
| 116. | VL BMS-663513 CDR3 | QQRSNWPPALT |
| 117. | VH h2E8 (CD52) | EVHLVESGGGLVQPGGSLRLSCAASGFTFSRYGMSWVRQAPGKGLELVAMMKT<br>KGGRTYYPDSVKGRFTISRDNAKNSLYLQMNSLRAEDTAIYYCASDGYYWGQG<br>TTVTVSS |
| 118. | VH h2E8 CDR1 | GFTFSRYG |
| 119. | VH h2E8 CDR2 | MKTKGGRT |
| 120. | VH h2E8 CDR3 | ASDGYY |
| 121. | VL h2E8 | DVVMTQTPLSLSVTLGQPASISCKSSQSLLHSDGKTYLNWLQQRPGQSPRRLIY<br>LVSKLDSGVPDRFSGSGSGTDFTLKISRVEAEDVGIYYCWQGTHLWTFGGGTK<br>VEIK |
| 122. | VL h2E8 CDR1 | QSLLHSDGKTY |
| 123. | VL h2E8 CDR3 | WQGTHLWT |
| 124. | constant region human HC IgG2-E345R | ASTKGPSVFPLAPCSRSTSESTAALGCLVKDYFPEPVTVSWNSGALTSGVHTFPAV<br>LQSSGLYSLSSVVTVPSSNFGTQTYTCNVDHKPSNTKVDKTVERKCCVECPPCPAP<br>PVAGPSVFLFPPKPKDTLMISRTPEVTCVVVDVSHEDPEVQFNWYVDGVEVHNAK<br>TKPREEQFNSTFRVVSVLTVVHQDWLNGKEYKCKVSNKGLPAPIEKTISKTKGQPR<br>RPQVYTLPPSREEMTKNQVSLTCLVKGFYPSDIAVEWESNGQPENNYKTTPPMLD<br>SDGSFFLYSKLTVDKSRWQQGNVFSCSVMHEALHNHYTQKSLSLSPGK |
| 125. | constant region human HC IgG2-E345R-K439E | ASTKGPSVFPLAPCSRSTSESTAALGCLVKDYFPEPVTVSWNSGALTSGVHTFPAV<br>LQSSGLYSLSSVVTVPSSNFGTQTYTCNVDHKPSNTKVDKTVERKCCVECPPCPAP<br>PVAGPSVFLFPPKPKDTLMISRTPEVTCVVVDVSHEDPEVQFNWYVDGVEVHNAK<br>TKPREEQFNSTFRVVSVLTVVHQDWLNGKEYKCKVSNKGLPAPIEKTISKTKGQPR<br>RPQVYTLPPSREEMTKNQVSLTCLVKGFYPSDIAVEWESNGQPENNYKTTPPMLD<br>SDGSFFLYSKLTVDKSRWQQGNVFSCSVMHEALHNHYTQESLSLSPGK |
| 126. | constant region human HC IgG2-E345R-S440K | ASTKGPSVFPLAPCSRSTSESTAALGCLVKDYFPEPVTVSWNSGALTSGVHTFPAV<br>LQSSGLYSLSSVVTVPSSNFGTQTYTCNVDHKPSNTKVDKTVERKCCVECPPCPAP<br>PVAGPSVFLFPPKPKDTLMISRTPEVTCVVVDVSHEDPEVQFNWYVDGVEVHNAK<br>TKPREEQFNSTFRVVSVLTVVHQDWLNGKEYKCKVSNKGLPAPIEKTISKTKGQPR<br>RPQVYTLPPSREEMTKNQVSLTCLVKGFYPSDIAVEWESNGQPENNYKTTPPMLD<br>SDGSFFLYSKLTVDKSRWQQGNVFSCSVMHEALHNHYTQKKLSLSPGK |
| 127. | constant region human HC IgG2-N297A-E345R-K439E | ASTKGPSVFPLAPCSRSTSESTAALGCLVKDYFPEPVTVSWNSGALTSGVHTFPAV<br>LQSSGLYSLSSVVTVPSSNFGTQTYTCNVDHKPSNTKVDKTVERKCCVECPPCPAP<br>PVAGPSVFLFPPKPKDTLMISRTPEVTCVVVDVSHEDPEVQFNWYVDGVEVHNAK<br>TKPREEQFASTFRVVSVLTVVHQDWLNGKEYKCKVSNKGLPAPIEKTISKTKGQPR<br>RPQVYTLPPSREEMTKNQVSLTCLVKGFYPSDIAVEWESNGQPENNYKTTPPMLD<br>SDGSFFLYSKLTVDKSRWQQGNVFSCSVMHEALHNHYTQESLSLSPGK |
| 128. | constant region human HC IgG2-N297A-E345R-S440K | ASTKGPSVFPLAPCSRSTSESTAALGCLVKDYFPEPVTVSWNSGALTSGVHTFPAV<br>LQSSGLYSLSSVVTVPSSNFGTQTYTCNVDHKPSNTKVDKTVERKCCVECPPCPAP<br>PVAGPSVFLFPPKPKDTLMISRTPEVTCVVVDVSHEDPEVQFNWYVDGVEVHNAK<br>TKPREEQFASTFRVVSVLTVVHQDWLNGKEYKCKVSNKGLPAPIEKTISKTKGQPR<br>RPQVYTLPPSREEMTKNQVSLTCLVKGFYPSDIAVEWESNGQPENNYKTTPPMLD<br>SDGSFFLYSKLTVDKSRWQQGNVFSCSVMHEALHNHYTQKKLSLSPGK |
| 129. | constant region human HC IgG4-E345R | ASTKGPSVFPLAPCSRSTSESTAALGCLVKDYFPEPVTVSWNSGALTSGVHTFPAV<br>LQSSGLYSLSSVVTVPSSSLGTKTYTCNVDHKPSNTKVDKRVESKYGPPCPSCPAP<br>EFLGGPSVFLFPPKPKDTLMISRTPEVTCVVVDVSQEDPEVQFNWYVDGVEVHNA<br>KTKPREEQFNSTYRVVSVLTVLHQDWLNGKEYKCKVSNKGLPSSIEKTISKAKGQ<br>PRRPQVYTLPPSQEEMTKNQVSLTCLVKGFYPSDIAVEWESNGQPENNYKTTPPVL<br>DSDGSFFLYSRLTVDKSRWQEGNVFSCSVMHEALHNHYTQKSLSLSLGK |
| 130. | constant region human HC IgG4-E345R-K439E | ASTKGPSVFPLAPCSRSTSESTAALGCLVKDYFPEPVTVSWNSGALTSGVHTFPAV<br>LQSSGLYSLSSVVTVPSSSLGTKTYTCNVDHKPSNTKVDKRVESKYGPPCPSCPAP<br>EFLGGPSVFLFPPKPKDTLMISRTPEVTCVVVDVSQEDPEVQFNWYVDGVEVHNA<br>KTKPREEQFNSTYRVVSVLTVLHQDWLNGKEYKCKVSNKGLPSSIEKTISKAKGQ<br>PRRPQVYTLPPSQEEMTKNQVSLTCLVKGFYPSDIAVEWESNGQPENNYKTTPPVL<br>DSDGSFFLYSRLTVDKSRWQEGNVFSCSVMHEALHNHYTQESLSLSLGK |
| 131. | constant region human HC IgG4-E345R-S440K | ASTKGPSVFPLAPCSRSTSESTAALGCLVKDYFPEPVTVSWNSGALTSGVHTFPAV<br>LQSSGLYSLSSVVTVPSSSLGTKTYTCNVDHKPSNTKVDKRVESKYGPPCPSCPAP<br>EFLGGPSVFLFPPKPKDTLMISRTPEVTCVVVDVSQEDPEVQFNWYVDGVEVHNA<br>KTKPREEQFNSTYRVVSVLTVLHQDWLNGKEYKCKVSNKGLPSSIEKTISKAKGQ<br>PRRPQVYTLPPSQEEMTKNQVSLTCLVKGFYPSDIAVEWESNGQPENNYKTTPPVL<br>DSDGSFFLYSRLTVDKSRWQEGNVFSCSVMHEALHNHYTQKKLSLSLGK |

TABLE 1-continued

| SEQ ID NO | Name | Sequence |
|---|---|---|
| 132. | constant region human HC IgG4-N297A-E345R-K439E | ASTKGPSVFPLAPCSRSTSESTAALGCLVKDYFPEPVTVSWNSGALTSGVHTFPAV LQSSGLYSLSSVVTVPSSSLGTKTYTCNVDHKPSNTKVDKRVESKYGPPCPSCPAP EFLGGPSVFLFPPKPKDTLMISRTPEVTCVVVDVSQEDPEVQFNWYVDGVEVHNA KTKPREEQFASTYRVVSVLTVLHQDWLNGKEYKCKVSNKGLPSSIEKTISKAKGQ PRRPQVYTLPPSQEEMTKNQVSLTCLVKGFYPSDIAVEWESNGQPENNYKTTPPVL DSDGSFFLYSRLTVDKSRWQEGNVFSCSVMHEALHNHYTQESLSLSLGK |
| 133. | constant region human HC IgG4-N297A-E345R-S440K | ASTKGPSVFPLAPCSRSTSESTAALGCLVKDYFPEPVTVSWNSGALTSGVHTFPAV LQSSGLYSLSSVVTVPSSSLGTKTYTCNVDHKPSNTKVDKRVESKYGPPCPSCPAP EFLGGPSVFLFPPKPKDTLMISRTPEVTCVVVDVSQEDPEVQFNWYVDGVEVHNA KTKPREEQFASTYRVVSVLTVLHQDWLNGKEYKCKVSNKGLPSSIEKTISKAKGQ PRRPQVYTLPPSQEEMTKNQVSLTCLVKGFYPSDIAVEWESNGQPENNYKTTPPVL DSDGSFFLYSRLTVDKSRWQEGNVFSCSVMHEALHNHYTQKKLSLSLGK |

The present invention is further illustrated by the following examples which should not be construed as further limiting.

EXAMPLES

Example 1

Antibody Expression Constructs

For the expression of human and humanized antibodies used herein, variable heavy (VH) chain and variable light (VL) chain sequences were prepared by gene synthesis (GeneArt Gene Synthesis; ThermoFisher Scientific) and cloned in pcDNA3.3 expression vectors (ThermoFisher Scientific) containing a constant region of a human IgG heavy chain (HC) (constant region human IgG1m(f) HC: SEQ ID NO 59) and or the constant region of the human kappa light chain (LC): SEQ ID NO 60. Desired mutations were introduced by gene synthesis. CD20 antibody variants in this application have VH and VL sequences derived from previously described CD20 antibody IgG1-CD20-11B8 (WO2004/035607; VH: SEQ ID NO 15; VL: SEQ ID NO 19). CD52 antibody variants in this application have VH and VL sequences derived from previously described CD52 antibody CAMPATH-1H (Crowe et al., 1992 Clin Exp Immunol. 87(1):105-110; VH: SEQ ID NO 1; VL: SEQ ID NO 5). CD37 antibody variants in this application have VH and VL sequences derived from previously described CD37 antibody IgG1-CD37-37.3 (WO2011/112978; VH: SEQ ID NO 8; VL: SEQ ID NO 12). The human IgG1 antibody b12, an HIV gp120-specific antibody was used as a negative control in some experiments (Barbas et al., J Mol Biol. 1993 Apr. 5; 230(3):812-23; VH: SEQ ID NO 22; VL: SEQ ID NO 26). Fas antibody variants in this application have VH and VL sequences derived from the previously described Fas antibody Fas-E09 (Chodorge et al., Cell Death Differ. 2012 July; 19(7):1187-95; VH: 103; VL: 107). DR5 antibody variants in this application have VH and VL sequences derived from previously described DR5 antibody DR5-01-G56T (WO 2017/093447; VH: SEQ ID NO 89; VL: SEQ ID NO 93) and DR5-05 (WO2014/009358; VH: SEQ ID NO 96; VL: SEQ ID NO 100). 4-1BB antibody variants in this application have VH and VL sequences derived from previously described 4-1BB antibody BMS-663513 (US 2005/0095244A1; VH: SEQ ID NO 110; VL: SEQ ID NO 114). Transient Expression Antibody Constructs Plasmid DNA mixtures encoding both heavy and light chains of antibodies were transiently transfected in human Expi293F cells (Gibco, Cat No A14635) using 293fectin (Life Technologies) essentially as described by Vink et al.

(Vink et al., 2014 Methods 65(1):5-10). Antibody concentrations in the supernatants were measured by absorbance at 280 nm. Antibody-containing supernatants were either directly used in in vitro assays, or antibodies were purified as described below.
Antibody Purification and Quality Assessment Antibodies were purified by Protein A affinity chromatography. Culture supernatants were filtered over a 0.20 µM dead-end filter and loaded on 5 mL MabSelect SuRe columns (GE Healthcare), washed and eluted with 0.02 M sodium citrate-NaOH, pH 3. The eluates were loaded on a HiPrep Desalting column (GE Healthcare) immediately after purification and the antibodies were buffer exchanged into 12.6 mM NaH2PO4, 140 mM NaCl, pH 7.4 buffer (B.Braun or Thermo Fisher). After buffer exchange, samples were sterile filtered over 0.2 µm dead-end filters. Purified proteins were analyzed by a number of bioanalytical assays including capillary electrophoresis on sodium dodecyl sulfate-polyacrylamide gels (CE-SDS) and high-performance size exclusion chromatography (HP-SEC). Concentration was measured by absorbance at 280 nm. Purified antibodies were stored at 2-8° C.

Example 2: Deglycosylated Antibody Variants Harboring Fc-Fc Interaction Enhancing Mutations Retain Potent CDC Capacity The glycosylation of antibody residue N297 positively impacts the potential of antibodies to engage in FcγR and complement-mediated effector functions. Complement activation may benefit from a contribution by the N297-linked glycan to inter-protein Fc-Fc interactions. Therefore, deglycosylation of antibody residue N297 may suppress Fc-Fc interactions and thus formation of antibody complexes. Here, it was tested whether the loss of CDC efficacy on Wien 133 cells by anti-CD52 and anti-CD20 antibody variants upon enzymatic deglycosylation could be restored by introducing an Fc-Fc interaction enhancing mutation.

Different mutations were introduced in the anti-CD52 IgG1-CAMPATH-1H antibody and anti-CD20 IgG1-11B8 antibody: E430G, E345K, or E345R, which induce enhanced Fc-Fc interactions. Single antibodies were mixed 1:1 with non-binding isotype control antibodies IgG1-b12 to enable direct comparison of the concentrations of individual components to mixtures composed thereof described in Examples 3 and 4. Deglycosylation was performed by use of the Remove-iT® PNGase F kit (New England Biolabs, Cat #P0706S) which contains an amidase that cleaves between asparagine residues and the innermost GlcNAc of high mannose, hybrid and complex oligosaccharides in N-linked glycoproteins. First, 1 µl of Remove-iT PNGase F was added per 10 µg of each of the antibody variants and subsequently incubated overnight at 37° C. Next, 50 µl of Chitin Magnetic Beads (New England Biolabs, Cat #E8036S) were pipetted into a reaction vial and placed in a DynaMag™-2 magnetic separation rack (Invitrogen, Cat #12321D). After letting the magnet attract the chitin beads, the liquid supernatant was pipetted off and discarded. With the vial on the magnetic separation rack, the magnetic chitin beads were washed twice with 500 µl of PBS (Braun, Cat #182478082). The supernatant was pipetted off and discarded. Then, the degly-cosylated glycoprotein sample was added into the vial with magnetic chitin beads, vortexed thoroughly and the sample was rocked for 1 hour at RT. The vial was placed back on the magnetic separation rack, in order to allow the magnet to attract the chitin beads. Supernatant was pipetted off and transferred to a new vial. The supernatant in the new vial was placed back on the magnet to remove any remaining magnetic beads, and the supernatant was pipetted off for further use.

To determine the glycosylation status of the enzyme-treated antibody samples and controls, all samples were analyzed by mass spectrometry on an Orbitrap Q Exactive plus (Thermo Scientific). Antibody samples that were either enzymatically deglycosylated, mock-treated by omitting the PNGase F enzyme during the procedure, or control samples that were not treated, were brought to a concentration of 0.2 µg/mL in PBS (B. Braun, Cat #3623140). To 10 µL of each sample, 1 µL 1M DTT (Sigma, Cat #D9163-5G) was added and subsequently vortexed and shortly centrifuged. After incubating the samples for 1 hour at 37° C., all samples were vortexed and centrifuged shortly, before acquisition on the Orbitrap Q Exactive plus. Data were analyzed using Gene-data Expressionist software.

Figure 1A:
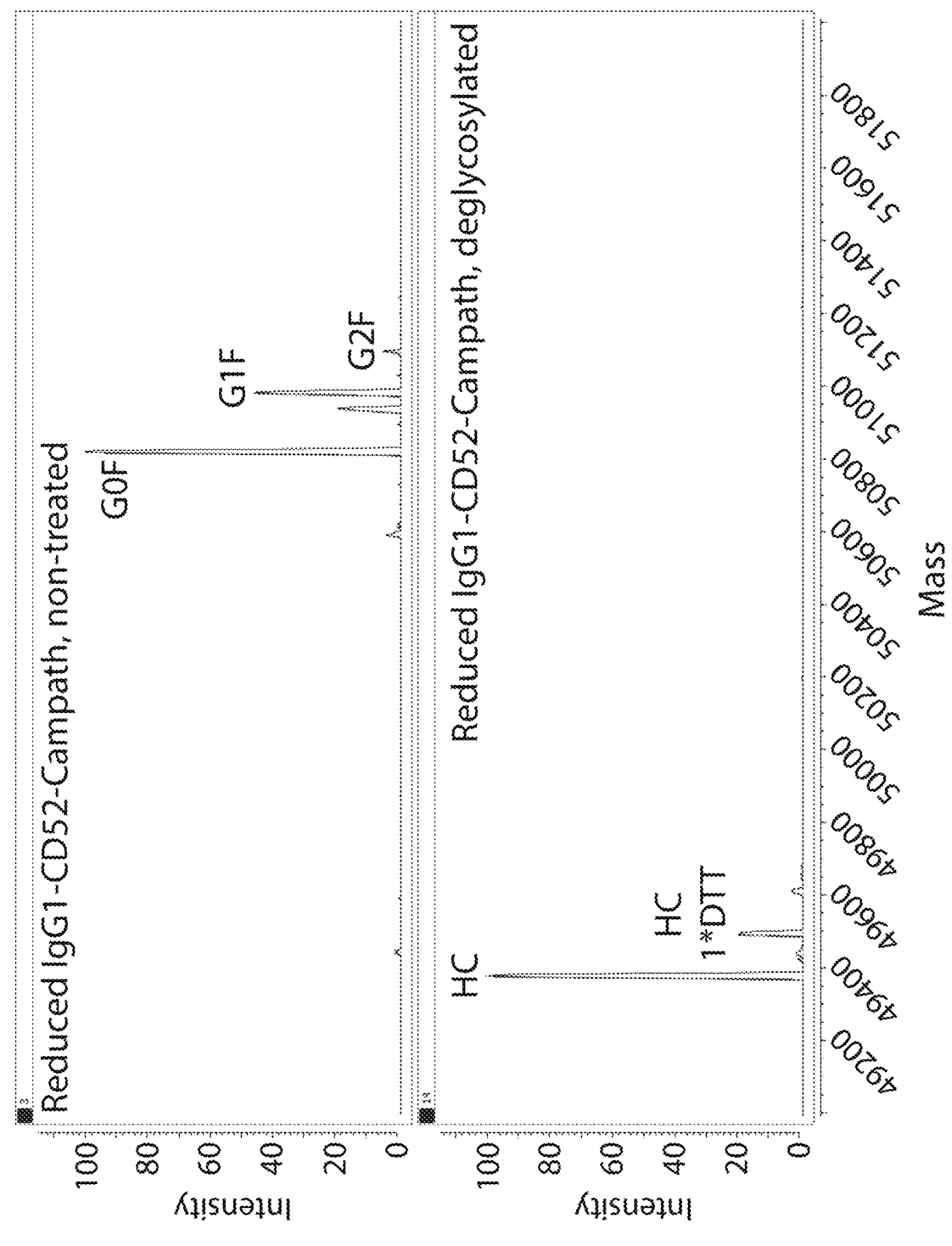
FIGS. 1A-1E shows that deglycosylated antibody variants harboring Fc-Fc interaction enhancing mutations retain potent CDC activity. Wien 133 cells were incubated with antibody concentration series in the presence of 20% NHS. The antibodies used in the experiments were either non-treated, enzymatically deglycosylated ('deg') or mock-treated ('trt'). Mass spectrometry spectra showing enzymatic deglycosylation efficiency for (FIG. 1A) wildtype IgG1-CAMPATH-1H, (FIG. 1B) IgG1-CAMPATH-1H-E430G-K439E and (FIG. 1C) IgG1-CAMPATH-1H-
Figure 1B:
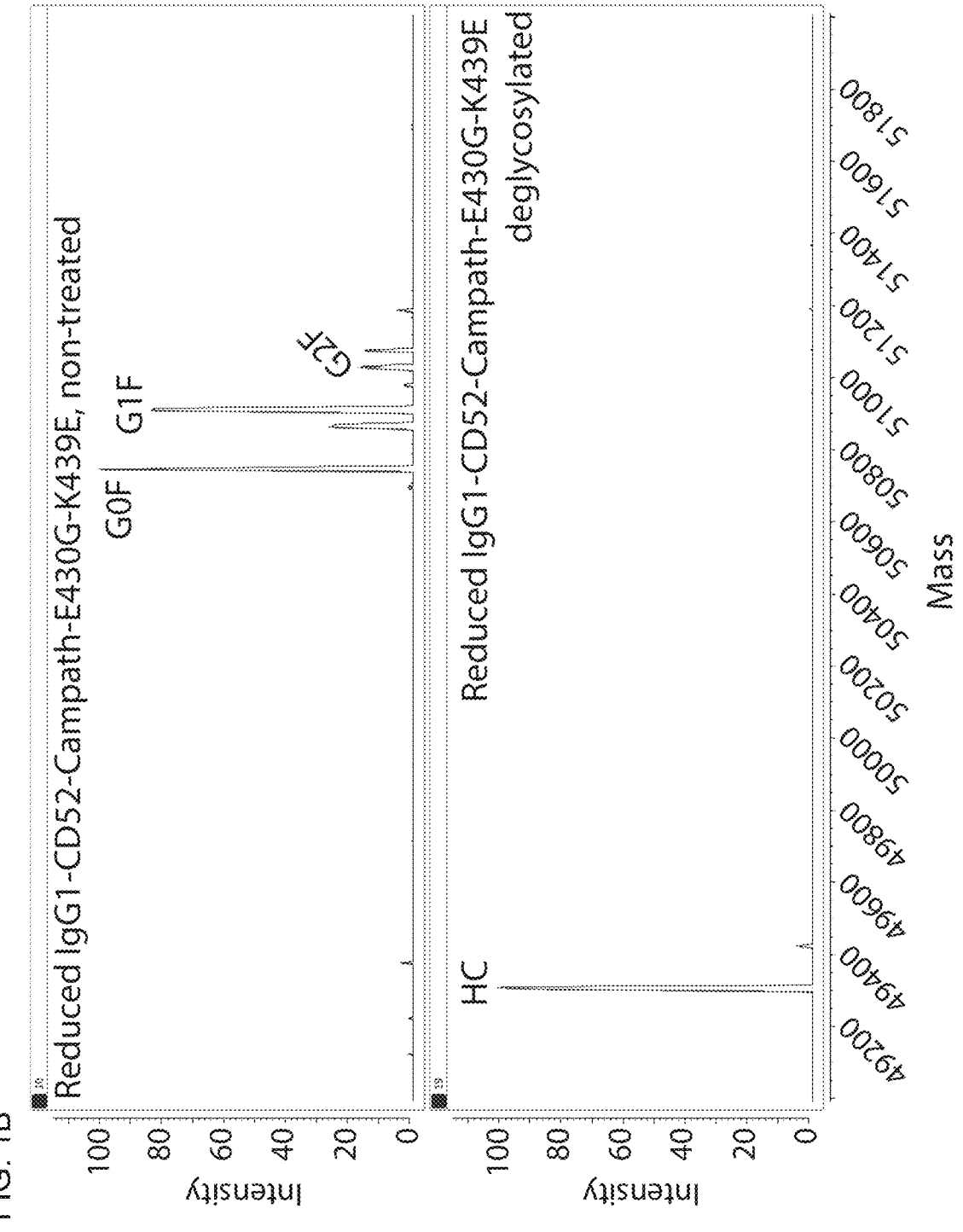
Figure 1C:
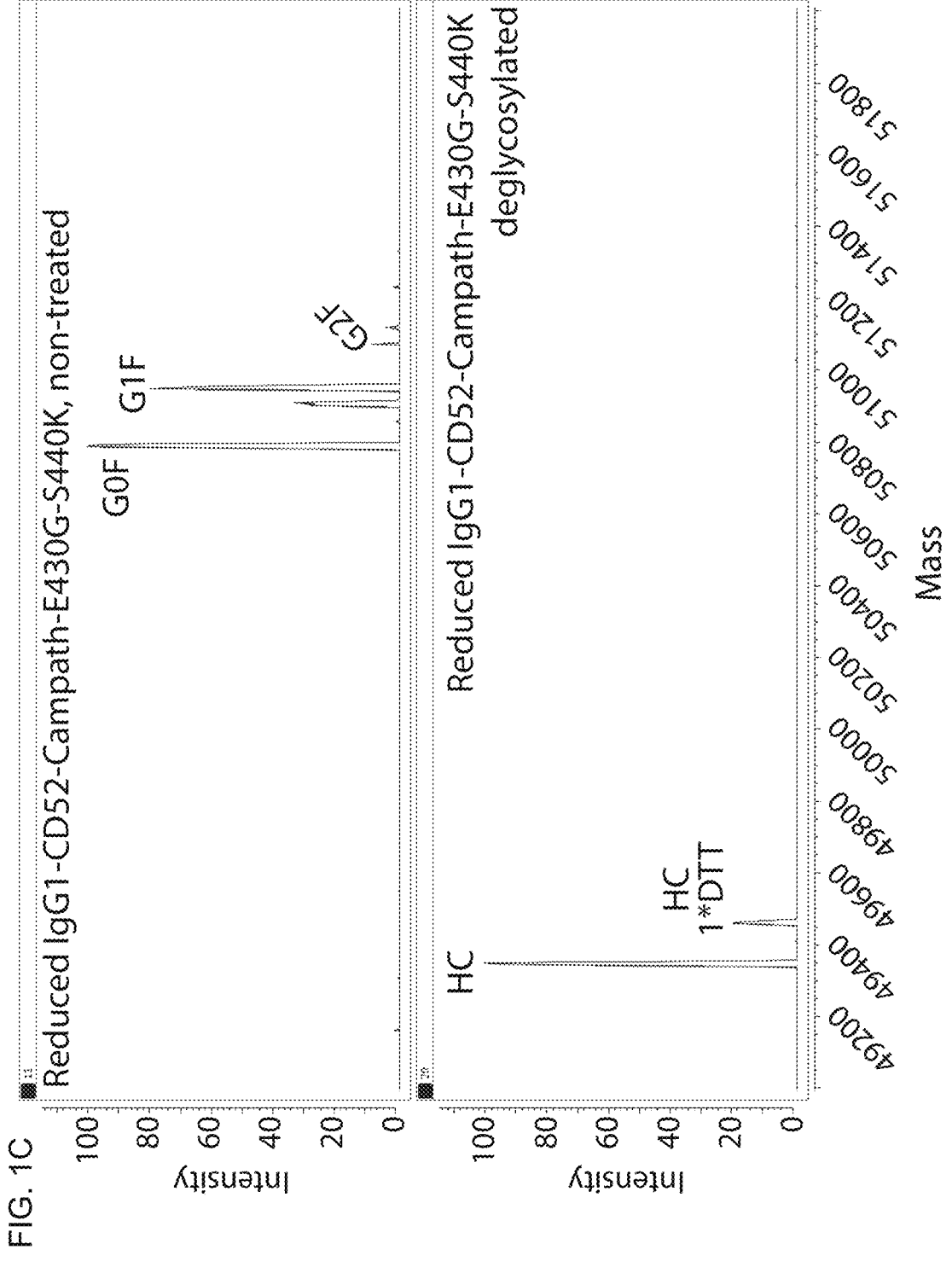
Figure 1D:
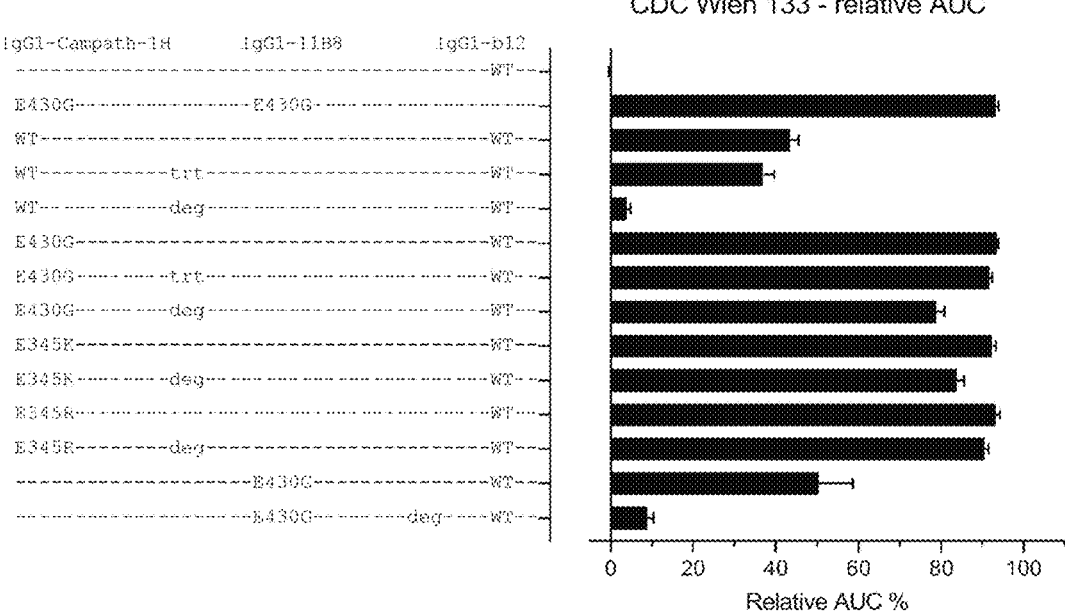

Mass spectrometry analysis of enzymatically deglycosy-lated and non-treated samples of wildtype IgG1-CAM-PATH-1IgG1-CAMPATH-1H-E430G-K439E (SEQ ID NO 57) and IgG1-CAMPATH-1H-E430G-S440K (SEQ ID NO 58) revealed highly efficient deglycosylation of the treated samples (<1% residual glycosylated sample; FIG. 1A, B, C). In addition, Table 2 provides a summary of the glycosylation status of IgG1-CAMPATH-1H and IgG1-11B8 antibody variants harboring Fc-Fc interaction enhancing and self-oligomerization inhibiting mutations that have undergone enzymatic deglycosylation and have been used in Examples 2, 3 and 4.

TABLE 2

Glycosylation status of antibody variants tested in
Examples 2, 3 and 4 upon enzymatic deglycoslation

| Antibody variant | Treated/non-treated | Glycosylation |
|---|---|---|
| IgG1-11B8-E430G | Non-treated | 100% |
| | Treated | <1% |
| IgG1-11B8-E430G-S440K | Non-treated | 100% |
| | Treated | <1% |
| IgG1-CD52-Campath-1H | Non-treated | 100% |
| | Mock-treated | 100% |
| | Treated | <1% |
| IgG1-CD52-Campath-1H-E345K | Non-treated | 100% |
| | Treated | <1% |
| IgG1-CD52-Campath-1H-E345R | Non-treated | 100% |
| | Treated | <1% |
| IgG1-CD52-Campath1H-E430G | Non-treated | 100% |
| | Mock-treated | 100% |
| | Treated | <1% |

TABLE 2-continued

Glycosylation status of antibody variants tested in
Examples 2, 3 and 4 upon enzymatic deglycoslation

| Antibody variant | Treated/non-treated | Glycosylation |
|---|---|---|
| IgG1-CD52-Campath-1H-E430G-K439E | Non-treated | 100% |
| | Treated | <1% |
| IgG1-CD52-Campath-1H-E430G-S440K | Non-treated | 100% |
| | Treated | <1% |

The deglycosylated samples were tested in a range of concentrations of purified antibodies (range 0.004-10.0 µg/mL final concentrations; 3-fold dilutions) in an in vitro CDC assay on Wien 133 cells with 20% NHS. For the CDC assay, $0.1 \times 10^6$ Wien 133 cells (kindly provided by Dr. Geoff Hale, BioAnaLab Limited, Oxford, UK), which co-express the CD20 and CD52 antigens, in RPMI (Lonza, Cat No. BE12-115F) with 0.2% bovine serum albumin (BSA; Roche, Cat No. 10735086001) were pre-incubated in poly-styrene round-bottom 96-well plates (Greiner Bio-One Cat #650101) with concentration series of purified antibodies in a total volume of 80 µL for 15 min on a shaker at RT. Next, 20 µL normal human serum (NHS; Sanquin, Reference No. M0008) was added as a source of complement and incubated in a 37° C. incubator for 45 min (20% final NHS concen-tration). The reaction was stopped by putting the plates on ice before pelleting the cells by centrifugation and replacing the supernatant replaced by 30 µL of 2 µg/mL propidium iodide solution (PI; Sigma Aldrich, Cat No. P4170). The number of PI-positive cells was determined by flow cytom-etry on an Intellicyt iQue screener (Westburg) and the percentage lysis was calculated as (number of PI-positive cells/total number of cells)×100%. As such, the CDC assay performed according to the methods described above will be referred to as the PI CDC assay from here on. The area under the dose-response curves of three experimental replicates was calculated using log-transformed concentrations in GraphPad PRISM. Relative areas under the curve (AUC) values were normalized to the AUC value measured for the non-binding negative control IgG1-b12 (0%) and the AUC value measured for the positive control mixture of IgG1-CAMPATH-1H-E430G+IgG1-11B8-E430G (100%).

Figure 1E:
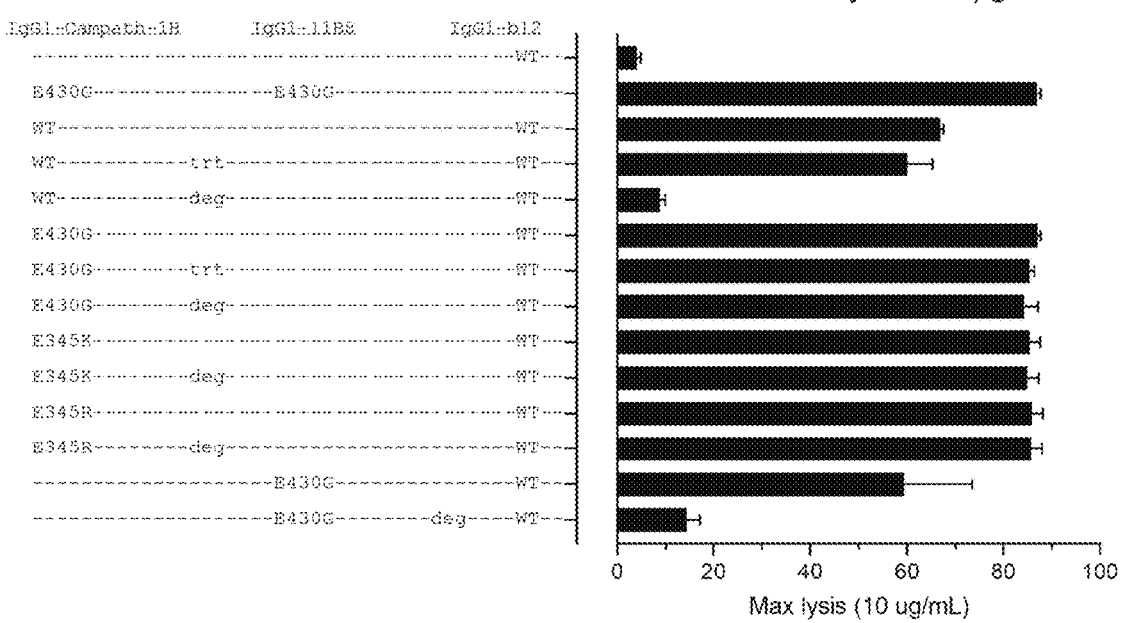

The wild-type IgG1-CAMPATH-1H antibody induced CDC on Wien 133 cells with intermediate efficacy (FIG. 1D) as compared to the positive control mixture of IgG1-CAM-PATH-1H-E430G+IgG1-11B8-E430G (both containing SEQ ID NO 54). Deglycosylation of wild-type IgG1-CAM-PATH-1H antibody (designated as 'deg' in the Figure) diminished CDC efficacy to background levels, while a (mock-treated) sample of the same antibody, which had undergone the same procedure without addition of the deglycosylating enzyme, showed comparable CDC efficacy to the non-treated antibody. Introduction of either of the Fc-Fc interaction enhancing mutations E430G, E345K (SEQ ID NO 55) or E345R (SEQ ID NO 56) strongly potentiated the CDC efficacy of IgG1-CAMPATH-1H. A mock treated IgG1-CAMPATH-1H-E430G antibody variant induced CDC with similar efficacy as the non-treated IgG1-CAM-PATH-1H-E430G antibody variant. Interestingly, deglyco-sylation only slightly impaired the CDC efficacy of the Fc-Fc interaction enhanced antibody variants IgG1-CAM-PATH-1H-E430G and IgG1-CAMPATH-1H-E345K. Degly-cosylation did not impact the CDC efficacy of IgG1-CAM-PATH-1H-E345R. At the highest IgG concentration tested, the deglycosylated IgG1-CAMPATH-1H variants harboring an Fc-Fc interaction enhancing mutation induced CDC with comparable efficacy as their glycosylated counterparts (FIG. 1E). In contrast, the CDC capacity of IgG1-11B8-E430G was strongly diminished after deglycosylation (FIG. 1), suggesting that the CDC potency of deglycosylated antibodies with Fc-Fc interaction enhancing mutations may be affected by to the antibody target- or epitope. Because wildtype IgG1-11B8 did not induce detectable CDC on Wien 133 cells, as shown in FIG. 4G, H (described in Example 5), the effect of deglycosylation on this antibody could not be assessed.

These data show that deglycosylation negatively impacted the CDC potency of the wild-type IgG1-CAM-PATH-1H antibody, while deglycosylation did not or only slightly impacted the CDC potency of IgG1-CAMPATH-1H antibody variants harboring Fc-Fc interaction enhancing mutations.

Figure 2A:
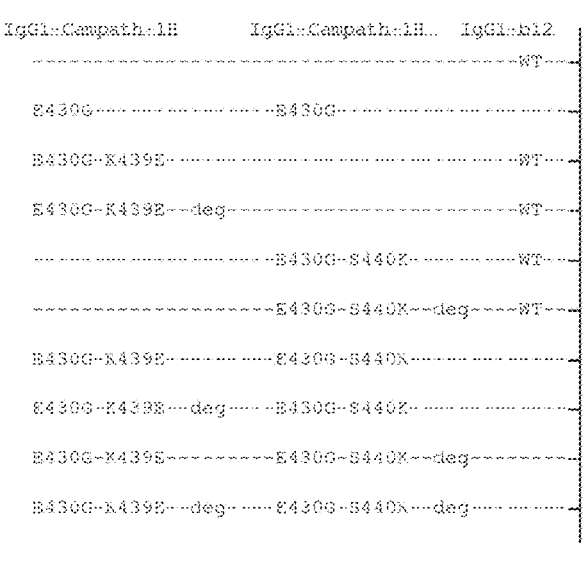
Figure 2A:
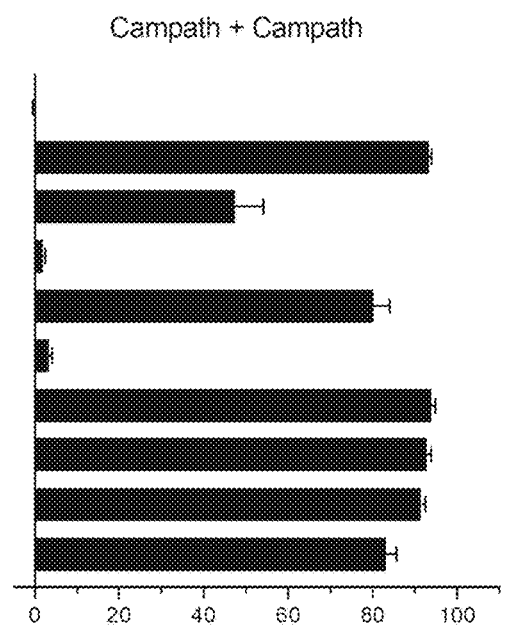

Example 3: Deglycosylation Increases Selectivity of Antibody Variants Containing an Fc-Fc Interaction Enhancing Mutation and a Self-Oligomerization Inhibiting Mutation When two antibodies containing Fc-Fc interaction enhancing mutations contain an additional self-oligomerization inhibiting mutation (either K439E or S440K), mixtures of such antibodies can induce lysis of cells expressing the two targets to which these antibodies are directed. While the activity of such co-dependent antibody combinations on cells expressing both targets was high, individual Campath-derived components still showed substantial activity, which may cause undesirable activity on cells expressing one of the two targets (FIG. 2A). Here, we tested whether the deglycosylation of anti-CD52 and anti-CD20 antibody variants that harbor an Fc-Fc interaction enhancing mutation in addition to a self-oligomerization inhibiting mutation could improve the selectivity of such co-dependent antibody mixtures by reducing the single agent CDC activity of the individual antibody variants.

Different mutations were introduced in the anti-CD52 IgG1-CAMPATH-1H antibody and anti-CD20 IgG1-11B8 antibody: E430G, E345K or E345R, which induce enhanced Fc-Fc interactions; K439E or S440K, which inhibit the formation of homo-hexameric antibody complexes through inhibition of the intermolecular Fc-Fc interactions and promote the formation of hetero-hexameric antibody complexes through cross-complementary Fc-Fc interactions. As controls, single antibodies were also mixed 1:1 with non-binding isotype control antibodies IgG1-b12 to enable direct comparison of the concentrations of individual components and mixtures composed thereof. Deglycosylation was performed by use of the Remove-iT® PNGase F kit (New England Biolabs), essentially as described in Example 2. The deglycosylated samples were tested in a range of concentrations of purified antibodies (range 0.0023-10.0 µg/mL final concentrations; 3-fold dilutions) in an in vitro CDC assay on Wien 133 cells with 20% NHS, essentially as described in Example 2. The percentage of cell lysis was calculated as (number of PI-positive cells/total number of cells)×100%. The area under the dose-response curves of three experimental replicates was calculated using log-transformed concentrations in GraphPad PRISM. Relative areas under the curve (AUC) values were normalized to the AUC value measured for the non-binding negative control IgG1-b12 (0%) and the AUC value measured for the positive control mixture of IgG1-CAMPATH-1H-E430G+IgG1-11B8-E430G (100%).

Figure 2B:
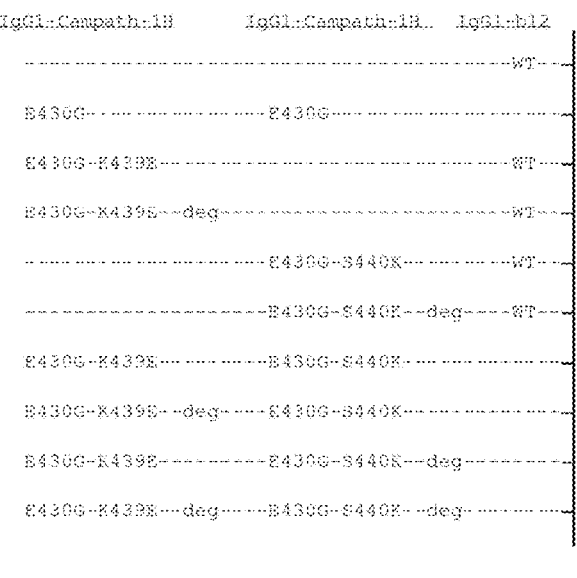
Figure 2B:
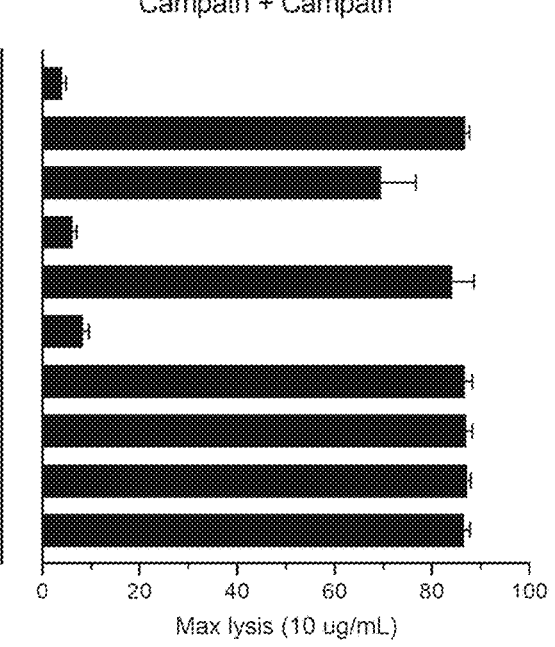

Strong CDC efficacy, close to the level induced by the positive control mixture IgG1-CAMPATH-1H-E430G+IgG1-11B8-E430G, was observed by the Fc-Fc enhanced antibody variant IgG1-CAMPATH-1H-E430G on Wien 133 cells, which express both CD20 and CD52 (FIG. 2A). Introduction of self-oligomerization inhibiting mutation K439E in IgG1-CAMPATH-1H-E430G only partially abrogated CDC efficacy as a single agent, while deglycosylation of this antibody variant fully abrogated the capacity to induce CDC. Antibody variant IgG1-CAMPATH-1H-E430G-S440K shows high residual activity when used as a single agent. Deglycosylation of this variant reduced CDC efficacy to only approximately 4% of the level induced by the glycosylated variant. Also at the highest concentration tested (10 µg/ml), the deglycosylated IgG1-CAMPATH-1H-E430G-S440K antibody variant induced CDC with an efficacy close to background levels, while the glycosylated counterpart induced CDC with an efficacy close to the level induced by glycosylated IgG1-CAMPATH-1H-E430G (FIG. 2B).

Mixtures of IgG1-CAMPATH-1H-E430G-K439E and IgG1-CAMPATH-1H-E430G-S440K recovered CDC efficacy to the level induced by IgG1-CAMPATH-1H-E430G. Surprisingly, for mixtures in which either the IgG1-CAMPATH-1H-E430G-K439E or IgG1-CAMPATH-1H-E430G-S440K were deglycosylated, no clear reduction in CDC efficacy was observed, even though single agent activity had been abolished. Furthermore, a mixture in which both antibody variants were deglycosylated only showed a slight reduction in CDC efficacy as compared with a mixture of the glycosylated variants, while at the highest concentration tested, the capacity to induce CDC by the mixture of deglycosylated IgG1-CAMPATH-1H antibody variants was comparable to that of the mixture of the glycosylated antibody variants (FIG. 2B).

Figure 2C:
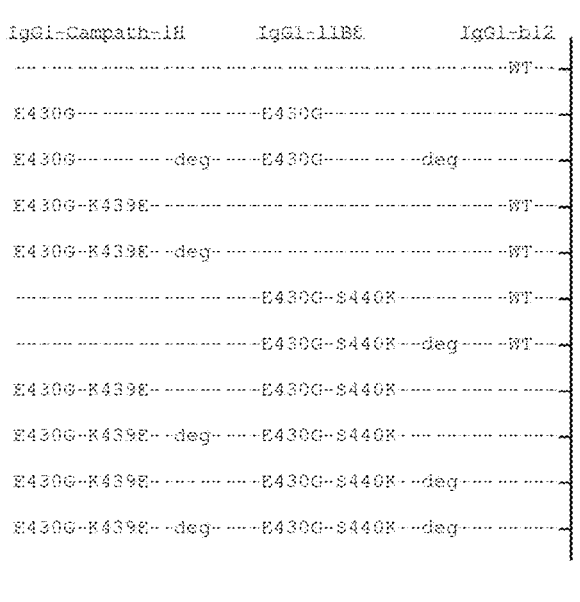
Figure 2C:
Figure 2D:
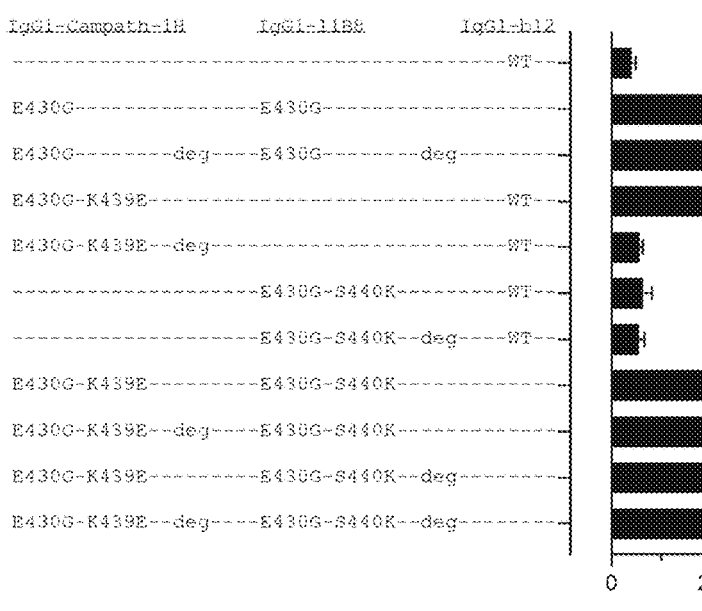
Figure 2D:
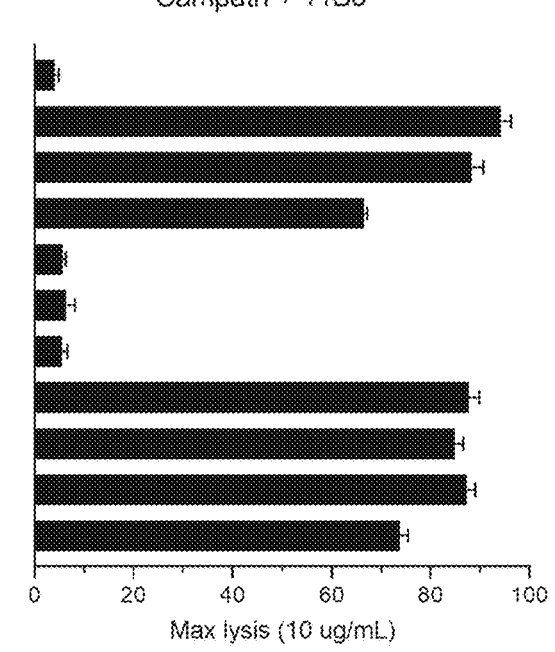

The impact of deglycosylation on CDC efficacy on Wien 133 cells was also assessed using mixtures of IgG1-CAMPATH-1H and IgG1-11B8 antibody variants harboring the E430G mutation and either of the K439E or S440K mutations. Strong CDC efficacy on Wien 133 cells was observed for the positive control mixture of IgG1-CAMPATH-1H-E430G and IgG1-11B8-E430G (FIG. 2C). A mixture in which both of these antibody variants had been deglycosylated showed a reduced capacity to induce CDC, to approximately 80% of the AUC measured for the glycosylated antibody variants. However, cell lysis induced by the deglycosylated antibody variants at the highest concentration tested was close to the level of the glycosylated variants (FIG. 2D). As previously seen in FIG. 2A, the introduction of self-oligomerization inhibiting mutation K439E in IgG1-CAMPATH-1H-E430G only partially abrogated CDC efficacy as a single agent, while deglycosylation of this antibody variant fully abrogated the capacity to induce CDC (FIG. 2C). Antibody variant IgG1-11B8 with the introduced mutations E430G and S440K did not induce CDC as a single agent, neither did the deglycosylated variant of this antibody. CDC efficacy could be recovered by a mixture of the co-dependent IgG1-CAMPATH-1H-E430G-K439E and IgG1-11B8-E430G-S440K antibody variants. Deglycosylation of either the IgG1-CAMPATH-1H-E430G-K439E or IgG1-11B8-E430G-S440K antibody variant in this mixture resulted in a 14% and 4% reduction in CDC efficacy, respectively, while the maximal cell lysis at the highest concentration tested in both cases was comparable to the mixture of glycosylated antibody variants (FIG. 2D). When both deglycosylated antibody variants were mixed 1:1, a reduction of approximately 35% in CDC efficacy as compared with a mixture of the glycosylated variants was noted (FIG. 2C). The maximal cell lysis at the highest concentration tested of the mixture containing both deglycosylated antibody variants was reduced from 87% lysis observed for the fully glycosylated mixture to approximately 74% lysis for the fully deglycosylated mixture (FIG. 2D).

Together, these data show that deglycosylation of IgG1-CAMPATH-1H antibody variants harboring the Fc-Fc interaction enhancing mutation E430G and self-oligomerization inhibiting mutations K439E or S440K reduces single agent CDC efficacy on Wien 133 cells. CDC efficacy could be recovered efficiently by mixing two deglycosylated co-dependent antibody variants at a level close to the CDC efficacy induced by a mixture of the glycosylated counterparts. While the single agent activity of both IgG1-CAMPATH-1H-E430G-K439E and IgG1-11B8-E430G-S440K could be fully abrogated by deglycosylation, a mixture of these antibody variants recovered potent CDC efficacy, albeit to a level lower than that of the less selective, glycosylated antibody counterparts.

Example 4: Recombinant Glycan Removal Increases Selectivity of Antibody Variants Containing an Fc-Fc Interaction Enhancing Mutation and a Self-Oligomerization Inhibiting Mutation In Example 3, it was described that enzymatic deglycosylation of antibody variants harboring an Fc-Fc interaction enhancing mutation and a self-oligomerization inhibiting mutation could reduce the single agent CDC activity, while CDC could (partially) be restored by mixing such deglycosylated antibody variants. The CH2 domain of IgG antibodies contains a highly conserved N-glycosylation site at amino acid position N297. Here, we tested whether the same effects as observed for enzymatically deglycosylated antibody variants could be observed for aglycosylated antibody variants containing the N297Q mutation.

Different mutations were introduced in the anti-CD52 IgG1-CAMPATH-1H antibody and anti-CD20 IgG1-11B8 antibody: E430G, E345K or E345R, which induce enhanced Fc-Fc interactions; K439E or S440K, which inhibit the formation of homo-hexameric antibody complexes through inhibition of the intermolecular Fc-Fc interactions and promote the formation of hetero-hexameric antibody complexes through cross-complementary Fc-Fc interactions; N297Q, which disrupts the N297 N-glycosylation consensus sequence (NX[S/T]), resulting in aglycosylated antibodies. As controls, single antibodies were also mixed 1:1 with non-binding isotype control antibodies IgG1-b12 to enable direct comparison of the concentrations of individual components and mixtures composed thereof. The aglycosylated samples were tested in a range of concentrations of purified antibodies (range 0.002-40 µg/mL final concentrations; 3-fold dilutions) in an in vitro CDC assay on Wien 133 cells with 20% NHS, essentially as described in Example 2. The percentage of cell lysis was calculated as (number of PI-positive cells/total number of cells)×100%. The area under the dose-response curves of three experimental replicates was calculated using log-transformed concentrations in GraphPad PRISM. Relative areas under the curve (AUC) values were normalized to the AUC value measured for non-binding negative control IgG1-b12 (0%) and the AUC value measured for the positive control mixture of IgG1-CAMPATH-1H-E430G+IgG1-11B8-E430G (100%).

Strong CDC efficacy on Wien 133 cells was observed by the positive control mixture of IgG1-CAMPATH-1H-E430G+IgG1-11B8-E430G (FIG. 3A). Similar to what is observed after enzymatic deglycosylation of antibody variant IgG1-CAMPATH-1H-E430G-K439E (Example 3), a variant of this antibody that is aglycosylated through the introduction of mutation N297Q (SEQ ID NO 61) lost its capacity to induce CDC as a single agent (FIG. 3A). A partial recovery of CDC, to approximately 65% of the level induced by the positive control mixture, could be attained by mixing IgG1-CAMPATH-1H-E430G-K439E-N297Q with IgG1-11B8-E430G-S440K. At the highest concentration tested, the latter mixture induced efficient cell lysis to approximately 97% of the level of cell lysis induced by the positive control mixture (FIG. 3B). CDC efficacy could also be partially restored, to approximately 45% of the level induced by the positive control mixture, by mixing the two aglycosylated antibody variants IgG1-CAMPATH-1H-E430G-K439E-N297Q and IgG1-11B8-E430G-S440K-N297Q (SEQ ID NO 62), while IgG1-11B8-E430G-S440K-N297Q showed no capacity to induce CDC (FIG. 3A). The mixture of IgG1-CAMPATH-1H-E430G-K439E-N297Q and IgG1-11B8-E430G-S440K-N297Q induced cell lysis with an efficiency of approximately 90% of the cell lysis level induced by the positive control mixture at the highest concentration tested (FIG. 3B).

Together, these data show that antibody variants of IgG1-CAMPATH-1H and IgG1-11B8 that are recombinantly agly-cosylated through the introduction of mutation N297Q, and also harbor an Fc-Fc interaction enhancing mutation and a self-oligomerization inhibiting mutation, loose their capacity to induce CDC on Wien 133 cells, similar to the loss of CDC efficacy upon enzymatic deglycosylation. CDC induced cell lysis could be recovered by mixing two co-dependent antibody variants harboring an Fc-Fc interaction enhancing and a self-oligomerization inhibiting mutation, when one, or both were aglycosylated.

Example 5: Fc-Fc Interaction Enhancing Mutations Promote CDC by Aglycosylated Anti-CD52 and Anti-CD20 Antibody Variants It was shown in Example 2 that enzymatic deglycosylation suppressed the CDC activity of wildtype anti-CD52 IgG1-CAMPATH-1H on Wien 133 cells. Here, we tested the effect on CDC activity by the introduction of different mutations at residues N297, and T299 in anti-CD52 IgG1-CAMPATH-1H and anti-CD20 IgG1-11B8 antibody variants harboring an Fc-Fc interaction enhancing mutation on Ramos and Wien 133 lymphoma cells.

Different mutations were introduced in the anti-CD52 IgG1-CAMPATH-1H antibody and anti-CD20 IgG1-11B8 antibody: E430G, E345K or E345R, which induce enhanced Fc-Fc interactions; N297A, N297G, N297Q, N297D, N297Y or T299A, which disrupt the N297 N-glycosylation consensus sequence (NX[S/T]), and yield aglycosylated antibodies. The purified antibody variants were tested in a range of concentrations (range 0.0088-40.0 µg/mL final concentrations, with 3.33-fold dilutions) on Ramos cells (N=3), which co-express the CD20 and CD52 antigens, in the presence of 10% NHS using an in vitro CellTiterGlo CDC assay detailed below, or on Wien 133 cells (N=3) in the presence of 20% NHS using the in vitro PI CDC assay described in Example 2.

For the CellTtiterGlo CDC assay, 50×10³ Ramos cells (ATCC, Cat #CRL-1596) in RPMI-1620 (Thermo, Cat #A1049101) with 10% heat inactivated FBS (Thermo, Cat #10082147) were pre-incubated in polystyrene opaque-walled flat-bottom 96-well plates (Corning, Cat #3917) with concentration series of purified antibodies in a total volume of 80 μL for 15 min on ice. Next, 20 μL normal human serum (diluted 1:1 in medium) (Complement Technologies, NHS Lot No. 42) was added as a source of complement and incubated in a 37° C. incubator for 45 min (10% final NHS concentration). CellTiterGlo® Reagent (Promega, cat #G7570) was added to all wells (50 μL per well) and mixed well using a pipette to induce cell lysis. After incubating the plates for 20 minutes in dark to stabilize the luminescence signal, luminescence was recorded on a microplate reader (Tecan Spark 20M). In the CellTiterGlo CDC assay, luminescence is detected by a luciferase-mediated conversion of luciferin that is dependent on ATP released from, and proportional to, the amount of viable cells remaining after incubation, upon addition of the CellTiterGlo reagent. Maximal cytotoxicity was determined using a positive control in which cells were lysed using a 0.02% Triton X-100 solution (10× Lysis Buffer from Thermo LDH Cytotoxicity Assay Kit Cat No. 88953, diluted to 1×), resulting in minimal remaining ATP and thus minimal luminescence values. Minimal cytotoxicity (negative control) was determined using cells incubated with serum in the absence of IgG, leading to maximal ATP remaining and thus maximal luminescence values. Luminescence values were converted to percentage cytotoxicity as follows: Cytotoxicity (%)=100%*(1−(luminescence of test sample—luminescence of Triton X-100 positive control)/(luminescence of no antibody negative control —luminescence of Triton X-100 positive control).

For both CellTiterGlo and PI CDC assays, the relative areas under dose-response curves with log transformed concentrations (AUC values) were normalized to the AUC value measured for the non-binding negative control IgG1-b12 (0%) and the AUC value measured for the positive control IgG1-CAMPATH-1H-E430G (100%).

Figure 4A:
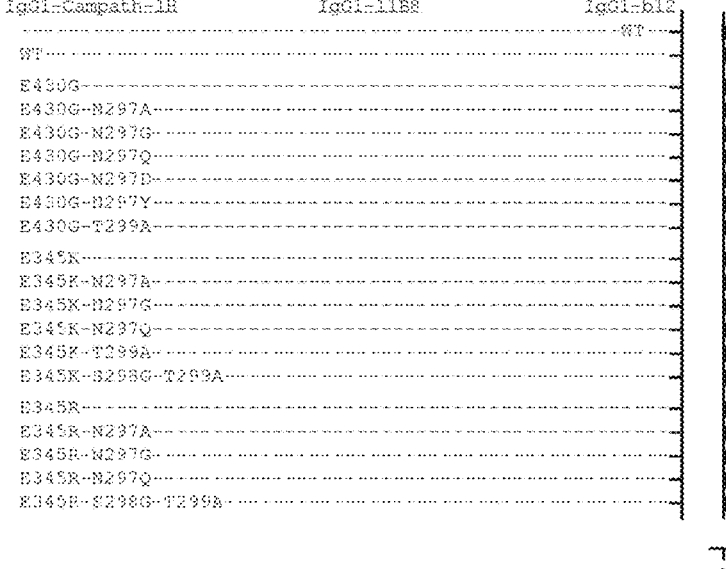
Figure 4A:
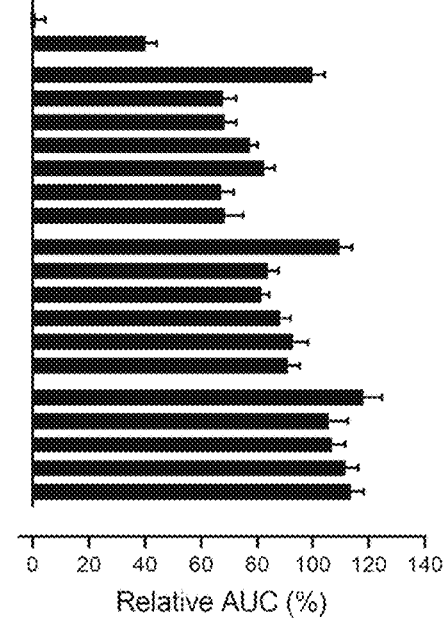
Figure 4B:
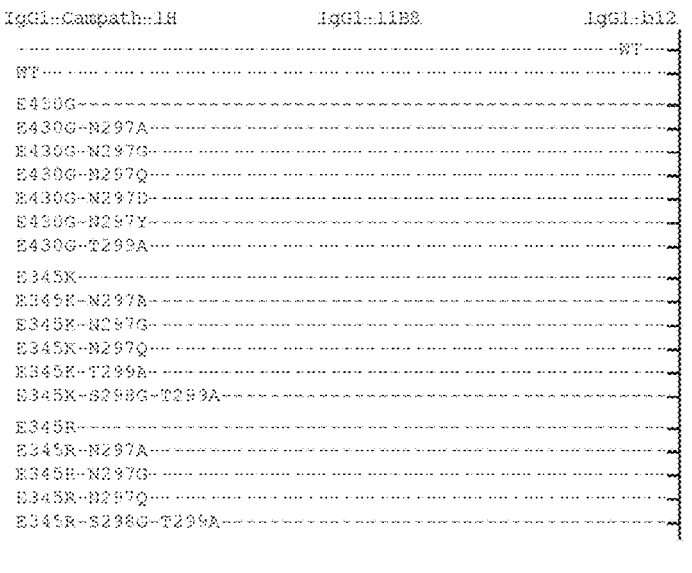
Figure 4B:
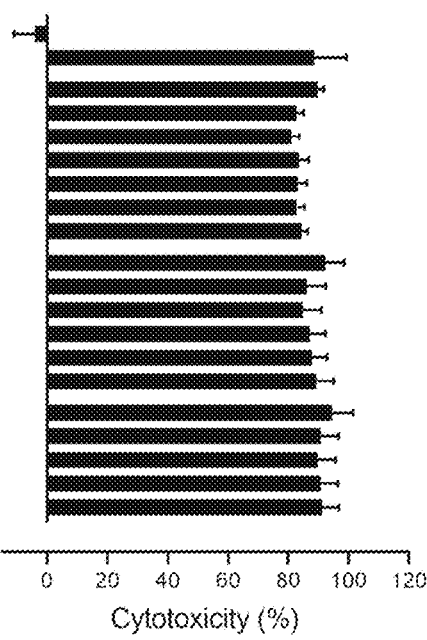

Wildtype IgG1-CAMPATH-1H antibody induced efficient CDC of Ramos cells, which was further potentiated by the introduction of either of the E430G, E345K or E345R mutations (FIG. 4A). Although the introduction of any of the glycosylation site mutations N297A (E430G-N297A: SEQ ID NO 29; E345K-N297A: SEQ ID NO 35; E345R-N297A: SEQ ID NO 39), N297G (E430G-N297G: SEQ ID NO 30; E345K-N297G: SEQ ID NO 36; E345R-N297G: SEQ ID NO 40), N297Q (E430G-N297Q: SEQ ID NO 31; E345K-N297Q: SEQ ID NO 37; E345R-N297Q: SEQ ID NO 41), N297D (E430G-N297D: SEQ ID NO 32), N297Y (E430G-N297Y: SEQ ID NO 33) or T299A (E430G-T299A: SEQ ID NO 34; E345K-T299A: SEQ ID NO 38) in IgG1-CAMPATH-1H antibody variants with Fc-Fc interaction enhancing mutations resulted in a slight suppression of CDC activity, all aglycosylated variants retained potent CDC activity. At the highest antibody concentration tested (40 μg/mL), all tested IgG1-CAMPATH-1H antibody variants induced similar levels of highly efficient CDC activity (FIG. 4B).

Figures 4C, 4D:
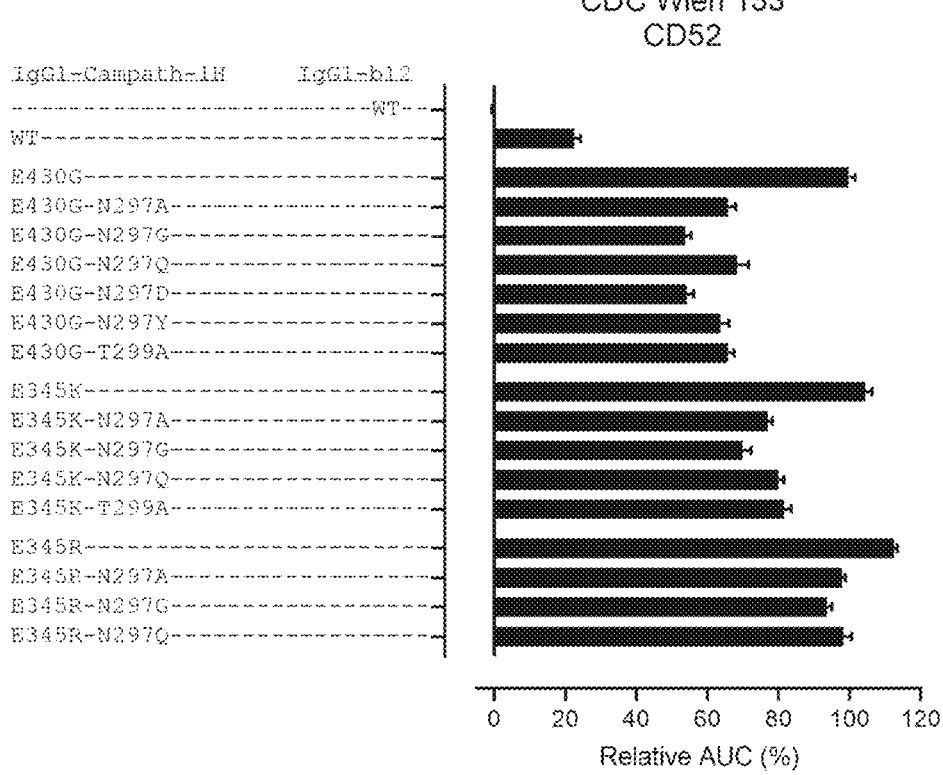

Although wildtype IgG1-CAMPATH-1H induced CDC on Wien 133 cells with lower efficiency than on Ramos cells, the introduction of aglycosylating mutations in IgG1-CAMPATH-1H antibody variants harboring an Fc-Fc interaction enhancing mutation led to similar results on Wien 133 cells as compared to Ramos cells. In short, introduction of an Fc-Fc interaction enhancing mutation strongly potentiated the CDC activity of IgG1-CAMPATH-1H (FIG. 4C). Aglycosylating mutations N297A, N297G, N297Q, N297D, N297Y or T299A only partially suppressed the CDC activity as measured through the AUC of the dose response curve, while the CDC activity of the aglycosylated variants was similar to the glycosylated counterparts at the highest antibody concentration tested (FIG. 4D). In particular, the E345R-containing antibody variants were least suppressed in their CDC activity upon the introduction of either of the aglycosylating mutations.

Figure 4E:
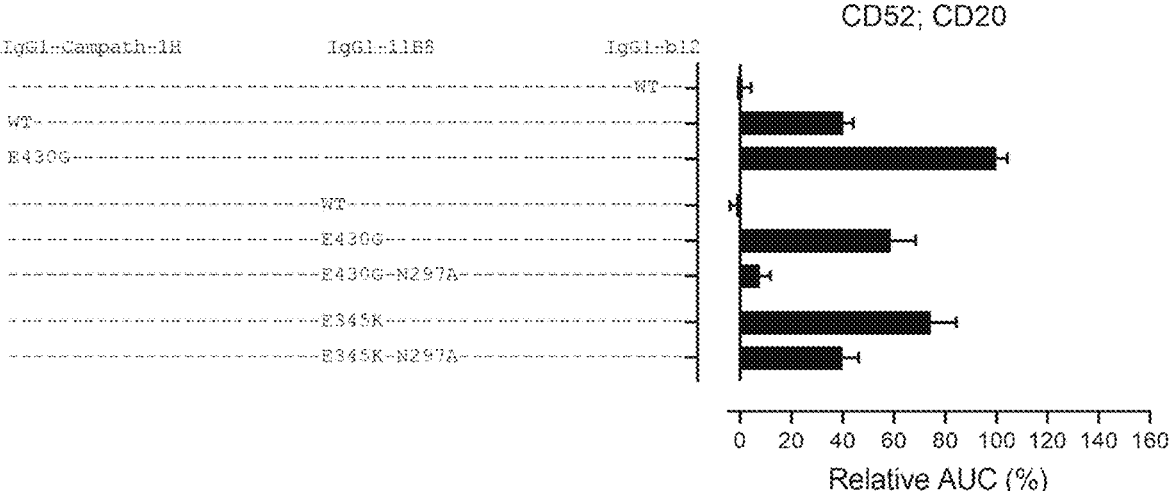
Figure 4F:
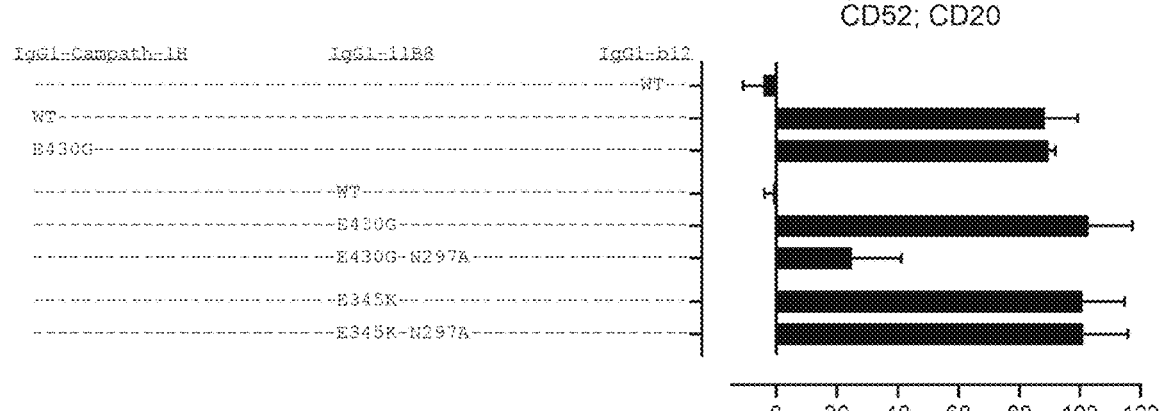
Figure 4G:
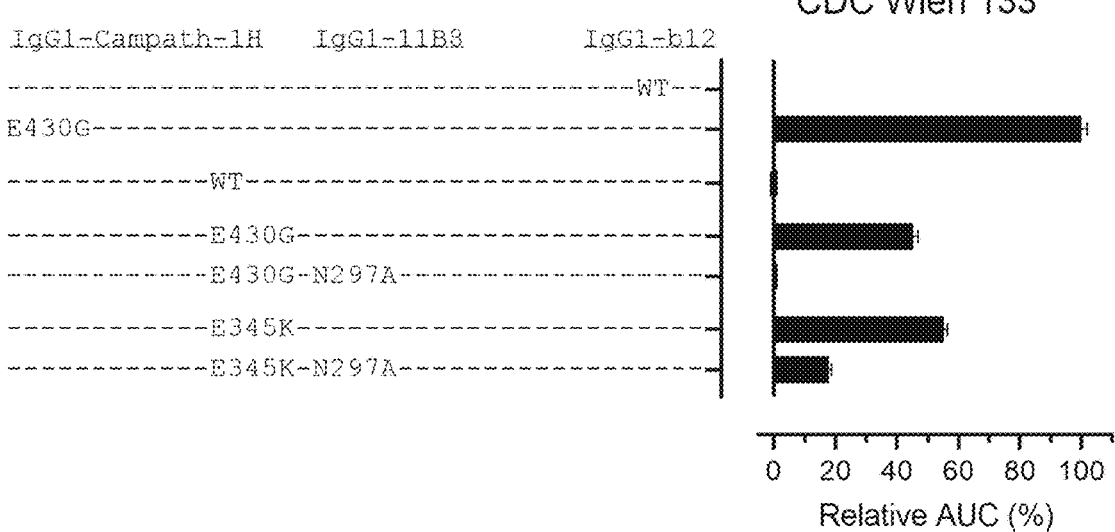

Wildtype IgG1-11B8 antibody did not induce detectable CDC of Ramos cells (FIG. 4E). Introduction of either the E430G or E345K mutation resulted in efficient CDC. Similar to the enzymatic deglycosylation described in Example 2, introduction of aglycosylating mutation N297A strongly suppressed the CDC activity of IgG1-11B8-E430G. In contrast, introduction of mutation N297A in IgG1-11B8-E345K only partially suppressed CDC activity. While the maximal cell lysis induced by IgG1-11B8-E430G-N297A at 40 μg/mL antibody concentration was considerably lower than the cell lysis induced by IgG1-11B8-E430G, the IgG1-11B8-E345K-N297A induced highly efficient CDC at the highest antibody concentration tested and was comparable to the level induced by IgG1-11B8-E345K (FIG. 4F).

Figure 4H:
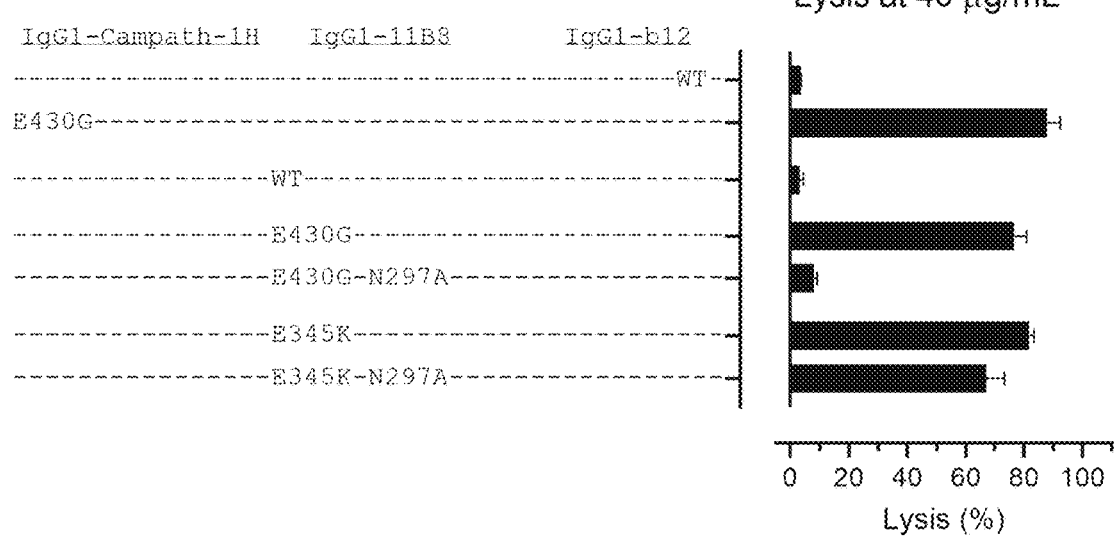
Figure 5A:
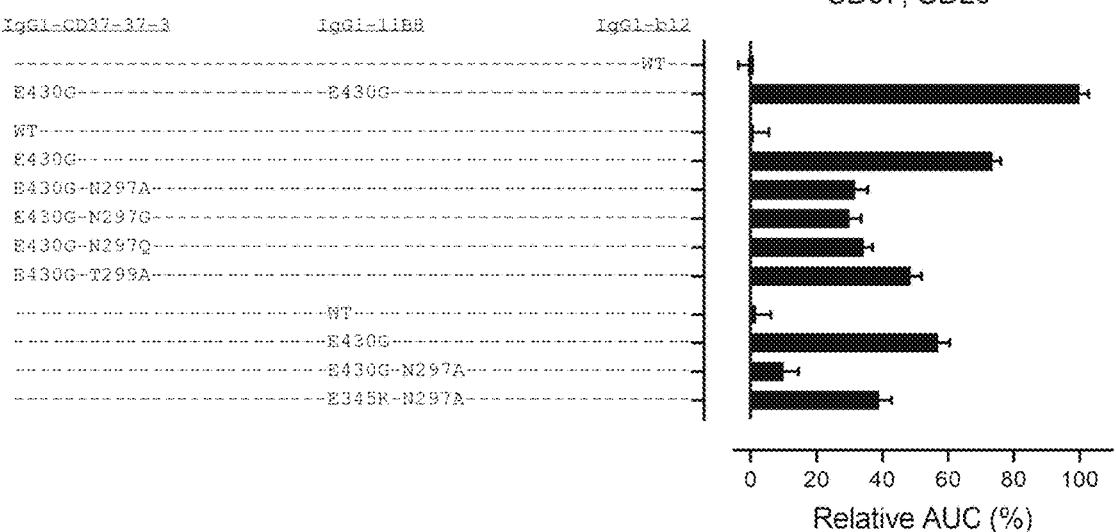
Figure 5B:
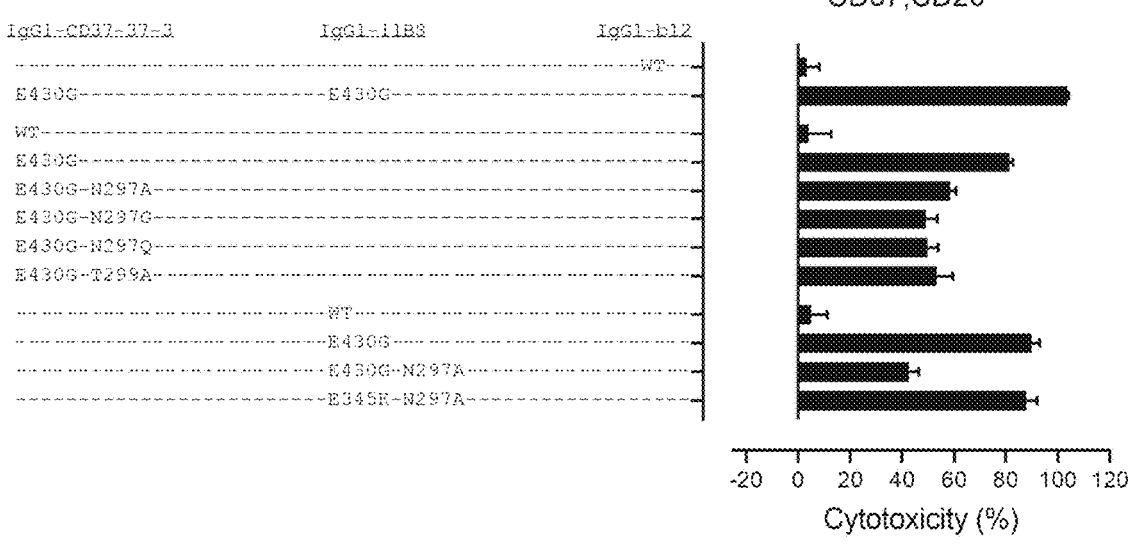
Figure 5C:
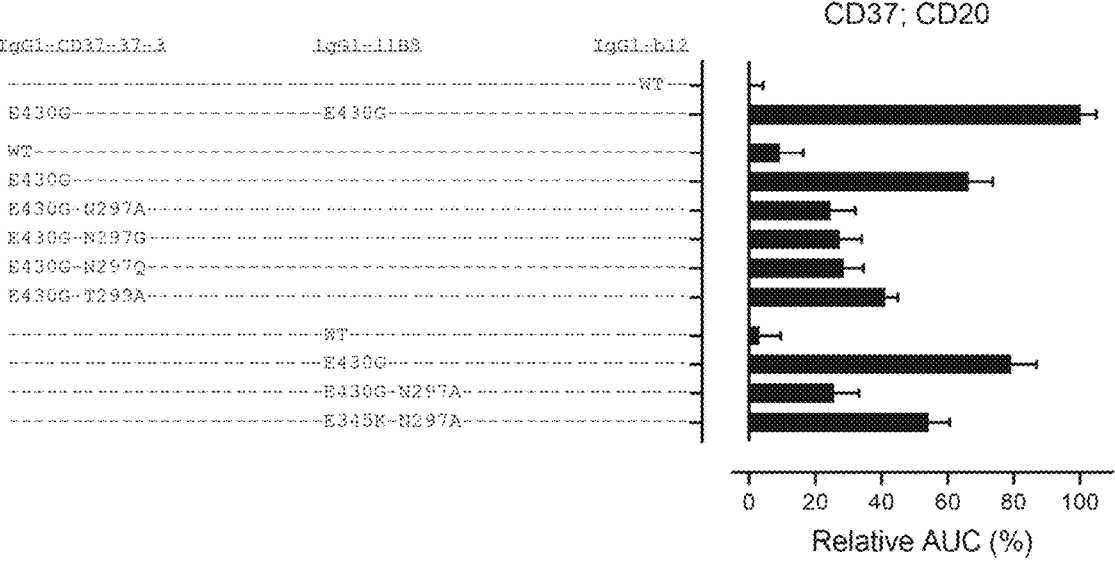
Figure 5D:
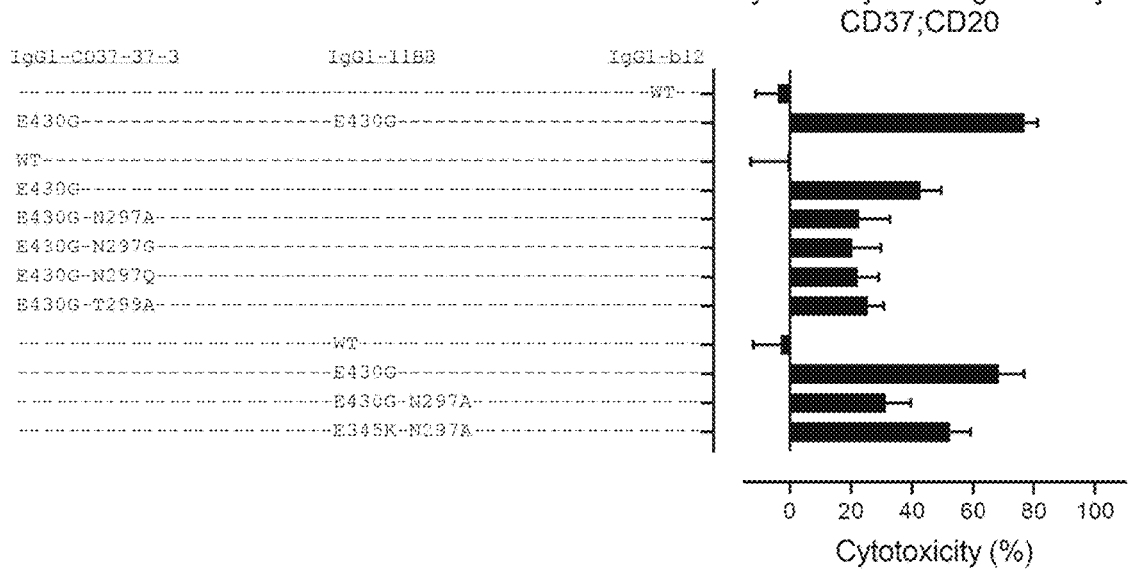

On Wien 133 cells, wildtype IgG1-11B8 did also not induce CDC at detectable levels (FIG. 4G). Introduction of the E430G or E345K mutation resulted in partial CDC of Wien 133 cells, which was fully abrogated upon the additional introduction of aglycosylating mutation N297A in IgG1-CAMPATH-1H-E430G, also at the highest antibody concentration tested (FIG. 4H). Introduction of N297A in IgG1-CAMPATH-1H-E345K resulted in a partial abrogation of CDC activity (FIG. 4G, H).

Together, these data show that IgG1-CAMPATH-1H antibody variants harboring an Fc-Fc interaction enhancing mutation retain high CDC activity on Ramos and Wien 133 cells upon the introduction of mutations preventing antibody glycosylation. While the introduction of glycosylation-inhibiting mutation N297A suppressed the CDC activity of IgG1-11B8-E430G, IgG1-11B8-E345K-N297A showed CDC activity comparable to IgG1-11B8-E345K at the highest concentration tested on the Ramos and Wien 133 cell lines.

Example 6: Aglycosylated Antibody Variants with Fc-Fc Interaction Mutations Retain Partial CDC Activity on Raji and Daudi Cells In Example 5, it was shown that aglycosylated IgG1-CAMPATH-1H and IgG1-11B8 antibody variants harboring Fc-Fc interaction enhancing mutations retained potent CDC activity on Ramos and Wien 133 cells. Here, we tested whether mutations that prevent glycosylation affected the CDC potency on Raji and Daudi cells of IgG1-CD37-37-3 and IgG1-11B8 antibody variants harboring Fc-Fc interaction enhancing mutations.

Different mutations were introduced in the anti-CD37 antibody IgG1-CD37-37-3 and anti-CD20 antibody IgG1-11B8: E430G or E345K, which induce enhanced Fc-Fc interactions; N297A, N297G, N297Q, or T299A, which disrupt the N297 N-glycosylation consensus sequence (NX [S/T]) and yield aglycosylated antibodies. The purified antibody variants were tested in a range of concentrations (range 0.0087-40.0 μg/mL final concentrations; 3.33-fold dilutions) in an in vitro CellTiterGlo CDC assay on Daudi (N=2) and Raji (N=3), which both express the CD20 and CD37 antigens, cells with 10% NHS, essentially as described in Example 5. Maximal cytotoxicity was determined using positive control 0.02% Triton X-100 solution (10× Lysis Buffer from Thermo LDH Cytotoxicity Assay Kit Cat No. 88953). Minimal cytotoxicity (negative control) was determined using cells incubated with serum in the absence of IgG. Luminescence values were converted to percentage cytotoxicity as follows: Cytotoxicity (%)=100%*(1−(luminescence of test sample —luminescence of Triton X-100 positive control)/(luminescence of no antibody negative control—luminescence of Triton X-100 positive control). The relative areas under dose-response curves with log transformed concentrations (AUC values) were normalized to the AUC value measured for the non-binding negative control IgG1-b12 (0%) and the AUC value measured for the positive control mixture of IgG1-CD37-37-3-E430G and IgG1-11B8-E430G.

Wildtype IgG1-CD37-37-3 and IgG1-11B8 showed no CDC activity against Daudi cells (FIG. 4A). Introduction of the Fc-Fc interaction enhancing E430G mutation enabled these antibody variants to efficiently induce CDC when used separately, and when combined. Disruption of the N297 glycosylation site by N297A, N297G, N297Q, or T299A mutations in antibody IgG1-CD37-37-3-E430G lowered CDC potency to variable levels. At the highest antibody concentration, aglycosylated IgG1-CD37-37-3-E430G variants retained substantial CDC activity, and all induced more CDC of Daudi cells than wild type IgG1-CD37-37-3 (FIG. 4B). Introduction of the N297A mutation in IgG1-11B8-E430G partially lowered its CDC potency, and partially inhibited Daudi cell lysis at the highest antibody concentration. An aglycosylated variant of IgG1-11B8 with another Fc-Fc interaction enhancing mutation (IgG1-11B8-E345K-N297A) killed Daudi cells as well, with a slightly higher efficiency than IgG1-11B8-E430G-N297A and a maximal cytotoxicity similar to IgG1-11B8-E430G.

Similar results were obtained in CDC assays on Raji cells (FIG. 4C-D). Wildtype IgG1-CD37-37-3 and IgG1-11B8 showed little to no CDC activity against Raji cells, but introduction of the Fc-Fc interaction enhancing E430G mutation in these variants resulted in efficient CDC (FIG. 4C). Disruption of the N297 glycosylation site by N297A, N297G, N297Q, or T299A mutations in IgG1-CD37-37-3-E430G lowered the CDC potential of the antibody variant, but retained substantial Raji cell lysis at the highest antibody concentration (FIG. 4D), which exceeded the lysis observed for wild type IgG1-CD37-37-3. Introduction of the N297A mutation in IgG1-11B8-E430G suppressed its CDC potency. An aglycosylated variant of IgG1-11B8 with a different Fc-Fc interaction enhancing mutation (IgG1-11B8-E345K-N297A) killed Raji cells with higher efficiency than IgG1-11B8-E430G-N297A. These data show that preventing glycosylation by modifications of the N-glycosylation consensus sequence only partially inhibited the CDC potency of IgG1-CD37-37-3 and IgG1-11B8 antibody variants with Fc-Fc interaction enhancing mutations.

Example 7: Disruption of the N297 Glycosylation Site Improves the Selectivity of CD52-Targeting Antibody Variants with Fc-Fc Interaction Enhancing and Self-Oligomerization Inhibiting Mutations In Example 4, we showed that the N297Q glycosylation site mutation in the CH2 domain of IgG antibodies resulted in improved selectivity of antibody variants with E430G Fc-Fc interaction enhancing and K439E/S440K self-oligomerization inhibiting mutations. Here, we tested whether this improved selectivity could also be observed with glycosylation site mutations (N297A, N297Q) in antibody variants bearing various Fc-Fc interaction enhancing and self-oligomerization inhibiting mutations.

Different mutations were introduced in the anti-CD52 IgG1-CAMPATH-1H antibody: E430G, E345K or E345R, which induce enhanced Fc-Fc interactions; K439E or S440K, which inhibit the formation of homo-hexameric antibody complexes through inhibition of intermolecular Fc-Fc interactions, and which promote the formation of hetero-hexameric antibody complexes through cross-complementary Fc-Fc interactions; N297A, N297Q, or S298G-T299A, which disrupt the N297 N-glycosylation consensus sequence (NX[S/T]) and yield aglycosylated antibodies. As controls, single antibodies were mixed 1:1 with non-binding isotype IgG1-b12 control antibodies to enable direct comparison of the concentrations of individual components and mixtures composed thereof. The purified antibody variants were tested in a range of concentrations (range 0.0088-40.0 µg/mL final concentrations, with 3.33-fold dilutions for the Ramos cells; 0.0018-40.0 µg/mL final concentrations, with 3-fold dilutions for the Wien 133 cells) in an in vitro CellTiterGlo CDC assay on Ramos cells (N=3) with 10% NHS, essentially as described in Example 5, or using a PI CDC assay on Wien 133 cells (N=3) with 20% NHS, essentially as described in Example 2. For both CellTiterGlo and PI CDC assays, the relative areas under dose-response curves with log transformed concentrations (AUC values) were normalized to the AUC value measured for the non-binding negative control IgG1-b12 (0%) and the AUC value measured for positive control IgG1-CAMPATH-1H-E430G.

Figure 6A:
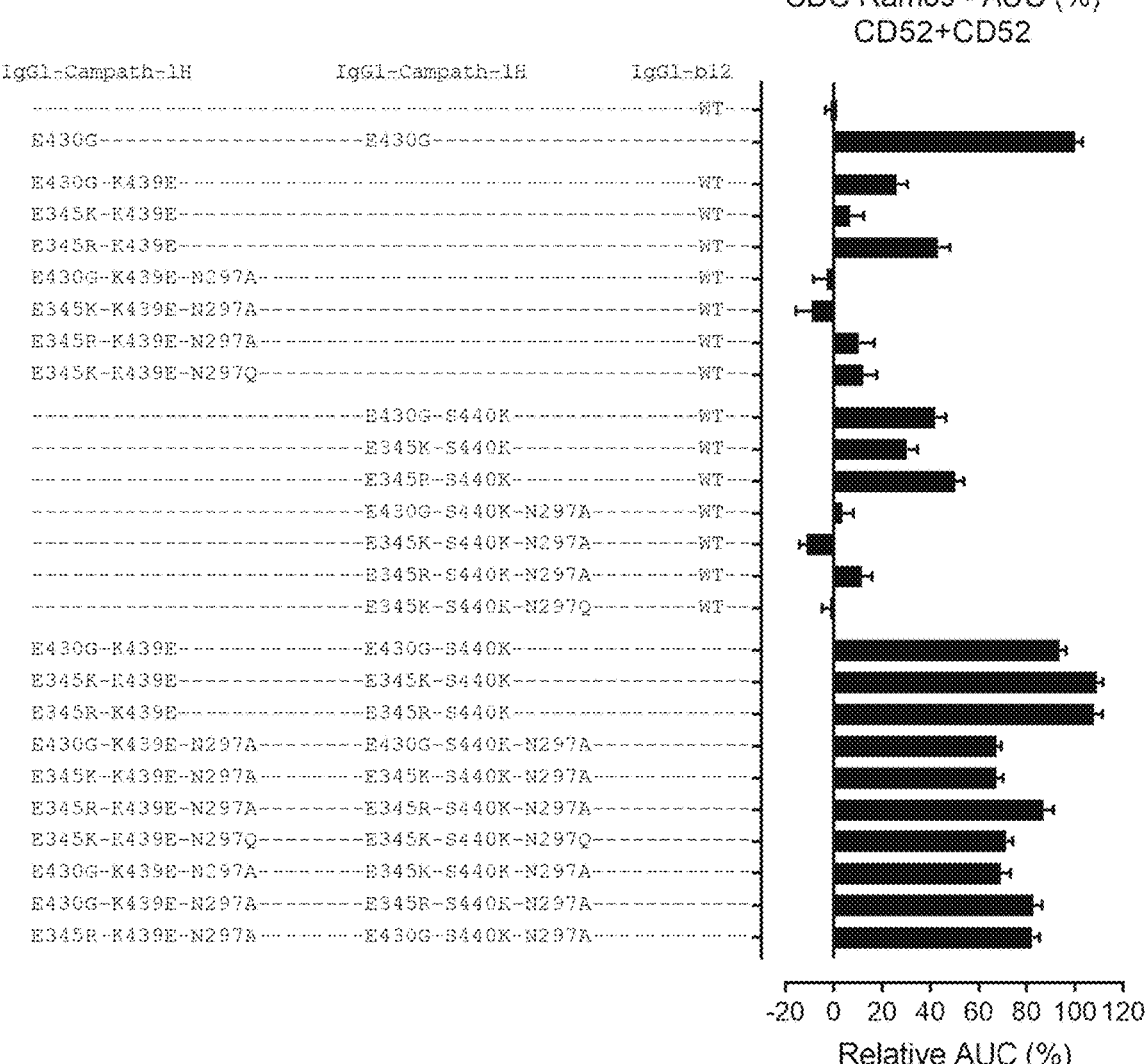
Figure 6B:
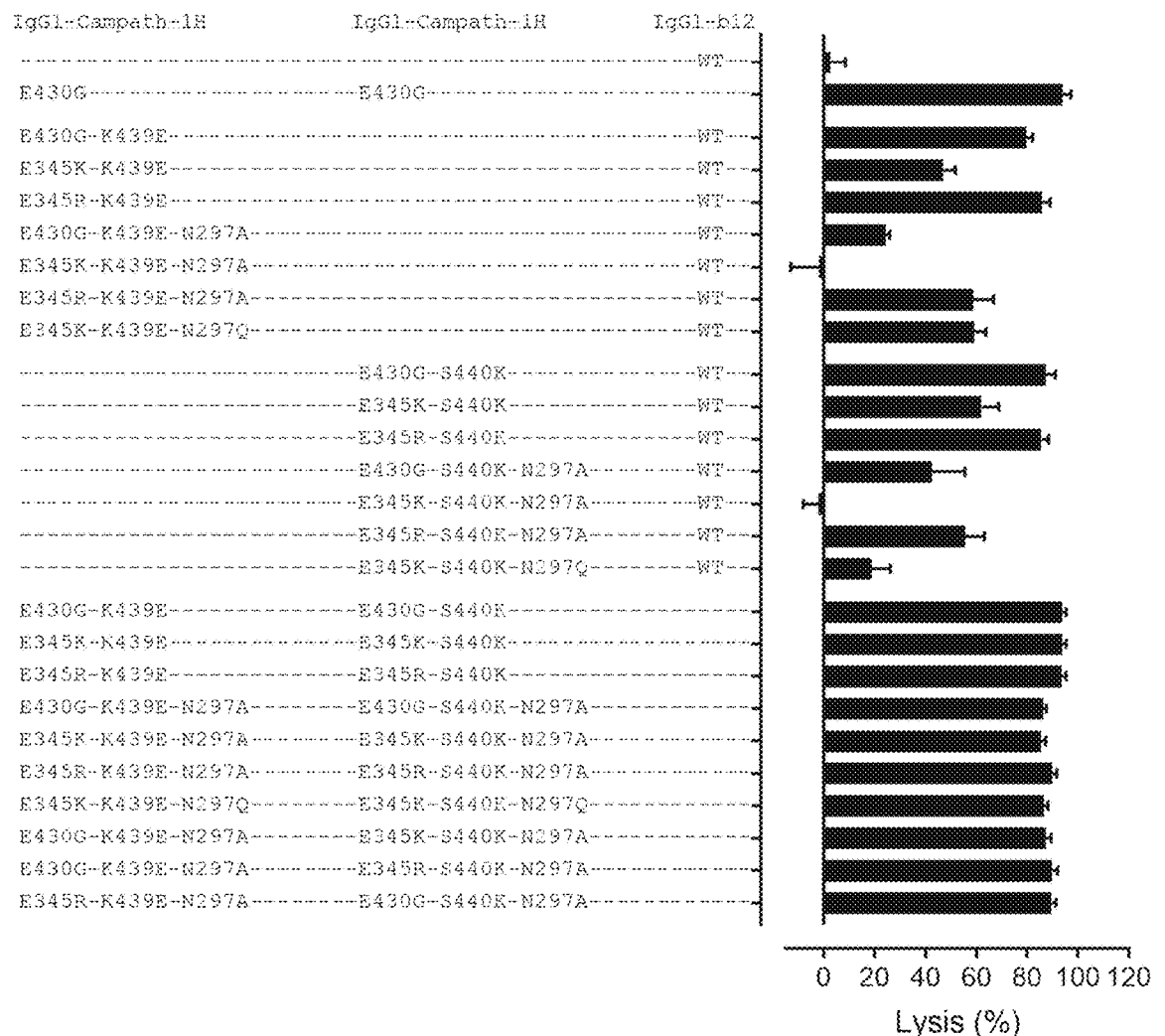

Introduction of the K439E/S440K self-oligomerization inhibiting mutations to the Fc-Fc interaction enhanced IgG1-CAMPATH-1H-E430G antibody variant reduced, but did not fully block, its CDC potency on Ramos cells (FIG. 6A). At the highest antibody concentration, the K439E and S440K variants displayed only slightly reduced CDC-mediated lysis (FIG. 6B), indicating substantial single agent activity. Similarly, IgG1-CAMPATH-1H antibody variants bearing the Fc-Fc interaction enhancing E345K or E345R mutation and the K439E (E345K-K439E: SEQ ID NO 50; E345R-K439E: SEQ ID NO 52) or S440K (E345K-S440K: SEQ ID NO 51; E345R-S440K: SEQ ID NO 53) self-oligomerization inhibiting mutation still demonstrated single agent activity, particularly at the highest antibody concentration tested. Disruption of the N297 glycosylation site via an N297A mutation (E430G-K439E-N297A: SEQ ID NO 42; E430G-S440K-N297A: SEQ ID NO 43; E345K-K439E-N297A: SEQ ID NO 44; E345K-S440K-N297A: SEQ ID NO 45; E345R-K439E-N297A: SEQ ID NO 46; E345R-S440K-N297A: SEQ ID NO 47), however, nearly fully inhibited the CDC potency of these antibody variants, and partially or fully inhibited CDC-mediated lysis of Ramos cells at the highest antibody concentration. Introduction of mutation N297Q reduced the single agent activity of IgG1-CAMPATH-1H-IgG1-CAMPATH-1H-E345K-S440K (SEQ ID NO 49), while introduction of the same mutation to E345K-K439E (SEQ ID NO 48) did not.

An almost full restoration of CDC potency (approximately 93%-109% of the activity of positive control IgG1-CAMPATH-1H-E430G was observed upon combining the complementary IgG1-CAMPATH-1H-K439E and -S440K antibody variants bearing the E430G, E345K, or E345R Fc-Fc interaction enhancing mutations. Disruption of the glycosylation site (N297A) in these antibody variants slightly reduced their CDC potency when mixed (approximately 67%-87% as compared to the positive control) and did not substantially affect the levels of lysis at the highest antibody concentration. Efficient CDC was also observed upon combining IgG1-CAMPATH-1H-E345K-K439E and IgG1-CAMPATH-1H-E345K-S440K antibody variants carrying the N297Q mutation.

When IgG1-CAMPATH-1H-K439E-N297A and IgG1-CAMPATH-1H-S440K-N297A antibody variants carrying two different Fc-Fc interaction enhancing (E430G, E345K, or E345R) mutations were combined, the resulting CDC was comparable to the level of CDC induced by two of these antibody variants carrying the same Fc-Fc interaction enhancing mutation, suggesting that the Fc-Fc enhancing mutations can be used interchangeably in the context of aglycosylated antibody variants.

Figure 6C:
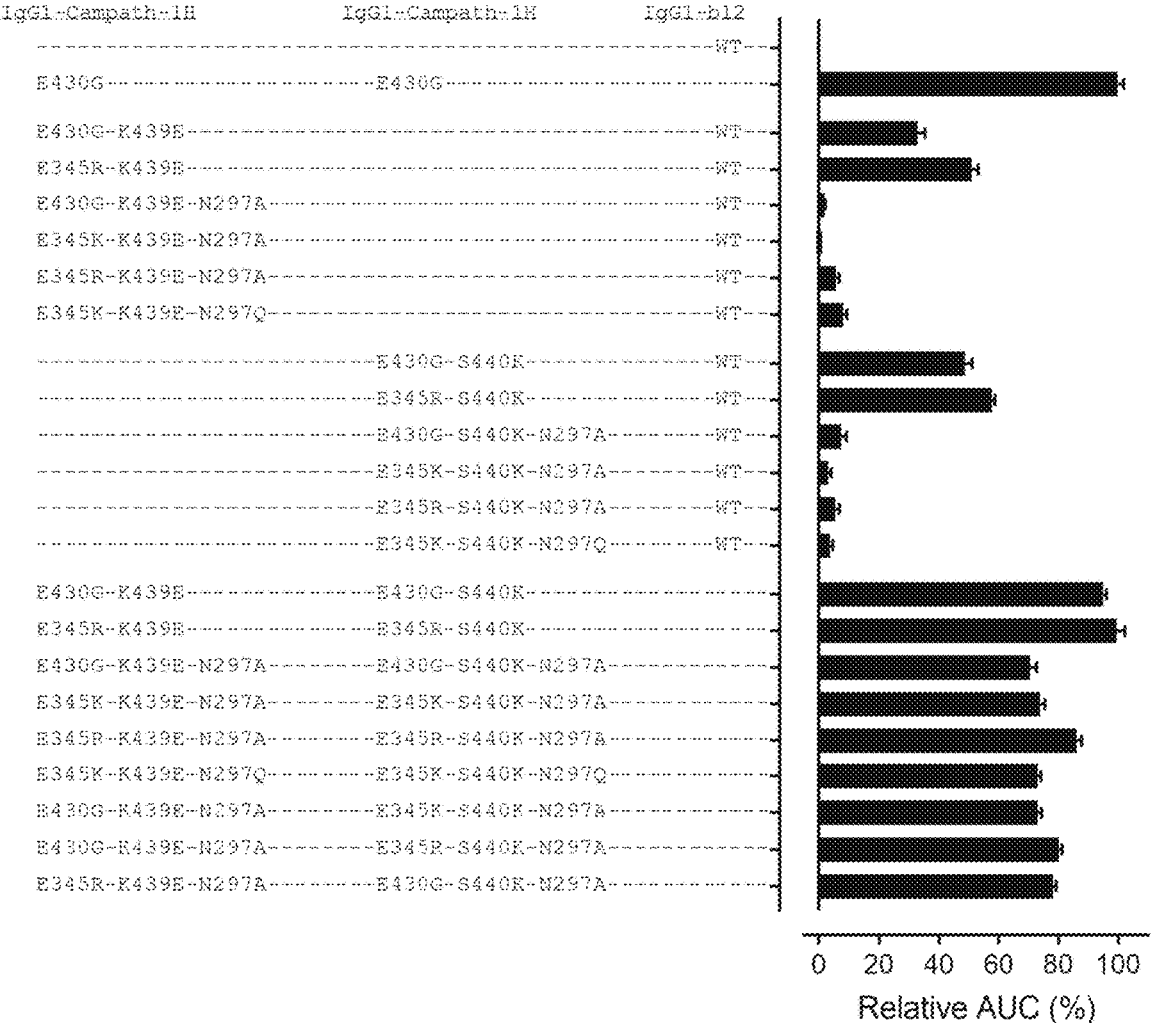
Figure 6D:
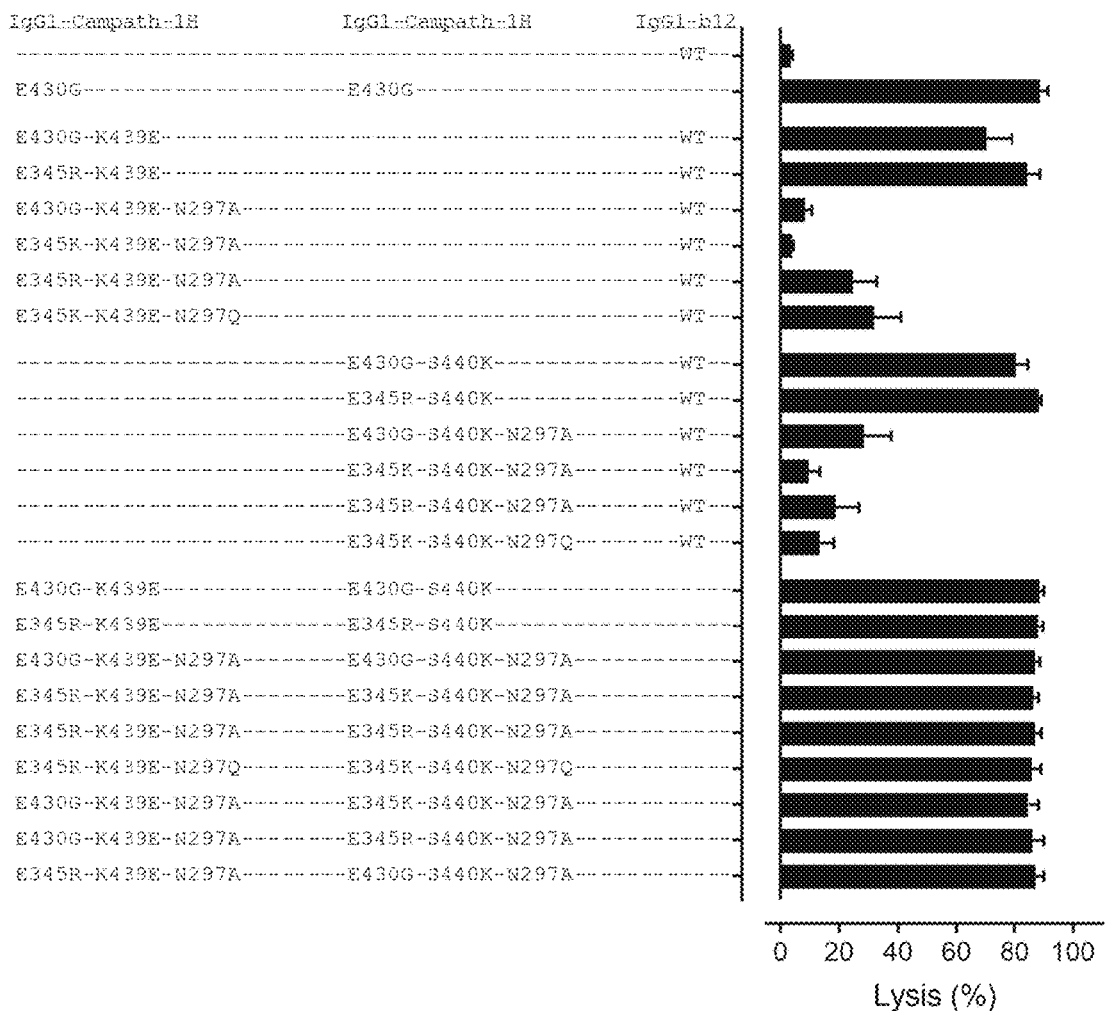

Similar results were obtained with Wien 133 cells (FIGS. 6C-D). The K439E and S440K self-oligomerization inhibiting mutations reduced, but did not fully abrogate, the CDC potency of IgG1-CAMPATH-1H-E430G on Wien 133 cells (FIG. 6C). Similarly, IgG1-CAMPATH-1H-E345R-K439E and -S440K still demonstrated substantial single agent activity, particularly at the highest antibody concentration (FIG. 6D). Aglycosylated variants of these antibodies via a N297A mutation virtually abrogated their CDC potency, and strongly inhibited CDC-mediated lysis of Wien 133 cells at the highest antibody concentration (approximately 8%-28% lysis remaining). The IgG1-CAMPATH-1H-E345K-K439E and -S440K antibody variants harboring the N297A or N297Q mutations also showed low CDC activity (approximately 4%-32%) on Wien 133 cells.

When combined, complementary IgG1-CAMPATH-1H-K439E and -S440K antibody variants harboring the E430G or E345R Fc-Fc interaction enhancing mutations displayed almost fully restored CDC potency against Wien 133 cells (to approximately 95%-99%). Aglycosylated variants (N297A) of these antibody variants slightly reduced their CDC potency when mixed (to approximately 70%-73%) and did not substantially affect the levels of lysis at the highest antibody concentration. Efficient CDC was also observed upon combining IgG1-CAMPATH-1H-E345K-K439E and IgG1-CAMPATH-1H-E345K-S440K antibody variants carrying the N297A or N297Q mutations.

When IgG1-CAMPATH-1H-K439E-N297A and IgG1-CAMPATH-1H-S440K-N297A antibody variants carrying two different Fc-Fc interaction enhancing (E430G, E345K, or E345R) mutations were combined, the resulting CDC was comparable to the level of CDC induced by two of these antibody variants carrying the same Fc-Fc interaction enhancing mutation, suggesting that the Fc-Fc enhancing mutations can be used interchangeably.

These data show that disruption of the N297 glycosylation site reduces the single agent activity of Fc-Fc interaction enhanced IgG1-CAMPATH-1H antibody variants harboring the self-oligomerization inhibiting K439E or S440K mutations. In contrast, combining these aglycosylated, Fc-Fc interaction enhanced, self-oligomerization inhibited antibody variants nearly fully restored their potency in CDC assays.

Example 8: Disruption of the N297 Glycosylation Site Improves the Selectivity of CD52- and CD20-Targeting Antibody Variants with Fc-Fc Interaction Enhancing and Self-Oligomerization Inhibiting Mutations In Example 7, disruption of the N297 glycosylation site in the CH2 domain of IgG1-CAMPATH-1H antibody variants harboring Fc-Fc interaction enhancing and self-oligomerization inhibiting mutations resulted in increased CDC selectivity. Here, we tested whether the same principle could be extended to a different combination of antibodies (anti-CD52 IgG1-CAMPATH-1H and anti-CD20 IgG1-11B8).

Different mutations were introduced in the anti-CD52 IgG1-CAMPATH-1H and anti-CD20 IgG1-11B8 antibodies: E430G, E345K or E345R, which induce enhanced Fc-Fc interactions; K439E or S440K, which inhibit the formation of homo-hexameric antibody complexes through inhibition of intermolecular Fc-Fc interactions, and which promote the formation of hetero-hexameric antibody complexes through cross-complementary Fc-Fc interactions; N297A, N297Q, or S298G-T299A, which disrupt the N297 N-glycosylation consensus sequence (NX[S/T]), resulting in aglycosylation. As controls, single antibodies were mixed 1:1 with non-binding isotype IgG1-b12 control antibodies to enable direct comparison of the concentrations of individual components and mixtures composed thereof. The purified antibody variants were tested in a range of concentrations (for the Wien 133 cells, 0.01-40.0 µg/mL, 3.3-fold dilutions; for the Ramos cells, 0.0088-40.0 µg/mL final concentrations, 3.33-fold dilutions) in an in vitro PI CDC assay on Wien 133 cells (N=3) with 20% NHS, essentially as described in Example 2, or in a CellTiterGlo CDC assay on Ramos cells (N=3) with 10% NHS, essentially as described in Example 5.

For both CellTiterGlo and PI CDC assays, the relative areas under dose-response curves with log transformed concentrations (AUC values) were normalized to the AUC value measured for the non-binding negative control IgG1-b12 (0%) and the AUC value measured for the positive control mixture of IgG1-CAMPATH-1H-E430G+IgG1-11B8-E430G (100%).

Figure 7A:
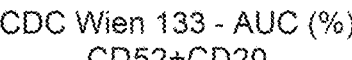
Figure 7A:
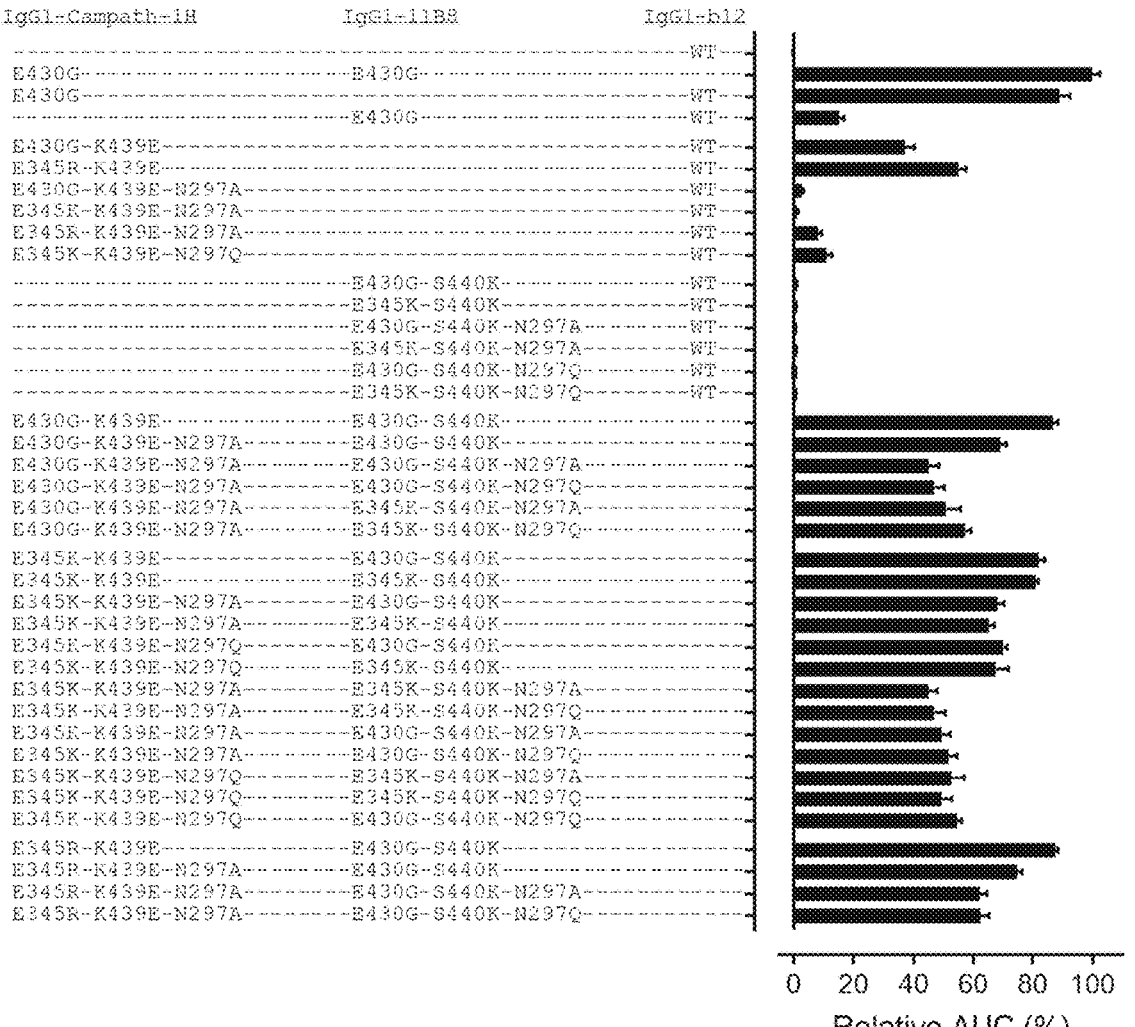
Figure 7B:
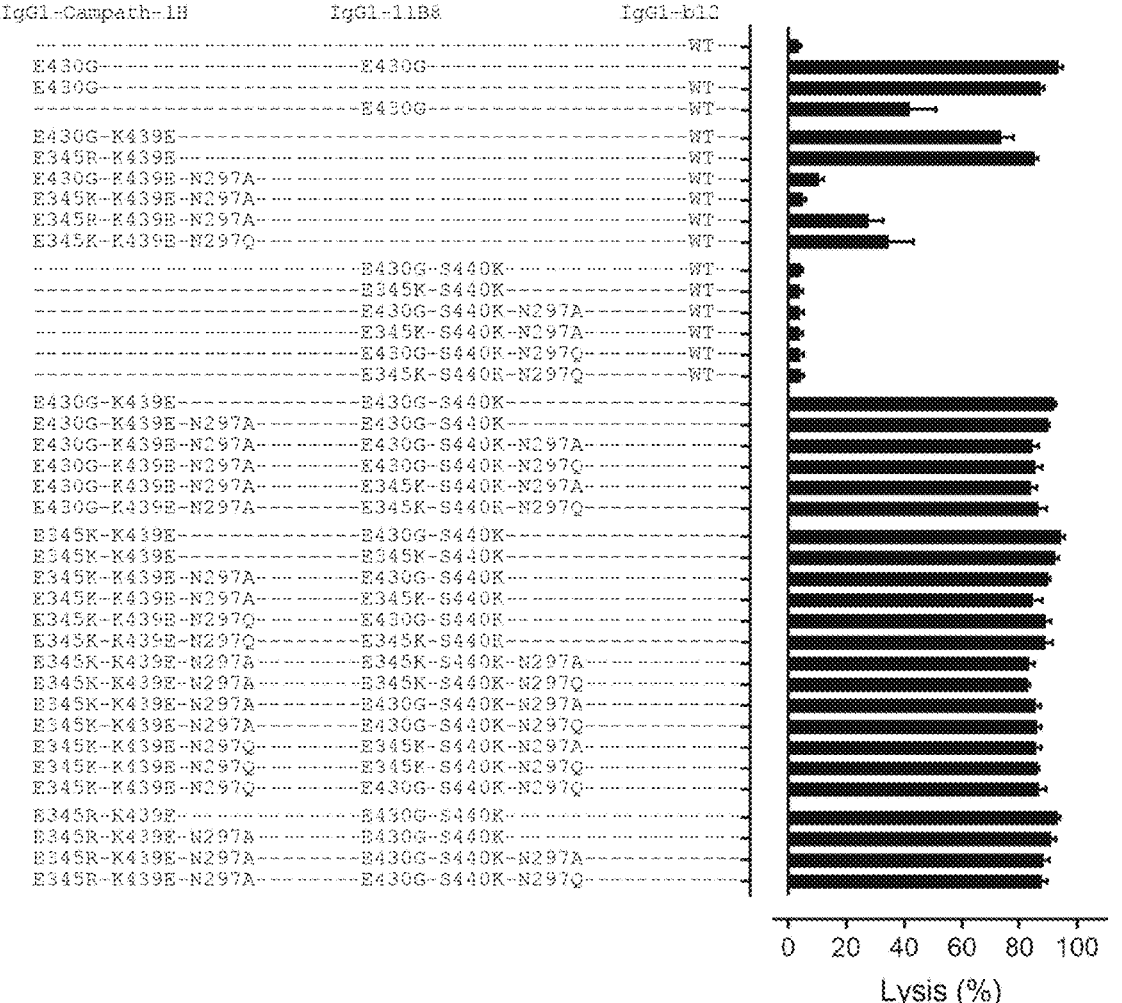

Treatment of Wien 133 cells with IgG1-CAMPATH-1H-E430G resulted in efficient CDC (FIG. 7A). Introduction of the K439E self-oligomerization inhibiting mutation reduced CDC potency, but had limited effect at single agent activity at antigen-saturating antibody concentrations. The additional introduction of the N297A mutation, which prevents glycosylation, reduced single agent activity of this antibody variant to background levels, also at elevated antibody concentrations. The N297A mutation also suppressed the CDC potency of an IgG1-CAMPATH-1H antibody variant harboring the E345R Fc-Fc interaction enhancing and K439E self-oligomerization inhibiting mutations. At the highest antibody concentration, treatment of Wien 133 cells with this IgG1-CAMPATH-1H-E345R-K439E-N297A antibody variant did result in low levels of CDC (approximately 28%) (FIG. 7B). The IgG1-CAMPATH-1H-E345K-K439E antibody variants carrying the N297A or N297Q mutations also displayed limited potency as single agents in CDC assays, but did display limited activity (approximately 5%-35%) at antigen-saturating antibody concentrations.

Compared to IgG1-CAMPATH-1H-E430G, IgG1-11B8-E430G showed limited CDC potency. Introduction of the S440K self-oligomerization inhibiting mutation fully abrogated single agent activity on Wien 133 cells, obscuring any potential additional inhibitory effects of mutations that prevent glycosylation (N297A or N297Q). Similarly, IgG1-11B8-E345K-S440K did not mediate CDC, thereby also obscuring any additional inhibitory effects of mutations that prevent glycosylation (N297A or N297Q).

IgG1-CAMPATH-1H-E430G-K439E and IgG1-11B8-E430G-S440K antibody variants efficiently induced CDC when combined, their potency only slightly lower than that of the positive control mixture IgG1-CAMPATH-1H-E430G+IgG1-11B8-E430G. The introduction of the N297A mutation to IgG1-CAMPATH-1H-E430G-K439E slightly reduced its CDC potency when combined with the IgG1-11B8-E430G-S440K antibody variant, and even more so when combined with the aglycosylated IgG1-11B8-E430G-S440K-N297A or IgG1-11B8-E430G-S440K-N297Q antibody variants. However, it did not substantially affect Wien 133 cell lysis mediated by these antibody combinations at the highest antibody concentrations (FIG. 7B). Similar levels of CDC potency were observed when IgG1-CAMPATH-1H-E430G-K439E-N297A was combined with IgG1-11B8-E345K-S440K-N297A or IgG1-11B8-E345K-S440K-N297Q, which carried the E345K instead of the E430G Fc-Fc interaction enhancing mutation.

The IgG1-CAMPATH-1H-E345K-K439E antibody variant efficiently induced CDC when combined with the IgG1-11B8-E430G-S440K or IgG1-11B8-E345K-S440K antibody variants, indicating that antibodies with different Fc-Fc interaction enhancing mutations can be combined into co-dependently acting mixtures. The introduction of the N297A or N297Q mutation to IgG1-CAMPATH-1H-E345K-K439E slightly reduced the CDC potency of this antibody variant in combination with the IgG1-11B8-E430G-S440K or IgG1-11B8-E345K-S440K antibody variants, but did not affect the level of Wien 133 cell lysis at the highest antibody concentration. When a mutation preventing glycosylation (N297A or N297Q) was present in both the IgG1-CAMPATH-1H-E345K-K439E antibody variant and in IgG1-11B8-E430G-S440K or IgG1-11B8-E345K-S440K, a more pronounced decrease in CDC potency was observed. The levels of maximal Wien 133 cell lysis, however, remained similar.

The IgG1-CAMPATH-1H-E345R-K439E variant efficiently induced CDC when combined with IgG1-11B8-E430G-S440K. The CDC potency of this combination was slightly reduced when IgG1-CAMPATH-1H-E345R-K439E carried the N297A mutation. When the IgG1-11B8-E430G-S440K antibody variant also carried a mutation which prevents glycosylation (N297A or N297Q), the decrease in CDC potency was more pronounced, although Wien 133 cell lysis at the highest antibody concentration was not affected.

Figure 7C:
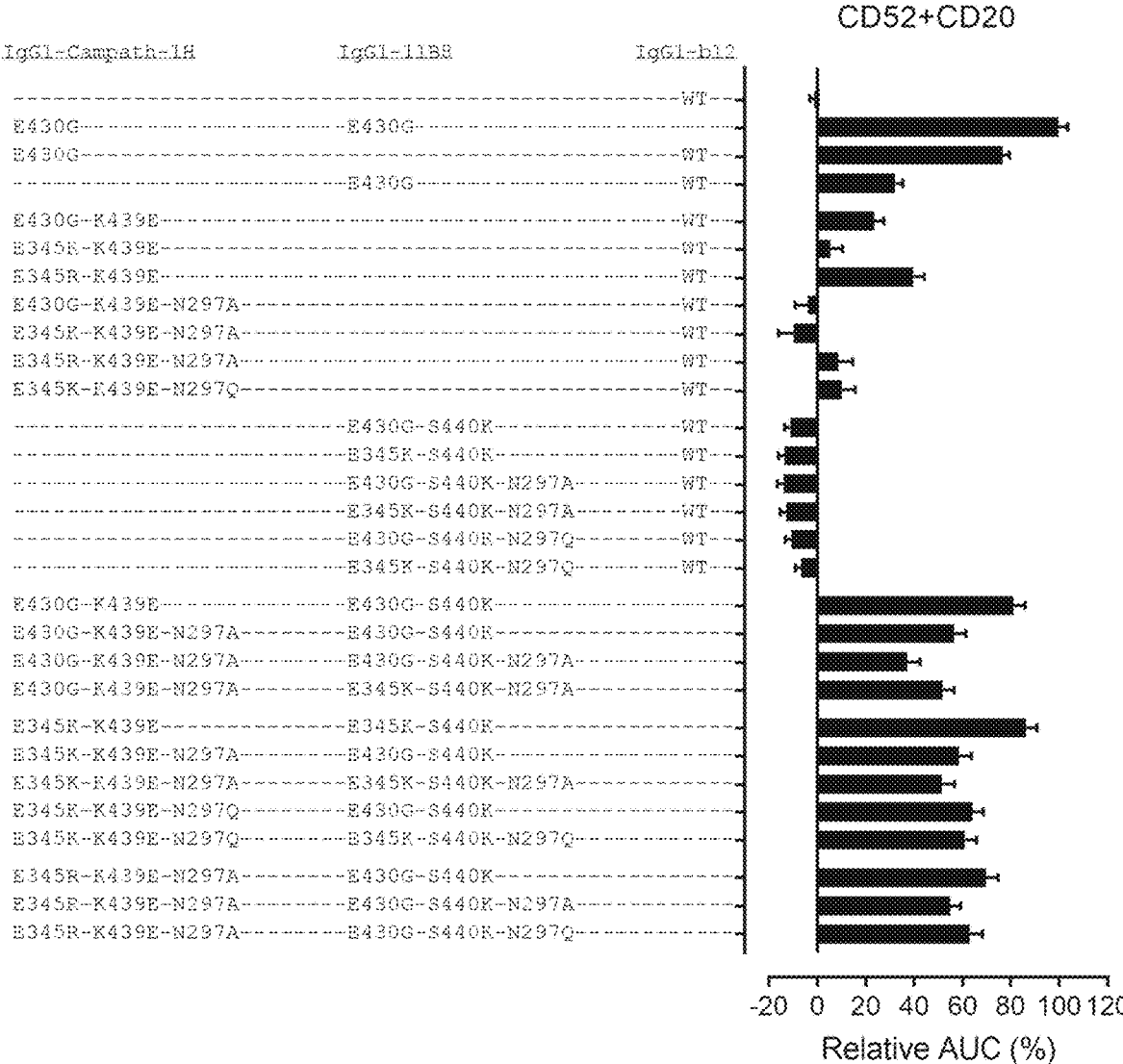
Figure 7D:
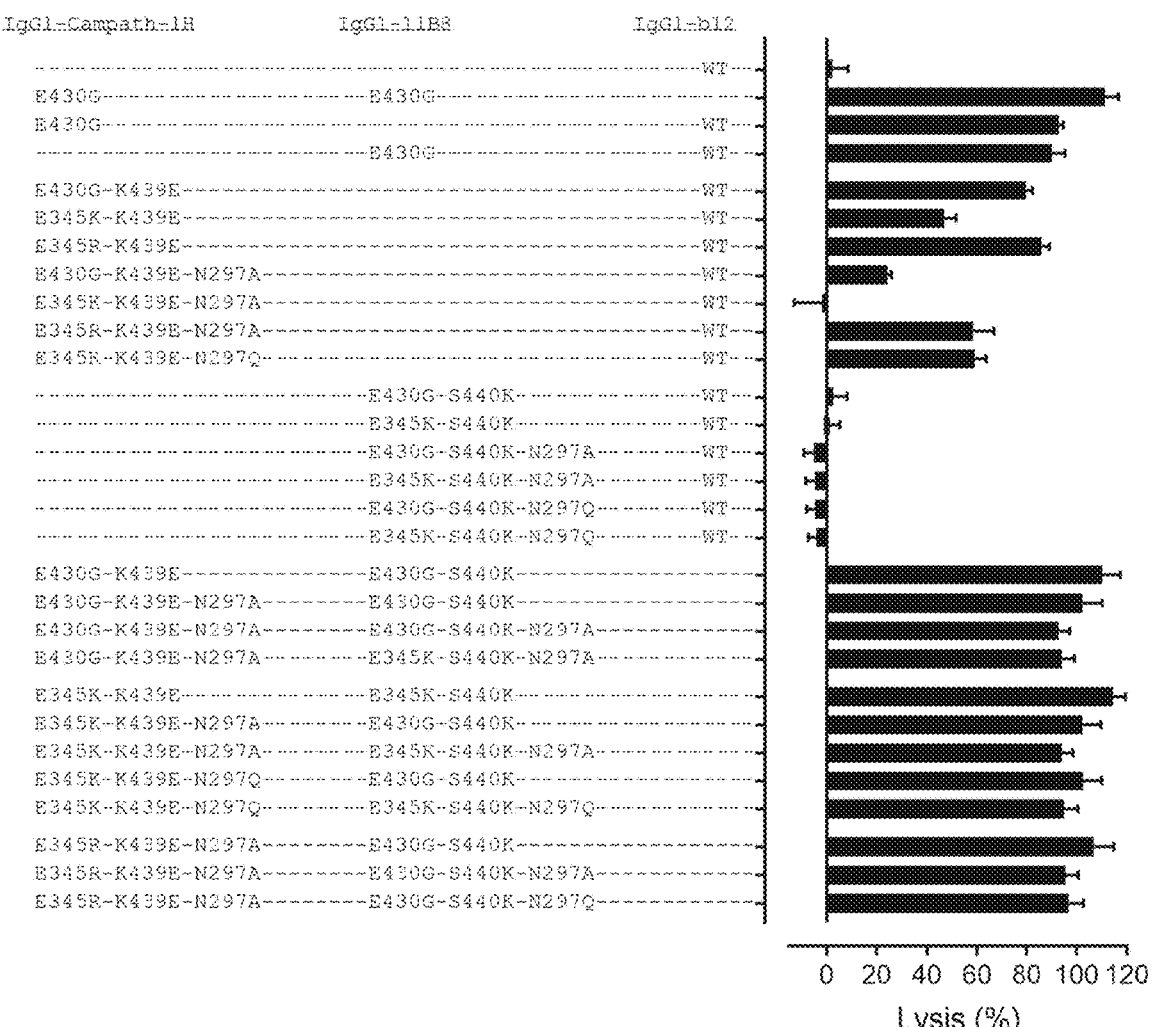

Similar results were observed using Ramos target cells (FIG. 7C-D). Introduction of the K439E self-oligomerization inhibiting mutation to IgG1-CAMPATH-1H-E430G reduced CDC potency (FIG. 7C), but not Ramos cell lysis at the highest antibody concentration (FIG. 7D). The N297A mutation reduced the single agent activity of this antibody variant to background levels. The N297A mutation also suppressed the single agent CDC potency of IgG1-CAMPATH-1H-E345R-K439E and IgG1-CAMPATH-1H-E345K-K439E. Introduction of the N297Q mutation had limited effect on the CDC potency of IgG1-CAMPATH-1H-E345K-K439E, in contrast to its inhibitory effect upon introduction into IgG1-CAMPATH-1H-E430G-K439E (Example 5, 4).

Compared to IgG1-CAMPATH-1H-E430G, IgG1-11B8-E430G showed limited CDC potency. Introduction of the S440K self-oligomerization inhibiting mutation fully abrogated single agent activity, obscuring any potential additional inhibitory effects of mutations which prevent glycosylation (N297A or N297Q). Similarly, IgG1-11B8-E345K-S440K did not mediate CDC, thereby obscuring any additional inhibitory effects of mutations which prevent glycosylation (N297A, N297Q, or S298G-T299A).

When combined, the IgG1-CAMPATH-1H-E430G-K439E and IgG1-11B8-E430G-S440K antibody variants efficiently induced CDC (approximately 81% of the positive control mixture). The introduction of the N297A mutation to IgG1-CAMPATH-1H-E430G-K439E slightly reduced its CDC potency when combined with the IgG1-11B8-E430G-S440K antibody variant (to approximately 56%), and even more so when combined with the aglycosylated IgG1-11B8-E430G-S440K-N297A or IgG1-11B8-E345K-S440K-

N297A antibody variants (to 37%-52%). However, it did not substantially affect Ramos cell lysis at the highest antibody concentration.

The IgG1-CAMPATH-1H-E345K-K439E antibody variant efficiently induced CDC when combined with IgG1-11B8-E345K-S440K. The presence of the N297A or N297Q mutation in IgG1-CAMPATH-1H-E345K-K439E and IgG1-11B8-E345K-S440K slightly reduced this CDC potency, but had limited effect on the levels of Ramos cell lysis at the highest antibody concentration. The combination of aglycosylated IgG1-CAMPATH-1H-E345K-K439E-N297A or -N297Q with IgG1-11B8-E430G-S440K also induced CDC. The combination of aglycosylated IgG1-CAMPATH-1H-E345R-K439E-N297A with IgG1-11B8-E430G-S440K or aglycosylated IgG1-11B8-E430G-S440K-N297A or -N297Q efficiently induced CDC.

These data show that disruption of the N297 glycosylation site inhibits the single agent activity of Fc-Fc interaction enhanced IgG1-CAMPATH-1H and IgG1-11B8 antibody variants harboring the self-oligomerization inhibiting K439E and S440K mutations. In contrast, combination of the complementary (K439E+S440K) aglycosylated Fc-Fc interaction enhanced antibody variants of IgG1-CAMPATH-1H and IgG1-11B8 partially restores their ability to induce CDC. At antigen-saturating concentrations, IgG1-CD52-CAMPATH-1H with E345K, K439E, and N297A mutations, in particular, showed the preferred phenotype of minimal activity as a single agent, while enabling high potency when used in co-dependent mixtures.

Example 9: Disruption of the N297 Glycosylation Site Improves the Selectivity of CD37- and CD20-Targeting Antibody Variants with Fc-Fc Interaction Enhancing and Self-Oligomerization Inhibiting Mutations In Examples 7 and 8, disruption of the N297 glycosylation site in IgG1-CAMPATH-1H and IgG1-11B8 antibody variants with Fc-Fc interaction enhancing and self-oligomerization inhibiting mutations improved their CDC selectivity. Here, we tested whether N297 mutations could also restrict the selectivity of a different combination of antibody variants (IgG1-CD37-37-3 and IgG1-11B8) with Fc-Fc interaction enhancing and self-oligomerization inhibiting mutations.

Different mutations were introduced in the anti-CD37 IgG1-CD37-37-3 and anti-CD20 IgG1-11B8 antibodies: E430G or E345K, which induce enhanced Fc-Fc interactions; K439E or S440K, which inhibit the formation of homo-hexameric antibody complexes through inhibition of intermolecular Fc-Fc interactions, and which promote the formation of hetero-hexameric antibody complexes through cross-complementary Fc-Fc interactions; N297A or N297Q, which disrupt the N297 N-glycosylation site, resulting in aglycosylation. As controls, single antibodies were mixed 1:1 with non-binding isotype IgG1-b12 control antibodies to enable direct comparison of the concentrations of individual components and mixtures composed thereof. The purified antibody variants were tested in a range of concentrations (range 0.0088-40.0 µg/mL final concentrations; 3.33-fold dilutions) in an in vitro CellTiterGlo CDC assay on Raji (N=3) or Daudi (N=2) cells with 10% NHS, essentially as described in Example 5. The relative area under dose-response curves with log transformed concentrations (AUC values) were normalized to the AUC value measured for the non-binding negative control IgG1-b12 (0%) and the AUC value measured for the positive control mixture of IgG1-CD37-37-3-E430G and IgG1-11B8-E430G (100%).

Figure 8A:
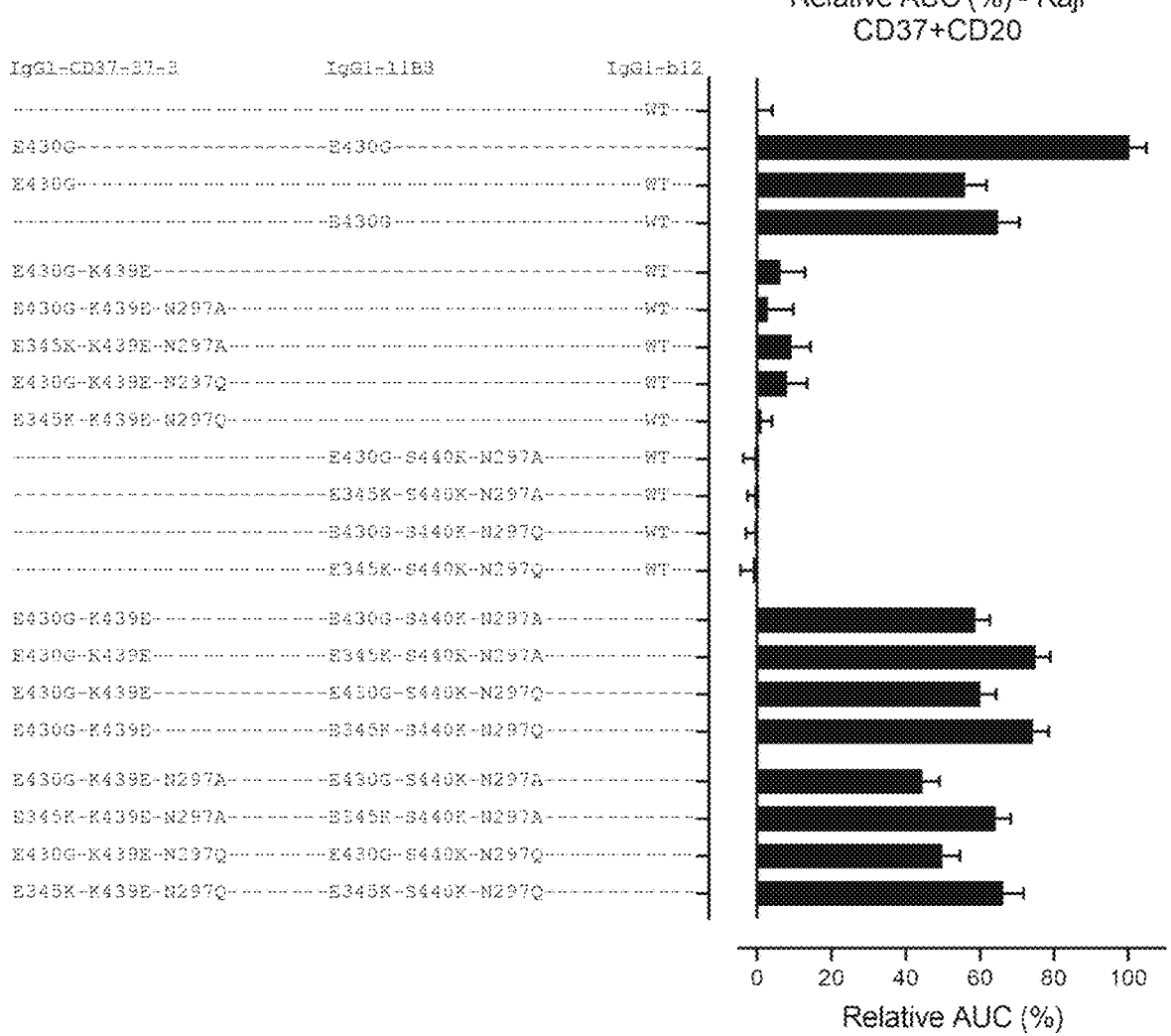
Figure 8B:
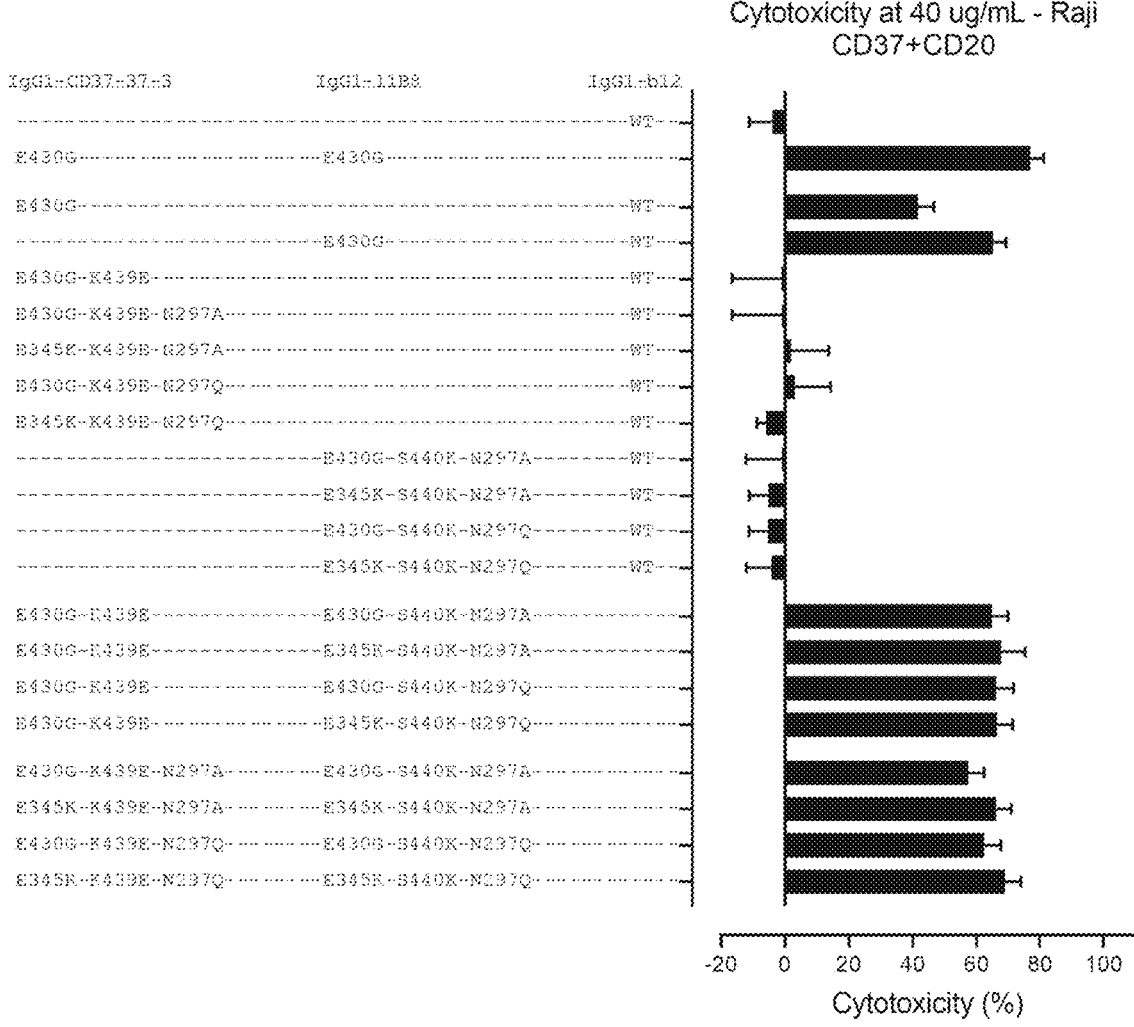

Treatment of Raji cells with IgG1-CD37-37-3-E430G or IgG1-11B8-E430G resulted in efficient CDC (FIG. 8A). Introduction of the K439E mutation alone or in combination with a mutation which prevents glycosylation (N297A or N297Q) strongly reduced the potency to induce CDC. Similarly, introduction of the K439E mutation in combination with either N297A or N297Q in IgG1-CD37-37-3-E345K resulted in a low residual potency to induce CDC. No single agent CDC activity was observed for IgG1-11B8-E430G or IgG1-11B8-E345K after introduction of the S440K mutation in combination with either N297A or N297Q. Upon mixing IgG1-CD37-37-3-E430G-K439E with either of the IgG1-11B8-S440K variants harboring the E430G or E345K mutation, and either the N297A or N297Q mutation, a partial recovery of CDC efficacy was observed. Mixing of IgG1-CD37-37-3-E430G-K439E with the E345K-containing IgG1-11B8 variants induced stronger CDC recovery, to approximately 75% of the level induced by the positive control, than mixing with the E430G-containing IgG1-11B8 variants (resulting in approximately 60% of the level induced by the positive control). Mixtures of an aglycosylated IgG1-CD37-37-3-K439E variant containing either the E430G or E345K mutation with an aglycosylated IgG1-11B8-S440K variant containing either the E430G or E345K mutation also resulted in partial recovery of CDC efficacy albeit to a lower recovery level than mixtures in which one of both antibody variants was glycosylated. Mixing two E430G-containing antibody variants with either the N297A or N297Q mutation resulted in CDC efficacy to approximately 45% or 50% of the level induced by the positive control, respectively. The CDC recovery was more efficient when mixing two E345K-containing antibody variants containing either the N297A or N297Q mutation with a recovery of approximately 64% and 66% of the level induced by the positive control, respectively. At the highest concentration tested (40 μg/mL), a similar CDC potency was attained by all mixtures, except for mixtures of the aglycosylated E430G-containing IgG1-CD37-37-3-K439E and IgG1-11B8-S440K variants which induced a slightly reduced level of CDC at this concentration (FIG. 8B).

Figure 8C:
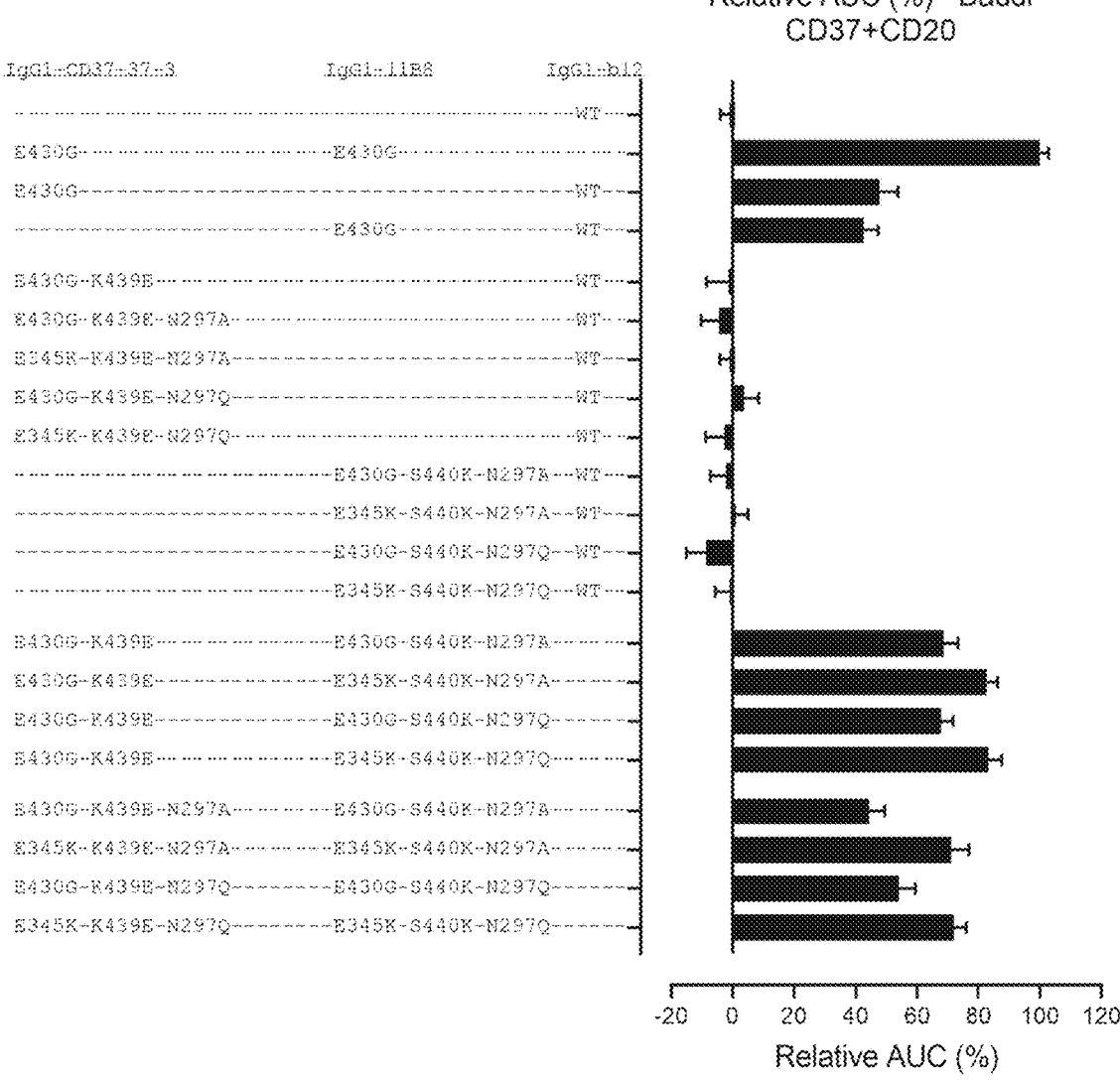
Figure 8D:
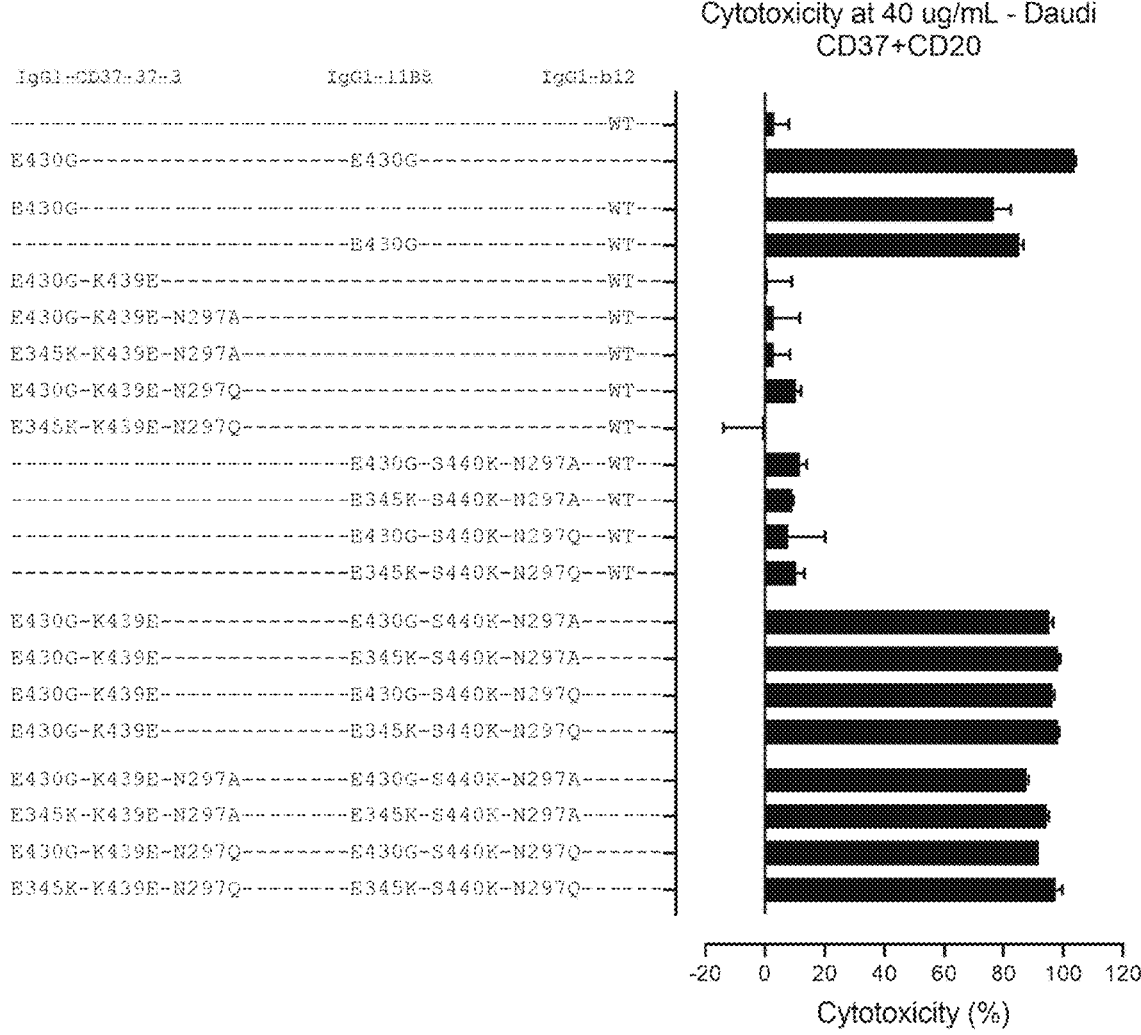

Similar results were obtained using Daudi target cells (FIG. 8C-D).I Introduction of the self-oligomerization inhibiting K439E mutation in combination with mutations which prevent glycosylation (N297A or N297Q) to IgG1-CD37-37-3-E430G or IgG1-CD37-37-3-E345K abrogated CDC efficacy (FIG. 8C). The single agent activity of IgG1-11B8-E430G and IgG1-11B8-E345K could be suppressed by introducing the S440K mutation in combination with a mutation disrupting the N-linked glycosylation site (N297A or N297Q). When combined with IgG1-CD37-37-3-E430G-K439E, the CDC potency of the aglycosylated IgG1-11B8-E430G-S440K-N297A and -N297Q antibody variants was partially restored, and Daudi cell lysis at the highest antibody concentrations was close to the level of CDC induced by the positive control (FIG. 8D). More efficient recovery of CDC efficacy was induced by mixtures of aglycosylated IgG1-11B8-E345K-S440K with IgG1-CD37-37-3-E430G-K439E. Mixing of aglycosylated IgG1-11B8-E430G-S440K-N297A and -N297Q antibody variants with IgG1-CD37-37-3-E430G-K439E or CD37-37-3-E345K-K439E antibody variants that also contain a mutation which prevents glycosylation (N297A or N297Q) also recovered CDC potency, albeit less efficiently.

These data show that the introduction of an Fc-Fc interaction enhancing mutation, a self-oligomerization inhibiting mutation and a mutation that disrupts the N297 glycosylation site abrogates the single agent activity of IgG1-CD37-37-3 and IgG1-11B8 antibody variants. In contrast, combinations of these aglycosylated Fc-Fc interaction enhanced antibody variants with their complementary aglycosylated Fc-Fc interaction enhanced counterpart largely restores their ability to induce CDC, especially at antigen-saturating antibody concentrations.

Example 10: Analysis of the Effect of Mutations Preventing Glycosylation in IgG1-CAMPATH-1H Antibody Variants Harboring an Fc-Fc Interaction Enhancing Mutation on Antibody-Dependent Cellular Phagocytosis Fcγ receptor 2a (FcγRIIa), also known as CD32a, is expressed by B cells, macrophages and monocytes and plays an important role in antibody-dependent cellular phagocytosis (ADCP). The interaction of Fc domains with Fcγ receptors is strongly dependent on glycosylation. Here, we tested whether the introduction of mutations preventing glycosylation affected the capacity of IgG1-CAMPATH-1H antibody variants harboring an Fc-Fc interaction enhancing mutation to activate FcγRIIa in a reporter cell assay, as a surrogate for ADCP.

For the ADCP reporter bioassay, antibody variants of IgG1-CAMPATH-1H and IgG1-11B8 were tested which harbor an Fc-Fc interaction enhancing mutation (E430G, E345K, or E345R), a self-oligomerization inhibiting mutation (K439E or S440K) and a mutation which disrupts the N297 N-glycosylation consensus sequence (NX[S/T]; N297A, N297G, N297Q, N297D, or N297Y) using the Bio-Glo Luciferase Assay System (Promega, Cat No. G7940) on Raji cells. As effector cells, the kit contains Jurkat human T cells that are engineered to stably express high affinity FcγRIIa (H131 allotype) and a nuclear factor of activated T cells (NFAT)-response element driving expression of firefly luciferase. Briefly, Raji cells (25 μL; 11,000 cells/well; Promega, Cat. #G870A) were seeded in 96-wells white opaque flat bottom plates (Corning, Cat. #3917) in RPMI-1640 [(Promega, Cat #G708A) supplemented with 4% low IgG serum (Promega, Cat. #G711A)]. The Raji cells were preincubated for 15 minutes with antibody concentration series (25 μL; 4-fold dilution series resulting in 0.15-40,000 ng/mL final concentrations after addition of effector cells) at 37° C./5% C02. Subsequently, thawed Jurkat FcγRIIa H131 allotype Effector cells (25 uL; 50,000 cells/well; Promega, Cat #G9991) were added, and the cells were incubated for 16-24 hours at 37° C./5% C02. After this incubation, the cells were equilibrated to room temperature for 15 minutes. Subsequently, 75 μL Bio-Glo Assay Luciferase Reagent [Bio-Glo Luciferase Assay Substrate (Promega Cat. #G720A) in Bio-Glo Luciferase Assay Buffer (Promega, Cat. #G719A)] was added per well and incubated for 20 minutes at RT in the dark. Luciferase production was quantified by luminescence readout on a Tecan Spark 20M luminescence plate reader (Tecan). The relative areas under dose-response curves with log transformed concentrations (AUC values) were normalized to the AUC value measured for the non-binding negative control IgG1-b12 (0%) and the AUC value measured for the positive control IgG1-CAMPATH-1H-E430G (100%; FIG. 9B).

The capacity to induce FcγRIIa activation by IgG1-CAMPATH-1H-E430G was fully suppressed by the introduction of N-linked glycosylation site mutations N297A, N297G, N297Q, N297D or N297Y (FIG. 9A). Similarly, while both IgG1-CAMPATH-1H-E345K and IgG1-CAM- PATH-1H-E345R induced efficient activation of FcγRIIa, the introduction of mutation N297A in these antibody variants fully abrogated their capacity to activate FcγRIIa.

A mixture of IgG1-CAMPATH-1H-E430G and IgG1-11B8-E430G efficiently induced FcγRIIa activation (FIG. 9B). In contrast, an IgG1-CAMPATH-1H-E430G antibody variant in which the K439E mutation was introduced did not induce FcγRIIa activation, thereby also obscuring any additional suppressive effects of mutation N297A. A low capacity to induce FcγRIIa activation was observed for IgG1-11B8-E430G-S440K as compared to the positive control mixture of IgG1-CAMPATH-1H-E430G-K439E and IgG1-11B8-E430G. Introduction of mutation N297A in the IgG1-11B8-E430G-S440K variant further suppressed its capacity to induce FcγRIIa activation. While a mixture of IgG1-CAMPATH-1H-E430G-K439E and IgG1-11B8-E430G-S440K slightly recovered FcγRIIa activation, a mixture of these antibody variants both harboring aglycosylating mutation N297A did not induce any FcγRIIa activation.

In summary, these data show that the introduction of an aglycosylating mutation in IgG1-CAMPATH-1H antibody variants harboring an Fc-Fc interaction enhancing mutation silences the capacity to induce ADCP as measured through an FcγRIIa activation reporter cell assay. While a mixture of co-dependent glycosylated antibody variants IgG1-CAMPATH-1H-E430G-K439E and IgG1-11B8-E430G-S440K induced partial recovery of ADCP, a mixture of aglycosylated variants IgG1-CAMPATH-1H-E430G-K439E-N297A and IgG1-11B8-E430G-S440K-N297A did not.

Example 11: Mutations Preventing Glycosylation in IgG1-CAMPATH-1H Antibody Variants Harboring an Fc-Fc Interaction Enhancing Mutation Inhibit Antibody-Dependent Cellular Cytotoxicity Fcγ receptor 3a (FcγRIIIa), also known as CD16a, is expressed predominantly on natural killer cells and macrophages, and plays an important role in antibody-dependent cellular cytotoxicity (ADCC). The interaction of Fc domains with Fcγ receptors strongly depends on their glycosylation. Here, we tested whether the introduction of mutations preventing glycosylation affected the capacity of IgG1-CAMPATH-1H antibody variants harboring an Fc-Fc interaction enhancing mutation to activate FcγRIIIa in a reporter cell assay, as a surrogate for ADCC.

For the ADCC reporter bioassay, antibody variants of IgG1-CAMPATH-1H were tested which harbor an Fc-Fc interaction enhancing mutation (E430G, E345K, or E345R), and a mutation which disrupts the N297 N-glycosylation consensus sequence (NX[S/T]; N297A, N297G, N297Q, N297D, or N297Y) using the Bio-Glo Luciferase ADCC Reporter Bioassay for the FcγRIIIa high affinity V158 allotype on Raji cells (Promega, Cat. #G7015). As effector cells, the kit contains Jurkat human T cells that are engineered to stably express the high affinity V158 allotype of FcγRIIIa and a nuclear factor of activated T cells (NFAT)-response element driving expression of firefly luciferase. Briefly, Raji cells (25 µL; 12,500 cells/well; Promega, Cat. #G870A) were seeded in 96-wells white opaque flat bottom plates (Corning, Cat. #3917) in RPMI-1640 [(Promega, Cat #G708A) supplemented with 10% low IgG serum (Promega, Cat. #G711A)]. The Raji cells were preincubated for 15 minutes with antibody concentration series (25 µL; 4-fold dilution series resulting in 0.15-40,000 ng/mL final concentrations after addition of effector cells) at 37° C./5% $CO_2$. Subsequently, thawed Jurkat FcγRIIIa (V158 high affinity allotype) Effector cells (25 µl; 75,000 cells/well; Promega, Cat. #G701A) were added, and the cells were incubated for 5 hours at 37° C./5% C02. After this incubation, the cells were equilibrated to room temperature for 15 minutes. Subsequently, 75 µL Bio-Glo Assay Luciferase Reagent [Bio-Glo Luciferase Assay Substrate (Promega Cat. #G720A) in Bio-Glo Luciferase Assay Buffer (Promega, Cat. #G719A)] was added per well and incubated for 20 minutes at RT in the dark. Luciferase production was quantified by luminescence readout on a Tecan Spark 20M luminescence plate reader (Tecan). The relative areas under dose-response curves with log transformed concentrations (AUC values) were normalized to the AUC value measured for the non-binding negative control IgG1-b12 (0%) and the AUC value measured for the positive control IgG1-CAMPATH-1H-E430G (100%).

The capacity of IgG1-CAMPATH-1H-E430G to induce FcγRIIIa activation was fully suppressed by the introduction of aglycosylating mutations N297A, N297G, N297Q, N297D, or N297Y (FIG. 10). Similarly, while both IgG1-CAMPATH-1H-E345K and IgG1-CAMPATH-1H-E345R induced efficient activation of FcγRIIIa, the introduction of mutation N297A in these antibody variants fully abrogated their capacity to activate FcγRIIIa.

In summary, these data show that the introduction of a mutation that prevents glycosylation in IgG1-CAMPATH-1H antibody variants harboring an Fc-Fc interaction enhancing mutation silences their capacity to induce ADCC as measured through an FcγRIIIa activation reporter cell assay.

Example 12: Disruption of the N297 Glycosylation Site in Antibody Variants with the Fc-Fc Interaction Enhancing Mutation K248E-T437R had Limited Effect on their CDC Activity It was shown in Example 5 that disruption of the N297 N-glycosylation site induced low or no inhibition of the CDC activity of antibody variants harboring E430G, E345K or E345R Fc-Fc interaction enhancing mutations. Here, we tested whether this also extended to the K248E-T437R Fc-Fc interaction enhancing mutation.

Different mutations were introduced in the anti-CD52 antibody IgG1-CAMPATH-1H: E430G or K248E-T437R, which induce enhanced Fc-Fc interactions; N297A, which disrupts the N297 N-glycosylation consensus sequence (NX [S/T]) and yields aglycosylated antibodies. The purified antibody variants were tested in a range of concentrations (range 0.0088-40.0 µg/mL final concentrations; 3.33-fold dilutions) in a PI CDC assay on Wien 133 cells (N=4) with 20% NHS, essentially as described in Example 2, or using an in vitro CellTiterGlo CDC assay on Ramos cells (N=3) with 10% NHS, essentially as described in Example 5. For both CellTiterGlo and PI CDC assays, the relative areas under dose-response curves with log transformed concentrations (AUC values) were normalized to the AUC value measured for the non-binding negative control IgG1-b12 (0%) and the AUC value measured for positive control IgG1-CAMPATH-1H-E430G.

Figure 11A:
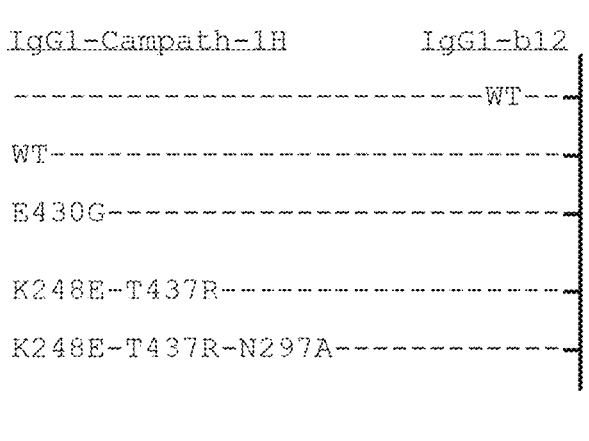
Figure 11A:
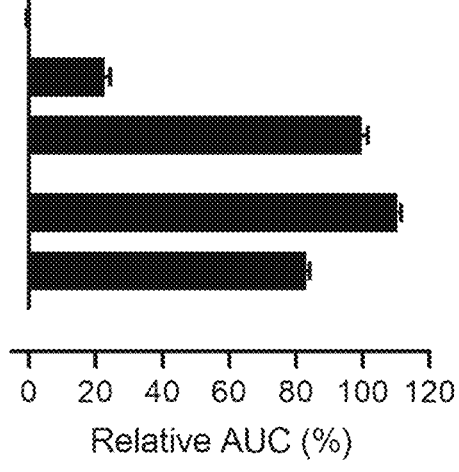
Figure 11B:
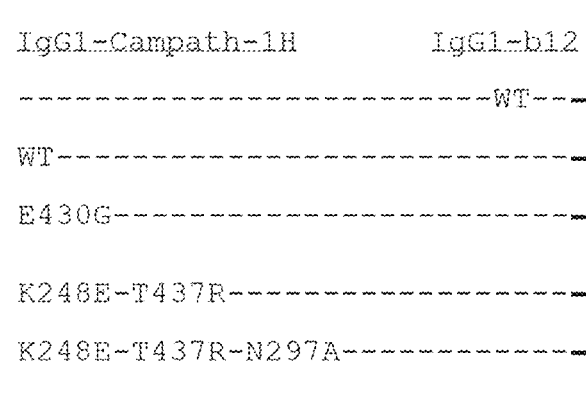
Figure 11B:
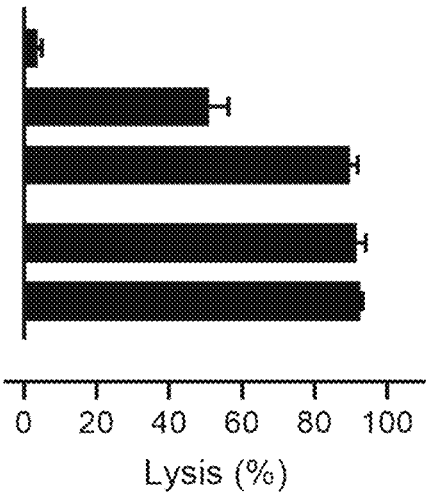

Introduction of the Fc-Fc interaction enhancing mutations E430G or K248E-T437R (SEQ ID NO 63) to IgG1-CAMPATH-1H strongly increased its CDC potency on Wien 133 cells (FIG. 11A). The increased CDC activity was also evident at antigen-saturating antibody concentrations (FIG. 11B). Disruption of the N297 glycosylation site with an N297A mutation (SEQ ID NO 64) slightly lowered the CDC potency of IgG1-CAMPATH-1H-K248E-T437R, and did not affect its CDC activity at the highest antibody concentration.

Figure 11C:
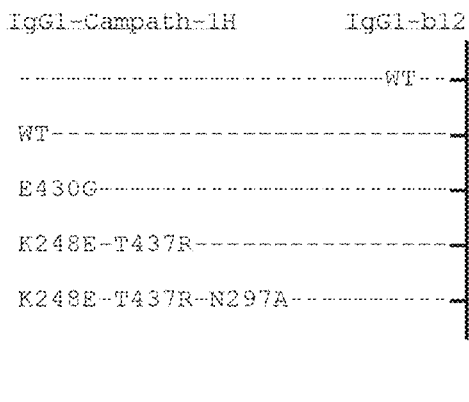
Figure 11C:
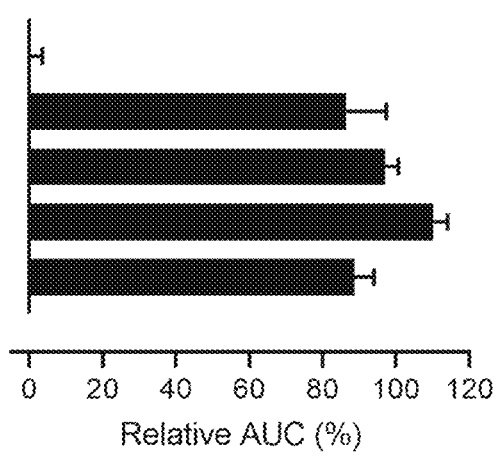
Figure 11D:
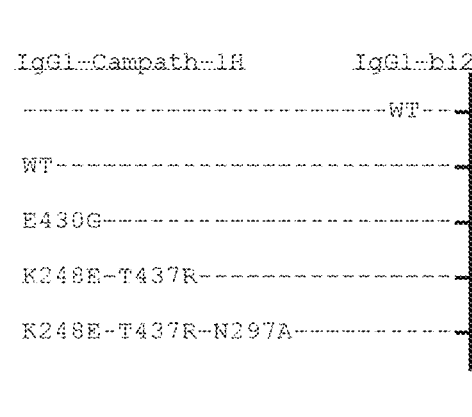
Figure 11D:
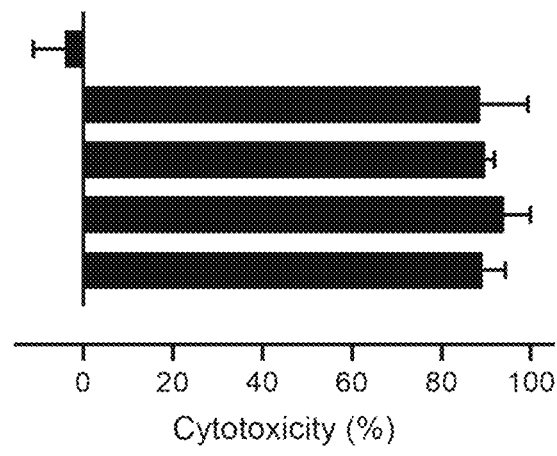

Similarly, IgG1-CAMPATH-1H antibody variants harboring the E430G or K248E-T437R Fc-Fc interaction enhancing mutations efficiently induced CDC in Ramos cells (FIG. 11C-D). Preventing N-linked glycosylation on N297 with an N297A mutation slightly lowered the CDC potency (FIG. 11C) of IgG1-CAMPATH-1H-K248E-T437R, but not its CDC activity at the antigen-saturating antibody dose (FIG. 11D). Together, these data show that the CDC activity of antibody variant IgG1-CAMPATH-1H-K248E-T437R was largely retained upon disruption of the N297 glycosylation site.

Example 13: Disruption of the N297 Glycosylation Site Improves the Selectivity of Antibody Variants Harboring the K248E-T437R Fc-Fc Interaction Enhancing and the K439E or S440K Self-Oligomerization Inhibiting Mutations It was shown in Examples 7-9 that disruption of the N297 glycosylation site improved the selectivity of antibody variants with an E430G, E345K, or E345R Fc-Fc interaction enhancing mutation and a K439E or S440K self-oligomerization inhibiting mutation. Here, we tested whether this also extended to antibody variants carrying the K248E-T437R Fc-Fc interaction enhancing mutation in combination with the self-oligomerization inhibiting K439E or S440K mutations.

Different mutations were introduced in the negative control antibody IgG1-b12, the anti-CD52 antibody IgG1-CAMPATH-1H, and the anti-CD20 antibody IgG1-11B8: E430G or K248E-T437R, which induce enhanced Fc-Fc interactions; K439E or S440K, which inhibit the formation of homo-hexameric antibody complexes through inhibition of intermolecular Fc-Fc interactions, and which promote the formation of hetero-hexameric antibody complexes through cross-complementary Fc-Fc interactions; N297A, which disrupts the N297 N-glycosylation consensus sequence (NX[S/T]) and yields aglycosylated antibodies. The purified antibody variants were tested in PI CDC assays on Wien 133 cells (N=3) with 20% NHS essentially as described in Example 2, in a range of concentrations (range of 0.002-40.0 µg/mL final concentrations; 4.0-fold dilutions (FIG. 12A); 0.0088-40.0 µg/mL final concentrations (FIGS. 12A-B); 3.33-fold dilutions (FIGS. 12C-D)). The purified antibody variants were also tested in in vitro CellTiterGlo CDC assays on Ramos cells (N=3) with 10% NHS (FIGS. 12E-F), essentially as described in Example 5. For both CellTiterGlo and PI CDC assays, the relative areas under dose-response curves with log transformed concentrations (AUC values) were normalized to the AUC value measured for the non-binding negative control IgG1-b12 (0%) and the AUC value measured for the positive control mixture IgG1-CAMPATH-1H-E430G+IgG1-B118-E430G (100%).

Figure 12A:
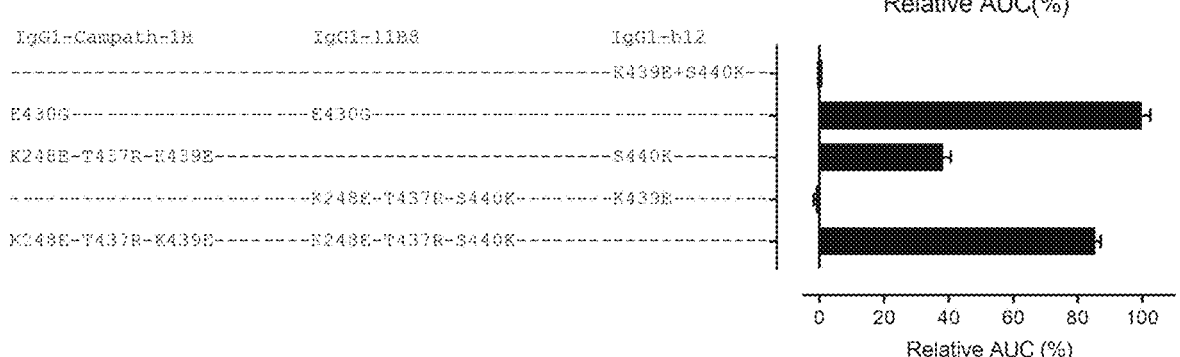
Figure 12B:
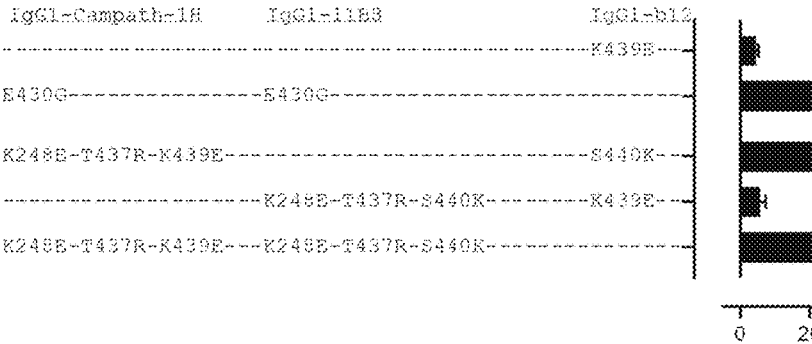
Figure 12B:
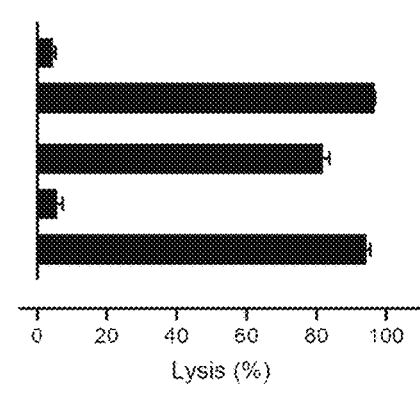

The combination of Fc-Fc interaction enhanced IgG1-CAMPATH-1H-E430G and IgG1-11B8-E430G efficiently induced CDC in Wien 133 cells (FIG. 12A). Fc-Fc interaction enhanced IgG1-CAMPATH-1H-K248E-T437R with the self-oligomerization inhibiting mutation K439E (SEQ ID NO 65) displayed single agent activity when combined with the IgG1-b12-S440K (SEQ ID NO 70) negative control antibody variant, while IgG1-CAMPATH-1H-K248E-T437R with the self-oligomerization inhibiting mutation S440K (SEQ ID NO 66) displayed single agent activity when combined with the IgG1-b12-K439E (SEQ ID NO 69) negative control antibody variant (FIG. 12A-B). Preventing N-linked glycosylation of the IgG1-CAMPATH-1H-K248E-T437R-K439E antibody variant with the N297A mutation (SEQ ID NO 67) efficiently inhibited its single agent CDC activity on Wien 133 cells (FIG. 12C-D).

The Fc-Fc interaction enhanced and self-oligomerization inhibited IgG1-11B8-K248E-T437R-S440K antibody variant already showed low single agent activity on Wien 133 cells (FIG. 12A-B), which was also the case after disruption of the N297 glycosylation site in this antibody variant (SEQ ID NO 68; FIGS. 12C-D). Upon combination of IgG1-CAMPATH-1H-K248E-T437R-N297A and IgG1-11B8-K248E-T437R-S440K-N297A, CDC potency was partially restored, and at the antigen-saturating antibody concentration, CDC activity was largely restored.

Figure 12C:
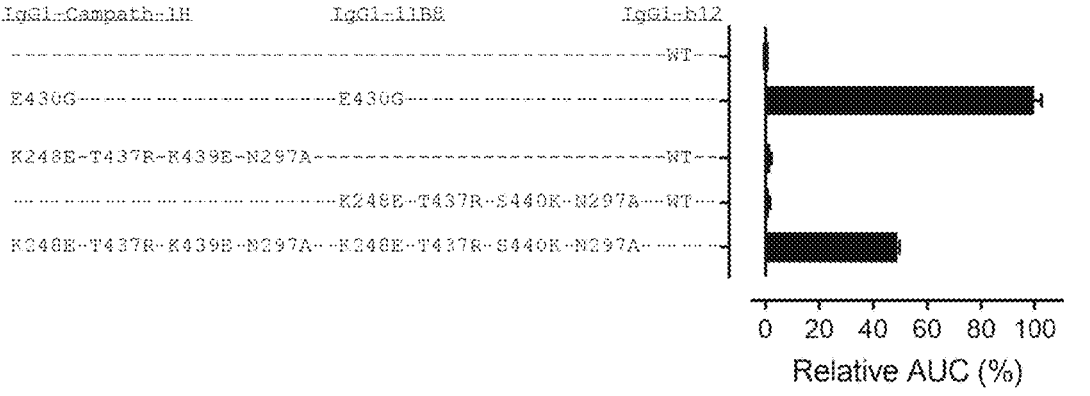
Figure 12D:
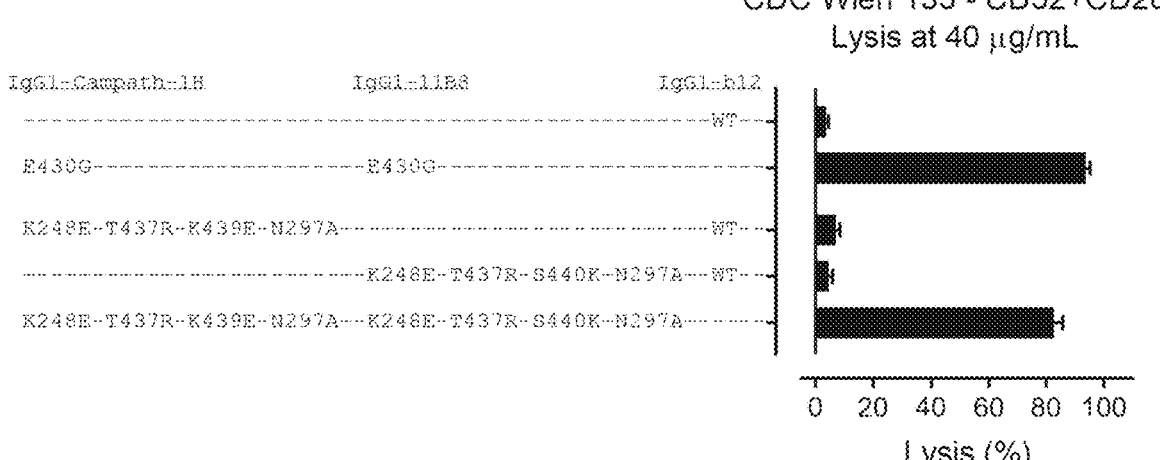

A similar co-dependent recovery of the CDC potency of aglycosylated IgG1-CAMPATH-1H-K248E-T437R-N297A and IgG1-11B8-K248E-T437R-S440K-N297A was observed using Ramos cells (FIG. 12C-D). Briefly, the IgG1-CAMPATH-1H-K248E-T437R-N297A and IgG1-11B8-K248E-T437R-S440K-N297A antibody variants displayed no CDC potency in Ramos cells (FIG. 12C), not even at the antigen-saturating antibody concentration (FIG. 12D). Combination of IgG1-CAMPATH-1H-K248E-T437R-N297A and IgG1-11B8-K248E-T437R-S440K-N297A partially restored the CDC potency of these antibody variants, and almost completely restored CDC activity at the antigen-saturating concentration, comparing to the IgG1-CAMPATH-1H-E430G+IgG1-11B8-E430G positive control.

Together, these data show that disruption of the N297 glycosylation site improves the selectivity of antibody variants harboring the Fc-Fc interaction enhancing K248E-T437R and the self-oligomerization inhibiting K439E or S440K mutations. Combination of the K248E-T437R Fc-Fc interaction enhanced antibody variants with the complementary K439E and S440K self-oligomerization inhibiting mutations partially restored their CDC activity.

Example 14: Aglycosylated CD37- and CD20-Targeting Antibody Variants with Fc-Fc Interaction Enhancing Mutation E345R and Self-Oligomerization Inhibiting Mutations Induce Mutually Dependent CDC Activation In Example 9, selective CDC could be induced by aglycosylated IgG1-CD37-37-3 and IgG1-11B8 antibody variants with Fc-Fc interaction enhancing mutation E430G or E345K and self-oligomerization inhibiting mutations. Here, we tested whether CDC could also be selectively induced by aglycosylated co-dependent IgG1-CD37-37-3 and IgG1-11B8 antibody variants harboring Fc-Fc interaction enhancing mutation E345R.

Different mutations were introduced in the anti-CD37 IgG1-CD37-37-3 and anti-CD20 IgG1-11B8 antibodies: E430G or E345R, which induce enhanced Fc-Fc interactions; K439E or S440K, which inhibit self-oligomerization; N297A, which disrupts the N297 N-glycosylation consensus sequence (NX[S/T]), resulting in aglycosylated antibodies. As controls, single antibodies were mixed 1:1 with non-binding isotype IgG1-b12 control antibodies to enable direct comparison of the concentrations of individual components and mixtures composed thereof. Where indicated, these mutations were introduced in IgG1-b12 non-binding control antibody as well. The purified antibody variants were tested in a range of concentrations (range 0.005-20.0 µg/mL final concentrations; 3.33-fold dilutions) in an in vitro CDC assay with 20% NHS on Daudi cells (N=3), which co-express the CD20 and CD37 antigens, essentially as described in Example 2, with the exception that in the current Example 30,000 cells/well were used. The relative area under dose-response curves with log transformed concentrations (AUC values) were normalized to the AUC value measured for the non-binding negative control IgG1-b12 (0%) and the AUC value measured for the positive control mixture of IgG1-CD37-37-3-E430G and IgG1-11B8-E430G (100%).

The low single agent CDC activity on Daudi cells of IgG1-CD37-37-3-E430G-K439E could not be further suppressed by introduction of mutation N297A (FIG. 13A). A similarly low residual single agent CDC activity was observed for IgG1-CD37-37-3-E345R-K439E-N297A when it was combined with IgG1-b12-E345R-S440K-N297A. The residual CDC potency induced by the IgG1-11B8-E430G-S440K antibody variant was lower than of IgG1-CD37-37-3-E430G-K439E and could also not be further suppressed by introduction of mutation N297A. IgG1-11B8-E345R-S440K-N297A demonstrated a similarly very low CDC activity when combined with IgG1-b12-E345R-K439E-N297A.

As compared to positive control mixture IgG1-CD37-37-3-E430G+IgG1-11B8-E430G, the introduction of self-oligomerization inhibiting mutations in these antibody variants resulted in approximately 12% less efficient CDC. Upon introducing the N297A mutation in the variants of the positive control, CDC was induced approximately 29% less efficiently. When both the K439E or S440K, and N297A mutations were introduced in IgG1-CD37-37-3-E430G and IgG1-11B8-E430G, CDC was induced approximately 45% less efficiently as compared to the positive control mixture. However, when E345R was introduced as the Fc-Fc interaction enhancing mutation instead of E430G, the CDC potency was reduced only by 14% as compared to the positive control mixture, which is a result comparable to the mixture of IgG1-CD37-37-3-E430G-K439E+IgG1-11B8-E430G-S440K. At the highest concentration tested (20 µg/mL), all mixtures described above induced a maximal lysis comparable to the positive control mixture, while all single agent CDC activity was limited to <14% lysis, retaining a substantial window between mixture and co-dependent mixture even at target saturation (FIG. 13B).

In conclusion, aglycosylated variants of IgG1-CD37-37-3 and IgG1-11B8 antibodies harboring an E430G or E345R Fc-Fc interaction enhancing mutation in addition to the K439E or S440K self-oligomerization inhibiting mutation could selectively and co-dependently induce CDC of Daudi cells. In particular, a mixture of antibody variants harboring the E345R mutation showed strong CDC selectivity. At the highest concentration tested, all mixtures studied in this Example induced efficient lysis of Daudi cells.

Example 15: Disruption of the N297 Glycosylation Site Improves Selectivity in CDC Efficacy by CD52- and CD20-Targeting Antibody Variants Harboring Fc-Fc Interaction Enhancing Mutation E430Y and Self-Oligomerization Inhibiting Mutations In Example 7 and 8, it was shown that single agent CDC efficacy on Wien 133 cells could be strongly reduced by the introduction of a mutation that prevents glycosylation of CD52-targeting IgG1-CAMPATH-1H and CD20-targeting IgG1-11B8 antibody variants that also harbor mutations that enhance Fc-Fc interactions and inhibit self-oligomerization. Co-dependent mixtures of such aglycosylated antibody variants could partially restore CDC efficacy. Here, it was studied whether aglycosylated co-dependent IgG1-CAMPATH-1H and IgG1-11B8 antibody variants harboring Fc- Fc interaction enhancing mutation E430Y could further optimize the CDC potency on Wien 133 cells in a selective fashion.

Different mutations were introduced in the anti-CD52 IgG1-CAMPATH-1H and anti-CD20 IgG1-11B8 antibodies: E430G, E345R or E430Y, which induce enhanced Fc-Fc interactions; K439E or S440K, which inhibit self-oligomerization; N297A, which disrupts the N297 N-glycosylation consensus sequence (NX[S/T]) and yields aglycosylated antibodies. As controls, single antibodies were mixed 1:1 with non-binding isotype IgG1-b12 control antibodies to enable direct comparison of the concentrations of individual components and mixtures composed thereof. Where indicated, mutations such as the abovementioned were introduced in IgG1-b12 non-binding control antibody as well. The purified antibody variants were tested in a range of concentrations (range 0.01-40.0 µg/mL final concentrations, with 3.33-fold dilutions) using a PI CDC assay on Wien 133 cells (N=3) with 20% NHS, essentially as described in Example 2, with the exception that in the current Example 30,000 cells/well were used. The relative areas under dose-response curves with log transformed concentrations (AUC values) were normalized to the AUC value measured for the non-binding negative control IgG1-b12 (0%) and the AUC value measured for positive control IgG1-CAMPATH-1H-E430G (100%; for the IgG1-CAMPATH-1H antibody variant mixtures) or positive control IgG1-CAMPATH-1H-E430G+IgG1-11B8-E430G (100%; for the IgG1-CAMPATH-1H-E430G+IgG1-11B8-E430G antibody variant mixtures).

In Example 7, it was observed that IgG1-CAMPATH-1H antibody variants harboring either E430G or E345R, and K439E or S440K had residual CDC activity on Wien 133 cells as compared to the level induced by the positive control (E430G-K439E: approximately 33%; E345R-K439E: approximately 51%; E430G-S440K: approximately 49%; E345R-S440K: approximately 58%). In the current Example, both IgG1-CAMPATH-1H-E430Y-K439E (SEQ ID NO 77) and IgG1-CAMPATH-1H-E430Y-S440K (SEQ ID NO 78) induced residual CDC to approximately 75% and 78%, respectively, of the level induced by the IgG1-CAM-PATH-1H-E430G positive control when combined with complementary non-binding control IgG1-b12 variants (FIG. 14A). In all cases, introduction of the N297A mutation partially suppressed the residual CDC activity (E430Y-K439-N297A: SEQ ID NO 79; E430Y-S440-N297A: SEQ ID NO 80).

The strongest recovery of CDC potency (to approximately 108% of the level induced by the positive control) was induced by a mixture of IgG1-CAMPATH-1H-E430Y-K439E+IgG1-CAMPATH-1H-E430Y-S440K, while mixtures of such variants containing the E345R (approximately 103% of level induced by positive control) or E430G mutation (approximately 97% of level induced by positive control) also efficiently recovered CDC activity. Although the CDC efficacy by mixtures of the aglycosylated IgG1-CAMPATH-1H variants was lower than by mixtures of glycosylated variants as compared to the level induced by the positive control (E430G: approximately 72%; E345R: approximately 88%; E430Y: approximately 94%), these combinations showed higher selectivity of CDC as the single agent CDC activity of aglycosylated variants was also considerably lower than of glycosylated antibody variants.

Similar CDC efficacy results were observed for IgG1-CAMPATH-1H and IgG1-11B8 antibody variants and mixtures thereof (FIG. 14B). Introduction of mutation N297A nearly abrogated the single agent activity of IgG1-CAM- PATH-1H-K439E variants harboring either the E430G or E345R mutation (both described in Example 8) while the single agent CDC activity of IgG1-CAMPATH-1H-E430Y-K439E (in a mixture with a complementary IgG1-b12 variant) was only partially suppressed by introduction of mutation N297A. While no single agent CDC activity could be detected for IgG1-11B8-E430G-S440K and IgG1-11B8-E345R-S440K (Example 8), a relatively high residual CDC activity was induced by IgG1-11B8-E430Y-S440K (to approximately 39% of the level induced by the positive control mixture). The residual CDC activity of IgG1-11B8-E430Y-S440K could partially be suppressed by introduction of mutation N297A, to approximately 10% of the level induced by the positive control mixture.

Strong recovery of CDC activity was observed for mixtures of the glycosylated IgG1-CAMPATH-1H and IgG1-11B8 variants harboring the E430G, E345R or E430Y and complementary self-oligomerization inhibiting mutations. Similar to what was observed for aglycosylated IgG1-CAMPATH-1H antibody variant mixtures in FIG. 14A, mixtures of aglycosylated IgG1-CAMPATH-1H and IgG1-11B8 antibody variants harboring the E430G, E345R or E430Y induced lower recovery of CDC potency. However, also here, the aglycosylated antibody variants showed a higher selectivity of CDC as the single agent CDC activity of the aglycosylated variants was considerably lower than that of glycosylated IgG1-CAMPATH-1H and IgG1-11B8 antibody variants.

In conclusion, introduction of the N297A mutation partially suppressed the single agent CDC activity on Wien 133 cells of IgG1-CAMPATH-1H-E430Y and IgG1-11B8-E430Y antibody variants that further contain a self-oligomerization inhibiting mutation. CDC efficacy could be efficiently restored by mixing such aglycosylated co-dependent antibody variants. Although the CDC potency of mixtures of glycosylated IgG1-CAMPATH-1H and IgG1-11B8 antibody variants was higher, the more strongly suppressed single agent CDC activity of aglycosylated variants resulted in a higher CDC selectivity. While IgG1-CAMPATH-1H variants harboring the E430Y Fc-Fc interaction enhancing mutation showed substantial residual single agent activity, reducing the selective window, variant IgG1-11B8-E430Y-S440K-N297A showed minimal single agent activity.

Example 16: CDC Efficacy of Mixed Aglycosylated Antibody Variants Containing Mutations that Enhance Fc-Fc Interactions and Inhibit Self-Oligomerization is Improved by Introducing Additional C1q Binding-Enhancing Mutations In Example 7 and 8, it was shown that single agent CDC efficacy could be strongly reduced by the introduction of a mutation that prevents glycosylation of CD52-targeting IgG1-CAMPATH-1H and CD20-targeting IgG1-11B8 antibody variants, that also harbor mutation E345K which enhances Fc-Fc interactions and mutations that which self-oligomerization. Co-dependent mixtures of such antibody variants could partially restore the CDC efficacy compared to the level of antibody variants containing only Fc-Fc interaction enhancing mutation E430G. Here, the effect of introducing additional C1q binding enhancing mutations on the recovery of CDC efficacy after mixing IgG1-CAMPATH-1H variants, or IgG1-CAMPATH-1H and IgG1-11B8 variants was studied for antibody variants harboring the Fc-Fc interaction enhancing mutation E345K.

Different mutations were introduced in the anti-CD52 IgG1-CAMPATH-1H and anti-CD20 IgG1-11B8 antibodies:

E430G or E345K, which induce enhanced Fc-Fc interactions; K439E or S440K, which inhibit self-oligomerization; N297A, which disrupts the N297 N-glycosylation consensus sequence (NX[S/T]) and yields aglycosylated antibodies. As controls, single antibodies were mixed 1:1 with non-binding isotype IgG1-b12 control antibodies to enable direct comparison of the concentrations of individual components and mixtures composed thereof. The purified antibody variants were tested in a range of concentrations (range 0.01-40.0 µg/mL final concentrations, with 3.33-fold dilutions) using a PI CDC assay on Wien 133 cells (N=3) with 20% NHS, essentially as described in Example 2 with the exception that in the current Example 30,000 cells/well were used. The relative areas under dose-response curves with log transformed concentrations (AUC values) were normalized to the AUC value measured for the non-binding negative control IgG1-b12 (0%) and the AUC value measured for positive control IgG1-CAMPATH-1H-E430G (100%; for the IgG1-CAMPATH-1H antibody variant mixtures) or positive control mixture IgG1-CAMPATH-1H-E430G+IgG1-11B8-E430G (100%; for the IgG1-CAMPATH-1H-E430G+IgG1-11B8-E430G antibody variant mixtures).

While no single agent CDC activity on Wien 133 cells by IgG1-CAMPATH-1H-E345K-K439E-N297A and IgG1-CAMPATH-1H-E345K-S440K-N297A could be detected in Example 7, the introduction of additional mutations that enhance C1q binding (K326A-E333S) in these constructs (E345K-K439E-N297A-K326A-E333S: SEQ ID NO 83; E345K-S440K-N297A-K326A-E333S: SEQ ID NO 84) increased single agent CDC activity (FIG. 15A). Mixing these complementary antibody variants resulted in a full co-dependent recovery of CDC potency equivalent to that of the IgG1-CAMPATH-1H-E430G positive control. Similarly, no single agent CDC activity could be detected for IgG1-11B8-E345K-S440K-N297A in Example 8, but partial CDC activity was observed after introducing the K326A-E333S mutations in this construct (FIG. 15B). A mixture of IgG1-CAMPATH-1H-E345K-K439E-N297A-K326A-E333S+ IgG1-11B8-E345K-S440K-N297A-K326A-E333S recovered a CDC potency similar to that of the IgG1-Campath-1H-E430G+IgG1-11B8-E430G positive control mixture.

Together, these data show that the introduction of C1q binding enhancing mutations K326A and E333S decreased the selectivity of CDC induction in Wien 133 cells by IgG1-CAMPATH-1H and IgG1-11B8 antibody variants harboring Fc-Fc interaction enhancing mutation E345K and self-oligomerization inhibiting mutations, but mutations K326A and E333S enabled the recovery of highly potent CDC after mixing.

Example 17: Selectivity of CDC Efficacy by Aglycosylated IgG2 and IgG4 Antibody Variants Harboring Fc-Fc Interaction Enhancing and Self-Oligomerization Inhibiting Mutations In the previous Examples, it was shown that aglycosylated variants of IgG1 antibodies harboring mutations that enhance Fc-Fc interactions and inhibit self-oligomerization could selectively and co-dependently induce CDC of target cells. Here, it was studied whether CDC could also be induced in a selective manner by aglycosylated variants of IgG2 and IgG4 antibodies harboring such mutations.

Different mutations were introduced in the anti-CD52 IgG2-CAMPATH-1H and IgG4-CAMPATH-1H antibodies, and anti-CD20 IgG2-11B8 and IgG4-11B8 antibodies: E430G or E345R, which induce enhanced Fc-Fc interactions; K439E or S440K, which inhibit self-oligomerization;

N297A, which disrupts the N297 N-glycosylation consensus sequence (NX[S/T]) and yields aglycosylated antibodies. As controls, single antibodies were mixed 1:1 with non-binding isotype IgG2-b12 control antibodies to enable direct comparison of the concentrations of individual components and mixtures composed thereof. The purified antibody variants were tested in a range of concentrations (range 0.01-40.0 μg/mL final concentrations, with 3.33-fold dilutions) using a PI CDC assay on Wien 133 cells (N=3) with 20% NHS, essentially as described in Example 2 with the exception that in the current Example 30,000 cells/well were used. The relative areas under dose-response curves with log transformed concentrations (AUC values) were normalized to the AUC value measured for the non-binding negative control IgG1-b12 (0%) and the AUC value measured for positive control mixture IgG1-CAMPATH-1H-E430G+IgG1-11B8-E430G (100%).

A mixture of IgG2 variants (SEQ ID NO 74) of the CAMPATH-1H and 11B8 antibodies both harboring the E345R (SEQ ID NO 124) mutation induced strong CDC of Wien 133 cells, to approximately 111% of the level induced by the positive control (FIG. 16A). Variant IgG2-CAM-PATH-1H-E345R-K439E (SEQ ID NO 125) induced residual CDC activity to approximately 34% of the level induced by the positive control, while introduction of mutation N297A (SEQ ID NO 127) in this variant resulted in single agent CDC activity of approximately 48% of the level induced by the positive control. When introducing mutation S440K (SEQ ID NO 126) in the IgG2-11B8-E345R variant, the single agent CDC activity dropped to approximately 18% of the level induced by the positive control, while the introduction of N297A (SEQ ID NO 128) in IgG2-11B8-E345R-S440K resulted in a single agent CDC activity of approximately 37% of the level induced by the positive control. A strong recovery of CDC potency was observed upon mixing IgG2-CAMPATH-1H-E345R-K439E+IgG2-11B8-E345R-S440K (to approximately 93% of the level induced by the positive control) or by mixing IgG2-CAM-PATH-1H-E345R-K439E-N297A+IgG2-11B8-E345R-S440K-N297A (to approximately 96% of the level induced by the positive control).

A mixture of IgG4 variants (SEQ ID NO 75) of the CAMPATH-1H and 11B8 antibodies both harboring the E345R (SEQ ID NO 129) mutation induced CDC of Wien 133 cells to approximately 71% of the level induced by the positive control (FIG. 16B). No substantial single agent CDC activity was detected for the IgG4-CAMPATH-1H-E345R variants harboring either the K439E (SEQ ID NO 130) or K439E-N297A (SEQ ID NO 132) mutations. Also, the IgG4-11B8-E345R variants harboring either the S440K (SEQ ID NO 131) or S440K-N297A (SEQ ID NO 133) mutations only induced CDC activity at very low levels. A partial recovery of CDC potency was observed by mixing IgG4-CAMPATH-1H-E345R-K439E+IgG4-11B8-E345R-S440K, to approximately 50% of the level induced by the positive control. Mixing aglycosylated variants of the latter antibody variants (IgG4-CAMPATH-1H-E345R-K439E-N297A+IgG4-11B8-E345R-S440K-N297A) only recovered CDC potency to approximately 14% of the level induced by the positive control.

In conclusion, mixtures of aglycosylated IgG2 antibody variants harboring Fc-Fc interaction enhancing mutation E345R and self-oligomerization inhibiting mutations K439E or S440K could induce selective CDC of Wien 133 cells in a co-dependent manner. The individual glycosylated IgG2 antibody variants induced a substantial level of residual single agent CDC activity, which could not be suppressed by introduction of mutation N297A. Although the window in CDC selectivity for IgG2 antibody variants is more limited than for comparable IgG1 variants, the lack of FcγR activation by aglycosylated IgG2 variants, as described in Example 23 and 24, may allow aglycosylated co-dependent IgG2 antibody variants to be used for applications in which single agent CDC activity does not pose a potential risk. No single agent CDC activity was observed for glycosylated and aglycosylated IgG4 antibody variants harboring mutations that enhance Fc-Fc interactions and inhibit self-oligomerization. However, only a partial recovery of CDC potency could be attained by mixing IgG4 antibody variants harboring the aforementioned mutations.

Example 18: Selectivity of CDC Induction by Aglycosylated IgG1-CAMPATH-1H Antibody Variants Harboring Fc-Fc Interaction Enhancing and Self-Oligomerization Inhibiting Mutations In previous Examples, the effect of disrupting the N-glycosylation consensus sequence of IgG1 antibody variants harboring Fc-Fc interaction enhancing and self-oligomerization inhibiting mutations on CDC efficacy was assessed for different antibody and target combinations. Here, CDC efficacy on Wien 133 cells induced by single agent antibody variants or mixtures of such variants was assessed for variants harboring self-oligomerization inhibiting mutations K439E or S440K, the N297A mutation, which disrupts the N-glycosylation consensus sequence, and either of the Fc-Fc interaction enhancing mutations E430G, E430Y, E345K or E345R.

Different mutations were introduced in the anti-CD52 IgG1-CAMPATH-1H antibody: E430G, E430Y, E345K or E345R, which enhance Fc-Fc interactions; K439E or S440K, which inhibit self-oligomerization; N297A, which disrupts the N297 N-glycosylation consensus sequence (NX[S/T]) and yields aglycosylated antibodies. As controls, single antibodies were mixed 1:1 with non-binding isotype IgG1-b12 control antibodies to enable direct comparison of the concentrations of individual components and mixtures composed thereof. Where indicated, mutations such as the abovementioned were introduced in IgG1-b12 non-binding control antibody as well. The purified antibody variants were tested in a range of concentrations (range 0.01-100.0 μg/mL final concentrations, with 2.5-fold dilutions) using a PI CDC assay on Wien 133 cells (N=3) with 20% NHS, essentially as described in Example 2 with the exception that in the current Example 30,000 cells/well were used. The relative areas under dose-response curves with log-transformed concentrations (AUC values) were normalized to the AUC value measured for the non-binding negative control IgG1-b12 (0%) and the AUC value measured for positive control IgG1-CAMPATH-1H-E430G (100%).

Upon introduction of mutation K439E or S440K in IgG1-CAMPATH-1H-E430Y, the single agent CDC efficacy was approximately 92% and 97% of the level induced by positive control IgG1-CAMPATH-1H-E430G, respectively (FIG. 17A). A mixture of these antibody variants increased the CDC efficacy to approximately 122% of the level induced by the positive control. IgG1-CAMPATH-1H variants harboring the K439E-N297A mutations induced varying levels of residual single agent CDC activity depending on the Fc-Fc interaction enhancing mutation that was introduced, ranging from approximately 5% (E345K), 12% (E430G), 36% (E345R) up to 60% (E430Y) of the level induced by the positive control. The single agent CDC activity of IgG1-CAMPATH-1H variants harboring S440K-

N297A also depended on the Fc-Fc interaction enhancing mutation that was introduced, but the residual CDC activity of variants containing the S440K-N297A mutations was overall higher than the constructs harboring mutations K439E-N297A. The residual CDC activity of the IgG1-CAMPATH-1H variants harboring the S440K-N297A mutations with an Fc-Fc interaction enhancing mutation ranged from approximately 20% (E345K), 27% (E430G), 47% (E345R) up to 65% (E430Y).

Mixtures of IgG1-CAMPATH-1H antibody variants harboring the K439E or S440K mutation in addition to mutation N297A and any of the Fc-Fc interaction enhancing mutations efficiently restored CDC efficacy. Mixtures of IgG1-CAMPATH-1H-E430Y-K439E-N297A+IgG1-CAM-PATH-1H-E430Y-S440K-N297A and IgG1-CAMPATH-1H-E345R-K439E-N297A+IgG1-CAMPATH-1H-E345R-S440K-N297A did so most efficiently to approximately 95% of the level induced by the positive control. Mixtures of the co-dependent IgG1-CAMPATH-1H variants harboring either the E430G or E345K mutations restored CDC efficacy to approximately 84 and 87% of the level induced by the positive control, respectively.

At the highest concentration tested, all mixtures induced CDC to a level that was comparable to the positive control (FIG. 17B). The IgG1-CAMPATH-1H variants harboring the K439E-N297A mutations and either of the E430G, E345K, E430Y or E345R mutations induced CDC with a varying level of potency ranging from 44% (E345K) to 82% (E430Y) while the IgG1-CAMPATH-1H variants harboring the S440K-N297A mutations and either of the E430G, E345K, E430Y or E345R mutations induced CDC with a potency ranging from 51% (E345K) to 82% (E430Y).

In conclusion, aglycosylated IgG1-CAMPATH-1H antibody variants harboring an Fc-Fc interaction enhancing mutation have a lower residual single agent CDC activity on Wien 133 cells upon introduction of the K439E mutation as compared to variants harboring the S440K mutation. In addition, the data presented in this Example indicate that CDC efficacy could be most potently restored by mixtures of co-dependent aglycosylated IgG1-CAMPATH-1H antibody variants harboring the E430Y or E345R Fc-Fc interaction enhancing mutations. However, such mixtures are associated with a lower CDC selectivity as the single agent CDC activity was relatively high. The most selective antibody variants are the variants harboring the E345K mutation, followed by the E430G mutation, which induced relatively lower single agent activity and relatively strong CDC recovery as a mixture.

Example 19: Analysis of the Effect of Introducing Glycosylation-Disrupting Mutation in IgG1-CAMPATH-1H Antibody Variants Harboring Fc-Fc Interaction Enhancing and Self-Oligomerization Inhibiting Mutations on FcγRIIa Activation In Example 10, it was shown that the introduction of a glycosylation-inhibiting mutation in IgG1-CAMPATH-1H antibody variants harboring an Fc-Fc interaction enhancing mutation silences the capacity to induce ADCP as measured through an FcγRIIa activation reporter cell assay. Here, we tested whether the introduction of glycosylation-inhibiting mutation N297A affected the capacity of IgG1-CAMPATH-1H and IgG1-11B8 antibody variants or mixtures thereof harboring Fc-Fc interaction enhancing mutation E430G, E430Y or E345R and a self-oligomerization inhibiting mutation to activate FcγRIIa in a reporter cell assay, as a surrogate for antibody-dependent cellular phagocytosis (ADCP).

For the ADCP reporter bioassay, antibody variants of IgG1-CAMPATH-1H and IgG1-11B8 were tested which harbor an Fc-Fc interaction enhancing mutation (E430G, E430Y, or E345R), a self-oligomerization inhibiting mutation (K439E or S440K) and a mutation which disrupts the N297 N-glycosylation consensus sequence (NX[S/T]; N297A) using the Bio-Glo Luciferase Assay System (Promega, Cat No. G7941) on Raji cells. As controls, single antibodies were mixed 1:1 with non-binding isotype IgG1-b12 control antibodies to enable direct comparison of the concentrations of individual components and mixtures composed thereof. As effector cells, the kit contains Jurkat human T cells that are engineered to stably express high affinity FcγRIIa (H131 allotype) and a nuclear factor of activated T cells (NFAT)-response element driving expression of firefly luciferase. Briefly, Raji cells (10 μL; 5,000 cells/well) were seeded in 384-wells white opaque flat bottom plates (Optiplate white; Perkin-Elmer; Cat #6007680) in RPMI-1640 [(Promega, Cat #G708A) supplemented with 4% low IgG serum (Promega, Cat. #G711A)]. The Raji cells were preincubated for 15 minutes with antibody concentration series (10 μL; 4-fold dilution series resulting in 0.2-40,000 ng/mL final concentrations after addition of effector cells) at 37° C./5% C02. Subsequently, thawed Jurkat FcγRIIa H131 allotype Effector cells (10 μL; 30,000 cells/well; Promega, Cat #G988A) were added, and the cells were incubated for 5.5 hours at 37° C./5% C02. After this incubation, the cells were equilibrated to room temperature for 15 minutes. Subsequently, 30 μL Bio-Glo Assay Luciferase Reagent [Bio-Glo Luciferase Assay Substrate (Promega Cat. #G720A) in Bio-Glo Luciferase Assay Buffer (Promega, Cat. #G719A)] was added per well and incubated for 15 minutes at RT in the dark. Luciferase production was quantified by luminescence readout on an EnVision Multilabel Reader (Perkin Elmer). Raw luminescence values were normalized prior to pooling relative to an internal IgG1 control antibody measured in each plate in triplicate, at a concentration of 40 μg/mL, to suppress plate-to-plate variation in absolute luminescence intensities. The relative areas under dose-response curves with log transformed concentrations (AUC values) were normalized to the AUC value measured for the non-binding negative control IgG1-b12 (0%) and the AUC value measured for the positive control IgG1-CAMPATH-1H-E430G (100%; FIG. 18A) or IgG1-CAMPATH-1H-E430G+IgG1-11B8-E430G (100%, FIG. 18B).

The capacity to induce FcγRIIa activation was enhanced by IgG1-CAMPATH-1H-E430Y (SEQ ID NO 76) as compared to IgG1-CAMPATH-1H-E430G (FIG. 18A). No FcγRIIa activation or levels close to background were induced by the single agent IgG1-CAMPATH-1H antibody variants harboring mutations E430Y-K439E, E430Y-K439E-N297A, E430G-K439E-N297A, or E345R-K439E-N297A. Such low levels of FcγRIIa activation should be seen in the perspective of the high sensitivity of the applied assay to any FcγRIIa activation. While IgG1-CAMPATH-1H-E430Y-S440K induced low levels of FcγRIIa activation, introduction of mutation N297A fully abrogated the FcγRIIa activation. Also, no FcγRIIa activation was detected for the aglycosylated S440K-containing antibody variants harboring the E430G or E345R instead of E430Y.

A mixture of IgG1-CAMPATH-1H-E430Y-K439E+IgG1-CAMPATH-1H-E430Y-S440K induced FcγRIIa activation to a level comparable to the positive control. When one of the IgG1-CAMPATH-1H antibody variants in the mixture harbored the N297A mutation, this FcγRIIa activation was strongly reduced but not completely abrogated. FcγRIIa activation was completely abrogated when a mixture contained two antibody variants that both contained the N297A mutation (E430G or E345R-containing variants) or reduced to low residual FcγRIIa activation for the E430Y-containing antibody variant mixture.

While the IgG1-11B8-E430G-S440K variant was shown to induce low levels of FcγRIIa activation in Example 10, the FcγRIIa activation induced by IgG1-11B8 single agents containing the E430G-S440K-N297A, E345R-S440K-N297A or E430Y-S440K-N297A mutations was abrogated (FIG. 18B). In Example 10, it was also shown that a mixture of IgG1-CAMPATH-1H-E430G-K439E+IgG1-11B8-E430G-S440K induced low levels of FcγRIIa activation as compared to the positive control. However, mixtures of IgG1-CAMPATH-1H and IgG1-11B8 variants in which both variants were aglycosylated, Fc-Fc interaction enhanced (E430G, E345R or E430Y mutation) and inhibited to self-oligomerize showed no FcγRIIa activation.

Taken together, the introduction of glycosylating site disrupting mutation N297A in Fc-Fc interaction enhanced and self-oligomerization-inhibited IgG1-CAMPATH1-H and IgG1-11B8 antibody variants efficiently suppressed the capacity to induce FcγRIIa activation in a highly sensitive reporter assay. Also, upon introducing the N297A mutation in both antibody variants in a mixture, such mixtures did not induce FcγRIIa activation, with the exception of a mixture of two IgG1-CAMPATH-1H variants containing the E430Y mutation which induced low residual FcγRIIa activation. This suggests that co-dependent mixtures of aglycosylated Fc-Fc interaction enhanced antibody variants lack the capacity to induce ADCP.

Example 20: Analysis of the effect of introducing a mutation disrupting glycosylation in IgG1-CAMPATH-1H antibody variants harboring Fc-Fc interaction enhancing, self-oligomerization inhibiting and C1q binding enhancing mutations on FcγRIIa activation In Example 19, it was shown that the introduction of mutation N297A disrupting the glycosylation of Fc-Fc interaction enhanced and self-oligomerization-inhibited IgG1-CAMPATH1-H and IgG1-11B8 antibody variants efficiently suppressed the capacity to induce ADCP as measured through an FcγRIIa activation reporter cell assay. Here, we tested whether the introduction of additional mutations that enhance C1q binding in such IgG1-CAMPATH-1H and IgG1-11B8 variants, or mixtures thereof, affected the capacity to activate FcγRIIa in a reporter cell assay, as a surrogate for ADCP.

For the ADCP reporter bioassay, antibody variants of IgG1-CAMPATH-1H and IgG1-11B8 were tested which harbor an Fc-Fc interaction enhancing mutation (E430G, E430Y, or E345R), a self-oligomerization inhibiting mutation (K439E or S440K), a mutation which disrupts the N297 N-glycosylation consensus sequence (NX[S/T]; N297A) and mutations that enhance the binding of C1q (K326A-E333S) using the Bio-Glo Luciferase Assay System (Promega, Cat No. G7941) on Raji cells, essentially as described in Example 19. As controls, single antibodies were mixed 1:1 with non-binding isotype IgG1-b12 control antibodies to enable direct comparison of the concentrations of individual components and mixtures composed thereof. Raw luminescence values were normalized prior to pooling relative to an internal IgG1 control antibody measured in each plate in triplicate, at a concentration of 40 μg/mL, to suppress plate-to-plate variation in absolute luminescence intensities. The relative areas under dose-response curves with log transformed concentrations (4-fold dilution series resulting in 0.2-40,000 ng/mL final concentrations after addition of effector cells; AUC values) were normalized to the AUC value measured for the non-binding negative control IgG1-b12 (0%) and the AUC value measured for the positive control IgG1-CAMPATH-1H-E430G (100%; FIG. 19A) or IgG1-CAMPATH-1H-E430G+IgG1-11B8-E430G (100%, FIG. 19B).

Strong FcγRIIa activation by the IgG1-CAMPATH-1H-E430G antibody variant was detected (FIG. 19A). No capacity to induce FcγRIIa activation was detected for the IgG1-CAMPATH-1H variants harboring the E345K-K439E-N297A or E345K-S440K-N297A mutations in addition to C1q binding enhancing mutations K326A-E333S. Also, a mixture of the latter two variants did not induce any FcγRIIa activation.

For an IgG1-11B8 antibody variant harboring the E345K-S440K-N297A-K326A-E333S mutations, the capacity to induce FcγRIIa activation as a single agent was highly comparable to the IgG1-CAMPATH-1H variants, as no single agent FcγRIIa activation was detected (FIG. 19B). Also, a mixture of IgG1-CAMPATH-1H-E345K-K439E-N297A-K326A-E333S+IgG1-11B8-E345K-S440K-N297A-K326A-E333S did not induce detectable FcγRIIa activation.

In conclusion, these data indicate that C1q binding-enhanced aglycosylated IgG1-CAMPATH-1H and IgG1-11B8 antibody variants harboring the E345K and either K439E or S440K mutations lack the capacity to induce FcγRIIa activation in a highly sensitive FcγRIIa reporter cell assay, both when tested as single agents or as a mixture.

Example 21: Analysis of the Effect of Introducing a Mutation Disrupting Glycosylation in IgG1-CAMPATH-1H Antibody Variants Harboring Fc-Fc Interaction Enhancing and Self-Oligomerization Inhibiting Mutations on FcγRIIIa Activation In Example 11, it was shown that the capacity to induce ADCC, as measured through an FcγRIIIa activation reporter cell assay, by IgG1-CAMPATH-1H antibody variants harboring an Fc-Fc interaction enhancing mutation could be efficiently suppressed by introduction of the N297A mutation that disrupts N-linked glycosylation. Here, we tested whether the introduction of mutation N297A affected the capacity of IgG1-CAMPATH-1H and IgG1-11B8 antibody variants harboring mutations that enhance Fc-Fc interactions and inhibit self-oligomerization, or mixtures thereof, to activate FcγRIIIa in a reporter cell assay as a surrogate for ADCC.

For the ADCC reporter bioassay, antibody variants of IgG1-CAMPATH-1H and IgG1-11B8 were tested which harbor an Fc-Fc interaction enhancing mutation (E430G, E430Y, or E345R), a self-oligomerization inhibiting mutation (K439E or S440K), and a mutation which disrupts the N297 N-glycosylation consensus sequence (NX[S/T]; N297A) using the Bio-Glo Luciferase ADCC Reporter Bioassay for the FcγRIIIa high affinity V158 allotype on Raji cells (Promega, Cat #G7018). As controls, single antibodies were mixed 1:1 with non-binding isotype IgG1-b12 control antibodies to enable direct comparison of the concentrations of individual components and mixtures composed thereof. As effector cells, the kit contains Jurkat human T cells that are engineered to stably express the high affinity V158 allotype of FcγRIIIa and a nuclear factor of activated T cells (NFAT)-response element driving expression of firefly luciferase. Except for using FcgammaRIIIa-V Effector Cells (Promega; Cat #G701A) in the current Example, the assay was performed essentially as described in Example 19. Raw luminescence values were normalized prior to pooling relative to an internal IgG1 control antibody measured in each plate in triplicate, at a concentration of 40 μg/mL, to suppress plate-to-plate variation in absolute luminescence intensities. The relative areas under dose-response curves with log transformed concentrations (4-fold dilution series resulting in 0.2-40,000 ng/mL final concentrations after addition of effector cells; AUC values) were normalized to the AUC value measured for the non-binding negative control IgG1-b12 (0%) and the AUC value measured for the positive control IgG1-CAMPATH-1H-E430G (100%; FIG. 20A) or IgG1-CAMPATH-1H-E430G+IgG1-11B8-E430G (100%, FIG. 20B).

The highly sensitive ADCC reporter assay indicated a strong capacity to induce FcγRIIIa activation by IgG1-CAMPATH-1H antibody variants, either as wild-type antibodies or when harboring Fc-Fc interaction enhancing mutations E430G or E430Y (FIG. 20A). The introduction of mutation K439E in IgG1-CAMPATH-1H-E430Y did not affect the capacity to induce FcγRIIIa activation. In contrast, no FcγRIIIa activation (E430G- or E345R-containing variants) or a strongly suppressed capacity to induce activation (E430Y-containing variant) was detected for the aglycosylated variants of IgG1-CAMPATH-1H-K439E. Similarly, an IgG1-CAMPATH-1H variant harboring the S440K mutation showed strong FcγRIIIa activation, while aglycosylated variants of Fc-Fc interaction enhanced IgG1-CAMPATH-1H-S440K variants showed strongly diminished (E430Y-containing variant) or no FcγRIIIa activation (E430G- or E345R-containing variants).

Introduction of the mutations K439E or S440K in a mixture of IgG1-CAMPATH-1H-E430Y antibody variants only mildly reduced the capacity to induce FcγRIIIa activation. Mixtures in which one of the antibody variants was glycosylated and the other aglycosylated also induced FcγRIIIa activation, the potency of which was dependent on which Fc-Fc interaction enhancing mutation was introduced: mixtures consisting of E430Y-containing variants induced the strongest FcγRIIIa activation, while E430G- and E345R-containing variants showed a reduced potency to induce FcγRIIIa activation. FcγRIIIa activation was strongly diminished by a mixture consisting of two aglycosylated (N297A-containing) IgG1-CAMPATH1-H-E430Y variants with the K439E or S440K mutation, while no FcγRIIIa activation could be detected for such mixtures consisting of two aglycosylated IgG1-CAMPATH-1H variants harboring the E430G or E345R mutations in addition to the K439E or S440K mutation.

Similar results were obtained for aglycosylated IgG1-11B8 variants and mixtures of IgG1-CAMPATH-1H and IgG1-11B8 variants (FIG. 20B). Aglycosylated variants of IgG1-11B8 harboring either the E430G, E345R or E430Y mutation did not induce FcγRIIIa activation. Also, no FcγRIIIa activation was observed for mixtures of aglycosylated IgG1-CAMPATH-1H and IgG1-11B8 variants harboring the K439E or S440K mutation in addition to any of the E430G, E345R or E430Y mutations.

In conclusion, the introduction of the N297A glycosylation site disrupting mutation in IgG1-CAMPATH-1H and IgG1-11B8 antibody variants harboring Fc-Fc interaction enhancing mutation E430G, E345R or E430Y and the K439E or S440K mutation either strongly reduced (in the case of E430Y-containing variants) or fully abrogated (in the case of E430G or E345R-containing variants) the capacity to induce FcγRIIIa activation when used as single agents. Also, no FcγRIIIa activation could be detected for mixtures of two co-dependent aglycosylated IgG1-CAMPATH-1H and/or IgG1-11B8 variants with an Fc-Fc interaction enhancing mutation, although a mixture of two IgG1-CAMPATH-1H variants harboring the E430Y mutation only induced low residual FcγRIIIa activation. It should be noted that the applied assay is highly sensitive for detection of FcγRIIIa activation. Both antibody variants in a mixture needed to be aglycosylated to fully eliminate FcγRIIIa activation, as a mixture of one aglycosylated and one glycosylated antibody variant still induced FcγRIIIa activation.

Example 22: Analysis of the Effect of Introducing a Mutation Disrupting Glycosylation in IgG1-CAMPATH-1H and IgG1-11B8 Antibody Variants Harboring Fc-Fc Interaction Enhancing, Self-Oligomerization Inhibiting and C1q Binding Enhancing Mutations on FcγRIIIa Activation In Example 21, it was shown that the capacity to induce ADCC, as measured through an FcγRIIIa activation reporter cell assay, by IgG1-CAMPATH-1H and IgG1-11B8 antibody variants harboring mutations that enhance Fc-Fc interactions and inhibit self-oligomerization could be efficiently suppressed by introduction of the N297A mutation disrupting N-linked glycosylation. Here, we tested whether the introduction of mutation N297A affected the capacity of such IgG1-CAMPATH-1H and IgG1-11B8 antibody variants that additionally harbor C1q binding enhancing mutations K326A-E333S, or mixtures thereof, to activate FcγRIIIa in a reporter cell assay as a surrogate for ADCC.

For the ADCC reporter bioassay, antibody variants of anti-CD52 IgG1-CAMPATH-1H and anti-CD20 IgG1-11B8 were tested which harbor an Fc-Fc interaction enhancing mutation (E430G or E345K), a self-oligomerization inhibiting mutation (K439E or S440K), mutations that enhance binding of C1q to antibody Fc domains (K326A-E333S) and a mutation which disrupts the N297 N-glycosylation consensus sequence (NX[S/T]; N297A) using the Bio-Glo Luciferase ADCC Reporter Bioassay for the FcγRIIIa high affinity V158 allotype on Raji cells (Promega, Cat #G7018). As controls, single antibodies were mixed 1:1 with non-binding isotype IgG1-b12 control antibodies to enable direct comparison of the concentrations of individual components and mixtures composed thereof. As effector cells, the kit contains Jurkat human T cells that are engineered to stably express the high affinity V158 allotype of FcγRIIIa and a nuclear factor of activated T cells (NFAT)-response element driving expression of firefly luciferase. Except for using FcgammaRIIIa-V Effector Cells (Promega; Cat #G701A) in the current Example, the assay was performed essentially as described in Example 19. Raw luminescence values were normalized prior to pooling relative to an internal IgG1 control antibody measured in each plate in triplicate, at a concentration of 40 μg/mL, to suppress plate-to-plate variation in absolute luminescence intensities. The relative areas under dose-response curves with log transformed concentrations (4-fold dilution series resulting in 0.2-40,000 ng/mL final concentrations after addition of effector cells; AUC values) were normalized to the AUC value measured for the non-binding negative control IgG1-b12 (0%) and the AUC value measured for the positive contro IgG1-CAMPATH- 1H-E430G (100%; FIG. 21A) or IgG1-CAMPATH-1H-E430G+IgG1-11B8-E430G (100%, FIG. 21B).

No potency to induce FcγRIIIa activation was detected in the highly sensitive ADCC reporter assay by single agents IgG1-CAMPATH-1H-E345K-K439E-N297A-K326A-E333S and IgG1-CAMPATH-1H-E345K-S440K-N297A-K326A-E333S (FIG. 21A). The potency to induce FcγRIIIa activation was not recovered by mixing the latter antibody variants.

The potency to induce FcγRIIIa activation was also studied for an IgG1-11B8 antibody variant harboring the E345K-S440K-N297A-K326A-E333S mutations (FIG. 21B). No FcγRIIIa activation was detected by this variant, either used as a single agent or mixed with IgG1-CAMPATH-1H-E345K-K439E-N297A-K326A-E333S.

In conclusion, aglycosylated IgG1-11B8 antibody variants harboring Fc-Fc interaction enhancing mutation E345K, a self-oligomerization inhibiting mutation (K439E or S440K) and C1q binding enhancing mutations K326A-E333S did not induce FcγRIIIa activation as single agents or when mixed with complementary IgG1-CAMPATH-1H antibody variants.

Example 23: Analysis of the Effect of Introducing a Mutation Disrupting Glycosylation in IgG2 and IgG4 Antibody Variants of CAMPATH-1H and 11B8 Harboring Fc-Fc Interaction Enhancing and Self-Oligomerization Inhibiting Mutations on FcγRIIa Activation In Example 17, it was shown that mixtures of IgG2 antibody variants harboring the E345R Fc-Fc interaction enhancing mutation and self-oligomerization inhibiting mutation K439E or S440K could selectively induce CDC of Wien 133 cells in a co-dependent manner. Mixtures of such aglycosylated antibody variants of the IgG4 subclass could also selectively induce CDC of Wien 133 cells but CDC recovery was limited. Here, it was tested whether the introduction of mutation N297A disrupting N-linked glycosylation affected the capacity of IgG2 and IgG4 antibody variants of CAMPATH-1H and 11B8 or mixtures thereof harboring Fc-Fc interaction enhancing mutation E345R and a self-oligomerization inhibiting mutation to activate FcγRIIa in a reporter cell assay, as a surrogate for ADCP.

For the ADCP reporter bioassay, antibody variants of anti-CD52 IgG2-CAMPATH-1H and anti-CD20 IgG2-11B8, as well as antibody variants of IgG4-CAMPATH-1H and IgG4-11B8 which harbor an Fc-Fc interaction enhancing mutation (E345R), a self-oligomerization inhibiting mutation (K439E or S440K) and a mutation which disrupts the N297 N-glycosylation consensus sequence (NX[S/T]; N297A) were tested using the Bio-Glo Luciferase Assay System (Promega, Cat No. G7940) on Raji cells, essentially as described in Example 19. As controls, single antibodies were mixed 1:1 with non-binding isotype IgG2- or IgG4-b12 control antibodies to enable direct comparison of the concentrations of individual components and mixtures composed thereof. The relative areas under dose-response curves with log transformed concentrations (4-fold dilution series resulting in 0.2-40 μg/mL final concentrations after addition of effector cells; AUC values) were normalized to the AUC value measured for the non-binding negative control IgG1-b12 (0%) and the AUC value measured for the positive control mixture of IgG1-CAMPATH-1H-E430G+IgG1-11B8-E430G (100%).

The capacity to induce FcγRIIa activation was enhanced by a mixture of IgG2 variants of CAMPATH-1H and 11B8 which harbor the E345R mutation as compared to the positive control mixture (FIG. 22A). While the introduction of K439E in IgG2-CAMPATH-1H strongly reduced the capacity to induce FcγRIIa activation, no remaining FcγRIIa activation was detected for the aglycosylated variant IgG2-CAMPATH-1H-E345R-K439E-N297A. While the IgG2-11B8-E345R-S440K antibody variant induced strong FcγRIIa activation to approximately 191% of the level induced by the positive control, the introduction of mutation N297A fully abrogated this activity. A mixture of IgG2-CAMPATH-1H-E345R-K439E+IgG2-11B8-E345R-S440K induced a high level of FcγRIIa activation (approximately 179% of the level induced by the positive control), a mixture of aglycosylated (N297A-containing) variants of these antibody variants fully abrogated the capacity to induce FcγRIIa activation.

A mixture of IgG4-CAMPATH-1H-E345R+IgG4-11B8-E345R enhanced the capacity to induce FcγRIIa activation as compared to the positive control mixture (FIG. 22B). When used as single agents, none of the IgG4-CAMPATH-1H-E345R or IgG4-11B8-E345R antibody variants harboring either mutation K439E or S440K, with or without the N297A mutation induced FcγRIIa activation. Low recovery of FcγRIIa activation was only observed for the mixture of IgG4-CAMPATH-1H-E345R-K439E+IgG4-11B8-E345R-S440K, and not by a mixture of IgG4-CAMPATH-1H-E345R-K439E-N297A+IgG4-11B8-E345R-S440K-N297A.

In conclusion, the introduction of glycosylation site disrupting mutation N297A in variants of the CAMPATH-1H and 11B8 antibodies of the IgG2 and IgG4 subclasses, harboring the E345R Fc-Fc interaction enhancing mutation and a self-oligomerization inhibiting mutation, fully abrogated the capacity to induce ADCP as measured through a surrogate FcγRIIa activation reporter cell assay. This applied to both the application as single agent antibody variants and co-dependent mixtures thereof.

Example 24: Analysis of the Effect of Introducing a Mutation Disrupting Glycosylation in IgG2 and IgG4 Antibody Variants of CAMPATH-1H and 11B8 Harboring Fc-Fc Interaction Enhancing and Self-Oligomerization Inhibiting Mutations on FcγRIIIa Activation In Example 23, it was shown that the introduction of mutation N297A disrupting glycosylation in CAMPATH-1H and 11B8 antibody variants of the IgG2 and IgG4 subclass, which harbored the E345R Fc-Fc interaction enhancing mutation and self-oligomerization inhibiting mutation K439E or S440K, resulted in full abrogation of the capacity to induce ADCP in a surrogate FcγRIIa activation reporter cell assay. Here, it was tested whether aglycosylated IgG2 and IgG4 antibody variants of CAMPATH-1H and 11B8, harboring Fc-Fc interaction enhancing mutation E345R and a self-oligomerization inhibiting mutation, or mixtures thereof, could activate FcγRIIIa in a reporter cell assay, as a surrogate for ADCC.

For the ADCC reporter bioassay, antibody variants of anti-CD52 IgG2-CAMPATH-1H and anti-CD20 IgG2-11B8, as well as antibody variants of IgG4-CAMPATH-1H and IgG4-11B8 which harbor an Fc-Fc interaction enhancing mutation (E345R), a self-oligomerization inhibiting mutation (K439E or S440K) and a mutation which disrupts the N297 N-glycosylation consensus sequence (NX[S/T]; N297A) were tested using the Bio-Glo Luciferase ADCC Reporter Bioassay for the FcγRIIIa high affinity V158 allotype on Raji cells (Promega, Cat #G7018). Except for using FcgammaRIIIa-V Effector Cells (Promega; Cat #G701A) in the current Example, the assay was performed essentially as described in Example 19. As controls, single antibodies were mixed 1:1 with non-binding isotype IgG2- or IgG4-b12 control antibodies to enable direct comparison of the concentrations of individual components and mixtures composed thereof. The relative areas under dose-response curves with log transformed concentrations (4-fold dilution series resulting in 0.2-40 µg/mL final concentrations after addition of effector cells; AUC values) were normalized to the AUC value measured for the non-binding negative control IgG1-b12 (0%) and the AUC value measured for the positive control mixture of IgG1-CAMPATH-1H-E430G+IgG1-11B8-E430G (100%).

While the positive control mixture of IgG1-CAMPATH-1H-E430G+IgG1-11B8-E430G efficiently induced FcγRIIIa activation, the capacity to induce FcγRIIIa activation by each of the tested IgG2 and IgG4 variants and mixtures thereof was below 5% of the level induced by the positive control mixture (FIG. 23A, B). Due to these low levels of FcγRIIIa activation, no conclusions can be drawn on the impact of introducing the glycosylation site disrupting mutation N297A in these antibody variants.

Example 25: Induction of Programmed Cell Death by Aglycosylated Anti-Fas Antibody Variants Harboring Mutations that Enhance Fc-Fc Interactions, Inhibit Self-Oligomerization and Enhance C1q Binding In previous Examples, co-dependent mixtures of aglycosylated antibody variants harboring mutations that enhance Fc-Fc interactions, inhibit self-oligomerization and/or modulate C1q binding were shown to selectively induce CDC of tumor cell lines. Here, it was studied whether mixtures of aglycosylated anti-Fas antibody variants harboring such mutations could induce selective co-dependent programmed cell death (PCD) of target cells.

Different mutations were introduced in the anti-Fas IgG1-Fas-E09 antibody: E345R, which enhances Fc-Fc interactions; K439E or S440K, which inhibit self-oligomerization; K326A and E333S, which enhance the binding of C1q to antibody Fc domains; N297A, which disrupts the N297 N-glycosylation consensus sequence (NX[S/T]) and yields aglycosylated antibodies. A range of antibody variant concentrations was tested in a programmed cell death assay using B lymphoblast WIL2S-SF cells. WIL2-S SF cells were derived from WIL2-S (ATCC, CRL-8885) B lymphoblasts and adapted to grow under serum-free conditions in culture medium formulated by HyQ-ADCF-Mab (Perbio, Cat #SH30349) containing 50 U/mL Pen/Strep and 1 mM sodium pyruvate. WIL2S-SF cells were harvested and passed through a cell strainer. Cells were pelleted by centrifugation for 5 minutes at 300 g and resuspended in serum-free culture medium (HyQ ADCF-Mab with L-Glutamine from HyClone. Cat SH30349+1 mM Sodium Pyruvate (Lonza, Cat #BE13-115E)). Per well, 50,000 cells of the single cell suspension were seeded in 46 µL in polystyrene 96-well flat-bottom plates (Greiner Bio-One, Cat #655180) and 24 µL purified human C1q stock solution (Complement Tech, Cat #A099, 2.5 µg/mL final concentration) was added. In addition, 50 µL samples of an antibody dilution series (final concentration range 0.05 ng/mL-20 µg/mL in 5-fold dilutions). As a positive control, cells were incubated with 5 µM staurosporine (Sigma Aldrich, Cat No. S6942). The viability of the cell cultures was determined in a CellTiter- Glo luminescence cell viability assay (Promega, Cat #G7571) after 24h of culture that quantifies the ATP present, which is an indicator of metabolically active cells. From the kit, 12 µL Luciferin Solution Reagent was added per well. Next, plates were incubated for 1.5 hours at 37° C. Luminescence was measured on an EnVision Multilabel Reader (PerkinElmer). The relative potency to induce cell death was calculated by comparing the area under dose-response curves with log transformed concentrations (AUC) using the following formula: Cell death induction potency=[AUC (IgG1-b12)—AUC (sample)], followed by normalization relative to the cell death induction potency determined for positive control IgG1-Fas-E09-E345R (100%).

While wild-type IgG1-Fas-E09 failed to induce programmed cell death of WIL2S-SF cells, introduction of the E345R mutation strongly enhanced PCD induction (FIG. 24A). No PCD was induced by an aglycosylated IgG1-Fas-E09 variant harboring the E345R and K439E mutations, or by a variant harboring the same mutations in addition to the C1q binding enhancing mutations K326A-E333S (SEQ ID NO 85). Also, the aglycosylated IgG1-Fas-E09 variant harboring the S440K mutation (SEQ ID NO 86), with or without the C1q binding enhancing mutations K326A-E3335, was not able to induce PCD of WIL2S-SF cells as a single agent. PCD potency was not observed at the highest concentration tested either (20 µg/mL; FIG. 24B). A mixture of the IgG1-Fas-E09-E345R-K439E-N297A+IgG1-Fas-E09-E345R-S440K-N297A antibody variants could partially recover the potency to induce PCD to approximately 49% of the level induced by the positive control mixture. At the highest concentration tested, this mixture was only able to partially recover PCD. A full recovery of PCD potency was induced by the co-dependent mixture of IgG1-Fas-E09-E345R-K439E-K326A-E333S-N297A+IgG1-Fas-E09-E345R-S440K-K326A-E333S-N297A.

In short, the capacity of anti-Fas-E09 antibodies to induce PCD of WIL2S-SF cells could be fully recovered by mixtures of aglycosylated antibody variants harboring mutations that enhance Fc-Fc interactions, inhibit self-oligomerization and enhance C1q binding, while a partial recovery was observed for a mixture of antibody variants lacking the C1q binding enhancing mutations. This indicates that the enhanced recruitment of C1q may be particularly favorable for agonistic applications of the mutually-dependent antibody mixtures of the present invention. Without being limited by theory, this may be explained by a stabilization of multimeric, PCD-signaling inducing Fas complexes after binding of Fas-directed antibodies that recruit the hexavalent C1q protein, which may act as a soluble crosslinker.

Example 26: Selective DR5 Agonist Activity on BxPC-3 Cells by a Mixture of Two Non-Competing Aglycosylated Anti-DR5 Antibody Variants Harboring Mutations that Enhance Fc-Fc Interactions, Inhibit Self-Oligomerization and Enhance C1q Binding The mixture of the two anti-death receptor 5 (DR5) antibodies IgG1-DR5-01-G56T-E430G+IgG1-DR5-05-E430G, that can bind independently to non-overlapping binding sites, acts as a DR5 agonist to induce killing of DR5-positive cancer cells (WO17093447). Here, it was studied whether aglycosylated variants of such DR5-targeting antibodies harboring mutations that enhance Fc-Fc interactions, inhibit self-oligomerization and enhance C1q binding could selectively induce killing of COL0205 colon cancer cells that are relatively sensitive to DR5-mediated PCD induction, and of BxPC-3 pancreatic cancer cells, which are relatively resilient to DR5-mediated PCD induction.

Different mutations were introduced in the anti-DR5 IgG1-hDR5-01-G56T and IgG1-hDR5-05 antibodies: E430G, E430Y or E345R, which enhances Fc-Fc interactions; K439E or S440K, which inhibit self-oligomerization; K326A and E333S, which enhance the binding of C1q to antibody Fc domains; N297A, which disrupts the N297 N-glycosylation consensus sequence (NX[S/T]) and yields aglycosylated antibodies. A range of antibody variant concentrations was tested in a killing assay using either BxPC-3 or COL0205 cells. BxPC-3 cells (ATCC, Cat #CRL-1687) and COL0205 cells (ATCC, Cat #CCL-222) were harvested by trypsinization and passed through a cell strainer. Cells were pelleted by centrifugation for 5 minutes at 300 g and resuspended in culture medium (RPMI 1640 Medium (ATCC Modification; Life Technologies, Cat #A10491-01)+ 10% DBSI (Life technologies, Cat #20371). Per well, 5,000 cells of the single cell suspension were seeded in 46 µL in polystyrene 96-well flat-bottom plates (Greiner Bio-One, Cat #655180) and 24 µL purified human C1q stock solution (Complement Tech, Cat #A099, 2.5 µg/mL final concentration) was added. The cells were allowed to adhere overnight at 37° C. The next day, 50 µL samples of an antibody dilution series (final concentration range 0.005-20 µg/mL in 3-fold dilutions) were added to each well. As a positive control, cells were incubated with 5 µM staurosporine (Sigma Aldrich, Cat No. S6942). The viability of the cell cultures was determined after 72h of incubation in a Cell-Titer-Glo luminescent cell viability assay (Promega, Cat #G7571), essentially as described in Example 25. Data were analyzed and plotted using non-linear regression (sigmoidal dose-response with variable slope) using GraphPad Prism software. The relative potency to induce cell death was calculated by comparing the area under dose-response curves with log transformed concentrations (AUC) using the following formula: Cell death induction potency=[AUC (IgG1-b12)—AUC (sample)], followed by normalization relative to the cell death induction potency determined for positive control IgG1-DR5-01-G56T-E430G+IgG1-DR5-05-E430G (100%).

Figures 25A, 25B:
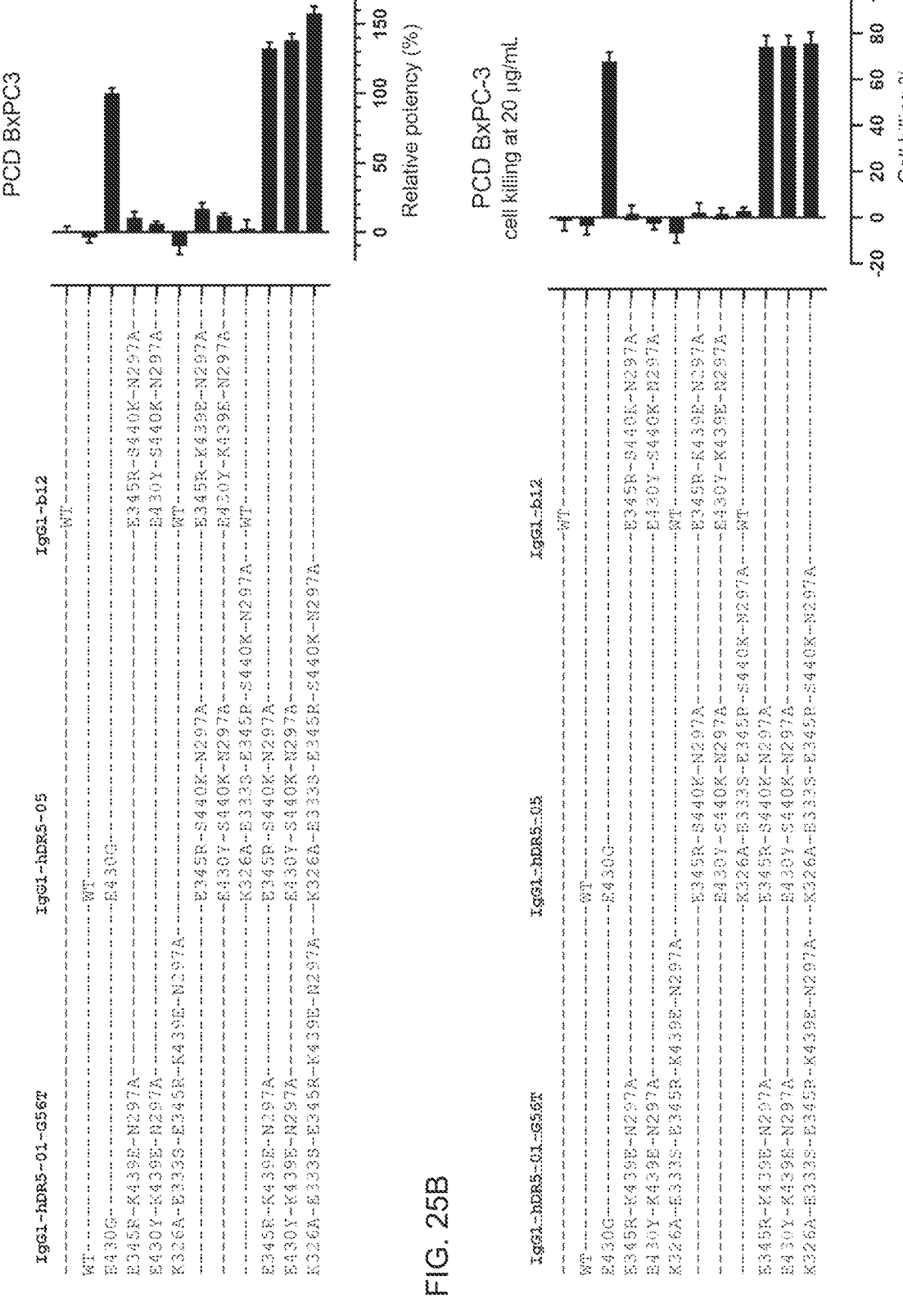

While a mixture of wild-type IgG1-hDR5-01-G56T+ IgG1-hDR-05 did not induce cell death of BxPC-3 cells, efficient cell death was observed upon introduction of the E430G mutation in both antibody variants (FIG. 25A). As a single agent, the potency to induce cell death was strongly reduced upon introducing mutations E345R-K439E-N297A in IgG1-hDR5-01-G56T or E345R-S440K-N297A in IgG1-hDR5-05. A mixture of these variants, however, induced potent cell death to approximately 132% of the level induced by the positive control mixture. Similar results were observed for such DR5-targeting antibody variants harboring the E430Y mutation instead of E345R: while single agent cell death activity was limited, a mixture of IgG1-hDR5-01-G56T-E430Y-K439E-N297A+IgG1-hDR5-05-E430Y-S440K-N297A induced highly efficient cell death of BxPC-3 cells, to approximately 139% of the level induced by the positive control mixture. The additional introduction of C1q binding enhancing mutations K326A-E333S to IgG1-hDR5-01-G56T-E345R-K439E-N297A or IgG1-hDR5-05-E345R-S440K-N297A did not induce an increase in single agent cell death potency. However, the potency to induce cell death of BxPC-3 cells was efficiently recovered by mixing IgG1-hDR5-01-G56T-E345R-K439E-N297A-K326A-E333S+IgG1-hDR5-05-E345R-S440K-N297A-K326A-E333S, which resulted in cell death to approximately 158% of the level induced by the positive control mixture. At the highest concentration tested (20 µg/mL), all the mixtures described above induced maximal cell death comparable to the potency of the positive control, while the individual antibody variants only partially induced cell death as single agents (FIG. 25B).

The mixture of wild-type IgG1-hDR5-01-G56T+IgG1-hDR-05 induced cell death of COL0205 cells, illustrating the increased sensitivity of this cell line to DR5-mediated PCD induction compared to BxPC-3 cells, albeit with reduced potency as compared to the mixture of the Fc-Fc enhanced antibody variants harboring the E430G mutation (FIG. 25C). No cell death was induced by the single agent aglycosylated antibody variants harboring either mutation E345R or E430Y and either mutation K439E or S440K. Mixtures of DR5-targeting aglycosylated antibody variants with an Fc-Fc interaction enhancing mutation (E345R or E430Y) and complementary self-oligomerization inhibiting mutations recovered the potency to induce cell death to approximately 105% (E345R) and 106% (E430Y) of the level induced by the positive control mixture. While the IgG1-hDR5-01-G56T-E345R-K439E-N297A antibody variant in which the C1q binding enhancing mutations K326A-E333S were introduced did not demonstrate any potency to induce cell death of COL0205 cells as a single agent, the IgG1-hDR5-05-E345R-S440K-N297A-K326A-E333S antibody variant induced residual single agent cell death to approximately 32% of the level induced by the positive control mixture. When the latter antibody variant was mixed with IgG1-hDR5-05-E345R-K439E-N297A-K326A-E333S, the potency to induce cell death was efficiently recovered to approximately 121% of the level induced by positive control. At the highest concentration tested (20 µg/mL), all mixtures consisting of Fc-Fc interaction enhanced antibody variants induced maximal cell death comparable to the positive control (FIG. 25D). The C1q binding-enhanced IgG1-hDR5-01-G56T-E345R-K439E-N297A-K326A-E333S was able to induce a low level of cell death as a single agent at the highest concentration, while the IgG1-hDR5-05-S440K-N297A variants harboring either the E345R or E430Y mutation could also induce cell death as single agents, albeit lower than the C1q binding-enhanced variant.

In conclusion, aglycosylated antibody variants of IgG1-hDR5-01-G56T and IgG1-hDR5-05 harboring mutations that enhance Fc-Fc interactions (E345R or E430Y) and inhibit self-oligomerization (K439E or S440K) co-dependently induce efficient cell death of BxPC-3 and COL0205 cancer cells in a highly selective manner. The additional introduction of C1q binding enhancing mutations K326A-E333S increased the residual single agent-induced cell death induced by IgG1-hDR5-05-E345R-S440K-N297A-K326A-E333S in COL0205 cells, reducing the selective window for this particular antibody variant on this relatively DR5-sensitive cell line. Overall, for applications involving induction of programmed cell death of cancer cells, mixtures of antibody variants harboring strong Fc-Fc interaction enhancing mutations, such as E345R or E430Y, show a high level of selectivity and strong potency to induce cell death.

Example 27: Selectivity of 4-1BB-Mediated Activation by Aglycosylated 4-1BB Antibody Variants with an Fc-Fc Interaction Enhancing Mutation and Self-Oligomerization Inhibiting Mutations Binding of specific ligands to receptors of the tumor necrosis factor receptor superfamily (TNFRSF) typically leads to clustering of such receptors into multimeric complexes on the cell surface. In the context of TNFRSF-expressing immune cells, these events can lead to activation of the immune cells. The TNFRSF member 4-1BB is mainly expressed on activated, antigen-experienced T cells and activated NK cells. Here, it was studied whether target cells engineered to express 4-1BB could be selectively activated in a co-dependent fashion by mixtures of aglycosylated 4-1BB-targeting antibody variants harboring mutations that enhance Fc-Fc interactions and inhibit self-oligomerization.

Different mutations were introduced in the agonistic anti-4-1BB IgG1-BMS663513 antibody: E345R, which induces enhanced Fc-Fc interactions; K439E or S440K, which inhibit self-oligomerization; N297A, which disrupts the N297 N-glycosylation consensus sequence (NX[S/T]) and yields aglycosylated antibodies; L234F, L235E and D265A, which eliminate Fc-mediated effector functions by suppressing FcγR and C1q binding; F405L, which promotes half-molecule hetero-dimerization with a complementary half-molecule harboring a K409R mutation only under controlled reducing conditions (Labrijn et al. PNAS 2013; 110(13): 5145-50). A range of antibody variant concentrations was tested using a Jurkat human T-cell line engineered to stably express 4-1BB and a nuclear factor of activated T cells (NFAT)-response element driving expression of firefly luciferase (Promega, Cat #J2332). As controls, single antibodies were mixed 1:1 with non-binding isotype IgG1-b12 control antibodies, harboring mutations such as the above-mentioned, to enable direct comparison of the concentrations of individual components and mixtures composed thereof. Antibody concentration series (0.005-20 μg/mL final concentrations in 4-fold dilutions) diluted in Assay Buffer (RPMI1640 containing 1% heat-inactivated FBS—Promega Cat #J121A) in a total volume of 30 μL were added to a 384-well optiplate (Perkin-Elmer, Cat #6007680). Purified human C1q (Quidel, cat #A400) was added to each well at a final concentration of 2.4 μg/mL. After thawing the reporter cells, cells were diluted 1:20 in RPMI1640 medium (Promega, G708A), 20 μL cell suspension per well was added to the 384-wells plates containing 10 μL of the antibody concentration series with C1q in a total V of 30 μL, and incubated for 5 hours at 37° C./5% C02. After incubating the plates for 15 minutes at room temperature (RT), 30 μL Bio Glo Assay Luciferase Reagent was added to each well and incubated for 10 minutes at RT in the dark. Luciferase production was quantified by luminescence read-out on an EnVision Multilabel Reader (Perkin Elmer). Prior to pooling data from experiments, raw luminescence signals were background-corrected by subtracting the luminescence signal determined from medium-only samples (no antibody and no reporter cells) and normalized to the averaged luminescence of 2.5 μg/mL IgG1-BMS663513-E345R measured in triplicate to suppress plate-to-plate variation. The area under dose-response curves using log-transformed concentrations of three experimental repeats was calculated in GraphPad PRISM. AUC values were normalized relative to the activity (AUC) observed for cells incubated with non-binding control IgG1-b12 (0%) and the activity (AUC) of IgG1-BMS663513-E345R (100%).

The IgG1-BMS663513 antibody harboring the L234F, L235E, D265A and F405L (FEAL; SEQ ID NO: 87) mutations, which are irrelevant in the context of this assay, demonstrated intrinsic agonistic 4-1BB activity (FIG. 26A). However, the potency to induce 4-1BB-mediated reporter cell activation by IgG1-BMS663513 could be strongly enhanced by the introduction of Fc-Fc interaction enhancing mutation E345R. The potency to induce 4-1BB-mediated reporter cell activation by IgG1-BMS663513-E345R-K439E-N297A or IgG1-BMS663513-E345R-S440K-N297A as single agents was reduced to the same level of potency induced by the IgG1-BMS663513 antibody variant harboring the irrelevant FEAL mutations. This was also the case at the concentration at which the strongest activation was observed for all variants (1.25 μg/mL; FIG. 26B). A strong recovery of 4-1BB-mediated reporter cell activation was observed for the mixture of IgG1-BMS663513-E345R-K439E-N297A+IgG1-BMS663513-E345R-S440K-N297A, to approximately 95% of the level induced by the positive control.

In conclusion, while the introduction of Fc-Fc interaction enhancing mutation E345R strongly potentiated the intrinsic agonistic activity of IgG1-BMS663513, the additional introduction of the K439E or S440K mutations, which inhibit self-oligomerization, and the N297A mutation, which yields aglycosylated antibodies, efficiently reduced the single agent potency to induce 4-1BB-mediated reporter cell activation. The potency to induce 4-1BB-mediated reporter cell activation was efficiently restored by a mixture of the latter antibody variants, providing favorable selectivity.

Example 28: Selectivity of 4-1BB-Mediated Activation by Aglycosylated 4-1BB Antibody Variants with an Fc-Fc Interaction Enhancing Mutation, Self-Oligomerization Inhibiting and C1q Binding Enhancing Mutations In Example 27, 4-1BB-mediated reporter cell activation was shown to be selectively and co-dependently induced by mixtures of aglycosylated 4-1BB targeting IgG1-BMS663513 antibody variants harboring Fc-Fc interaction enhancing and self-oligomerization inhibiting mutations. Here, the effect of the additional introduction of C1q binding enhancing mutations in such IgG1-BMS663513 variants on the selective induction of 4-1BB-mediated reporter cell activation was studied.

Different mutations were introduced in the agonistic anti-4-1BB IgG1-BMS663513 antibody: E345R, which induces enhanced Fc-Fc interactions; K439E or S440K, which inhibit self-oligomerization; N297A, which disrupts the N297 N-glycosylation consensus sequence (NX[S/T]) and yields aglycosylated antibodies; L234F, L235E and D265A, which eliminate Fc-mediated effector functions by suppressing FcγR and C1q binding; F405L, which promotes half-molecule hetero-dimerization with a complementary half-molecule harboring a K409R mutation only under controlled reducing conditions (Labrijn et al. PNAS 2013; 110(13): 5145-50); K326A and E333S, which enhance the binding of C1q to antibody Fc domains. A range of antibody variant concentrations was tested in a reporter cell activation assay, essentially as described in Example 27, using a Jurkat human T-cell line engineered to stably express 4-1BB and a nuclear factor of activated T cells (NFAT)-response element driving expression of firefly luciferase (Promega, Cat #J2332). As controls, single antibodies were mixed 1:1 with non-binding isotype IgG1-b12 control antibodies to enable direct comparison of the concentrations of individual components and mixtures composed thereof.

The IgG1-BMS663513 antibody harboring the L234F, L235E, D265A and F405L (FEAL) mutations, which are irrelevant in the context of this assay, demonstrated intrinsic agonistic 4-1BB activity (FIG. 27A). However, the potency to induce 4-1BB-mediated reporter cell activation by IgG1-BMS663513 could be strongly enhanced by the introduction of Fc-Fc interaction enhancing mutation E345R. Both the IgG1-BMS663513 variants harboring the E345R, N297A, K326A and E333S in addition to either K439E or S440K showed substantial single agent potency to induce 4-1BB-mediated reporter cell activation. This residual activity was also observed at the highest concentration at which the strongest activation was observed for all variants (1.25 ug/mL), with single agent activity of approximately 62% (K439E-containing variant) and 57% (S440K-containing variant) of the level induced by the positive control (FIG. 27B). The potency to induce 4-1BB-mediated reporter cell activation could be recovered by mixing IgG1-BMS66313-E345R-K439E-N297A-K326A-E333S+IgG1-BMS663513-

E345R-S440K-N297A-K326A-E333S, to approximately 85% of the level induced by the positive control.

In conclusion, mixtures of aglycosylated IgG1-BMS663513 antibody variants harboring the E345R, K439E or S440K, N297A mutations and C1q binding enhancing mutations K326A-E333S could selectively recover the potency to induce 4-1BB-mediated reporter cell activation. However, as the individual antibody variants harboring Clq binding enhancing mutations induced residual single agent activity, these variants displayed reduced selectivity than variants without Clq binding enhancing mutations when applied to antibody IgG1-BMS663513.

The invention claimed is:

1. A method of treating cancer, the method comprising administering an effective amount of a first antibody comprising a first Fc region of a human IgG and a first antigen-binding region capable of binding to a first antigen and a second antibody comprising a second Fc region of a human IgG and a second antigen-binding region capable of binding to a second antigen, wherein said first Fc region comprises:

a. a substitution at position E430, a substitution at position E345, or a combination of the substitutions K248E and T437R, and b. a K439E or S440K substitution, and said second Fc region comprises c. a substitution at position E430, a substitution at position E345, or a combination of the substitutions K248E and T437R, and d. a K439E or S440K substitution, wherein the first Fc region has a K439E substitution and the second Fc region has an S440K substitution, or the first Fc region has an S440K substitution and the second Fc region has a K439E substitution, wherein the first antibody and/or the second antibody does not comprise N-linked glycosylation at position N297, and wherein the amino acid positions correspond to human IgG1 according to the Eu numbering system.

2. The method of claim 1, wherein the first Fc region and/or second Fc region comprises an amino acid substitution at position N297 or at position T299, wherein the substitution at position T299 is not T299S.

3. The method of claim 1, wherein a. the first Fc region comprises a K439E substitution and a Y436N substitution and the second Fc region comprises a S440K substitution and a Q438R substitution, or b. the first Fc region comprises a K439E substitution and a Q438R substitution and the second Fc region comprises a S440K substitution and a Y436N substitution, or c. the first Fc region comprises a S440K substitution and a Y436N substitution and the second Fc region comprises a K439E substitution and a Q438R substitution, or d. the first Fc region comprises a S440K substitution and a Q438R substitution and the second Fc region comprises a K439E substitution and a Y436N substitution.

4. The method of claim 1, wherein the first Fc region and the second Fc region comprise a substitution selected from the group consisting of: E345K, E430G, E345R, E430Y, E345Q, E345Y, E430S, E430T, and E430F, and/or the combination of the substitutions K248E and T437R.

5. The method of claim 1, wherein the first Fc region and the second Fc region comprise:

a. a substitution selected from the group consisting of: E345K, E430G, E345R, and E430Y, b. a substitution selected from the group consisting of: E430G and E345K, c. a substitution selected from the group consisting of: E345R and E430Y, or d. a combination of the substitutions K248E and T437R.

6. The method of claim 1, wherein the first Fc region and/or the second Fc region comprise one or more substitution(s) selected from the group consisting of: E333S, K326A, E333A, and K326W.

7. The method of claim 1, wherein the first antibody and/or second antibody is human, humanized or chimeric.

8. The method of claim 1, wherein the first antibody and/or second antibody is a monoclonal antibody.

9. The method of claim 1, wherein the first antibody and/or second antibody is a human IgG1, IgG2, IgG3 or IgG4 subclass.

10. The method of claim 1, wherein:

a. the first and second antigens are both cell surface-expressed molecules, b. the first and second antigens are co-expressed in cells or tissues that are target cells or target tissue for the disease or disorder to be treated, c. the first and second antigens are not identical, d. the first antibody and second antibody in combination deplete a cell population co-expressing the first and second antigen, e. the first antibody and second antibody in combination induces cell death in a cell population co-expressing the first and second antigen, and/or f. the first antibody and second antibody in combination induces cell death in a cell population co-expressing the first and second antigen.

11. The method of claim 10, wherein the cell population is a tumor cell population.

12. The method of claim 10, wherein the cell population is a leukocyte, lymphocyte, B cell, T cell, regulatory T cell, NK cell, myeloid derived suppressor cell, or tumor associated macrophage cell population.

13. The method of claim 1, wherein the antigen-binding region of the first or second antibody is capable of binding to an antigen selected from the group consisting of: DR4, DR5, CD20, CD37, CD52, HLA-DR, CD3, CDS, 4-1BB, PD1, and FAS.

14. The method of claim 1, wherein the antigen-binding region of the first or second antibody comprises:

a. a VH region comprising a CDR1 sequence as set forth in SEQ ID NO:9, a CDR2 sequence as set forth in SEQ ID NO:10 and a CDR3 sequence as set forth in SEQ ID NO:11, and a VL region comprising a CDR1 sequence as set forth in SEQ ID NO:13, a CDR2 sequence as set forth in: DAS and a CDR3 sequence as set forth in SEQ ID NO:14, b. a VH region comprising a CDR1 sequence as set forth in SEQ ID NO:43, a CDR2 sequence as set forth in SEQ ID NO:44 and a CDR3 sequence as set forth in SEQ ID NO:45, and a VL region comprising a CDR1 sequence as set forth in SEQ ID NO:47, a CDR2 sequence as set forth in: VAT and a CDR3 sequence as set forth in SEQ ID NO:48, c. a VH region comprising a CDR1 sequence as set forth in SEQ ID NO:2, a CDR2 sequence as set forth in SEQ ID NO:3 and a CDR3 sequence as set forth in SEQ ID NO:4, and a VL region comprising a CDR1 sequence as set forth in SEQ ID NO:6, a CDR2 sequence as set forth in: NTN, and a CDR3 sequence as set forth in SEQ ID NO:7, d. a VH region comprising a CDR1 sequence as set forth in SEQ ID NO: 118, a CDR2 sequence as set forth in SEQ ID NO:119, and a CDR3 sequence as set forth in SEQ ID NO:120 and a VL region comprising a CDR1 sequence as set forth in SEQ ID NO:122, a CDR2 sequence as set forth in SEQ ID NO: 123 and a CDR3 sequence as set forth in SEQ ID NO:124, e. a VH region comprising a CDR1 sequence as set forth in SEQ ID NO:104, a CDR2 sequence as set forth in SEQ ID NO:105 and a CDR3 sequence as set forth in SEQ ID NO:106, and a VL region comprising a CDR1 sequence as set forth in SEQ ID NO:108, a CDR2 sequence as set forth in: YNN and a CDR3 sequence as set forth in SEQ ID NO:109, f. a VH region comprising a CDR1 sequence as set forth in SEQ ID NO:111, a CDR2 sequence as set forth in SEQ ID NO: 112 and a CDR3 sequence as set forth in SEQ ID NO: 113, and a VL region comprising a CDR1 sequence as set forth in SEQ ID NO:115, a CDR2 sequence as set forth in: DAS and a CDR3 sequence as set forth SEQ ID NO:116, g. a VH region comprising a CDR1 sequence as set forth in SEQ ID NO:90, a CDR2 sequence as set forth in SEQ ID NO:91 and a CDR3 sequence as set forth in SEQ ID NO:92, and a VL region comprising a CDR1 sequence as set forth in SEQ ID NO:94, a CDR2 sequence as set forth in: FAS, and a CDR3 sequence as set forth in SEQ ID NO:95, or h. a VH region comprising a CDR1 sequence as set forth in SEQ ID NO:97, a CDR2 sequence as set forth in SEQ ID NO:98 and a CDR3 sequence as set forth in SEQ ID NO:99, and a VL region comprising a CDR1 sequence as set forth in SEQ ID NO:101, a CDR2 sequence as set forth in: RTS, and a CDR3 sequence as set forth in SEQ ID NO:102.

15. The method according to claim 1, wherein the method comprises administering an additional therapeutic agent.

16. The method of claim 1, wherein said method depletes a cell population expressing said first antigen and said second antigen.

17. The method according to claim 1, wherein the first antigen and/or second antigen is a member of the TNFR-SF.

\*    \*    \*    \*    \*

SEQUENCE LISTING

```
<160> NUMBER OF SEQ ID NOS: 133

<210> SEQ ID NO 1
<211> LENGTH: 121
<212> TYPE: PRT
<213> ORGANISM: Artificial sequence
<220> FEATURE:
<223> OTHER INFORMATION: Humanized VH region

<400> SEQUENCE: 1

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser
        115                 120

<210> SEQ ID NO 2
<211> LENGTH: 8
<212> TYPE: PRT
<213> ORGANISM: Artificial sequence
<220> FEATURE:
<223> OTHER INFORMATION: CDR sequence

<400> SEQUENCE: 2

Gly Phe Thr Phe Thr Asp Phe Tyr
1               5

<210> SEQ ID NO 3
<211> LENGTH: 10
<212> TYPE: PRT
<213> ORGANISM: Artificial sequence
<220> FEATURE:
<223> OTHER INFORMATION: CDR Sequence

<400> SEQUENCE: 3

Ile Arg Asp Lys Ala Lys Gly Tyr Thr Thr
1               5                   10
```

<210> SEQ ID NO 4
<211> LENGTH: 12
<212> TYPE: PRT
<213> ORGANISM: Artificial sequence
<220> FEATURE:
<223> OTHER INFORMATION: CDR sequence

<400> SEQUENCE: 4

Ala Arg Glu Gly His Thr Ala Ala Pro Phe Asp Tyr
1               5                   10

<210> SEQ ID NO 5
<211> LENGTH: 107
<212> TYPE: PRT
<213> ORGANISM: Artificial sequence
<220> FEATURE:
<223> OTHER INFORMATION: Humanized VL region

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys
            100                 105

<210> SEQ ID NO 6
<211> LENGTH: 6
<212> TYPE: PRT
<213> ORGANISM: Artificial sequence
<220> FEATURE:
<223> OTHER INFORMATION: CDR sequence

<400> SEQUENCE: 6

Gln Asn Ile Asp Lys Tyr
1               5

<210> SEQ ID NO 7
<211> LENGTH: 9
<212> TYPE: PRT
<213> ORGANISM: Artificial sequence
<220> FEATURE:
<223> OTHER INFORMATION: CDR sequence

<400> SEQUENCE: 7

Leu Gln His Ile Ser Arg Pro Arg Thr
1               5

<210> SEQ ID NO 8
<211> LENGTH: 115
<212> TYPE: PRT
<213> ORGANISM: Artificial sequence
<220> FEATURE:
<223> OTHER INFORMATION: Humanized VH region

<400> SEQUENCE: 8

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
                100                 105                 110

Val Ser Ala
        115

<210> SEQ ID NO 9
<211> LENGTH: 8
<212> TYPE: PRT
<213> ORGANISM: Artificial sequence
<220> FEATURE:
<223> OTHER INFORMATION: CDR sequence

<400> SEQUENCE: 9

Gly Phe Ser Leu Thr Thr Ser Gly
1               5

<210> SEQ ID NO 10
<211> LENGTH: 7
<212> TYPE: PRT
<213> ORGANISM: Artificial sequence
<220> FEATURE:
<223> OTHER INFORMATION: CDR sequence

<400> SEQUENCE: 10

Ile Trp Gly Asp Gly Ser Thr
1               5

<210> SEQ ID NO 11
<211> LENGTH: 9
<212> TYPE: PRT
<213> ORGANISM: Artificial sequence
<220> FEATURE:
<223> OTHER INFORMATION: CDR sequence

<400> SEQUENCE: 11

Ala Lys Gly Gly Tyr Ser Leu Ala His
1               5

<210> SEQ ID NO 12
<211> LENGTH: 107
<212> TYPE: PRT
<213> ORGANISM: Artificial sequence
<220> FEATURE:
<223> OTHER INFORMATION: Humanized VL region

<400> SEQUENCE: 12

Asp Ile Gln Met Thr Gln Ser Pro Ala Ser Leu Ser Val Ser Val Gly
1               5                   10                  15

```
Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
            35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys
            100                 105
```

<210> SEQ ID NO 13
<211> LENGTH: 6
<212> TYPE: PRT
<213> ORGANISM: Artificial sequence
<220> FEATURE:
<223> OTHER INFORMATION: CDR sequence

<400> SEQUENCE: 13

```
Glu Asn Ile Arg Ser Asn
1               5
```

<210> SEQ ID NO 14
<211> LENGTH: 9
<212> TYPE: PRT
<213> ORGANISM: Artificial sequence
<220> FEATURE:
<223> OTHER INFORMATION: CDR sequence

<400> SEQUENCE: 14

```
Gln His Tyr Trp Gly Thr Thr Trp Thr
1               5
```

<210> SEQ ID NO 15
<211> LENGTH: 125
<212> TYPE: PRT
<213> ORGANISM: Artificial sequence
<220> FEATURE:
<223> OTHER INFORMATION: VH region

<400> SEQUENCE: 15

```
Glu Val Gln Leu Val Gln Ser Gly Gly Gly Leu Val His Pro Gly Gly
1               5                   10                  15

Ser Leu Arg Leu Ser Cys Thr Gly Ser Gly Phe Thr Phe Ser Tyr His
            20                  25                  30

Ala Met His Trp Val Arg Gln Ala Pro Gly Lys Gly Leu Glu Trp Val
            35                  40                  45

Ser Ile Ile Gly Thr Gly Gly Val Thr Tyr Tyr Ala Asp Ser Val Lys
    50                  55                  60

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Tyr Tyr Gly Ala Gly Ser Phe Tyr Asp Gly Leu Tyr Gly Met
                100                 105                 110

Asp Val Trp Gly Gln Gly Thr Thr Val Thr Val Ser Ser
            115                 120                 125
```

```
<210> SEQ ID NO 16
<211> LENGTH: 8
<212> TYPE: PRT
<213> ORGANISM: Artificial sequence
<220> FEATURE:
<223> OTHER INFORMATION: CDR sequence

<400> SEQUENCE: 16

Gly Phe Thr Phe Ser Tyr His Ala
1               5

<210> SEQ ID NO 17
<211> LENGTH: 7
<212> TYPE: PRT
<213> ORGANISM: Artificial sequence
<220> FEATURE:
<223> OTHER INFORMATION: CDR sequence

<400> SEQUENCE: 17

Ile Gly Thr Gly Gly Val Thr
1               5

<210> SEQ ID NO 18
<211> LENGTH: 19
<212> TYPE: PRT
<213> ORGANISM: Artificial sequence
<220> FEATURE:
<223> OTHER INFORMATION: CDR sequence

<400> SEQUENCE: 18

Ala Arg Asp Tyr Tyr Gly Ala Gly Ser Phe Tyr Asp Gly Leu Tyr Gly
1               5                   10                  15

Met Asp Val

<210> SEQ ID NO 19
<211> LENGTH: 107
<212> TYPE: PRT
<213> ORGANISM: Artificial sequence
<220> FEATURE:
<223> OTHER INFORMATION: VL region

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys
            100                 105

<210> SEQ ID NO 20
<211> LENGTH: 6
<212> TYPE: PRT
<213> ORGANISM: Artificial sequence
<220> FEATURE:
<223> OTHER INFORMATION: CDR sequence
```

<400> SEQUENCE: 20

Gln Ser Val Ser Ser Tyr
1               5

<210> SEQ ID NO 21
<211> LENGTH: 9
<212> TYPE: PRT
<213> ORGANISM: Artificial sequence
<220> FEATURE:
<223> OTHER INFORMATION: CDR sequence

<400> SEQUENCE: 21

Gln Gln Arg Ser Asp Trp Pro Leu Thr
1               5

<210> SEQ ID NO 22
<211> LENGTH: 127
<212> TYPE: PRT
<213> ORGANISM: Artificial sequence
<220> FEATURE:
<223> OTHER INFORMATION: VH region

<400> SEQUENCE: 22

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
        50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser
        115                 120                 125

<210> SEQ ID NO 23
<211> LENGTH: 8
<212> TYPE: PRT
<213> ORGANISM: Artificial sequence
<220> FEATURE:
<223> OTHER INFORMATION: CDR sequence

<400> SEQUENCE: 23

Gly Tyr Arg Phe Ser Asn Phe Val
1               5

<210> SEQ ID NO 24
<211> LENGTH: 8
<212> TYPE: PRT
<213> ORGANISM: Artificial sequence
<220> FEATURE:
<223> OTHER INFORMATION: CDR sequence

<400> SEQUENCE: 24

Ile Asn Pro Tyr Asn Gly Asn Lys
1               5

-continued

```
<210> SEQ ID NO 25
<211> LENGTH: 20
<212> TYPE: PRT
<213> ORGANISM: Artificial sequence
<220> FEATURE:
<223> OTHER INFORMATION: VH region

<400> SEQUENCE: 25

Ala Arg Val Gly Pro Tyr Ser Trp Asp Asp Ser Pro Gln Asp Asn Tyr
1               5                   10                  15

Tyr Met Asp Val
            20

<210> SEQ ID NO 26
<211> LENGTH: 108
<212> TYPE: PRT
<213> ORGANISM: Artificial sequence
<220> FEATURE:
<223> OTHER INFORMATION: VL region

<400> SEQUENCE: 26

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20                  25                  30

Arg Val Ala Trp Tyr Gln His Lys Pro Gly Gln Ala Pro Arg Leu Val
        35                  40                  45

Ile His Gly Val Ser Asn Arg Ala Ser Gly Ile Ser Asp Arg Phe Ser
    50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105

<210> SEQ ID NO 27
<211> LENGTH: 7
<212> TYPE: PRT
<213> ORGANISM: Artificial sequence
<220> FEATURE:
<223> OTHER INFORMATION: VL region

<400> SEQUENCE: 27

His Ser Ile Arg Ser Arg Arg
1               5

<210> SEQ ID NO 28
<211> LENGTH: 9
<212> TYPE: PRT
<213> ORGANISM: Artificial sequence
<220> FEATURE:
<223> OTHER INFORMATION: CDR sequence

<400> SEQUENCE: 28

Gln Val Tyr Gly Ala Ser Ser Tyr Thr
1               5

<210> SEQ ID NO 29
<211> LENGTH: 330
<212> TYPE: PRT
<213> ORGANISM: Artificial sequence
<220> FEATURE:
<223> OTHER INFORMATION: Modified heavy chain constant region
```

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
            325                 330

<210> SEQ ID NO 30
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 30

Ala Ser Thr Lys Gly Pro Ser Val Phe Pro Leu Ala Pro Ser Ser Lys
1               5                   10                  15

-continued

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
            325                 330

<210> SEQ ID NO 31
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

-continued

```
Gly Val His Thr Phe Pro Ala Val Leu Gln Ser Ser Gly Leu Tyr Ser
    50              55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

```
<210> SEQ ID NO 32
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 32
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50              55                  60

Leu Ser Ser Val Val Thr Val Pro Ser Ser Ser Leu Gly Thr Gln Thr
65              70                  75                  80
```

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asp Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

```
<210> SEQ ID NO 33
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 33
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

-continued

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Tyr Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

```
<210> SEQ ID NO 34
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 34
```

```
Ala Ser Thr Lys Gly Pro Ser Val Phe Pro Leu Ala Pro Ser Ser Lys
1                 5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140
```

-continued

```
Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175

Glu Gln Tyr Asn Ser Ala Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

```
<210> SEQ ID NO 35
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 35
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175
```

_____

```
Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

-continued

```
Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240
```

-continued

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 38
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 38
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Ala Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 39
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

-continued

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 40
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

-continued

<210> SEQ ID NO 41
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 330
<212> TYPE: PRT
<213> ORGANISM: Artificial sequence
<220> FEATURE:

-continued

```
<223> OTHER INFORMATION: Modified heavy chain constant region

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 43
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 43

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
        20              25                  30

Phe Pro Glu Pro Val Thr Val Ser Trp Asn Ser Gly Ala Leu Thr Ser
        35              40                  45

Gly Val His Thr Phe Pro Ala Val Leu Gln Ser Ser Gly Leu Tyr Ser
    50              55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330
```

```
<210> SEQ ID NO 44
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 44
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
        20              25                  30

Phe Pro Glu Pro Val Thr Val Ser Trp Asn Ser Gly Ala Leu Thr Ser
        35              40                  45
```

-continued

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 45
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330
```

```
<210> SEQ ID NO 46
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 46
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 47
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140
```

```
Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Ala Ser Thr Tyr Arg Val Val Ser Val Leu Thr Val Leu
        180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Arg Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Lys Leu Ser Leu Ser Pro Gly Lys
            325             330
```

```
<210> SEQ ID NO 48
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 48
```

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175
```

```
Glu Gln Tyr Gln Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330
```

<210> SEQ ID NO 49
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 49

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330

<210> SEQ ID NO 50
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330
```

```
<210> SEQ ID NO 51
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 51
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330

<210> SEQ ID NO 52
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300
```

-continued

```
Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 53
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330
```

```
<210> SEQ ID NO 54
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 55
<211> LENGTH: 330
<212> TYPE: PRT
<213> ORGANISM: Artificial sequence
```

<220> FEATURE:
<223> OTHER INFORMATION: Modified heavy chain constant region

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 56
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 57
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 57

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
         20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
         130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
             180                 185                 190

His Gln Asp Trp Leu Asn Gly Lys Glu Tyr Lys Cys Lys Val Ser Asn
             195                 200                 205

Lys Ala Leu Pro Ala Pro Ile Glu Lys Thr Ile Ser Lys Ala Lys Gly
         210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
             260                 265                 270

Asn Tyr Lys Thr Thr Pro Pro Val Leu Asp Ser Asp Gly Ser Phe Phe
             275                 280                 285

Leu Tyr Ser Lys Leu Thr Val Asp Lys Ser Arg Trp Gln Gln Gly Asn
         290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                    325                 330
```

```
<210> SEQ ID NO 58
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 58

Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
         20                  25                  30

Phe Pro Glu Pro Val Thr Val Ser Trp Asn Ser Gly Ala Leu Thr Ser
         35                  40                  45
```

-continued

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330
```

```
<210> SEQ ID NO 59
<211> LENGTH: 330
<212> TYPE: PRT
<213> ORGANISM: Human

<400> SEQUENCE: 59
```

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

-continued

```
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 60
<211> LENGTH: 107
<212> TYPE: PRT
<213> ORGANISM: Human

<400> SEQUENCE: 60

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 61
<211> LENGTH: 330
<212> TYPE: PRT
```

-continued

```
<213> ORGANISM: Artificial sequence
<220> FEATURE:
<223> OTHER INFORMATION: Modified heavy chain constant region

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 62
<211> LENGTH: 330
<212> TYPE: PRT
<213> ORGANISM: Artificial sequence
<220> FEATURE:
<223> OTHER INFORMATION: Modified heavy chain constant region
```

<400> SEQUENCE: 62

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330
```

<210> SEQ ID NO 63
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 63

```
Ala Ser Thr Lys Gly Pro Ser Val Phe Pro Leu Ala Pro Ser Ser Lys
1               5                   10                  15
```

-continued

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Glu Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Arg
305                 310                 315                 320

Gln Lys Ser Leu Ser Leu Ser Pro Gly Lys
                325                 330
```

```
<210> SEQ ID NO 64
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 64
```

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

-continued

```
Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Glu Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Ala Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Arg
305             310             315             320

Gln Lys Ser Leu Ser Leu Ser Pro Gly Lys
            325             330
```

```
<210> SEQ ID NO 65
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 65
```

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80
```

```
Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Glu Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Arg
305             310             315             320

Gln Glu Ser Leu Ser Leu Ser Pro Gly Lys
                325             330
```

<210> SEQ ID NO 66
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 66

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110
```

```
Pro Ala Pro Glu Leu Leu Gly Gly Pro Ser Val Phe Leu Phe Pro Pro
        115                 120                 125

Lys Pro Glu Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Arg
305                 310                 315                 320

Gln Lys Lys Leu Ser Leu Ser Pro Gly Lys
                325                 330

<210> SEQ ID NO 67
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Glu Asp Thr Leu Met Ile Ser Arg Thr Pro Glu Val Thr Cys
        130                 135                 140
```

```
Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Arg
305                 310                 315                 320

Gln Glu Ser Leu Ser Leu Ser Pro Gly Lys
                325                 330
```

```
<210> SEQ ID NO 68
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 68
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Glu Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175
```

-continued

```
Glu Gln Tyr Ala Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
            210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
            290             295             300

Val Phe Ser Cys Ser Val Met His Glu Ala Leu His Asn His Tyr Arg
305             310             315             320

Gln Lys Lys Leu Ser Leu Ser Pro Gly Lys
            325             330

<210> SEQ ID NO 69
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 69

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
            50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
            130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205
```

-continued

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330
```

```
<210> SEQ ID NO 70
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 70
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

-continued

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330
```

<210> SEQ ID NO 71
<211> LENGTH: 330
<212> TYPE: PRT
<213> ORGANISM: Human

<400> SEQUENCE: 71

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

-continued

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 72
<211> LENGTH: 330
<212> TYPE: PRT
<213> ORGANISM: Human

<400> SEQUENCE: 72

Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Pro Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

-continued

```
Val Phe Ser Cys Ser Val Met His Glu Ala Leu His Asn His Tyr Thr
305                 310             315                 320

Gln Lys Ser Leu Ser Leu Ser Pro Gly Lys
            325             330

<210> SEQ ID NO 73
<211> LENGTH: 330
<212> TYPE: PRT
<213> ORGANISM: Human

<400> SEQUENCE: 73

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75                  80

Tyr Ile Cys Asn Val Asn His Lys Pro Ser Asn Thr Lys Val Asp Lys
                85              90                  95

Pro Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155                 160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235                 240

Met Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Glu Gly Leu His Asn His Tyr Thr
305             310             315                 320

Gln Lys Ser Leu Ser Leu Ser Pro Gly Lys
            325             330
```

-continued

```
<210> SEQ ID NO 74
<211> LENGTH: 326
<212> TYPE: PRT
<213> ORGANISM: Human

<400> SEQUENCE: 74

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 75
<211> LENGTH: 327
<212> TYPE: PRT
<213> ORGANISM: Human
```

-continued

<400> SEQUENCE: 75

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 76
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 76

Ala Ser Thr Lys Gly Pro Ser Val Phe Pro Leu Ala Pro Ser Ser Lys
1               5                   10                  15

-continued

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Tyr Ala Leu His Asn His Tyr Thr
305                 310                 315                 320

Gln Lys Ser Leu Ser Leu Ser Pro Gly Lys
                325                 330
```

<210> SEQ ID NO 77
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 77

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Tyr Ala Leu His Asn His Tyr Thr
305                 310                 315                 320

Gln Glu Ser Leu Ser Leu Ser Pro Gly Lys
                325                 330

<210> SEQ ID NO 78
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

-continued

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Tyr Ala Leu His Asn His Tyr Thr
305                 310                 315                 320

Gln Lys Lys Leu Ser Leu Ser Pro Gly Lys
                325                 330

<210> SEQ ID NO 79
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Tyr Ala Leu His Asn His Tyr Thr
305                 310                 315                 320

Gln Glu Ser Leu Ser Leu Ser Pro Gly Lys
                325                 330

<210> SEQ ID NO 80
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 80

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

-continued

```
Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Tyr Ala Leu His Asn His Tyr Thr
305                 310                 315                 320

Gln Lys Lys Leu Ser Leu Ser Pro Gly Lys
                325                 330

<210> SEQ ID NO 81
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 81

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175
```

-continued

```
Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Ala Ala Leu Pro Ala Pro Ile Ser Lys Thr Ile Ser Lys Ala Lys Gly
            210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 82
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

-continued

```
Ala Ala Leu Pro Ala Pro Ile Ser Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 83
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 83

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Ala Ala Leu Pro Ala Pro Ile Ser Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240
```

-continued

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 84
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 84

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Ala Ala Leu Pro Ala Pro Ile Ser Lys Thr Ile Ser Lys Ala Lys Gly
        210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

-continued

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
            325                 330

<210> SEQ ID NO 85
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Ala Ala Leu Pro Ala Pro Ile Ser Lys Thr Ile Ser Lys Ala Lys Gly
        210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

-continued

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 86
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Ala Ala Leu Pro Ala Pro Ile Ser Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330

-continued

<210> SEQ ID NO 87
<211> LENGTH: 330
<212> TYPE: PRT
<213> ORGANISM: Artificial sequence
<220> FEATURE:
<223> OTHER INFORMATION: Modified heavy chain constant region

<400> SEQUENCE: 87

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 88
<211> LENGTH: 106
<212> TYPE: PRT
<213> ORGANISM: Human

-continued

```
<400> SEQUENCE: 88

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 89
<211> LENGTH: 118
<212> TYPE: PRT
<213> ORGANISM: Artificial sequence
<220> FEATURE:
<223> OTHER INFORMATION: Humanized VH region

<400> SEQUENCE: 89

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

Gly Arg Ile Asp Pro Ala Asn Thr Asn Thr Lys Tyr Asp Pro Lys Phe
    50                  55                  60

Gln Gly Lys Ala Thr Ile Thr Thr Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
            100                 105                 110

Leu Val Thr Val Ser Ser
        115

<210> SEQ ID NO 90
<211> LENGTH: 8
<212> TYPE: PRT
<213> ORGANISM: Artificial sequence
<220> FEATURE:
<223> OTHER INFORMATION: CDR sequence

<400> SEQUENCE: 90

Gly Phe Asn Ile Lys Asp Thr Phe
1               5

<210> SEQ ID NO 91
<211> LENGTH: 8
<212> TYPE: PRT
<213> ORGANISM: Artificial sequence
<220> FEATURE:
<223> OTHER INFORMATION: CDR sequence
```

-continued

```
<400> SEQUENCE: 91

Ile Asp Pro Ala Asn Thr Asn Thr
1               5

<210> SEQ ID NO 92
<211> LENGTH: 11
<212> TYPE: PRT
<213> ORGANISM: Artificial sequence
<220> FEATURE:
<223> OTHER INFORMATION: CDR sequence

<400> SEQUENCE: 92

Val Arg Gly Leu Tyr Thr Tyr Tyr Phe Asp Tyr
1               5               10

<210> SEQ ID NO 93
<211> LENGTH: 107
<212> TYPE: PRT
<213> ORGANISM: Artificial sequence
<220> FEATURE:
<223> OTHER INFORMATION: CDR sequence

<400> SEQUENCE: 93

Glu Ile Val Met Thr Gln Ser Pro Ala Thr Leu Ser Val Ser Pro Gly
1               5               10              15

Glu Arg Ala Thr Leu Ser Cys Arg Ala Ser Gln Ser Ile Ser Asn Asn
            20              25              30

Leu His Trp Tyr Gln Gln Lys Pro Gly Gln Ala Pro Arg Leu Leu Ile
        35              40              45

Lys Phe Ala Ser Gln Ser Ile Thr Gly Ile Pro Ala Arg Phe Ser Gly
    50              55              60

Ser Gly Ser Gly Thr Glu Phe Thr Leu Thr Ile Ser Ser Leu Gln Ser
65              70              75              80

Glu Asp Phe Ala Val Tyr Tyr Cys Gln Gln Gly Asn Ser Trp Pro Tyr
                85              90              95

Thr Phe Gly Gln Gly Thr Lys Leu Glu Ile Lys
            100             105

<210> SEQ ID NO 94
<211> LENGTH: 6
<212> TYPE: PRT
<213> ORGANISM: Artificial sequence
<220> FEATURE:
<223> OTHER INFORMATION: CDR sequence

<400> SEQUENCE: 94

Gln Ser Ile Ser Asn Asn
1               5

<210> SEQ ID NO 95
<211> LENGTH: 9
<212> TYPE: PRT
<213> ORGANISM: Artificial sequence
<220> FEATURE:
<223> OTHER INFORMATION: CDR sequence

<400> SEQUENCE: 95

Gln Gln Gly Asn Ser Trp Pro Tyr Thr
1               5

<210> SEQ ID NO 96
<211> LENGTH: 118
```

-continued

```
<212> TYPE: PRT
<213> ORGANISM: Artificial sequence
<220> FEATURE:
<223> OTHER INFORMATION: Humanized VL region

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

His Met His Trp Val Arg Gln Ala Pro Gly Gln Arg Leu Glu Trp Ile
        35                  40                  45

Gly Arg Ile Asp Pro Ala Asn Gly Asn Thr Glu Tyr Asp Gln Lys Phe
    50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Thr Asn Val Tyr Phe Ala Tyr Trp Gly Gln Gly Thr
            100                 105                 110

Leu Val Thr Val Ser Ser
        115

<210> SEQ ID NO 97
<211> LENGTH: 8
<212> TYPE: PRT
<213> ORGANISM: Artificial sequence
<220> FEATURE:
<223> OTHER INFORMATION: CDR sequence

<400> SEQUENCE: 97

Gly Phe Asn Ile Lys Asp Thr His
1               5

<210> SEQ ID NO 98
<211> LENGTH: 8
<212> TYPE: PRT
<213> ORGANISM: Artificial sequence
<220> FEATURE:
<223> OTHER INFORMATION: CDR sequence

<400> SEQUENCE: 98

Ile Asp Pro Ala Asn Gly Asn Thr
1               5

<210> SEQ ID NO 99
<211> LENGTH: 11
<212> TYPE: PRT
<213> ORGANISM: Artificial sequence
<220> FEATURE:
<223> OTHER INFORMATION: CDR sequence

<400> SEQUENCE: 99

Ala Arg Trp Gly Thr Asn Val Tyr Phe Ala Tyr
1               5                   10

<210> SEQ ID NO 100
<211> LENGTH: 106
<212> TYPE: PRT
<213> ORGANISM: Artificial sequence
<220> FEATURE:
<223> OTHER INFORMATION: Humanized VL region
```

<400> SEQUENCE: 100

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr His Ser Tyr Pro Pro Thr
                85                  90                  95

Phe Gly Gly Gly Thr Lys Val Glu Ile Lys
            100                 105
```

<210> SEQ ID NO 101
<211> LENGTH: 5
<212> TYPE: PRT
<213> ORGANISM: Artificial sequence
<220> FEATURE:
<223> OTHER INFORMATION: CDR sequence

<400> SEQUENCE: 101

```
Ser Ser Val Ser Tyr
1               5
```

<210> SEQ ID NO 102
<211> LENGTH: 9
<212> TYPE: PRT
<213> ORGANISM: Artificial sequence
<220> FEATURE:
<223> OTHER INFORMATION: CDR sequence

<400> SEQUENCE: 102

```
Gln Gln Tyr His Ser Tyr Pro Pro Thr
1               5
```

<210> SEQ ID NO 103
<211> LENGTH: 132
<212> TYPE: PRT
<213> ORGANISM: Artificial sequence
<220> FEATURE:
<223> OTHER INFORMATION: VH region

<400> SEQUENCE: 103

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ala Asn
            20                  25                  30

Ser Tyr Tyr Gly Val Trp Val Arg Gln Ser Pro Gly Lys Gly Leu Glu
        35                  40                  45

Trp Val Gly Ser Ile Ala Tyr Arg Gly Asn Ser Asn Ser Gly Ser Thr
    50                  55                  60

Tyr Tyr Asn Pro Ser Leu Lys Ser Arg Ala Thr Val Ser Val Asp Thr
65                  70                  75                  80

Ser Lys Asn Gln Val Ser Leu Arg Leu Thr Ser Val Thr Ala Ala Asp
                85                  90                  95
```

```
Thr Ala Leu Tyr Tyr Cys Ala Arg Arg Gln Leu Leu Asp Asp Gly Thr
            100                 105                 110

Gly Tyr Gln Trp Ala Ala Phe Asp Val Trp Gly Gln Gly Thr Met Val
        115                 120                 125

Thr Val Ser Ser
    130

<210> SEQ ID NO 104
<211> LENGTH: 10
<212> TYPE: PRT
<213> ORGANISM: Artificial sequence
<220> FEATURE:
<223> OTHER INFORMATION: CDR sequence

<400> SEQUENCE: 104

Gly Ala Ser Ile Ser Ala Asn Ser Tyr Tyr
1               5                   10

<210> SEQ ID NO 105
<211> LENGTH: 19
<212> TYPE: PRT
<213> ORGANISM: Artificial sequence
<220> FEATURE:
<223> OTHER INFORMATION: CDR sequence

<400> SEQUENCE: 105

Ala Arg Arg Gln Leu Leu Asp Asp Gly Thr Gly Tyr Gln Trp Ala Ala
1               5                   10                  15

Phe Asp Val

<210> SEQ ID NO 106
<211> LENGTH: 19
<212> TYPE: PRT
<213> ORGANISM: Artificial sequence
<220> FEATURE:
<223> OTHER INFORMATION: CDR sequence

<400> SEQUENCE: 106

Ala Arg Arg Gln Leu Leu Asp Asp Gly Thr Gly Tyr Gln Trp Ala Ala
1               5                   10                  15

Phe Asp Val

<210> SEQ ID NO 107
<211> LENGTH: 110
<212> TYPE: PRT
<213> ORGANISM: Artificial sequence
<220> FEATURE:
<223> OTHER INFORMATION: VL region

<400> SEQUENCE: 107

Gln Ser Val Leu Thr Gln Pro Pro Ser Val Ser Glu Ala Pro Arg Gln
1               5                   10                  15

Thr Val Thr Ile Ser Cys Ser Gly Asn Ser Phe Asn Ile Gly Arg Tyr
            20                  25                  30

Pro Val Asn Trp Tyr Gln Gln Leu Pro Gly Lys Ala Pro Lys Leu Leu
        35                  40                  45

Ile Tyr Tyr Asn Asn Leu Arg Phe Ser Gly Val Ser Asp Arg Phe Ser
    50                  55                  60

Gly Ser Lys Ser Gly Thr Ser Ala Ser Leu Ala Ile Arg Asp Leu Leu
65                  70                  75                  80
```

-continued

```
Ser Glu Asp Glu Ala Asp Tyr Tyr Cys Ser Thr Trp Asp Asp Thr Leu
                85                  90                  95

Lys Gly Trp Val Phe Gly Gly Gly Thr Lys Val Thr Val Leu
            100                 105                 110

<210> SEQ ID NO 108
<211> LENGTH: 8
<212> TYPE: PRT
<213> ORGANISM: Artificial sequence
<220> FEATURE:
<223> OTHER INFORMATION: CDR sequence

<400> SEQUENCE: 108

Ser Phe Asn Ile Gly Arg Tyr Pro
1               5

<210> SEQ ID NO 109
<211> LENGTH: 11
<212> TYPE: PRT
<213> ORGANISM: Artificial sequence
<220> FEATURE:
<223> OTHER INFORMATION: CDR sequence

<400> SEQUENCE: 109

Ser Thr Trp Asp Asp Thr Leu Lys Gly Trp Val
1               5                   10

<210> SEQ ID NO 110
<211> LENGTH: 121
<212> TYPE: PRT
<213> ORGANISM: Artificial sequence
<220> FEATURE:
<223> OTHER INFORMATION: VH region

<400> SEQUENCE: 110

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120

<210> SEQ ID NO 111
<211> LENGTH: 8
<212> TYPE: PRT
<213> ORGANISM: Artificial sequence
<220> FEATURE:
<223> OTHER INFORMATION: CDR sequence

<400> SEQUENCE: 111

Gly Gly Ser Phe Ser Gly Tyr Tyr
1               5
```

```
<210> SEQ ID NO 112
<211> LENGTH: 7
<212> TYPE: PRT
<213> ORGANISM: Artificial sequence
<220> FEATURE:
<223> OTHER INFORMATION: CDR sequence

<400> SEQUENCE: 112

Ile Asn His Gly Gly Tyr Val
1               5

<210> SEQ ID NO 113
<211> LENGTH: 15
<212> TYPE: PRT
<213> ORGANISM: Artificial sequence
<220> FEATURE:
<223> OTHER INFORMATION: CDR sequence

<400> SEQUENCE: 113

Ala Arg Asp Tyr Gly Pro Gly Asn Tyr Asp Trp Tyr Phe Asp Leu
1               5                   10                  15

<210> SEQ ID NO 114
<211> LENGTH: 109
<212> TYPE: PRT
<213> ORGANISM: Artificial sequence
<220> FEATURE:
<223> OTHER INFORMATION: VL region

<400> SEQUENCE: 114

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105

<210> SEQ ID NO 115
<211> LENGTH: 6
<212> TYPE: PRT
<213> ORGANISM: Artificial sequence
<220> FEATURE:
<223> OTHER INFORMATION: CDR sequence

<400> SEQUENCE: 115

Gln Ser Val Ser Ser Tyr
1               5

<210> SEQ ID NO 116
<211> LENGTH: 11
<212> TYPE: PRT
<213> ORGANISM: Artificial sequence
<220> FEATURE:
<223> OTHER INFORMATION: CDR sequence
```

```
<400> SEQUENCE: 116

Gln Gln Arg Ser Asn Trp Pro Pro Ala Leu Thr
1               5               10

<210> SEQ ID NO 117
<211> LENGTH: 113
<212> TYPE: PRT
<213> ORGANISM: Artificial sequence
<220> FEATURE:
<223> OTHER INFORMATION: VH region

<400> SEQUENCE: 117

Glu Val His Leu Val Glu Ser Gly Gly Gly Leu Val Gln Pro Gly Gly
1               5               10                  15

Ser Leu Arg Leu Ser Cys Ala Ala Ser Gly Phe Thr Phe Ser Arg Tyr
            20              25                  30

Gly Met Ser Trp Val Arg Gln Ala Pro Gly Lys Gly Leu Glu Leu Val
            35              40                  45

Ala Met Met Lys Thr Lys Gly Gly Arg Thr Tyr Tyr Pro Asp Ser Val
        50              55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Ser Asp Gly Tyr Tyr Trp Gly Gln Gly Thr Thr Val Thr Val Ser
            100                 105                 110

Ser

<210> SEQ ID NO 118
<211> LENGTH: 8
<212> TYPE: PRT
<213> ORGANISM: Artificial sequence
<220> FEATURE:
<223> OTHER INFORMATION: CDR sequence

<400> SEQUENCE: 118

Gly Phe Thr Phe Ser Arg Tyr Gly
1               5

<210> SEQ ID NO 119
<211> LENGTH: 8
<212> TYPE: PRT
<213> ORGANISM: Artificial sequence
<220> FEATURE:
<223> OTHER INFORMATION: CDR sequence

<400> SEQUENCE: 119

Met Lys Thr Lys Gly Gly Arg Thr
1               5

<210> SEQ ID NO 120
<211> LENGTH: 6
<212> TYPE: PRT
<213> ORGANISM: Artificial sequence
<220> FEATURE:
<223> OTHER INFORMATION: CDR sequence

<400> SEQUENCE: 120

Ala Ser Asp Gly Tyr Tyr
1               5

<210> SEQ ID NO 121
```

-continued

<211> LENGTH: 111
<212> TYPE: PRT
<213> ORGANISM: Artificial sequence
<220> FEATURE:
<223> OTHER INFORMATION: VL region

<400> SEQUENCE: 121

Asp Val Val Met Thr Gln Thr Pro Leu Ser Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Trp Gln Gly
                85                  90                  95

Thr His Leu Trp Thr Phe Gly Gly Gly Thr Lys Val Glu Ile Lys
            100                 105                 110

<210> SEQ ID NO 122
<211> LENGTH: 11
<212> TYPE: PRT
<213> ORGANISM: Artificial sequence
<220> FEATURE:
<223> OTHER INFORMATION: CDR sequence

<400> SEQUENCE: 122

Gln Ser Leu Leu His Ser Asp Gly Lys Thr Tyr
1               5                   10

<210> SEQ ID NO 123
<211> LENGTH: 8
<212> TYPE: PRT
<213> ORGANISM: Artificial sequence
<220> FEATURE:
<223> OTHER INFORMATION: CDR sequence

<400> SEQUENCE: 123

Trp Gln Gly Thr His Leu Trp Thr
1               5

<210> SEQ ID NO 124
<211> LENGTH: 326
<212> TYPE: PRT
<213> ORGANISM: Artificial sequence
<220> FEATURE:
<223> OTHER INFORMATION: Modified heavy chain constant region

<400> SEQUENCE: 124

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

-continued

```
Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Arg
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 125
<211> LENGTH: 326
<212> TYPE: PRT
<213> ORGANISM: Artificial sequence
<220> FEATURE:
<223> OTHER INFORMATION: Modified heavy chain constant region

<400> SEQUENCE: 125

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

-continued

```
Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Arg
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Glu Ser Leu
305                 310                 315                 320

Ser Leu Ser Pro Gly Lys
                325
```

```
<210> SEQ ID NO 126
<211> LENGTH: 326
<212> TYPE: PRT
<213> ORGANISM: Artificial sequence
<220> FEATURE:
<223> OTHER INFORMATION: Modified heavy chain constant region

<400> SEQUENCE: 126
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
        130                 135                 140
```

-continued

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Arg
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Lys Leu
305                 310                 315                 320

Ser Leu Ser Pro Gly Lys
                325
```

```
<210> SEQ ID NO 127
<211> LENGTH: 326
<212> TYPE: PRT
<213> ORGANISM: Artificial sequence
<220> FEATURE:
<223> OTHER INFORMATION: Modified heavy chain constant region

<400> SEQUENCE: 127
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175
```

```
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Arg
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Glu Ser Leu
305                 310                 315                 320

Ser Leu Ser Pro Gly Lys
                325
```

```
<210> SEQ ID NO 128
<211> LENGTH: 326
<212> TYPE: PRT
<213> ORGANISM: Artificial sequence
<220> FEATURE:
<223> OTHER INFORMATION: Modified heavy chain constant region

<400> SEQUENCE: 128
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205
```

-continued

Ala Pro Ile Glu Lys Thr Ile Ser Lys Thr Lys Gly Gln Pro Arg Arg
    210             215         220

Pro Gln Val Tyr Thr Leu Pro Pro Ser Arg Glu Glu Met Thr Lys Asn
225             230             235             240

Gln Val Ser Leu Thr Cys Leu Val Lys Gly Phe Tyr Pro Ser Asp Ile
            245             250             255

Ala Val Glu Trp Glu Ser Asn Gly Gln Pro Glu Asn Asn Tyr Lys Thr
            260             265             270

Thr Pro Pro Met Leu Asp Ser Asp Gly Ser Phe Phe Leu Tyr Ser Lys
        275             280             285

Leu Thr Val Asp Lys Ser Arg Trp Gln Gln Gly Asn Val Phe Ser Cys
    290             295             300

Ser Val Met His Glu Ala Leu His Asn His Tyr Thr Gln Lys Lys Leu
305             310             315             320

Ser Leu Ser Pro Gly Lys
            325

<210> SEQ ID NO 129
<211> LENGTH: 327
<212> TYPE: PRT
<213> ORGANISM: Artificial sequence
<220> FEATURE:
<223> OTHER INFORMATION: Modified heavy chain constant region

<400> SEQUENCE: 129

Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Lys Thr
65              70              75              80

Tyr Thr Cys Asn Val Asp His Lys Pro Ser Asn Thr Lys Val Asp Lys
            85              90              95

Arg Val Glu Ser Lys Tyr Gly Pro Pro Cys Pro Ser Cys Pro Ala Pro
            100             105             110

Glu Phe Leu Gly Gly Pro Ser Val Phe Leu Phe Pro Pro Lys Pro Lys
        115             120             125

Asp Thr Leu Met Ile Ser Arg Thr Pro Glu Val Thr Cys Val Val Val
    130             135             140

Asp Val Ser Gln Glu Asp Pro Glu Val Gln Phe Asn Trp Tyr Val Asp
145             150             155             160

Gly Val Glu Val His Asn Ala Lys Thr Lys Pro Arg Glu Glu Gln Phe
            165             170             175

Asn Ser Thr Tyr Arg Val Val Ser Val Leu Thr Val Leu His Gln Asp
            180             185             190

Trp Leu Asn Gly Lys Glu Tyr Lys Cys Lys Val Ser Asn Lys Gly Leu
        195             200             205

Pro Ser Ser Ile Glu Lys Thr Ile Ser Lys Ala Lys Gly Gln Pro Arg
    210             215             220

Arg Pro Gln Val Tyr Thr Leu Pro Pro Ser Gln Glu Glu Met Thr Lys
225             230             235             240

-continued

```
Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 130
<211> LENGTH: 327
<212> TYPE: PRT
<213> ORGANISM: Artificial sequence
<220> FEATURE:
<223> OTHER INFORMATION: Modified heavy chain constant region

<400> SEQUENCE: 130

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Arg Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270
```

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 131
<211> LENGTH: 327
<212> TYPE: PRT
<213> ORGANISM: Artificial sequence
<220> FEATURE:
<223> OTHER INFORMATION: Modified heavy chain constant region

<400> SEQUENCE: 131

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Arg Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Lys
305                     310                 315                 320

Leu Ser Leu Ser Leu Gly Lys
                325

<210> SEQ ID NO 132
<211> LENGTH: 327
<212> TYPE: PRT
<213> ORGANISM: Artificial sequence
<220> FEATURE:
<223> OTHER INFORMATION: Modified heavy chain constant region

<400> SEQUENCE: 132

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Ala Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Arg Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

-continued

<210> SEQ ID NO 133
<211> LENGTH: 327
<212> TYPE: PRT
<213> ORGANISM: Artificial sequence
<220> FEATURE:
<223> OTHER INFORMATION: Modified heavy chain constant region

<400> SEQUENCE: 133

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Ala Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Arg Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Lys
305                 310                 315                 320

Leu Ser Leu Ser Leu Gly Lys
                325
```